(12) United States Patent
Lapointe et al.

(10) Patent No.: US 10,287,272 B2
(45) Date of Patent: May 14, 2019

(54) SUBSTITUTED INDAZOLE COMPOUNDS AS RORGAMMAT INHIBITORS AND USES THEREOF

(71) Applicant: Merck Sharp & Dohme Corp., Rahway, NJ (US)

(72) Inventors: Blair T. Lapointe, Brookline, MA (US); Peter H. Fuller, Ashland, MA (US); Hakan Gunaydin, Somerville, MA (US); Kun Liu, Needham, MA (US); Mark E. Scott, Edmonton (CA); B. Wesley Trotter, Medfield, MA (US); Hongjun Zhang, Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/770,256

(22) PCT Filed: Oct. 27, 2016

(86) PCT No.: PCT/US2016/059063
§ 371 (c)(1),
(2) Date: Apr. 23, 2018

(87) PCT Pub. No.: WO2017/075182
PCT Pub. Date: May 4, 2017

(65) Prior Publication Data
US 2018/0312489 A1    Nov. 1, 2018

Related U.S. Application Data

(60) Provisional application No. 62/372,544, filed on Aug. 9, 2016, provisional application No. 62/246,921, filed on Oct. 27, 2015.

(51) Int. Cl.
| | |
|---|---|
| *C07D 403/08* | (2006.01) |
| *C07D 403/12* | (2006.01) |
| *C07D 231/56* | (2006.01) |
| *C07D 403/06* | (2006.01) |
| *C07D 403/14* | (2006.01) |
| *C07D 405/12* | (2006.01) |
| *C07D 487/04* | (2006.01) |
| *C07D 487/10* | (2006.01) |
| *C07D 491/107* | (2006.01) |
| *C07D 491/048* | (2006.01) |
| *C07D 401/06* | (2006.01) |
| *C07D 401/12* | (2006.01) |

(Continued)

(52) U.S. Cl.
CPC ............ *C07D 403/08* (2013.01); *A61P 19/02* (2018.01); *C07D 231/56* (2013.01); *C07D 401/06* (2013.01); *C07D 401/12* (2013.01); *C07D 403/06* (2013.01); *C07D 403/12* (2013.01); *C07D 403/14* (2013.01); *C07D 405/12* (2013.01); *C07D 487/04* (2013.01); *C07D 487/10* (2013.01); *C07D 491/048* (2013.01); *C07D 491/107* (2013.01)

(58) Field of Classification Search
CPC .. C07D 403/08; C07D 401/06; C07D 401/12; C07D 491/107; C07D 403/12; C07D 487/10; C07D 405/12; C07D 403/06; C07D 487/04; C07D 491/048; C07D 231/56; C07D 403/14; A61P 19/02
See application file for complete search history.

(56) References Cited

U.S. PATENT DOCUMENTS

| 4,670,447 A | 6/1987 | Strupczewski |
| 4,751,235 A | 6/1988 | Anderson |

(Continued)

FOREIGN PATENT DOCUMENTS

| EP | 0429257 A2 | 5/1991 |
| EP | 0882718 A1 | 12/1998 |

(Continued)

OTHER PUBLICATIONS

U.S. Appl. No. 15/647,437, 4-Heteroaryl Substituted Benzoic Acid Compounds as RORgammaT Inhibitors and Uses Thereof, filed Jul. 12, 2017.

(Continued)

*Primary Examiner* — John M Mauro
(74) *Attorney, Agent, or Firm* — Dechert LLP

(57) ABSTRACT

The present invention relates to compounds according to Formula (I) and pharmaceutically acceptable salts thereof. Such compounds can be used in the treatment o RORgammaT-mediated diseases or conditions.

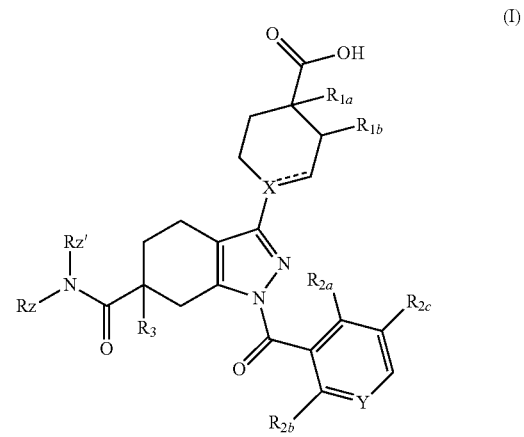

30 Claims, 5 Drawing Sheets

(51) Int. Cl.
*A61P 19/02* (2006.01)
*A61K 31/416* (2006.01)

(56) References Cited

U.S. PATENT DOCUMENTS

| | | |
|---|---|---|
| 5,583,152 A | 12/1996 | Bernstein et al. |
| 5,639,780 A | 6/1997 | Lau et al. |
| 5,985,903 A | 11/1999 | Assmann et al. |
| 6,020,354 A | 2/2000 | Assmann et al. |
| 6,037,367 A | 3/2000 | Christensen, IV et al. |
| 6,133,290 A | 10/2000 | Krushinski, Jr. et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,115,750 B1 | 10/2006 | Kato et al. |
| 7,138,401 B2 | 11/2006 | Kasibhatla et al. |
| 7,329,675 B2 | 2/2008 | Cox et al. |
| 7,355,042 B2 | 4/2008 | Edgar et al. |
| 7,420,059 B2 | 9/2008 | O'Connor et al. |
| 7,482,342 B2 | 1/2009 | D'Orchymont et al. |
| 7,514,465 B2 | 4/2009 | Kuo et al. |
| 7,569,571 B2 | 8/2009 | Dong et al. |
| 7,696,200 B2 | 4/2010 | Ackermann et al. |
| 7,696,229 B2 | 4/2010 | Dunn et al. |
| 7,713,996 B2 | 5/2010 | Ackermann et al. |
| 7,741,495 B2 | 6/2010 | Liou et al. |
| 7,772,252 B2 | 8/2010 | Hendrix et al. |
| 7,799,933 B2 | 9/2010 | Ceccarelli et al. |
| 9,095,583 B2 | 8/2015 | Karstens et al. |
| 9,266,827 B2 | 2/2016 | Aicher et al. |
| 9,273,070 B2 | 3/2016 | Knochel et al. |
| 9,487,490 B2 | 11/2016 | Barr et al. |
| 9,512,111 B2 | 12/2016 | Glick et al. |
| 9,556,168 B2 | 1/2017 | Barr et al. |
| 9,603,838 B2 | 3/2017 | Karstens et al. |
| 9,657,033 B2 | 5/2017 | Aicher et al. |
| 9,663,522 B2 | 5/2017 | Barr et al. |
| 9,745,265 B2 | 8/2017 | Barr et al. |
| 9,884,043 B2 | 2/2018 | Karstens et al. |
| 2006/0004000 A1 | 1/2006 | D'Orchymont et al. |
| 2006/0030612 A1 | 2/2006 | Steffan et al. |
| 2006/0100218 A1 | 5/2006 | Ibrahim et al. |
| 2006/0100230 A1 | 5/2006 | Bischoff et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0191603 A1 | 8/2007 | Ackermann et al. |
| 2007/0197782 A1 | 8/2007 | Clough et al. |
| 2007/0281922 A1 | 12/2007 | Liu et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0305169 A1 | 12/2008 | Miki et al. |
| 2009/0005410 A1 | 1/2009 | Charvat et al. |
| 2009/0075973 A1 | 3/2009 | Newcom et al. |
| 2009/0124616 A1 | 5/2009 | Song et al. |
| 2009/0233955 A1 | 9/2009 | Frazee et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0130484 A1 | 5/2010 | Ackermann et al. |
| 2010/0234340 A1 | 9/2010 | Schunk et al. |
| 2010/0317863 A1 | 12/2010 | Kuzmich et al. |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0150864 A1 | 6/2011 | Bignan et al. |
| 2011/0178063 A1 | 7/2011 | Baldwin et al. |
| 2011/0263046 A1 | 10/2011 | Deuschle et al. |
| 2014/0088094 A1 | 3/2014 | Glick et al. |
| 2015/0111877 A1 | 4/2015 | Aicher et al. |
| 2015/0126493 A1 | 5/2015 | Aicher et al. |
| 2015/0191434 A1 | 7/2015 | Barr et al. |
| 2015/0210687 A1 | 7/2015 | Barr et al. |
| 2015/0218096 A1 | 8/2015 | Barr et al. |
| 2015/0218169 A1 | 8/2015 | Barr et al. |
| 2015/0297566 A1 | 10/2015 | Karstens et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |
| 2017/0313722 A1 | 11/2017 | Aicher et al. |
| 2017/0340610 A1 | 11/2017 | Karstens et al. |
| 2018/0016239 A1 | 1/2018 | Lapointe et al. |
| 2018/0022701 A1 | 1/2018 | Barr et al. |
| 2018/0305320 A1 | 10/2018 | Lapointe et al. |

FOREIGN PATENT DOCUMENTS

| | | |
|---|---|---|
| EP | 1820515 A1 | 8/2007 |
| EP | 2181710 A1 | 5/2010 |
| EP | 2487159 A1 | 8/2012 |
| JP | 6-250441 A | 9/1994 |
| JP | 2004307487 A | 11/2004 |
| JP | 2007238463 A | 9/2007 |
| JP | 2016-141632 A | 8/2016 |
| WO | WO-92/13856 A1 | 8/1992 |
| WO | WO-1996/37467 A1 | 11/1996 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/012600 A1 | 2/2001 |
| WO | WO-02/100819 A1 | 12/2002 |
| WO | WO-03/014075 A2 | 2/2003 |
| WO | WO-2004/056830 A1 | 7/2004 |
| WO | WO-05/028434 A2 | 3/2005 |
| WO | WO-2005/037834 A1 | 4/2005 |
| WO | WO-2006/007486 A2 | 1/2006 |
| WO | WO-2006/026754 A2 | 3/2006 |
| WO | WO-2006/052190 A1 | 5/2006 |
| WO | WO-2006/057460 A1 | 6/2006 |
| WO | WO-2006/063167 A1 | 6/2006 |
| WO | WO-2007/024944 A1 | 3/2007 |
| WO | WO-2007/031429 A1 | 3/2007 |
| WO | WO-2007/093507 A1 | 8/2007 |
| WO | WO-2007/103308 A2 | 9/2007 |
| WO | WO-2007/125405 A2 | 11/2007 |
| WO | WO-2007/138998 A1 | 12/2007 |
| WO | WO-2007/144327 A2 | 12/2007 |
| WO | WO-2008/003703 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/132434 A2 | 11/2008 |
| WO | WO-2008/138889 A2 | 11/2008 |
| WO | WO-2008/150827 A1 | 12/2008 |
| WO | WO-2008/153858 A1 | 12/2008 |
| WO | WO-2009/015067 | 1/2009 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/038901 A1 | 4/2010 |
| WO | WO-2010/50837 A1 | 5/2010 |
| WO | WO-2010/057101 A2 | 5/2010 |
| WO | WO-2010/059602 A2 | 5/2010 |

(56) References Cited

FOREIGN PATENT DOCUMENTS

| | | |
|---|---|---|
| WO | WO-2010/068483 A2 | 6/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2010/150837 A1 | 12/2010 |
| WO | WO-2011/14775 A1 | 2/2011 |
| WO | WO-2011/014775 A1 | 2/2011 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/103189 A1 | 8/2011 |
| WO | WO-2011/109059 A1 | 9/2011 |
| WO | WO-2011/146313 A1 | 11/2011 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/077932 A2 | 6/2012 |
| WO | WO-2012/106995 A1 | 8/2012 |
| WO | WO-2012/139775 A1 | 10/2012 |
| WO | WO-2012/176763 A1 | 12/2012 |
| WO | WO-2013/169704 A2 | 11/2013 |
| WO | WO-2014/026327 A1 | 2/2014 |
| WO | WO-2014/026329 A1 | 2/2014 |
| WO | WO-2014/028589 A2 | 2/2014 |
| WO | WO-2014/028591 A2 | 2/2014 |
| WO | WO-2014/028597 A2 | 2/2014 |
| WO | WO-2014/028600 A2 | 2/2014 |
| WO | WO-2015/008234 A1 | 1/2015 |
| WO | WO-2015/087234 A1 | 6/2015 |
| WO | WO-2015/139621 | 9/2015 |
| WO | WO-2016/128908 A1 | 8/2016 |
| WO | WO-2016/130818 A1 | 8/2016 |

OTHER PUBLICATIONS

U.S. Appl. No. 15/549,465, Substituted Pyrazole Compounds as RORgammaT Inhibitors and Uses Thereof, filed Aug. 8, 2017.

U.S. Appl. No. 15/770,255, Substituted Bicyclic Pyrazole Compounds as RORgammaT Inhibtors and Uses Thereof, filed Apr. 23, 2018.

U.S. Appl. No. 15/770,257, Heteroaryl Substituted Benzoic Acids as RORgammaT Inhibitors and Uses Thereof, filed Apr. 23, 2018.

International Search Report from PCT/CN2012/071017, dated May 24, 2012.

Bundgaard (ed.). Design of Prodrugs, Elsevier (1985).

Buonocore et al., "Innate lymphoid cells drive interleukin-23-dependent innate intestinal pathology," 464 Nature 1371-75 (2010).

Cheng et al., "Design and synthesis of heterocyclic malonyl-CoA decarboxylase inhibitors," 16 Bioorg. Med. Chem. Lett. 695-700 (2006).

Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).

Gennaro (ed.), Remington: The Science and Practice of Pharmacy, 20th edition (2000).

Higuchi et al. (eds.), Pro-drugs as Novel Delivery Systems, 14 A.C.S. Symposium Series (1975).

Hueber et al., "Cutting Edge: Mast Cells Express IL-17A in Rheumatoid Arthritis Synovium," 184 J. Immunol. 3336-40 (2010).

Jia et al., "The T helper type 17/regulatory T cell imbalance in patients with acute Kawasaki disease," 162 Clin. Exp. Immunol. 131-37 (2010).

Kastelein et al., "Discovery and Biology of IL-23 and IL-27: Related but Functionally Distinct Regulators of Inflammation," 25 Annu. Rev. Immunol. 221-42 (2007).

Louten et al., "Development and function of TH17 cells in health and disease," 123(5) J. Allergy Clin. Immunol. 1004-11 (2009).

Roche (ed.), Biorevesible Carriers in Drug Design, Pergamon Press (1987).

Zhou et al., "Use of Homogeneous Time-Resolved Fluorescence Energy Transfer in the Measurement of Nuclear Receptor Activation," 25 Methods 54-61 (2001).

Extended European Search Report, EP Application No. 12744370.3, Sep. 9, 2014.

Ciattini et al., "An Efficient Synthesis of 3-Substituted Indoles by Palladium-Catalyzed Coupling Reaction of 3-Tributylstannylindoles with Organic Triflates and Halides," 35(15) Tetrahedron Letters 2405-08 (1994).

Inamoto et al., "Palladium-Catalyzed C-H Activation/Intramolecular Amination Reaction: A New Route to 3-Aryl/Alkylindazoles," 9(15) Org. Letts. 2931-34 (2007).

Larhed et al., "Rapid Microwave-Assisted Suzuki Coupling on Solid-Phase," 37(45) Tetrahedron Letters 8219-22 (1996).

Reckenbeil et al., "Supramolekulare Phosphorylierung kationischer Alkohole mit 3-Arylindol-4-carboxamidin-Struktur," Liebigs Ann. Chem. 1219-29 (1994).

Chen, Hua-Sin et al., "Synthesis and antiplatelet activity of ethyl 4-(1-benzyl-1H-indazol-3-yl)benzoate (YD-3) derivatives," *Bioorganic & Medicinal Chemistry*, vol. 16, pp. 1262-1278, (2008).

Annunziato et al., "Type 17 T helper cells-origins, features and possible roles in rheumatic disease," 5 Nat. Rev. Rheumatol. 325-31 (2009).

Boaventura et al., "Human mucosal leishmaniasis: Neutrophils infiltrate areas of tissue damage that express high levels of Th17-related cytokines," 40 Eur. J. Immunol. 2830-36 (2010).

Eberl et al., "An essential function for the nuclear receptor RORγt in the generation of fetal lymphoid tissue inducer cells," 5(1) Nat. Immunol. 64-73 (2004).

He et al., "RORγt, a Novel Isoform of an Orphan Receptor, Negatively Regulates Fas Ligand Expression and IL-2 Production in T Cells," 9 Immunity 797-806 (1998).

Hirose et al., "RORγ: the third member of ROR/RZR orphan receptor subfamily that is highly expressed in skeletal muscle," 205 Biochem. Biophys. Res. Comm. 1976-83 (1994).

Ivanov et al., "The Orphan Nuclear Receptor RORγt Directs the Differentiation Program of Proinflammatory IL-17+ T Helper Cells," 126 Cell 1121-33 (2006).

Jin et al., "Structural Basis for Hydroxycholesterols as Natural Ligands of Orphan Nuclear Receptor RORγ," *Mol. Endocrinol.* (2010) vol. 24, No. 5, pp. 923-929.

Kurebayashi et al., "Selective LXXLL peptides antagonize transcriptional activation by the retinoid-related orphan receptor RORγ," 315 Biochem. Biophys. Res. Comm. 919-27 (2004).

Miossec et al., "Interleukin-17 and Type 17 Helper T Cells," 361(9) New Eng. J. Med. 888-98 (2009).

Sun et al., "Requirement for RORγ in Thymocyte Survival and Lymphoid Organ Development," 288 Science 2369-72 (2000).

Sutton et al., "Interleukin-1 and IL-23 Induce Innate IL-17 Production from γσ T Cells, Amplifying Th17 Responses and Autoimmunity," 31 Immunity 331-41 (2009).

Varnavas et al., "Anthranilic acid based CCK1 receptor antagonists: preliminary investigation on their second 'touch point,'" 40(6) Euro. J. Med. Chem. 563-81 (2005).

Wang et al., "Identification of SR1078, a Synthetic Agonist for the Orphan Nuclear Receptors RORα and RORγ," 5(11) ACS Chem. Biol. 1029-34 (2010).

Wang et al., "Modulation of Retinoic Acid Receptor-related Orphan Receptor α and γ Activity by 7-Oxygenated Sterol Ligands," J. Biol. Chem. (2010) vol. 285, No. 7, pp. 5013-5025.

Xie et al., "RORγt Recruits Steroid Receptor Coactivators to Ensure Thymocyte Survival," 175(6) J. Immunol. 3800-09 (2005).

Yang et al., "T Helper 17 Lineage Differentiation is programmed by Orphan Nuclear Receptors RORα and RORγ," 28 Immunity 29-39 (2008).

International Search Report and Written Opinion for PCT/US2013/054168, dated Feb. 14, 2014 (5 pages).

(56) References Cited

OTHER PUBLICATIONS

Lee et al., "Synthesis of 1-Benzyl-3-(5'-hydroxymethyl-2'-furyl)indazole Analogues as Novel Antiplatelet Agents," 44 J. Med. Chem. 3746-49 (2001).
André et al., "Disruption of retinoid-related orphan receptor β changes circadian behaviour, causes retinal degeneration and leads to vacillans phenotype in mice," 17(14) The EMBO J. 3867-3877 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Bernhardt et al., "Preparation of Solid Salt-Stabilized Functionalized Organozinc Compounds and their Application to Cross-Coupling and Carbonyl Addition Reactions," 50(39) Angew. Chem. Int. Ed. 9205-9209 (2011).
Boltze et al., "Chemische Struktur and antiphlogistische Wirkung in der Reihe der substituierten Indol-3-essigsauren," 30(8A) Arzneimittel-Forschung 1314-25 (1980).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γσ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
El-Sawy et al., "Synthesis, antimicrobial and anti-cancer activities of some new N-ethyl, N-benzyl and N-benzoyl-3-indolyl heterocycles," 62 Acta Pharm. 157-179 (2012).
Giguère et al., "Isoform-specific amino-terminal domains dictate DNA-binding properties of RORα, a novel family of orphan hormone nuclear receptors," 8 Genes & Develop. 538-53 (1994).
Guo et al., "Stereospecific microbial reduction of ethyl 1-benzyl-3-oxo-piperidine-4-carboxylate," 17(13) Tetrahedron: Asymmetry 2015-2020 (2006).
Hirose et al., "Benzoheterocyclic derivatives. XI. Synthesis and pharmacological actions of indoline derivatives. 2," CA76:46035 (1971).
Huh et al., "Small molecule inhibitors of RORγt: Targeting Th17 cells and other applications," 42 Eur. J. Immunol. 2232-2237 (2012).
Julia et al., "Research in the indole series. IX. Certain 3-indolylsuccinic acids and the corresponding succinimides and pyrrolidines," CA61:92261 (1964).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.

Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, J. et al. "Pharmacologic Inhibition of RORγt Regulates Th17 Signature Gene Expression and Suppresses Cutaneous Inflammation in Vivo," downloaded from the Internet at http://www.jimmunol.org/cgi/doi/10.4049/jimmunol.1302190 on Feb. 17, 2014, published in final edited form in J. Immunol. (2014) vol. 192, No. 6, pp. 2564-2575.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Whelligan et al., "Aminopyrazine Inhibitors Binding to an Unusual Inactive Conformation of the Mitotic Kinase Nek2: SAR and Structural Characterization," 53 J. Med. Chem. 7682-98 (2010).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
International Search Report and Written Opinion for PCT/US2013/054887, dated Mar. 18, 2014 (5 pages).
International Search Report and Written Opinion for PCT/US2013/054902, dated Feb. 28, 2014 (5 pages).
International Search Report and Written Opinion for PCT/US2013/054911 dated Mar. 4, 2014 (9 pages).
Database Caplus [Online] Chemical Abstracts Service, Columbus, Ohio, US; Kusakabe, Kanekazu et al: "Preparation of condensed pyrazole compounds as TTK protein kinase inhibitors", retrieved from STN Database accession No. 2011:1578140 ; & Kusakabe, Kanekazu et al: "Preparation of condensed pyrazole compounds as TTK protein kinase inhibitors", Jpn. Kokai Tokkyo Koho, 134PP. Coden: JKXXAF.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation-Isomerization-Acylation Cascade," 13 Org. Lett. 5456-59 (2011).

(56) References Cited

OTHER PUBLICATIONS

De et al., Methods in Molecular Biology 1184, second edition, Human Press (2014).
Gould, "Salt selection for basic drugs," 33 Intl J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N-O Bond as a Handle for C-N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).
Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2011/059788 dated May 23, 2012 (23 pages).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
International Search Report and Written Opinion for PCT/US2013/040085 dated Oct. 23, 2013 (9 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C-H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).

Santilli et al., "Synthesis of 5,6,7,8-Tetrahydro-5-oxopyrido[2,3-d]pyrimidine-6-carbonitriles and -6-carboxylic Acid Esters," 12 J. Het. Chem. 311-16 (1975).
Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (−)-desmosterol," 14 J. Chem. Soc., Chem. Commun. 760-61 (1983).
van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).
Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071671 dated Apr. 28, 2015 (10 pages).
International Search Report and Written Opinion for PCT/US2014/071663 dated Apr. 17, 2015 (6 pages).
International Search Report and Written Opinion for PCT/US2014/071656 dated Mar. 12, 2015 (8 pages).
International Search Report and Written Opinion for PCT/US2016/017566 dated May 6, 2016 (12 pages).
International Search Report and Written Opinion for PCT/US2016/059057 dated Dec. 9, 2016 (13 pages).
International Search Report and Written Opinion for PCT/US2016/059063 dated Jan. 20, 2017 (12 pages).
International Search Report and Written Opinion for PCT/US2016/059067 dated Jan. 11, 2017 (10 pages).
CAS Registry Numbers: 886371-27-3 and 886370-74-7, STN entry date: Jun. 1, 2006.
Fauber Benjamin P. "Modulators of the Nuclear Receptor Retinoic Acid Receptor-Related Orphan Receptor-[gamma] (ROR[gamma] or RORc," *Journal of Medicinal Chemistry*, vol. 57, No. 14, Jul. 24, 2014 (Jul. 24, 2014), pp. 5871-5892, XP055242989.
Fauber Benjamin P. "Discovery of Imidazo[1,5-a]pyridines and -pyrimidines as potent and selective RORc inverse agonists," *Bioorganic & Medical Chemistry Letters*, vol. 25, No. 15, May 28, 2015 (May 28, 2015 ), pp. 2907-2912, XP029160601.
International Search Report and Written Opinion for PCT/US2013/054893 dated Feb. 24, 2014 (6 pages).

SUBSTITUTED INDAZOLE COMPOUNDS AS RORGAMMAT INHIBITORS AND USES THEREOF

CROSS REFERENCE TO RELATED APPLICATIONS

This application is the national stage of International (PCT) Patent Application Ser. No. PCT/US2016/059063, filed Oct. 27, 2016, which claims the benefit of and priority to U.S. Provisional Patent Application Ser. No. 62/246,921, filed Oct. 27, 2015, and U.S. Provisional Patent Application Ser. No. 62/372,544, filed Aug. 9, 2016; the contents of each of which are hereby incorporated by reference.

BACKGROUND

Upon activation by antigen-presenting cells naïve T helper cells undergo clonal expansion and will ultimately differentiate into cytokine secreting effector T cells, such as Th1 and Th2 subtypes. A third and distinct effector subset has been identified, which plays a key role in providing immunity to bacteria and fungi at mucosal surfaces (Kastelein et al., *Annu. Rev. Immunol.* 25: 221-242, 2007). This effector T helper cell subset can be distinguished based on its ability to produce large quantities of IL-17/F, IL-21 and IL-22, and is named Th17 (Miossec et al., *New Eng. J. Med.* 2361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., *Immunity* 9: 797-806, 1998). RORgammaT belongs to the nuclear hormone receptor superfamily (Hirose et al., *Biochem. Biophys. Res. Comm.* 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver, and muscle), exclusively expressed in cells of the lymphoid lineage and embryonic lymphoid tissue inducers (Sun et al., *Science* 288: 2369-2372, 2000; Eberl et al., *Nat. Immunol.* 5: 64-73, 2004).

Studies using heterozygous knock-in mice replacing the RORgammaT open reading frame with GFP (green fluorescent protein), revealed a constitutive expression of GFP in approximately 10% of the CD4+ T cells in the small intestinal lamina propria (LP), co-expressing the Th17 cytokines IL-17/F and IL-22 (Ivanov et al., *Cell* 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., *Cell* 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., *Immunity* 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., *Nature* 464: 1371-1375, 2010). In addition, RORgammaT was shown to play a crucial role in other non-Th17 cells, such as mast cells (Hueber et al., *J. Immunol.* 184: 3336-3340, 2010). Finally, RORgammaT expression and secretion of Th17-type of cytokines was reported for Lymphoid Tissue Inducer cells, NK T-cells, NK cells (Eberl et al., *Nat. Immunol.* 5: 64-73, 2004), and gamma-delta T-cells (Sutton et al., *Nat. Immunol.* 31: 331-341, 2009; Louten et al., *J. Allergy Clin. Immunol.* 123: 1004-1011, 2009), suggesting an important function for RORgammaT in these subtypes of cells.

Based on the role of IL-17 producing cells (either Th117 or non-Th17 cells), RORgammaT has been identified as a key mediator in the pathogenesis of several diseases (Louten et al., *J. Allergy Clin. Immunol.* 123: 1004-1011, 2009; Annuziato et al., *Nat. Rev. Rheumatol.* 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., *Cell* 126:1121-33, 2006; Buonocore et al., *Nature* 464: 1371-1375, 2010).

With RORgammaT being a critical mediator in Th17 cells and non-Th17 cells, antagonism of the transcriptional activity of RORgammaT is expected to have a beneficial effect on autoimmune diseases such as, but not limited to, rheumatoid arthritis, psoriasis, multiple sclerosis, inflammatory bowel disease, Crohn's disease, and asthma (Annunziato et al., *Nat. Rev. Immunol.* 5: 325-331, 2009; Louten et al., *J. Allergy Clin. Immunol.* 123: 1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., *Clin. Exp. Immunol.* 162: 131-137, 2010) and Hashimoto's thyroiditis (Figueroa-Vega et al., *J. Clin. Endocrinol. Metab.* 95: 953-962, 2010). Other examples include various infectious diseases such as, but not limited to, mucosal leishmaniasis (Boaventura et al., *Eur. J. Immunol.* 40: 2830-2836, 2010). In each of the above examples the inhibition may be enhanced by simultaneous inhibition of RORalpha.

Compounds modulating RORgammaT have been reported. Examples of agonists include SR1078 (Wang et al., *ACS Chem. Biol.* 5:1029-1034, 2010). In addition, antagonists have been reported such as T0901317 and 7-oxygenated sterols (Wang et al., *J. Biol. Chem.* 285: 5013-5025, 2009) and compounds described in EP2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies. Another exemplary disorder in need of better therapy is cancer.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT (and thereby, as commonly observed for nuclear hormone receptors, antagonize RORgammaT-mediated transcriptional activity; see e.g. "Differential Biochemical and Cellular Actions of Premarin Estrogens: Distinct Pharmacology of Bazedoxifene-Conjugate Estrogens Combination". Berrodin, T. J., Chang, K. C. N., Komm, B. S., Freedman, L. P., Nagpal, S. Molecular Endocrinology, January 2009, 23(1): 74-85) and are useful for the treatment of RORgammaT-mediated diseases or conditions, in particular autoimmune diseases and inflammatory diseases, as well as pharmaceutical compositions comprising such compounds and pharmaceutical carriers.

DETAILED DESCRIPTION OF THE INVENTION

Definitions

Figure 1:
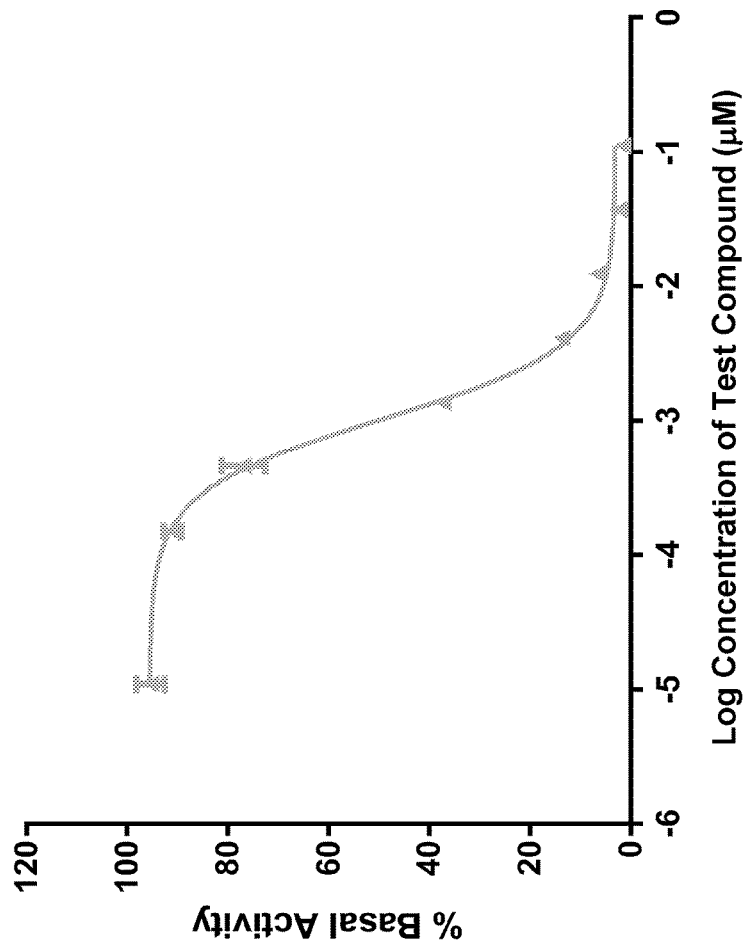
FIG. 1 is a line graph showing assay results, as described in Example 22.

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In an embodiment, an alkyl group contains, for example, from 1 to 4 carbon atoms ($C_{1-4}$)alkyl. Non-limiting examples of alkyl groups include methyl, ethyl, n-propyl, isopropyl, n-butyl, sec-butyl, isobutyl and tert-butyl. In one embodiment, an alkyl group is linear. In another embodiment, an alkyl group is branched.

The term "cycloalkyl," as used herein, refers to a monocyclic saturated aliphatic hydrocarbon group having the specified number of carbon atoms, such as from 1-6 carbon atoms or 1-4 carbon atoms referred to as $C_1$-$C_6$cycloalkyl and $C_1$-$C_4$cycloalkyl, respectively. For example, "cycloalkyl" includes cyclopropyl, cyclobutyl, cyclopentyl and cyclohexyl. In one embodiment, cycloalkyl is cyclopropyl or cyclobutyl.

The term "heterocyclyl," as used herein, refers to a 3- to 10-membered aromatic or nonaromatic heterocycle containing from 1 to 4 heteroatoms selected from the group consisting of O, N and S, and includes monocyclic or bicyclic groups (fused, bridged or spirocyclic). "Heterocycle" therefore includes heteroaryls, as well as dihydro and tetrathydro analogs thereof. Further examples of "heterocycle" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

In one embodiment, heterocycle is selected from benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

In another embodiment, heterocycle is selected from benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl and thiomorpholinyl.

In another embodiment, heterocycle is selected from: oxazoline, oxetanyl, pyranyl, pyrazinyl, pyrazolyl, pyridazinyl, pyridyl, pyrimidyl, pyrrolyl, tetrazolyl, thiadiazolyl, thiazolyl, thienyl, triazolyl, azetidinyl, piperazinyl, piperidinyl, pyrrolidinyl, and morpholinyl.

In another embodiment, heterocycle is selected from: azetidinyl, piperazinyl, piperidinyl, pyrrolidinyl, thiomorpholinyl, and morpholinyl.

The term "bicyclic," as used herein, refers to a fused ring system in which two rings are fused across two adjacent ring carbon atoms. An example of a bicyclic moiety is

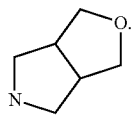

The term "spirocyclic," as used herein, refers to a spiro ring system which is a bicyclic ring wherein the two rings are joined through a common ring carbon atom. Nonlimiting examples of a spirocyclic moiety include azaspiro[4.4]nonane, azaspiro[3.4]octane and so on.

The term "halogen" (or "halo") refers to fluorine, chlorine, bromine and iodine (alternatively referred to as fluoro (F), chloro (Cl), bromo (Br), and iodo (I)). In one embodiment, a halogen is F or Cl. In another embodiment, halogen is F.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means that a substitution with the specified groups, radicals, or moieties may or may not be made on the specified group.

When any substituent or variable occurs more than one time in any constituent or in the compound of Formulas (I-II), its definition on each occurrence is independent of its definition at every other occurrence, unless otherwise indicated.

The term "purified" as used herein, refers to the physical state of a compound after the compound has been isolated through a synthetic process (e.g., from a reaction mixture), from a natural source, or a combination thereof. The term "purified" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

The term "amount" or "effective amount" as used herein refers to an amount of the compound of Formulas (I-II) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human.

It should be noted that any carbon as well as heteroatom with unsatisfied valences in the text, schemes, examples and tables herein is assumed to have the sufficient number of hydrogen atom(s) to satisfy the valences.

Compounds of the Invention

The present invention provides a compound according to Formula I:

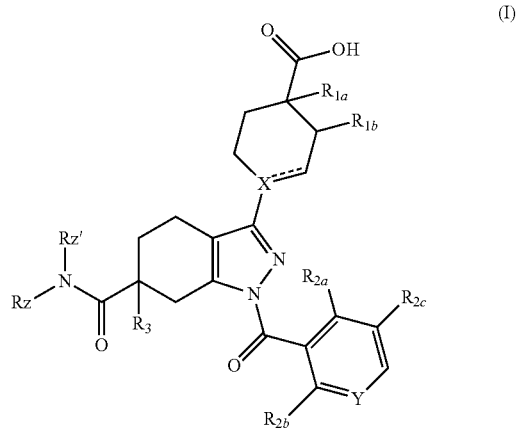

wherein:
Rz and Rz' are independently selected from H, $(C_{1-4})$alkyl, $O(C_{1-4})$alkyl, $(C=O)O(C_{1-4})$alkyl, halogen, OH, oxo, cycloalkyl, $—((C_{1-4})$alkylene)-cycloalkyl, heterocyclyl, phenyl, $NH_2$, $N(R_b)_2$, $S(O)_2—Z$, $CF_3$, $CHF_2$ and CN, said $N(R_b)_2$, alkyl, cycloalkyl and heterocyclyl are optionally substituted with OH, oxo, CN, halogen, $NH_2$, $(C_{1-4})$alkyl, $O(C_{1-4})$alkyl, heterocyclyl and $N(R_b)_2$, and said alkyl and phenyl are optionally substituted with halogen, $O(C_{1-4})$alkyl and $N(R_b)_2$; or Rz and Rz' can come together with the nitrogen to which they are attached and form a cyclic, bicyclic or spirocyclic moiety containing 3-9 atoms selected from C, O, N and S, said cyclic, bicyclic or spirocyclic moiety optionally substituted with one to three substituents independently selected from H, $(C_{1-4})$alkyl, $O(C_{1-4})$alkyl, $(C=O)O(C_{1-4})$alkyl, halogen, OH, oxo, cycloalkyl, heterocyclyl, $NH_2$, $N(R_b)_2$, $S(O)_2—Z$, $CF_3$, $CHF_2$ and CN, wherein said $N(R_b)_2$, alkyl, cycloalkyl and heterocyclyl are optionally substituted with OH, oxo, halogen, $NH_2$, $(C_{1-4})$alkyl, O($C_{1-4}$)alkyl and N($R_b$)$_2$, and said alkyl is optionally substituted with halogen, O($C_{1-4}$)alkyl and N($R_b$)$_2$;

Z is ($C_{1-4}$)alkyl;

X is N or C, wherein when X is N then the dashed line is absent and when X is C the dashed line represents a double bond;

Y is N or CH;

$R_{1a}$ is H or ($C_{1-4}$)alkyl;

$R_{1b}$ is H, OH or ($C_{1-4}$)alkyl;

$R_{2a}$ is Cl or ($C_{1-4}$)alkyl;

$R_{2b}$ is cyclopropyl, cyclobutyl, oxetanyl or azetidinyl, each optionally substituted with ($C_{1-4}$)alkyl, F, $CF_3$, $CHF_2$ or CN;

$R_{2c}$ is H or F;

$R_b$ is selected from H and ($C_{1-4}$)alkyl; and $R_3$ is H or ($C_{1-4}$)alkyl;

or a pharmaceutically acceptable salt thereof.

A more specific collection of compounds may be described according to the following definitions for certain variables for Formula I. In certain embodiments, Rz and Rz' are taken together with the nitrogen to which they are attached and form a cyclic, bicyclic or spirocyclic moiety containing 3-9 atoms selected from C, O, N and S, said cyclic, bicyclic or spirocyclic moiety optionally substituted with one to three substituents independently selected from H, ($C_{1-4}$)alkyl, O($C_{1-4}$)alkyl, (C=O)O($C_{1-4}$)alkyl, halogen, OH, oxo, cycloalkyl, heterocyclyl, $NH_2$, N($R_b$)$_2$, S(O)$_2$—Z, $CF_3$, $CHF_2$ and CN, wherein said N($R_b$)$_2$, alkyl, cycloalkyl and heterocyclyl optionally substituted with OH, oxo, halogen, $NH_2$, ($C_{1-4}$)alkyl, O($C_{1-4}$)alkyl and N($R_b$)$_2$, and said alkyl is optionally substituted with halogen, O($C_{1-4}$)alkyl and N($R_b$)$_2$. In certain embodiments, Rz and Rz' are taken together with the nitrogen to which they are attached and form a cyclic, bicyclic or spirocyclic moiety containing 3-9 atoms selected from C, O, and N, said cyclic, bicyclic or spirocyclic moiety optionally substituted with one to two substituents independently selected from H, ($C_{1-4}$)alkyl, O($C_{1-4}$)alkyl, halogen, and OH. In certain embodiments, Rz and Rz' are taken together with the nitrogen to which they are attached and form a spirocyclic moiety containing 7-9 atoms selected from C, O, and N, wherein said spirocyclic moiety is optionally substituted with one to two substituents independently selected from H, ($C_{1-4}$)alkyl, O($C_{1-4}$)alkyl, halogen, and OH. In certain embodiments, X is C. In certain embodiments, Y is CH. In certain embodiments, $R_{1a}$ is H. In certain embodiments, $R_{1b}$ is H. In certain embodiments, $R_{2a}$ is Cl. In certain embodiments, $R_{2b}$ is cyclopropyl optionally substituted with $CF_3$. In certain embodiments, $R_{2c}$ is H. In certain embodiments, $R_3$ is H. In certain embodiments, $R_3$ is ($C_{1-4}$)alkyl. In certain embodiments, the compound is in the form of a free acid. The invention embraces all combinations of such embodiments.

In another embodiment, the present invention provides a compound according to Formula I wherein:

Rz and Rz' are independently selected from H, ($C_{1-4}$)alkyl, O($C_{1-4}$)alkyl, (C=O)O($C_{1-4}$)alkyl, halogen, OH, oxo, cycloalkyl, heterocyclyl, $NH_2$, N($R_b$)$_2$, S(O)$_2$—Z, $CF_3$, $CHF_2$ and CN, said N($R_b$)$_2$, alkyl, cycloalkyl and heterocyclyl are optionally substituted with OH, oxo, CN, halogen, $NH_2$, ($C_{1-4}$)alkyl, O($C_{1-4}$)alkyl, heterocyclyl and N($R_b$)$_2$, and said alkyl is optionally substituted with halogen, O($C_{1-4}$)alkyl and N($R_b$)$_2$; or Rz and Rz' can come together with the nitrogen to which they are attached and form a cyclic, bicyclic or spirocyclic moiety containing 3-9 atoms selected from C, O, N and S, said cyclic, bicyclic or spirocyclic moiety optionally substituted with one to three substituents independently selected from H, ($C_{1-4}$)alkyl, O($C_{1-4}$)alkyl, (C=O)O($C_{1-4}$)alkyl, halogen, OH, oxo, cycloalkyl, heterocyclyl, $NH_2$, N($R_b$)$_2$, S(O)$_2$—Z, $CF_3$, $CHF_2$ and CN, wherein said N($R_b$)$_2$, alkyl, cycloalkyl and heterocyclyl are optionally substituted with OH, oxo, halogen, $NH_2$, ($C_{1-4}$)alkyl, O($C_{1-4}$)alkyl and N($R_b$)$_2$, and said alkyl is optionally substituted with halogen, O($C_{1-4}$)alkyl and N($R_b$)$_2$;

Z is ($C_{1-4}$)alkyl;

X is N or C, wherein when X is N then the dashed line is absent and when X is C the dashed line represents a double bond;

Y is N or CH;

$R_{1a}$ is H or methyl;

$R_{1b}$ is H, OH or methyl;

$R_{2a}$ is Cl or methyl;

$R_{2b}$ is cyclopropyl, cyclobutyl, oxetanyl or azetidinyl, each optionally substituted with methyl, F, $CF_3$, $CHF_2$ and CN;

$R_{2c}$ is H or F; and $R_3$ is H;

or a pharmaceutically acceptable salt thereof.

In another embodiment, the present invention provides a compound according to Formula II:

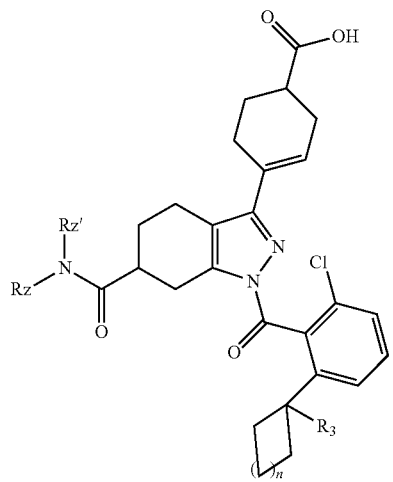

(II)

wherein:

Rz and Rz' are independently selected from H, ($C_{1-4}$)alkyl, O($C_{1-4}$)alkyl, (C=O)O($C_{1-4}$)alkyl, halogen, OH, oxo, cycloalkyl, heterocyclyl, $NH_2$, N($R_b$)$_2$, S(O)$_2$—Z, $CF_3$, $CHF_2$ and CN, said N($R_b$)$_2$, alkyl, cycloalkyl and heterocyclyl are optionally substituted with OH, oxo, CN, halogen, $NH_2$, ($C_{1-4}$)alkyl, O($C_{1-4}$)alkyl, heterocyclyl and N($R_b$)$_2$, wherein said alkyl is optionally substituted with halogen, O($C_{1-4}$)alkyl and N($R_b$)$_2$; or Rz and Rz' can come together with the nitrogen to which they are attached and form a cyclic, bicyclic or spirocyclic moiety containing 3-9 atoms selected from C, O, N and S, said cyclic, bicyclic or spirocyclic moiety optionally substituted with one to three substituents independently selected from H, ($C_{1-4}$)alkyl, O($C_{1-4}$)alkyl, (C=O)O($C_{1-4}$)alkyl, halogen, OH, oxo, cycloalkyl, heterocyclyl, $NH_2$, N($R_b$)$_2$, S(O)$_2$—Z, $CF_3$, $CHF_2$ and CN, wherein said N($R_b$)$_2$, alkyl, cycloalkyl and heterocyclyl are optionally substituted with OH, oxo, halogen, $NH_2$, ($C_{1-4}$)alkyl, O($C_{1-4}$)alkyl and N($R_b$)$_2$, and said alkyl is optionally substituted with halogen, O($C_{1-4}$)alkyl and N($R_b$)$_2$;

Z is (C$_{1-4}$)alkyl;
n is 0 or 1;
R$_b$ is selected from H and (C$_{1-4}$)alkyl; and
R$_3$ is methyl, F, CF$_3$, CHF$_2$ or CN;
or a pharmaceutically acceptable salt thereof.

In another embodiment, the present invention provides a compound according to Formula II-A:

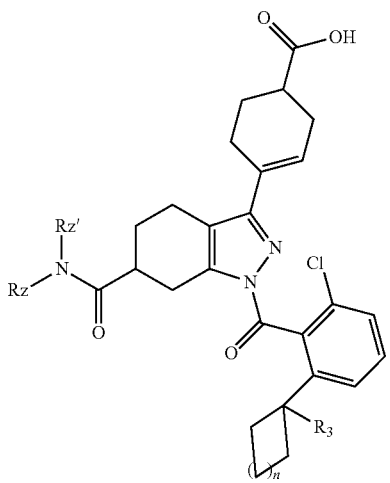
(II-A)

wherein:
Rz and Rz' are taken together with the nitrogen to which they are attached and form a spirocyclic moiety containing 7-9 atoms selected from C, O, and N, wherein said spirocyclic moiety is optionally substituted with one to three substituents independently selected from (C$_{1-4}$)alkyl, O(C$_{1-4}$)alkyl, (C═O)O(C$_{1-4}$)alkyl, halogen, and OH;
n is 0 or 1; and
R$_3$ is methyl, F, CF$_3$, CHF$_2$;
or a pharmaceutically acceptable salt thereof.

In certain embodiments, the compound is a compound of Formula II-A wherein Rz and Rz' are taken together with the nitrogen to which they are attached and form a spirocyclic moiety that is one of the following:

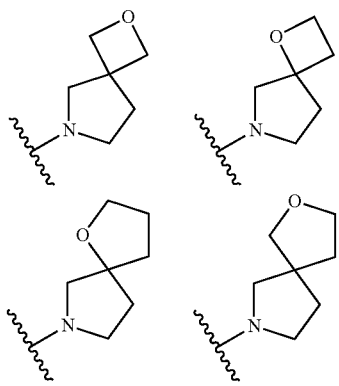

each of which is optionally substituted with (C$_{1-4}$)alkyl or O(C$_{1-4}$)alkyl. In certain embodiments, the compound is a compound of Formula II-A wherein Rz and Rz' are taken together with the nitrogen to which they are attached and form a spirocyclic moiety that is one of the following:

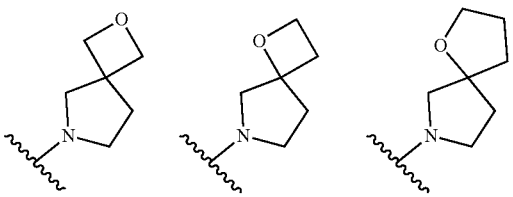

In certain embodiments, the compound is a compound of Formula II-A wherein Rz and Rz' are taken together with the nitrogen to which they are attached and form a spirocyclic moiety that is

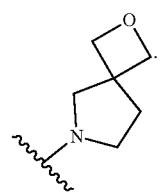 [SMILES: *N1CCC2(COC2)C1]

Exemplary specific compounds according to the instant invention include, for example:
4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(6-methyl-2,6-diazaspiro[3.3]heptane-2-carbonyl)-4,5,6,7-tetrahydro-1H-indazol-3-yl)cyclohex-3-ene-1-carboxylic acid;
4-((R or S)-6-(azetidine-1-carbonyl)-1-(2-chloro-6-cyclopropylbenzoyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-fluoroazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3,3-difluoroazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-hydroxyazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-cyclopropyl-3-hydroxyazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-hydroxy-3-(trifluoromethyl)azetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-hydroxy-3-methylazetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-methoxy-3-methylazetidine-1-carbonyl)-4,5,6,7-tetrahydro-1H-indazol-3-yl)cyclohex-3-ene-1-carboxylic acid;

4-((R or S)-6-(3-(1H-pyrazol-1-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid;

4-((R or S)-6-(3-(1H-imidazol-1-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid;

4-((R or S)-6-(3-(4H-1,2,4-triazol-4-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid;

4-((R or S)-6-(3-(4H-1,2,4-triazol-3-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid;

4-((R or S)-6-(3-aminoazetidine-1-carbonyl)-1-(2-chloro-6-cyclopropylbenzoyl)-4,5,6,7-tetrahydro-1H-indazol-3-yl)cyclohex-3-ene-1-carboxylic acid;

4-((R or S)-6-(3-(aminomethyl)-3-methylazetidine-1-carbonyl)-1-(2-chloro-6-cyclopropylbenzoyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-(2-hydroxypropan-2-yl)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-(dimethylamino)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(5-methyl-2,5-diazaspiro[3.4]octane-2-carbonyl)-4,5,6,7-tetrahydro-1H-indazol-3-yl)cyclohex-3-ene-1-carboxylic acid;

4-((R or S)-6-(azetidin-3-yl(methyl)carbamoyl)-1-(2-chloro-6-cyclopropylbenzoyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-(difluoromethyl)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-cyano-3-fluoroazetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-2-(hydroxymethyl)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(1-oxa-6-azaspiro[3.3]heptane-6-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(5-oxa-2-azaspiro[3.4]octane-2-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(1-methyloctahydropyrrolo[3,4-b]pyrrole-5-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-2-(methoxymethyl)pyrrolidine-1-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(2-(1-methyl-1H-1,2,4-triazol-3-yl)pyrrolidine-1-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(2-((methylamino)methyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-2-(methoxymethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-2-(fluoromethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-2-(fluoromethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-2-(hydroxymethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-2-(hydroxymethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-3-methoxypyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-3-methoxypyrrolidine-1-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(3-hydroxy-3-methylpyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(5-methyl-2-oxa-5,8-diazaspiro[3.5]nonane-8-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-3-(dimethylamino)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-3-(dimethylamino)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(6-oxa-2-azaspiro[3.4]octane-2-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(1-oxa-6-azaspiro[3.4]octane-6-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(2-oxa-7-azaspiro[4.4]nonane-7-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(hexahydro-1H-furo[3,4-c]pyrrole-5-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(1-oxa-7-azaspiro[4.4]nonane-7-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-fluoro-[1,3'-biazetidine]-1'-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(2-oxa-6-azaspiro[3.4]octane-6-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(1-methyl-1,6-diazaspiro[3.4]octane-6-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((3aR,6aS)-hexahydro-1H-furo[3,4-c]pyrrole-5-carbonyl)-4,5,6,7-tetrahydro-1H-indazol-3-yl)cyclohex-3-ene-1-carboxylic acid;

4-[(6R or S)-1-[(2-chloro-6-cyclopropylphenyl)carbonyl]-6-{[6-(1-methylethyl)-2,6-diazaspiro[3.3]hept-2-yl]carbonyl}-4,5,6,7-tetrahydro-1H-indazol-3-yl]cyclohex-3-ene-1-carboxylic acid;

4-{(6R or S)-1-[(2-chloro-6-cyclopropylphenyl)carbonyl]-6-[(6-pyrimidin-2-yl-2,6-diazaspiro[3.3]hept-2-yl)carbonyl]-4,5,6,7-tetrahydro-1H-indazol-3-yl}cyclohex-3-ene-1-carboxylic acid;

4-{(6R or S)-6-{[6-(tert-butoxycarbonyl)-2,6-diazaspiro[3.3]hept-2-yl]carbonyl}-1-[(2-chloro-6-cyclopropylphenyl)carbonyl]-4,5,6,7-tetrahydro-1H-indazol-3-yl}cyclohex-3-ene-1-carboxylic acid;

4-((6R or S)-1-(2-chloro-6-cyclopropylbenzoyl)-6-(((1-methylpyrrolidin-3-yl)oxy)carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(4-methyl-3-oxopiperazine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-(methylsulfonyl)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(2-oxa-6-azaspiro[3.3]heptane-6-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-(methylsulfonyl)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(4-methyl-3-oxopiperazine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(2-oxa-6-azaspiro[3.3]heptane-6-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-((R)-3-(dimethylamino)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-(3-fluoro-[1,3'-biazetidine]-1'-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-(6-oxa-2-azaspiro[3.4]octane-2-carbonyl)-4,5,6,7-tetrahydro-1H-indazol-3-yl)cyclohex-3-ene-1-carboxylic acid;

4-((6R or S)-1-(2-chloro-6-cyclopropyl-3-fluorobenzoyl)-6-(1,6-diazaspiro[3.4]octane-6-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-(3-methoxyazetidine-1-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-(5-oxa-2-azaspiro[3.4]octane-2-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((1R,2S)-2-hydroxycyclopentyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((1S,2R)-2-fluorocyclopentyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((1R,2R)-2-hydroxycyclopentyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((1S,2R)-2-hydroxycyclopentyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3R,4S)-4-fluoropyrrolidin-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3S,4S)-4-fluoropyrrolidin-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3R,4R)-4-fluorotetrahydrofuran-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3S,4R)-4-fluorotetrahydrofuran-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3-fluoroazetidin-3-yl)methyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((4-fluoropiperidin-4-yl)methyl)carbamoyl)-4,5,6,7-tetrahydro-1H-indazol-3-yl)cyclohex-3-ene-1-carboxylic acid;

(1R or S)-4-((6R or S)-1-(2-chloro-6-(1-(trifluoromethyl)cyclopropyl)benzoyl)-6-((3,3-difluoropiperidin-4-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((((S)-3-fluoropiperidin-3-yl)methyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3-(dimethylamino)-2,2-difluoropropyl)carbamoyl)-4,5,6,7-tetrahydro-1H-indazol-3-yl)cyclohex-3-ene-1-carboxylic acid;

(1R or S)-4-((6R or 5)-1-(2-chloro-6-(1-(trifluoromethyl)cyclopropyl)benzoyl)-6-((2,2-difluorocyclopropyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((1-(2,2,2-trifluoroethyl)-1H-pyrazol-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((2-fluorophenyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3-fluoropyridin-2-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(methyl(pyridin-2-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(pyridin-2-ylcarbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4S)-3-hydroxy-4-methoxypyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4S)-3-(dimethylamino)-4-hydroxypyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4R)-3-fluoro-4-hydroxypyrrolidine-1-carbonyl)-4,5,6,7-tetrahydro-1H-indazol-3-yl)cyclohex-3-ene-1-carboxylic acid;

(1R or S)-4-((6R or S)-1-(2-chloro-6-(1-(trifluoromethyl)cyclopropyl)benzoyl)-6-(4-(dimethylamino)-3,3-difluoropyrrolidine-1-carbonyl)-4,5,6,7-tetrahydro-1H-indazol-3-yl)cyclohex-3-ene-1-carboxylic acid;

(1R or S)-4-((6R or S)-6-(3-(azetidin-1-yl)pyrrolidine-1-carbonyl)-1-(2-chloro-6-(1-(trifluoromethyl)cyclopropyl)benzoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4R)-3-(dimethylamino)-4-fluoropyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-methoxy-3-methylazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4S)-3-(dimethylamino)-4-fluoropyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(methyl((1-methyl-1H-pyrazol-4-yl)methyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(1-methyl-1,4,5,6-tetrahydropyrrolo[3,4-c]pyrazole-5-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-((R)-3-cyanopyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(methyl((1-methyl-1H-pyrazol-4-yl)methyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(1-methyl-1,4,5,6-tetrahydropyrrolo[3,4-c]pyrazole-5-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4S)-3-(dimethylamino)-4-fluoropyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-methoxy-3-methylazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4R)-3-(dimethylamino)-4-fluoropyrrolidine-1-carbonyl)-4,5,6,7-tetrahydro-1H-indazol-3-yl)cyclohex-3-ene-1-carboxylic acid;

(1R or S)-4-((6R or S)-6-(3-(azetidin-1-yl)pyrrolidine-1-carbonyl)-1-(2-chloro-6-(1-(trifluoromethyl)cyclopropyl)benzoyl)-4,5,6,7-tetrahydro-1H-indazol-3-yl)cyclohex-3-ene-1-carboxylic acid;

(1R or S)-4-((6R or S)-1-(2-chloro-6-(1-(trifluoromethyl)cyclopropyl)benzoyl)-6-(4-(dimethylamino)-3,3-difluoropyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(methyl(pyrazin-2-ylmethyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-hydroxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-hydroxy-3-methylazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4R)-3-fluoro-4-hydroxypyrrolidine-1-carbonyl)-4,5,6,7-tetrahydro-1H-indazol-3-yl)cyclohex-3-ene-1-carboxylic acid;

4-((R or S)-1-(2-chloro-6-(1-(difluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-(3-fluoro-[1,3'-biazetidine]-1'-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid;

4-((R or S)-1-(2-chloro-6-cyclopropylbenzoyl)-6-(3-methoxyazetidine-1-carbonyl)-6-methyl-4,5,6,7-tetrahydro-1H-indazol-3-yl)cyclohex-3-ene-1-carboxylic acid;

4-((R or S)-1-(2-(azetidin-1-yl)-4-methylnicotinoyl)-6-(3-methoxyazetidine-1-carbonyl)-4,5,6,7-tetrahydro-1H-indazol-3-yl)cyclohex-3-ene-1-carboxylic acid;

4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid;

4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid;

4-((6R or S)-1-(2-chloro-6-(1-(trifluoromethyl)cyclopropyl)benzoyl)-6-(3-hydroxypyrrolidine-1-carbonyl)-4,5,6,7-tetrahydro-1H-indazol-3-yl)cyclohex-3-ene-1-carboxylic acid;

4-((6R or 5)-1-(2-chloro-6-(1-(trifluoromethyl)cyclopropyl)benzoyl)-6-(3-methoxy-3-methylpyrrolidine-1-carbonyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-((2-methoxyethyl)(methyl)carbamoyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-((2-(dimethylamino)ethyl)(methyl)carbamoyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-((2-(dimethylamino)ethyl)carbamoyl)-4,5,6,7-tetrahydro-1H-indazol-3-yl)cyclohex-3-ene-1-carboxylic acid;

4-((6R or S)-1-(2-chloro-6-(1-(trifluoromethyl)cyclopropyl)benzoyl)-6-(3-hydroxy-3-methylpyrrolidine-1-carbonyl)-4,5,6,7-tetrahydro-1H-indazol-3-yl)cyclohex-3-ene-1-carboxylic acid;

4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylic acid;

4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylic acid;

(1R,2S or 1S,2R)-4-((R or S)-1-(2-chloro-6-(1-(trifluoromethyl)cyclopropyl)benzoyl)-6-(3-hydroxy-3-methylazetidine-1-carbonyl)-4,5,6,7-tetrahydro-1H-indazol-3-yl)-2-methylcyclohex-3-ene-1-carboxylic acid;

(1R,2S or 1S,2R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-2-methylcyclohex-3-ene-1-carboxylic acid;

(1R,2S or 1S,2R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-2-methylcyclohex-3-ene-1-carboxylic acid;

(1R,6S or 1S, 6R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-6-methylcyclohex-3-ene-1-carboxylic acid;

(1R,6S or 1S, 6R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-6-methylcyclohex-3-ene-1-carboxylic acid;

(1R,2S or 1S,2R)-4-((S or R)-1-(2-chloro-6-(1-(trifluoromethyl)cyclopropyl)benzoyl)-6-(3-hydroxyazetidine-1-carbonyl)-4,5,6,7-tetrahydro-1H-indazol-3-yl)-2-methylcyclohex-3-ene-1-carboxylic acid;

(1R,6S or 1S,6R)-4-((S or R)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)-6-methylcyclohex-3-ene-1-carboxylic acid;

(1R,6S or 1S,6R)-4-((S or R)-1-(2-chloro-6-(1-(trifluoromethyl)cyclopropyl)benzoyl)-6-(4-hydroxypiperidine-1-carbonyl)-4,5,6,7-tetrahydro-1H-indazol-3-yl)-6-methylcyclohex-3-ene-1-carboxylic acid;

(R or S)-1-(1-(2-chloro-6-cyclopropylbenzoyl)-6-(3-methoxyazetidine-1-carbonyl)-4,5,6,7-tetrahydro-1H-indazol-3-yl)piperidine-4-carboxylic acid; and (R or S)-1-(1-(2-chloro-6-(1-(trifluoromethyl)cyclopropyl)benzoyl)-6-(3-methoxyazetidine-1-carbonyl)-4,5,6,7-tetrahydro-1H-indazol-3-yl)piperidine-4-carboxylic acid;

or a pharmaceutically acceptable salt thereof.

Collections of compounds defined by Formulae I and II may be more specifically described according to the following embodiments specifying certain definitions for variables Rz and Rz'. In an embodiment, when Rz and Rz' are taken together with the nitrogen atom to which they are attached and form a spirocyclic moiety, said spirocyclic moiety is selected from

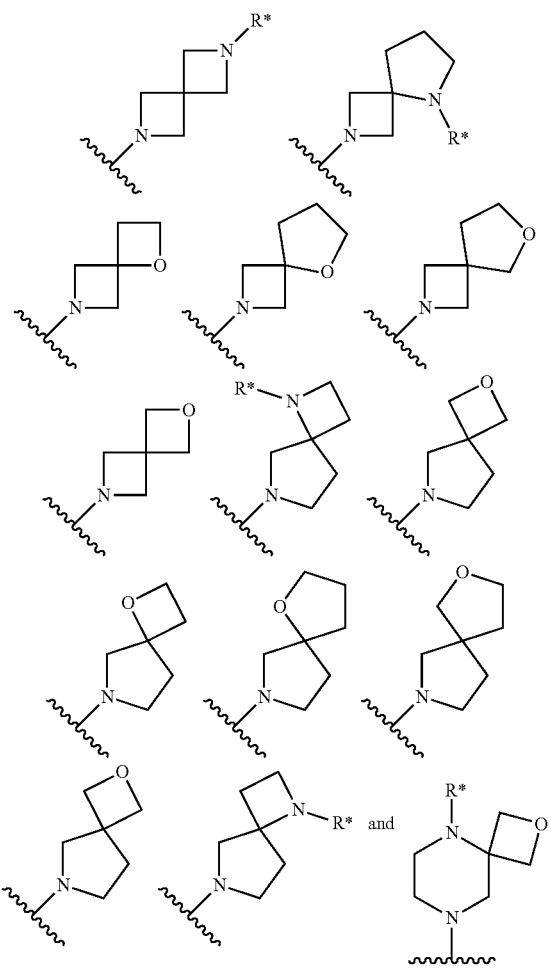

wherein
R* is hydrogen or $C_1$-$C_4$alkyl. In an embodiment, when Rz and Rz' are taken together with the nitrogen atom to which they are attached and form a bicyclic moiety, said bicyclic moiety is selected from

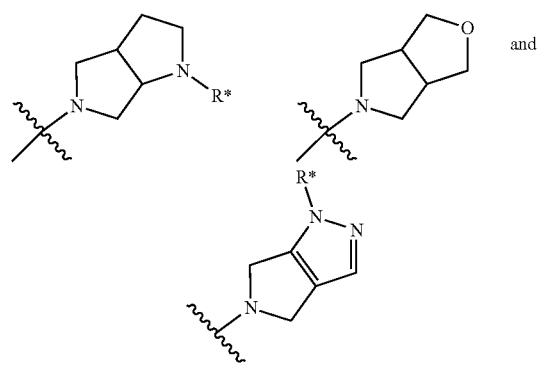

wherein R* is hydrogen or $C_1$-$C_4$alkyl.

In an embodiment, when Rz and Rz' are taken together with the nitrogen atom to which they are attached and form a cyclic moiety, said cyclic moiety is selected from

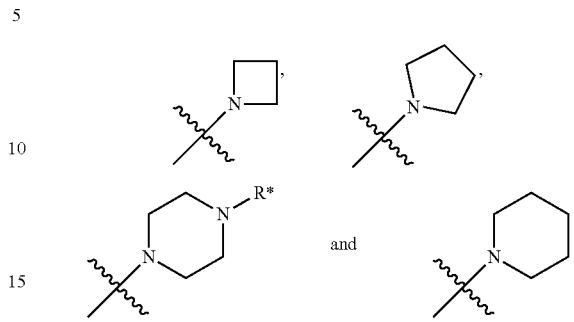

wherein R* is hydrogen or $C_1$-$C_4$alkyl.

In an embodiment, heterocyclyl is selected from pyrazole, imidazole, triazole, azetidine, pyrimidine, pyrrolidine, furan, piperidine, pyridine and pyrazine.

In an embodiment, heterocyclyl is selected from pyrazolyl, imidazolyl, triazolyl, azetidinyl, pyrimidinyl, pyrrolidinyl, furanyl, piperidinyl, pyridinyl and pyrazinyl.

In an embodiment, a spirocyclic moiety, bicyclic moiety, heterocyclyl and cycloakyl are each optionally substituted with one or two substituents independently selected from $(C_{1-4})$alkyl, $O(C_{1-4})$alkyl, $(C=O)O(C_{1-4})$alkyl, F, OH, oxo, cycloalkyl, heterocyclyl, $NH_2$, $N(R_b)_2$, $S(O)_2$, $CF_3$, $CHF_2$ and CN.

The invention also provides a compound of Formulas I-II, or a pharmaceutically acceptable salt thereof in purified form.

In certain embodiments, a compound of Formula I or II is provided in the form of a free base or free acid (i.e., not a salt form).

In certain embodiments, the compound is:

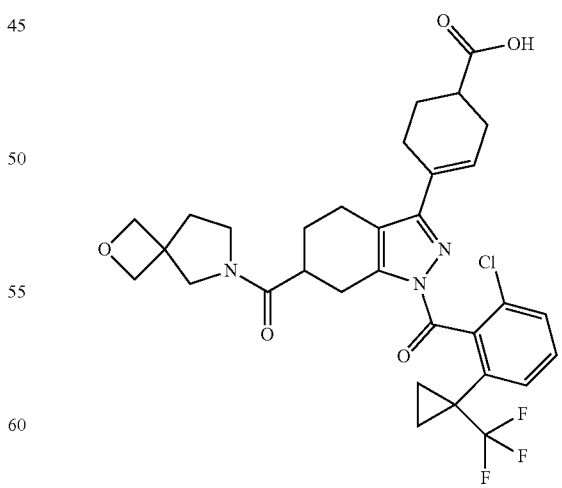

or a pharmaceutically acceptable salt thereof. In certain other embodiments, the compound is

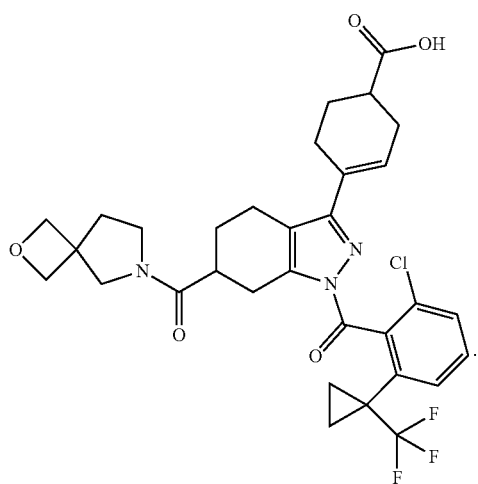 [SMILES: O=C(O)C1CC=C(c2nn(C(=O)c3c(Cl)cccc3C3(C(F)(F)F)CC3)c3c2CCC(C(=O)N2CCC4(COC4)C2)C3)CC1]

In yet other embodiments, the compound is

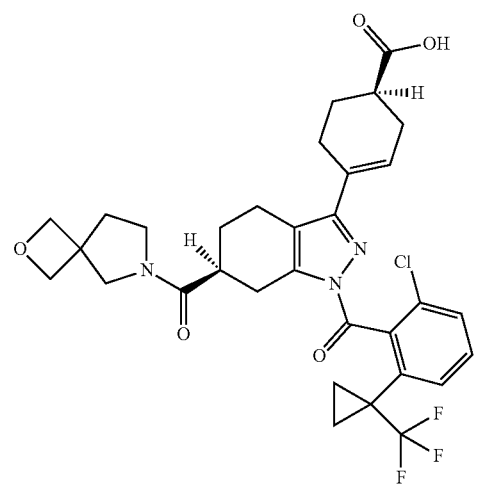 [SMILES: O=C(O)[C@H]1CC=C(c2nn(C(=O)c3c(Cl)cccc3C3(C(F)(F)F)CC3)c3c2CC[C@H](C(=O)N2CCC4(COC4)C2)C3)CC1]

or a pharmaceutically acceptable salt thereof. In yet other embodiments, the compound is

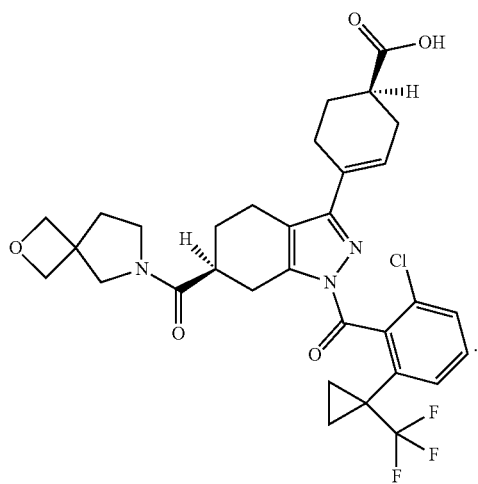 [SMILES: O=C(O)[C@H]1CC=C(c2nn(C(=O)c3c(Cl)cccc3C3(C(F)(F)F)CC3)c3c2CC[C@H](C(=O)N2CCC4(COC4)C2)C3)CC1]

In certain embodiments, the foregoing compound is further characterized by a stereochemical purity, such as a diastereomeric excess of at least 90%. In certain embodiments, the foregoing compound is further characterized by a stereochemical purity, such as a diastereomeric excess of at least 95%, 97%, or 99%.

In yet other embodiments, the compound is

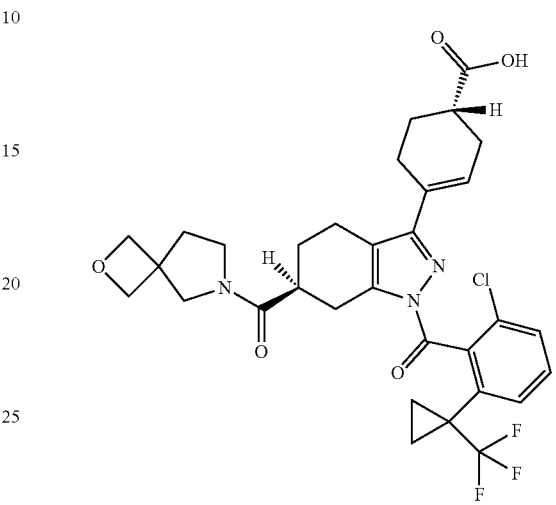

or a pharmaceutically acceptable salt thereof. In yet other embodiments, the compound is

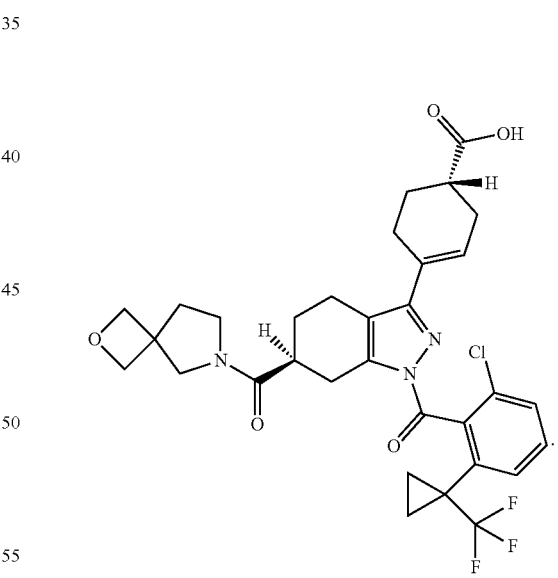

In certain embodiments, the foregoing compound is further characterized by a stereochemical purity, such as a diastereomeric excess of at least 90%. In certain embodiments, the foregoing compound is further characterized by a stereochemical purity, such as a diastereomeric excess of at least 95%, 97%, or 99%.

In yet other embodiments, the compound is

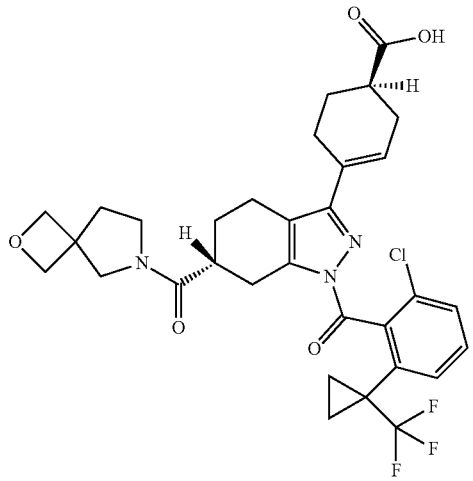 [SMILES: O=C(O)[C@H]1CC=C(c2nn(C(=O)c3c(Cl)cccc3C3(C(F)(F)F)CC3)c3c2CC[C@@H](C(=O)N2CCC4(COC4)C2)C3)CC1]

or a pharmaceutically acceptable salt thereof. In yet other embodiments, the compound is

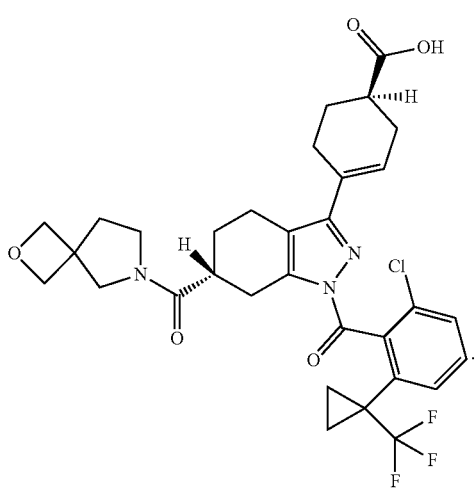 [SMILES: O=C(O)[C@H]1CC=C(c2nn(C(=O)c3c(Cl)cccc3C3(C(F)(F)F)CC3)c3c2CC[C@@H](C(=O)N2CCC4(COC4)C2)C3)CC1]

In certain embodiments, the foregoing compound is further characterized by a stereochemical purity, such as a diastereomeric excess of at least 90%. In certain embodiments, the foregoing compound is further characterized by a stereochemical purity, such as a diastereomeric excess of at least 95%, 97%, or 99%.

In yet other embodiments, the compound is

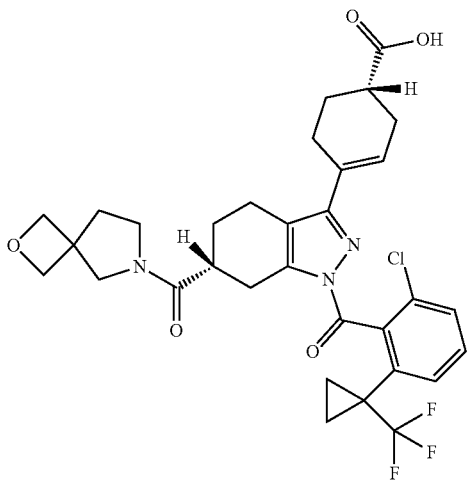 [SMILES: O=C(O)[C@@H]1CC=C(c2nn(C(=O)c3c(Cl)cccc3C3(C(F)(F)F)CC3)c3c2CC[C@@H](C(=O)N2CCC4(COC4)C2)C3)CC1]

is a pharmaceutically acceptable salt thereof. In yet other embodiments, the compound is

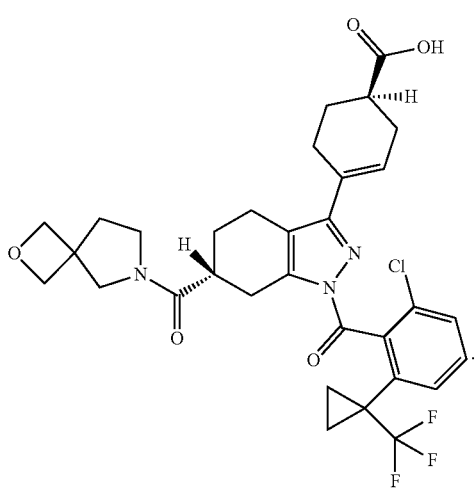 [SMILES: O=C(O)[C@H]1CC=C(c2nn(C(=O)c3c(Cl)cccc3C3(C(F)(F)F)CC3)c3c2CC[C@@H](C(=O)N2CCC4(COC4)C2)C3)CC1]

In certain embodiments, the foregoing compound is further characterized by a stereochemical purity, such as a diastereomeric excess of at least 90%. In certain embodiments, the foregoing compound is further characterized by a stereochemical purity, such as a diastereomeric excess of at least 95%, 97%, or 99%.

In certain embodiments, the compound is a compound in any one of Tables 7-16 or a pharmaceutically acceptable salt thereof.

The invention includes prodrugs, hydrates or solvates of compounds described herein. The use of the terms "prodrug", "hydrate", "salt", "solvate", "ester", and the like is intended to equally apply to the salt, solvate, ester, and prodrug of enantiomers, stereoisomers, rotamers, tautomers, positional isomers, racemates, or prodrugs of the inventive compounds.

Optical Isomers—Diastereomers—Geometric Isomers—Tautomers

The compounds of Formulas (I-II) may contain asymmetric or chiral centers, and, therefore, exist in different stereoisomeric forms. It is intended that all stereoisomeric forms of the compounds of Formulas (I-II) as well as mixtures thereof, including racemic mixtures, form part of the present invention. In addition, the present invention embraces all geometric and positional isomers. For example, if a compound of Formulas (I-II) incorporates a double bond or a fused ring, both the cis- and trans-forms, as well as mixtures, are embraced within the scope of the invention.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formulas (I-II) are shown without a definitive stereochemistry at certain positions. The present invention includes all stereoisomers of Formulas (I-II) and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formulas (I-II) may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen. Such compounds are referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are included within the scope of the present invention. The compounds of Formulas I-II may exist in different tautomeric forms, and all such forms are embraced within the scope of the invention. Also, for example, imine-enamine forms of the compounds are included in the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formulas (I-II) may be atropisomers (e.g. substituted biaryls) and are considered as part of this invention. Enantiomers can also be separated by use of chiral HPLC column.

All stereoisomers (for example, geometric isomers, optical isomers and the like) of the present compounds (including those of the salts, solvates, esters, and prodrugs of the compounds as well as the salts, solvates, and esters of the prodrugs), such as those that may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (-ic and -ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

The compounds of Formulas I-II can form salts which are also within the scope of this invention. Reference to a compound of Formulas I-II herein is understood to include reference to salts thereof, unless otherwise indicated.

The term pharmaceutically acceptable salt represents those salts that are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide, calcium hydroxide, calcium carbonate, ammonium (e.g. diethylamine) or lithium hydroxide.

Solvates

The present invention includes within its scope solvates of compounds of Formulas (I-II). As used herein, the term "solvate" refers to a complex of variable stoichiometry formed by a solute (i.e., a compound of Formulas (I-II)) or a pharmaceutically acceptable salt thereof and a solvent that does not interfere with the biological activity of the solute. Examples of solvents include but are not limited to water, ethanol, and acetic acid. When the solvent is water, the solvate is known as hydrate; hydrate includes, but is not limited to, hemi-, mono, sesqui-, di- and trihydrates.

The compounds of the invention may form hydrates or solvates. It is known to those of skill in the art that charged compounds form hydrated species when lyophilized with water, or form solvated species when concentrated in a solution with an appropriate organic solvent. One or more compounds of the invention may exist in unsolvated as well as solvated forms with pharmaceutically acceptable solvents such as water, ethanol, and the like, and it is intended that the invention embrace both solvated and unsolvated forms. "Solvate" may also mean a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of Formulas I-II or with a compound that may not be a compound of Formulas I-II, but that converts to a compound of Formulas I-II in vivo after administration to the patient. Conventional procedures for the selection and preparation of suitable prodrug derivatives are described, for example, in "Design of Prodrugs," ed. H. Bundgaard, Elsevier, 1985.

The term "prodrug" means a compound (e.g., a drug precursor) that is transformed in vivo to yield a compound of Formulas I-II or a pharmaceutically acceptable salt, hydrate or solvate of the compound. The transformation may occur by various mechanisms (e.g., by metabolic or chemical processes), such as, for example, through hydrolysis in blood. A discussion of prodrugs and the use of prodrugs is provided by T. Higuchi and W. Stella, "Pro-drugs as Novel Delivery Systems," Vol. 14 of the A.C.S. Symposium Series, 1987; and in Bioreversible Carriers in Drug Design, ed. Edward B. Roche, American Pharmaceutical Association and Pergamon Press, 1987.

Isotopes

In the compounds of generic Formulas (I-II), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formulas I-II. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formulas (I-II) can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound having Formulas I-II, or a pharmaceutically acceptable salt thereof, that is effective for treating the disease or condition mediated by RORgammaT in the subject.

The compounds according to the invention can be used in therapy.

A further aspect of the invention resides in the use of compounds according to the invention or a pharmaceutically acceptable salt thereof for the treatment of RORgammaT-mediated diseases or RORgammaT mediated conditions.

Another aspect of the invention resides in the use of compounds or a pharmaceutically acceptable salt thereof having the general Formulas (I-II) for the treatment of autoimmune diseases, in particular those diseases in which Th17 cells and non-Th17 cells, which express Th117 hallmark cytokines, play a prominent role. These include, but are not limited to, the treatment of rheumatoid arthritis, psoriasis, inflammatory bowel disease, Crohn's disease, ankylosing spondylitis and multiple sclerosis.

In another aspect, compounds or a pharmaceutically acceptable salt thereof having the general Formulas (I-II) can be used for treatment of inflammatory diseases in which Th17 cells and/or non-Th17 cells, which express Th17 hallmark cytokines, play a prominent role, such as but not limited to respiratory diseases, osteoarthritis and asthma. Also, compounds or a pharmaceutically acceptable salt thereof having the general Formulas (I-II) can be used for treatment of infectious diseases in which Th117 cells and/or non-Th17 cells, which express Th17 hallmark cytokines, play a prominent role, such as but not limited to mucosal leishmaniasis.

Accordingly, in certain embodiments, the invention provides a method of treating a disorder selected from the group consisting of an autoimmune disorder and an inflammatory disorder, where the method comprises administering to a subject in need thereof a therapeutically effective amount of a compound described herein (e.g., a compound of Formula I or II) to treat the disorder. In certain embodiments, the disorder is an autoimmune disorder. In certain embodiments, the autoimmune disorder is rheumatoid arthritis, psoriasis, Crohn's disease, inflammatory bowel disease, multiple sclerosis, psoriasis, ankylosing spondylitis, systemic lupus erythematosus, chronic graft-versus-host disease, acute graft-versus-host disease, Celiac Sprue, idiopathic thrombocytopenic thrombotic purpura, myasthenia gravis, Sjogren's syndrome, scleroderma, ulcerative colitis, or epidermal hyperplasia. In certain other embodiments, the autoimmune disorder is rheumatoid arthritis, psoriasis, Crohn's disease, inflammatory bowel disease, multiple sclerosis, or psoriasis. In certain embodiments, the disorder is an inflammatory disorder. In certain embodiments, the inflammatory disorder is a respiratory disease or osteoarthritis. In certain other embodiments, the inflammatory disorder is osteoarthritis or asthma. In certain embodiments, the disorder to be treated is psoriasis. In certain embodiments, the disorder to be treated is ankylosing spondylitis.

Compounds or a pharmaceutically acceptable salt thereof having the general Formulas (I-II) can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect the disease or condition is an autoimmune disease or an inflammatory disease. The disease or condition includes, but is not limited to, multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis or mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis.

In another aspect the compounds according to the invention can be used to treat or prevent psoriasis.

In another aspect the compounds according to the invention can be used to treat or prevent ankylosing spondylitis In yet another aspect the compounds according to the invention can be used to treat inflammatory bowel disease.

In yet other embodiments, the invention provides a method of treating a disorder selected from the group consisting of ankylosing spondylitis, psoriasis, asthma, diabetic nephropathy, atopic dermatitis, cystic fibrosis, Type 1 diabetes, ischemia reperfusion injury, lupus nephritis, Crohn's disease, Sjogren's syndrome, psoriatic arthritis, vitiligo, systemic lupus erythematosus, giant cell arthritis, ulcerative colitis, primary biliary cirrhosis, Behcet's disease, polymyalgia rheumatica, nonalcoholic steatohepatitis, graft-versus-host disease (e.g., acute graft-versus-host disease and chronic graft-versus-host disease), rheumatoid arthritis, Graves Disease, chronic obstructive pulmonary disease, Celiac disease, uveitis, multiple sclerosis, atherosclerosis, alopecia areata, myasthenia gravis, Hashimoto's disease, and autosomal dominant polycystic kidney disease (ADPKD), where the method comprises administering to a subject in need thereof a therapeutically effective amount of a compound described herein (e.g., a compound of Formula I or II) to treat the disorder.

In yet another aspect the compounds according to the invention can be used to treat cancer. The term cancer includes, but is not limited to, colorectal, lung, and pancreatic cancer. Additional exemplary cancers contemplated for treatment include, for example, ovarian cancer, a melanoma, breast cancer, prostate cancer, renal cell carcinoma, testicular cancer, uterine cancer, brain cancer, bladder cancer, leukemia, a B-cell lymphoma, and non-Hodgkin lymphoma.

In yet other embodiments, the cancer to be treated is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, and hemangioblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In another aspect the compounds according to the invention can be used to treat colorectal cancer.

In another aspect the compounds according to the invention can be used to treat lung cancer.

In another aspect the compounds according to the invention can be used to treat pancreatic cancer.

Another aspect of the invention provides a method of inhibiting the activity of RORγ. The method comprises exposing a RORγ to an effective amount of a compound described herein (e.g., a compound of Formula I or II) to inhibit the activity of said RORγ.

Another aspect of the present invention further includes the use of a compound of Formulas I-II, or a pharmaceutically acceptable salt thereof, in the manufacture of a medicament for the treatment of a disease or condition mediated by RORgammaT.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration that include subcutaneous, intravenous, intramuscular, intraarticular injection or infusion, intrastemal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., autoimmune and inflammatory diseases and disorders.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formulas I-II, or a pharmaceutically acceptable salt thereof, and one or more pharmaceutically acceptable excipients or carriers. In a more specific embodiment, the invention provides pharmaceutical compositions comprising a compound described herein (e.g., a compound prepared in one of the Examples, such as Example 5HH), or a pharmaceutically acceptable salt thereof, and one or more pharmaceutically acceptable excipients or carriers. The term "excipient" and "carrier" may be used interchangeably. The term "composition", as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formulas I-II, additional active ingredient(s), and pharmaceutically acceptable excipients.

In one embodiment, the pharmaceutical compositions of the present invention comprise a compound represented by Formulas I-II (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formulas I-II in suitable propellants, such as fluorocarbons or hydrocarbons.

For ocular administration, an ophthalmic preparation may be formulated with an appropriate weight percent solution or suspension of the compounds of Formulas I-II in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules may be prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules may be washed and dried.

A large number of tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection may be prepared by stirring 1.5% by weight of active ingredient in 10% by volume propylene glycol. The solution may be made to volume with water for injection and sterilized.

An aqueous suspension may be prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The present invention also relates to a pharmaceutical composition comprising compounds or pharmaceutically acceptable salts thereof having the general Formulas I-II in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of the present invention, and their salts and solvates, and physiologically functional derivatives thereof, may be employed alone or in combination with other therapeutic agents for the treatment of diseases and conditions associated with inappropriate IL-17 pathway activity. Combination therapies according to the present invention thus comprise the administration of at least one compound of formulas (I-II) or a pharmaceutically acceptable salt thereof, or a physiologically functional derivative thereof, and the use of at least one other pharmaceutically active agent. The compound(s) of formulas (I-II) and the other pharmaceutically active agent(s) may be administered together or separately and, when administered separately this may occur simultaneously or sequentially in any order. The amounts of the compound(s) of formulas (I-II) and the other pharmaceutically active agent(s) and the relative timings of administration will be selected in order to achieve the desired combined therapeutic effect. For the treatment of the inflammatory and autoimmune diseases, rheumatoid arthritis, psoriasis, inflammatory bowel disease, ankylosing spondylitis, SLE, uveitis, atopic dermatitis, COPD, asthma and allergic rhinitis a compound of Formulas (I-II) may be combined with one or more other active agents such as: (1) TNF-α inhibitors; (2) non-selective COX-I/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. It could also be combined with anti-IL17 antibodies to obtain additive/synergistic responses for the treatment of inflammatory and autoimmune diseases.

Compounds of the present invention, and their salts and solvates, and physiologically functional derivatives thereof, may be employed alone or in combination with other anti-cancer agents for the treatment of cancer.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formulas I-II.

The invention further includes a compound of Formulas I-II in combination with one or more other drug(s).

Methods of Preparing the Compounds of Formulas (I-II)

Methods for preparing the compounds of this invention are illustrated in the following schemes and examples. Other synthetic protocols will be readily apparent to those skilled in the art in light of the present disclosure. The examples illustrate the preparation of the compounds of Formulas (I-II) and as such are not to be considered as limiting the invention set forth in the claims appended hereto. Unless otherwise indicated, all variables are as previously defined.

All the end products of the Formulas (I-II) were analyzed by NMR and/or LCMS. Intermediates were analyzed by NMR and/or TLC and/or LCMS. Most compounds were purified by reverse phase HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

Abbreviations used herein are as follows: EtOAc: Ethyl acetate; PE: Petroleum ether; EA: Ethyl acetate; DCM: Dichloro methane; Dppf: 1,1'-Bis(diphenylphosphino) ferrocene; AcOH: Acetic acid; DMAC: N,N-Dimethylacetamide; Pd(PPh$_3$)$_4$: Tetrakis(Triphenylphosphine)Palladium (0); Pd(dppf)Cl$_2$: [1,1'-Bis(diphenylphosphino) ferrocene] dichloropalladium (II); Ac$_2$O: Acetic anhydride; LiHMDS: Lithium bis(trimethylsilyl)amide; PhNTf$_2$: N-Phenyl-bis(trifluoromethanesulfonimide); S-Phos: 2-Dicyclohexylphosphino-2',6'-dimethoxybiphenyl; X-Phos: 2-Dicyclohexylphosphino-2',4',6'-triisopropylbiphenyl; CPME: Cyclopentyl methyl ether; DMAP: 4-Dimethylaminopyridine; TEA: Triethylamine; THF: Tetrahydrofuran; PYAOP: (7-Azabenzotriazol-1-yloxy)tripyrrolidinophosphonium hexafluorophosphate.

Schemes

Scheme 1 illustrates a general method toward the preparation of compounds of the instant invention. Starting with the halogenation of compound A followed by N-acylation with either carboxylic acids or acid chlorides in the presence of base led to the formation of compound C. Subsequent cross coupling followed by ester hydrolysis afforded the compound E. Standard amide coupling furnished intermediate F. Ester deprotection led to the formation of the final product I.

Scheme 1

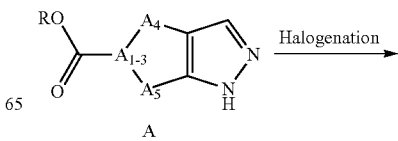

A

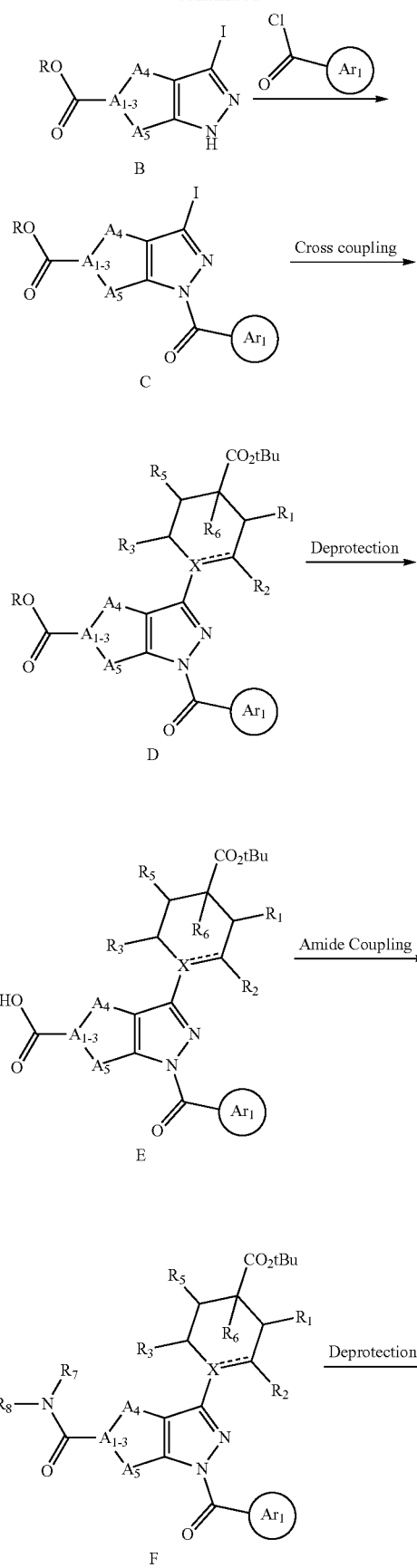
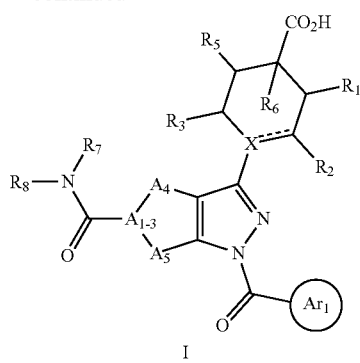
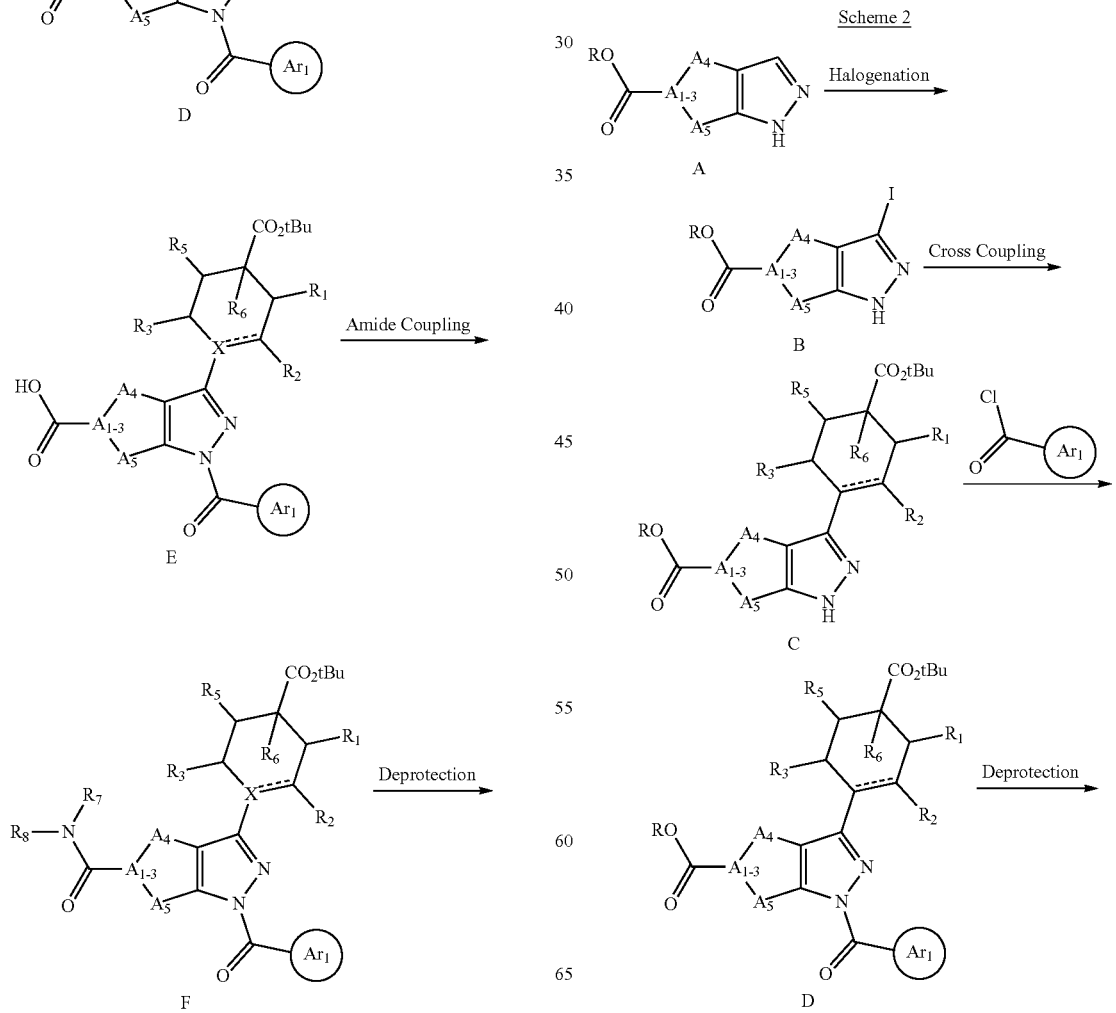

Scheme 2 illustrates a general method toward the preparation of compounds of the instant invention. Starting with the halogenation of compound A followed by a Suzuki cross coupling yielded compound C. N-acylation with either carboxylic acids or acid chlorides in the presence of base led to the formation of compound D. Ester hydrolysis led to compound E which underwent a standard amide coupling to give compound F. Ester deprotection led to the formation of the final product II.

Scheme 2

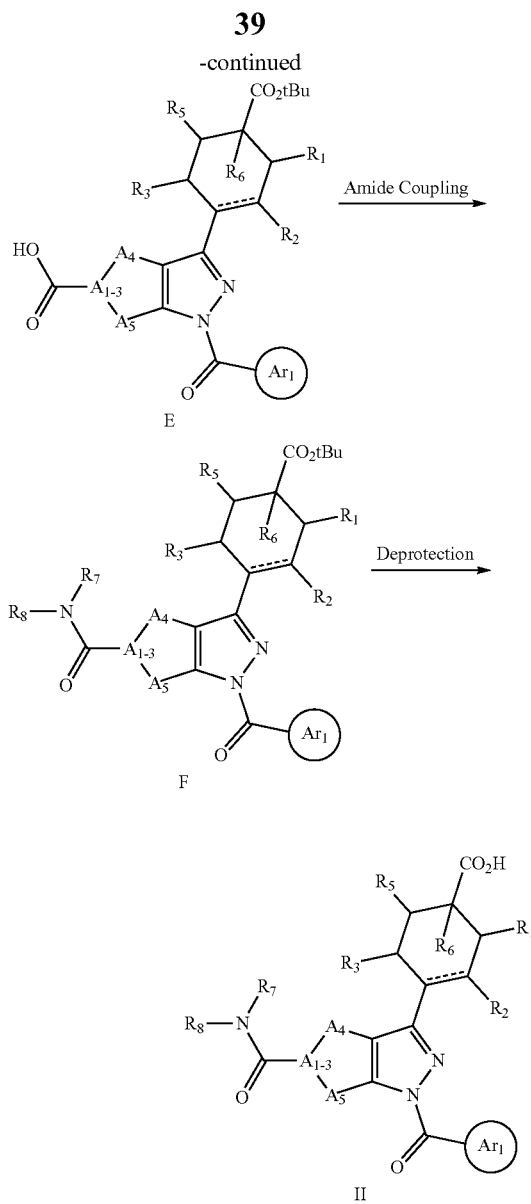

COMMERCIALLY AVAILABLE/PREVIOUSLY DESCRIBED MATERIALS

The following table lists commercial sources, and previously disclosed synthetic routes for chemical materials employed in the synthesis of intermediates, and examples of the instant invention. The list is not intended to be exhaustive, exclusive, or limiting in any way.

| Structure | Source |
|---|---|
| | Matrix Scientific |
| | Sigma Aldrich |
| 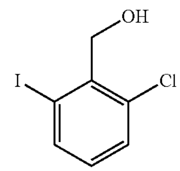 | Spectra Group Limited Inc |
| | Sigma Aldrich |
| | Sigma Aldrich |
| | Matrix Scientific |
| 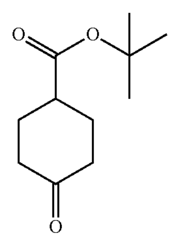 | Astatech Inc |
| | Sigma Aldrich |
| | Matrix Scientific |

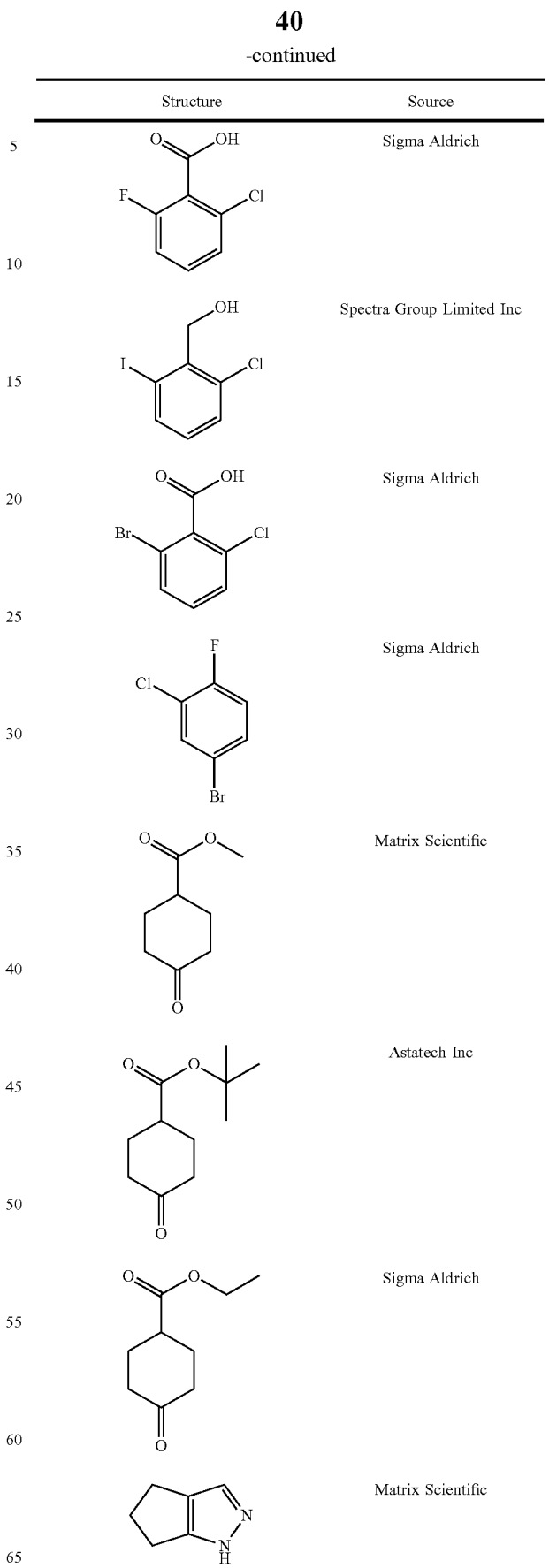

| Structure | Source |
|---|---|
| | Enamine |
| 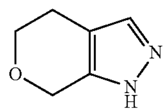 | Anichem Inc |
| | Enamine |
| 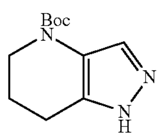 | Combi-Blocks Inc |
| 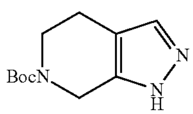 [SMILES: CC(C)(C)OC(=O)N1CCc2cn[nH]c2C1] | Enovation Chemicals Llc |
| 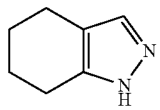 | Sigma Aldrich |
| 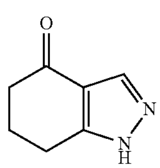 | Chembridge Corporation |

INTERMEDIATES

Intermediate i-1

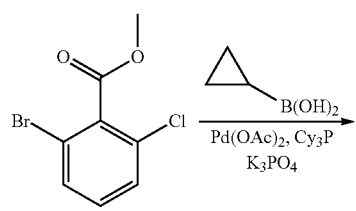

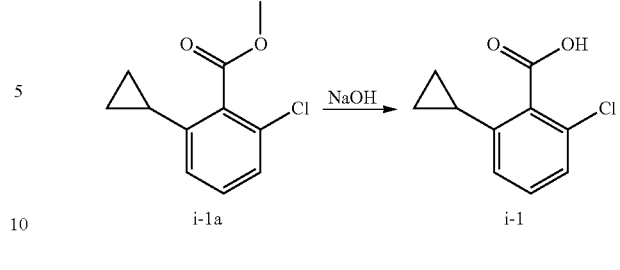

2-chloro-6-cyclopropylbenzoic acid

Step 1. Preparation of methyl 2-chloro-6-cyclopropylbenzoate (i-1a)

Methyl 2-bromo-6-chlorobenzoate (1.0 g, 4.0 mmol), cyclopropylboronic acid (516 mg, 6.0 mmol), Pd(OAc)$_2$ (90 mg, 0.4 mmol), Cy$_3$P (224 mg, 0.8 mmol) and K$_3$PO$_4$ (2.5 g, 12.0 mmol) were mixed in toluene (20 mL) and H$_2$O (2.5 mL). The mixture was stirred at 100° C. for 14 h under N$_2$ atmosphere. The mixture was cooled down and poured into water. The mixture was extracted with EtOAc and the organic layer was dried over Na$_2$SO$_4$ and concentrated. The residue was purified by flash chromatography (Petroleum/EtOAc 15/1) to give the title compound. MS: 211 (M+1).

Step 2. Preparation of 2-chloro-6-cyclopropylbenzoic acid (i-1)

NaOH (380 mg, 9.5 mmol) was added to a solution of methyl 2-chloro-6-cyclopropylbenzoate (200 mg, 0.95 mmol) in EtOH (15 mL) and H$_2$O (6 mL). The resultant solution was stirred at 80° C. overnight. The mixture was cooled down and acidified with 2N HCl to pH=2~3. Then the mixture was extracted with EtOAc. The organic layer was dried over Na$_2$SO$_4$ and concentrated to afford the title compound. MS: 197 (M+1).

Intermediate i-2

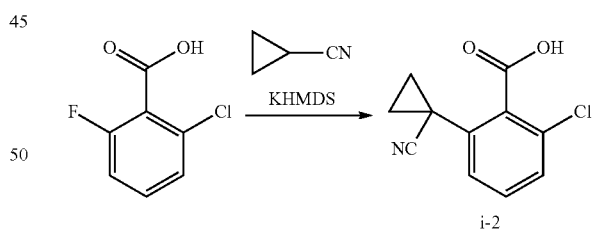

2-chloro-6-(1-cyanocyclopropyl)benzoic acid

To a solution of 2-chloro-6-fluorobenzoic acid (5.00 g, 28.6 mmol) and cyclopropanecarbonitrile (20.0 g, 298 mmol) in THF (5 mL) at −40° C. was added KHMDS (75 mL, 1.0M in THF 75 mmol) dropwise. The reaction mixture was slowly warmed up and heated at 70° C. for 16 hrs, then cooled to room temperature. The reaction was acidified with 1N HCl, and extracted with EtOAc. The combined organic layers were concentrated and the residue was purified by chromatography (0-80% ethyl acetate/Pentanes) and re-purified by prep. HPLC (CH$_3$CN/H$_2$O+0.1% TFA) to afford 2-chloro-6-(1-cyanocyclopropyl)benzoic acid. MS: 222 (M+1). ¹H NMR (600 MHz, DMSO-d6): δ 12.9-13.1 (brs, 1H), 7.53 (dd, 1H, J=8.4, 1.2 Hz), 7.48 (dd, 1H, J=8.4, 1.2 Hz), 7.45 (t, 1H, J=8.4 Hz), 1.60-1.63 (m, 2H), 1.35-1.38 (m, 2H).

Intermediate i-3

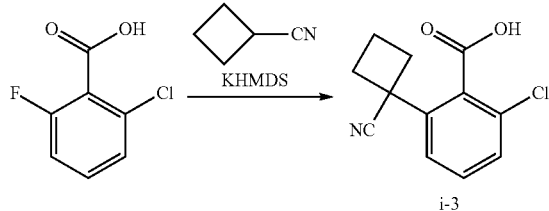 [SMILES: O=C(O)c1c(F)cccc1Cl ; N#CC1CCC1 ; N#CC1(c2cccc(Cl)c2C(=O)O)CCC1]

i-3

2-chloro-6-(1-cyanocyclobutyl)benzoic acid

To a mixture of cyclobutanecarbonitrile (0.70 g, 8.6 mmol) and 2-chloro-6-fluorobenzoic acid (0.5 g, 2.9 mmol) in THF (9.6 mL) at 0° C. was added KHMDS (0.5M in toluene, 12.6 mL, 6.3 mmol). The resulting mixture was heated at 70° C. for 3 h, then cooled down, concentrated in vacuo. The residue was taken up in 20 mL H₂O, and extracted with Et₂O for three times. The aqueous layer was acidified with 2N HCl, and extracted with CHCl₃/i-PrOH (3:1). The combined organics were dried over Na₂SO₄, concentrated. The crude residue was used directly. MS: 236 (M+1). ¹H NMR (600 MHz, DMSO-d6): δ 12.9-13.1 (brs, 1H), 7.51 (dd, 1H, J=8.4, 1.2 Hz), 7.46 (t, 1H, J=8.4 Hz), 7.30 (dd, 1H, J=8.4, 1.2 Hz), 2.56-2.68 (m, 4H), 2.22-2.32 (m, 1H), 1.84-1.90 (m, 1H).

Intermediate i-4

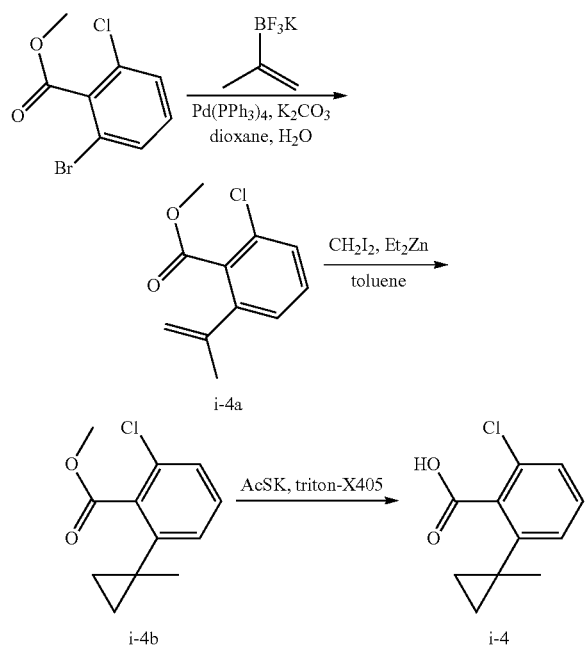

2-chloro-6-(1-methylcyclopropyl)benzoic acid

Step 1. Preparation of 2-chloro-6-(prop-1-en-2-yl) benzoate (i-4a)

To a solution of methyl 2-bromo-6-chlorobenzoate (5.00 g, 20.0 mmol) and potassium trifluoro(prop-1-en-2-yl)borate (4.00 g, 27.0 mmol) in dioxane (30 mL) and water (5 mL) was added Pd(PPh₃)₄ (460 mg, 0.40 mmol) under N₂ atmosphere. The resulting mixture was stirred at 100° C. for 16 h, then cooled to room temperature, filtered and washed with DCM and water. The organic layer was washed with brine, dried over Na₂SO₄, filtered and concentrated. The residue was purified by flash chromatography (0-5% EtOAc in petroleum ether) to give the title compound. ¹H NMR (400 MHz, CDCl₃) δ 7.25-7.31 (m, 2H), 7.11-7.17 (m, 1H), 5.13 (s, 1H), 4.95 (s, 1H), 3.85 (s, 3H), 2.04 (s, 3H).

Step 2. Preparation of methyl 2-chloro-6-(1-methylcyclopropyl)benzoate (i-4b)

To a solution of methyl 2-chloro-6-(prop-1-en-2-yl)benzoate (2.00 g, 9.50 mmol) in toluene (6 mL) at 0° C. was added diiodomethane (4.0 mL, 47.5 mmol), followed by the addition of 1.0 M Et₂Zn (47.4 mL, 47.4 mmol) under N₂ atmosphere. The reaction mixture was warmed to room temperature, stirred for 1 h, then heated at 60° C. for 2 days. The reaction mixture was then cooled to 0° C., additional diiodomethane (4.0 mL, 47.5 mmol) was added, followed by Et₂Zn (47.4 mL, 47.4 mmol) under N₂ atmosphere. The reaction was then heated at 60° C. overnight. The reaction mixture was cooled down, quenched with NH₄Cl solution, and extracted with EtOAc. The organic layer washed with brine, dried over Na₂SO₄, filtered and concentrated, the residue was purified by flash chromatography (0 to 10% EtOAc in petroleum ether) to afford crude product contained some starting material. The product was dissolved in CH₃CN (10 mL) and water (1 mL), followed by the addition of NMO (500 mg, 4.27 mmol) and potassium osmate(vi) dihydrate (20 mg, 0.05 mmol) at 0° C. The resulting mixture was warmed to room temperature, stirred for 24 h, quenched with Na₂SO₃ solution, extracted with EtOAc. The organic layer was washed with brine, dried over Na₂SO₄, filtered and concentrated. The residue was purified by flash chromatography (0-10% EtOAc in petroleum ether) and then preparative TLC (petroleum ether:EtOAc=20:1) to give the title compound. MS: 225 (M+1). ¹H NMR (400 MHz, CDCl₃) δ 7.23-7.28 (m, 2H), 7.08-7.15 (m, 1H), 3.90 (m, 3H), 1.28 (s, 3H), 0.71-0.74 (m, 2H), 0.55-0.60 (m, 2H).

Step 3. Preparation of 2-chloro-6-(1-methylcyclopropyl)benzoic acid (i-4)

To a solution of methyl 2-chloro-6-(1-methylcyclopropyl) benzoate (320 mg, 1.42 mmol) in DMF (5 mL) was added potassium thioacetate (651 mg, 5.70 mmol), followed by polyethylene glycol tert-octylphenyl ether (73 mg, 0.14 mmol). The resulting mixture was stirred at 130° C. for 5 h, cooled to room temperature, diluted with water and extracted with EtOAc. The organic layer was washed with brine, dried over MgSO₄, filtered and concentrated. The residue was purified by preparative TLC (EtOAc:DCM=2:1) and then preparative HPLC to give the title compound. MS: 211 (M+1). ¹H NMR (400 MHz, CDCl₃) δ 7.31-7.36 (m, 1H), 7.25-7.29 (m, 2H), 1.39 (s, 3H), 0.85-0.90 (m, 2H), 0.67-0.74 (m, 2H).

Intermediate i-5

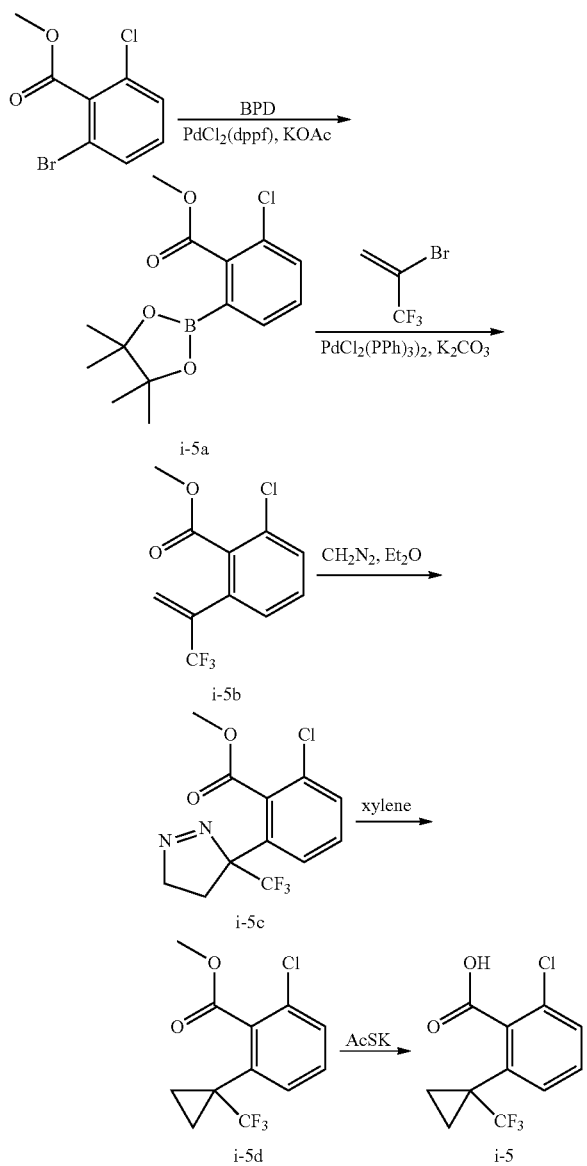

2-chloro-6-(1-(trifluoromethyl)cyclopropyl)benzoic acid

Step 1. Preparation of methyl 2-chloro-6-(4,4,5,5-tetramethyl-1,3,2-dioxaborolan-2-yl)benzoate (i-5a)

To a solution of methyl 2-bromo-6-chlorobenzoate (7.50 g, 30.1 mmol) in dioxane (65 mL) was added Bis(pinacolato)diboron (15.3 g, 60.3 mmol), AcOK (3.54 g, 36.1 mmol) and PdCl$_2$(dppf) (0.66 g, 0.90 mmol) under N$_2$ atmosphere, then the resulting mixture was stirred at 100° C. for 18 h, cooled to room temperature, filtered and concentrated, the residue was purified by chromatography (0-3% EtOAc in petroleum ether) to give the title compound. MS: 297 (M+1). $^1$H NMR (400 MHz, CDCl$_3$) δ 7.67 (d, J=7.4 Hz, 1H), 7.46 (d, J=7.8 Hz, 1H), 7.29-7.39 (m, 1H), 3.92 (s, 3H), 1.32 (s, 12H).

Step 2. Preparation of methyl 2-chloro-6-(3,3,3-trifluoroprop-1-en-2-yl)benzoate (i-5b)

Bis(triphenylphosphine)palladium(ii) dichloride (120 mg, 0.171 mmol) was added to a solution of methyl 2-chloro-6-(4,4,5,5-tetramethyl-1,3,2-dioxaborolan-2-yl)benzoate (2.00 g, 6.74 mmol), 2-bromo-3,3,3-trifluoroprop-1-ene (3.54 g, 20.23 mmol) and K$_2$CO$_3$ (1.86 g, 13.49 mmol) in THF (25 mL) and water (2 mL). The resultant mixture was stirred at 70° C. for 5 h. The mixture was concentrated in vacuo and purified by chromatography (0-5% EtOAc in petroleum ether) to give the title compound. $^1$H NMR (400 MHz, CDCl$_3$) δ 7.43-7.49 (m, 1H), 7.37 (t, J=7.8 Hz, 1H), 7.27-7.32 (m, 1H), 6.08 (s, 1H), 5.66 (s, 1H), 3.86 (s, 3H).

Step 3. Preparation of methyl 2-chloro-6-(3-(trifluoromethyl)-4,5-dihydro-3H-pyrazol-3-yl)benzoate (i-5c)

Diazomethane (300 mL, 75.0 mmol in Et$_2$O) was added to a solution of methyl 2-chloro-6-(3,3,3-trifluoroprop-1-en-2-yl)benzoate (1.03 g, 3.89 mmol) in DCM (10 mL). The resultant mixture was stirred at 0° C. for 24 h, and quenched with AcOH (1 mL). Then the reaction mixture was concentrated in vacuo and purified by column chromatography on silica gel (0-10% EtOAc in petroleum ether) to give the title compound. MS: 307 (M+1). $^1$H NMR (400 MHz, CDCl$_3$) δ 7.60 (d, J=7.8 Hz, 1H), 7.46-7.52 (m, 1H), 7.43 (d, J=7.8 Hz, 1H), 4.83-4.96 (m, 1H), 4.63 (td, J=17.8 Hz, 8.7 Hz, 1H), 3.93 (s, 3H), 2.45 (m, 1H), 1.94-2.06 (m, 1H).

Step 4. Preparation of methyl 2-chloro-6-(1-(trifluoromethyl)cyclopropyl)benzoate (i-5d)

A solution of methyl 2-chloro-6-(3-(trifluoromethyl)-4,5-dihydro-3H-pyrazol-3-yl)benzoate (900 mg, 2.93 mmol) in xylene (5.0 mL) was heated at 130° C. for 6 h, then cooled to room temperature, purified by chromatography on silica gel (petroleum ether:EtOAc=10:1) to give the title compound. $^1$H NMR (400 MHz, CDCl$_3$) δ 7.45 (d, J=7.8 Hz, 1H), 7.38-7.43 (m, 1H), 7.35 (d, J=7.8 Hz, 1H), 3.95 (s, 3H), 1.33-1.40 (m, 2H), 1.11-1.19 (m, 2H).

Step 5. Preparation of 2-chloro-6-(1-(trifluoromethyl)cyclopropyl)benzoic acid (i-5)

To a solution of methyl 2-chloro-6-(1-(trifluoromethyl)cyclopropyl)benzoate (600 mg, 2.15 mmol) in DMF (1 mL) was added potassium thioacetate (984 mg, 8.61 mmol), followed by Polyethylene glycol-tert-octylphenyl ether (111 mg, 0.22 mmol). The resulting mixture was heated at 130° C. for 2 h, and then cooled to room temperature. The mixture was purified by Prep-HPLC to give the title compound. $^1$H NMR (400 MHz, CDCl$_3$) δ 7.36-7.48 (m, 2H), 7.28-7.36 (m, 1H), 1.32-1.41 (m, 2H), 1.15-1.19 (m, 2H).

Intermediate i-6

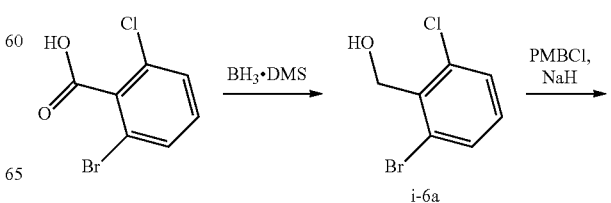

-continued

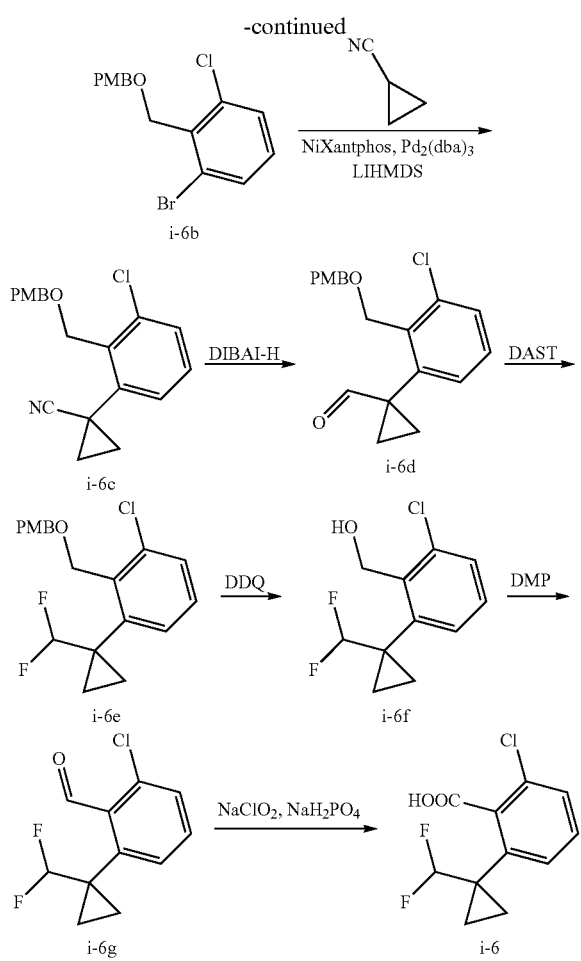

2-chloro-6-(1-(difluoromethyl)cyclopropyl)benzoic acid

Step 1. Preparation of (2-bromo-6-chlorophenyl)methanol (i-6a)

To a solution of 2-bromo-6-chlorobenzoic acid (20 g, 85 mmol) in THF (200 mL) was added BH₃-DMS (42.5 mL, 425 mmol) slowly at 0° C. The resulting solution was heated at 80° C. for 17 h. The reaction was cooled and quenched with MeOH (100 mL) and NaClO (aq., 100 mL) carefully, then most of THF and MeOH were removed under reduced pressure and the remaining aqueous phase was filtered. The filtrate was extracted with EtOAc (4×30 mL). The combined organic layers were washed with brine (50 mL), dried over Na₂SO₄, filtered and concentrated in vacuo. The residue was purified by silica gel column chromatography (petroleum ether:EtOAc=50:1-20:1) to give the title compound. ¹H NMR (400 MHz, CDCl₃) δ 7.52 (d, J=8.0 Hz, 1H), 7.38 (d, J=8.0 Hz, 1H), 7.12 (t, J=8.0 Hz, 1H), 4.99 (d, J=3.5 Hz, 2H), 2.08-2.29 (m, 1H).

Step 2. Preparation of 1-bromo-3-chloro-2-(((4-methoxybenzyl)oxy)methyl)benzene (i-6b)

To a solution of (2-bromo-6-chlorophenyl)methanol (18.41 g, 83 mmol) in THF (200 mL) was added NaH (60%, 4.99 g, 125 mmol) at 0° C. After the mixture was stirred for 0.5 h, 1-(chloromethyl)-4-methoxybenzene (15.62 g, 100 mmol) was added. The mixture was stirred at 0° C. for 3 h and then at room temperature for 17 h. The mixture was quenched with H₂O (80 mL), extracted with EtOAc (3×100 mL). The combined organic layers were washed with brine (80 mL), dried over Na₂SO₄, filtered and concentrated in vacuo. The residue was purified by silica gel column chromatography (petroleum ether:EtOAc=100:1-50:1) to give the title compound. ¹H NMR (400 MHz, CDCl₃) δ 7.51 (d, J=8.0 Hz, 1H), 7.30-7.43 (m, 3H), 7.07-7.15 (m, 1H), 6.89 (d, J=8.6 Hz, 2H), 4.80 (s, 2H), 4.58 (s, 2H), 3.81 (s, 3H).

Step 3. Preparation of 1-(3-chloro-2-(((4-methoxybenzyl)oxy)methyl)phenyl)-cyclopropanecarbonitrile (i-6c)

4,6-Bis(diphenylphosphino)-10H-phenoxazine (1.94 g, 3.51 mmol) and Pd₂(dba)₃ (1.61 g, 1.76 mmol) was dissolved in THF (100 mL). The mixture was stirred at room temperature for 30 min under N₂. 1-bromo-3-chloro-2-(((4-methoxybenzyl)oxy)methyl)benzene (12 g, 35.13 mmol) and cyclopropanecarbonitrile (2.88 g, 42.85 mmol) was added. Then LHMDS (52.8 mL, 52.8 mmol) (1.0 Min THF) was added immediately. The mixture was stirred at 80° C. for 18 h under N₂. The mixture was cooled and quenched with sat. NH₄Cl (100 mL) and the mixture was extracted with ethyl acetate (4×60 mL). The combined organic fractions were washed with brine (50 mL), dried over Na₂SO₄, filtered and the solvent was evaporated under reduced pressure. The residue was purified by silica gel column flash chromatography, eluting with EtOAc/petroleum ether=0-20% to give the title compound. ¹H NMR (400 MHz, CDCl₃) δ 7.35-7.42 (m, 3H), 7.27-7.32 (m, 1H), 7.21-7.26 (m, 1H), 6.92 (d, J=8.6 Hz, 2H), 4.80-4.91 (m, 2H), 4.65 (s, 2H), 3.77-3.91 (m, 3H), 1.57-1.60 (m, 2H), 1.38-1.45 (m, 2H).

Step 4. Preparation of 1-(3-chloro-2-(((4-methoxybenzyl)oxy)methyl)phenyl)-cyclopropanecarbaldehyde (i-6d)

Diisobutylaluminum hydride (55 mL, 55.0 mmol) (1.0 M in toluene) was added to a stirred mixture of 1-(3-chloro-2-(((4-methoxybenzyl)oxy)methyl)phenyl)-cyclopropanecarbonitrile (9 g, 27.5 mmol) in toluene (60 mL) at room temperature and the mixture was stirred at room temperature for 2 h. The mixture was cooled to 0° C., i-PrOH (12 mL) was added. After stirring at 0° C. for 30 min, hydrochloric acid (1 M, 60 mL) was added and the mixture was extracted with ethyl acetate (4×50 mL). The combined organic fractions were washed with brine (saturated, 50 mL), dried (Na₂SO₄), filtered and the solvent was evaporated under reduced pressure. The residue was purified by silica gel column flash chromatography, (EtOAc/petroleum ether=0-10%) to give the title compound. ¹H NMR (400 MHz, CDCl₃) δ 9.16 (s, 1H), 7.39 (d, J=7.5 Hz, 1H), 7.31 (d, J=8.4 Hz, 2H), 7.23 (d, J=7.9 Hz, 1H), 7.16-7.22 (m, 1H), 6.89 (d, J=8.6 Hz, 2H), 4.61 (s, 2H), 4.52 (s, 2H), 3.82 (s, 3H), 1.58 (d, J=2.9 Hz, 2H), 1.38-1.47 (m, 2H).

Step 5. Preparation of methyl 1-chloro-3-(1-(difluoromethyl)cyclopropyl)-2-(((4-methoxybenzyl)oxy)methyl)benzene (i-6e)

DAST (2.80 mL, 21.16 mmol) was added to a stirred mixture of 1-(3-chloro-2-(((4-methoxybenzyl)oxy)methyl)phenyl)cyclopropanecarbaldehyde (3.5 g, 10.58 mmol) in DCM (40 mL) at room temperature and the mixture was stirred at 30° C. for 18 h. The mixture was concentrated to dryness. The residue was purified by silica gel column flash chromatography, (EtOAc/petroleum ether=0-5%) to give the title compound. ¹H NMR (400 MHz, CDCl₃) δ 7.29-7.40 (m, 4H), 7.19-7.25 (m, 1H), 6.89-6.93 (m, 2H), 5.57-5.91 (m, 1H), 4.71-4.82 (m, 2H), 4.61 (s, 2H), 3.82 (s, 3H), 1.17 (s, 2H), 1.04 (d, J=2.3 Hz, 2H).

Step 6. Preparation of (2-chloro-6-(1-(difluoromethyl)cyclopropyl)phenyl)methanol (i-6f)

DDQ (1.930 g, 8.50 mmol) was added to a stirred mixture of 1-chloro-3-(1-(difluoromethyl)cyclopropyl)-2-(((4-methoxybenzyl)oxy)methyl)benzene (2 g, 5.67 mmol) in DCM (12 mL) and water (2 mL) at room temperature and the mixture was stirred at room temperature for 18 h. The mixture was filtered and the filter cake was washed with dichloromethane (30 mL), the combined organic fractions were washed with Na₂SO₃ (Saturated, 2×20 mL), dried (Na₂SO₄), filtered and concentrated. The residue was dissolved in MeOH (10 mL), added NaBH₄ (0.643 g, 17.01 mmol) at 0° C. After the mixture was stirred at 0° C. for 2 h, water (5 mL) was added. The mixture was concentrated in vacuo to remove the most of MeOH, and then extracted with ethyl acetate (3×15 mL). The combined organic fractions were washed with brine (20 mL), dried over Na₂SO₄, filtered and the solvent was evaporated under reduced pressure. The residue was purified by silica gel column flash chromatography, (EtOAc/petroleum ether=0-15%) to give the title compound. ¹H NMR (400 MHz, CDCl₃) δ 7.38 (dd, J=14.0 Hz, 7.8 Hz, 2H), 7.22-7.27 (m, 1H), 5.52-5.87 (m, 1H), 4.93-5.13 (m, 2H), 2.10-2.21 (m, 1H), 1.30 (s, 2H), 1.09 (brs, 2H).

Step 7. Preparation of 2-chloro-6-(1-(difluoromethyl)cyclopropyl)benzaldehyde (i-6g)

DMP (3.10 g, 7.31 mmol) was added to a stirred mixture of (2-chloro-6-(1-(difluoromethyl)cyclopropyl)phenyl)methanol (0.85 g, 3.65 mmol) in DCM (10 mL) at room temperature and the mixture was stirred at room temperature for 5 h. The mixture was diluted with DCM (20 mL), filtered and the filter cake was washed with dichloromethane (20 mL). The filtrate was concentrated and purified by silica gel column flash chromatography, (EtOAc/petroleum ether=0-10%) to give the title compound. ¹H NMR (400 MHz, CDCl₃) δ 10.61 (s, 1H), 7.41-7.55 (m, 3H), 5.97-6.28 (m, 1H), 1.33-1.39 (m, 2H), 0.80 (brs, 2H).

Step 8. Preparation of 2-chloro-6-(1-(difluoromethyl)cyclopropyl)benzoic acid (i-6)

2-Methylbut-2-ene (1.672 g, 23.85 mmol) was added to a stirred mixture of 2-chloro-6-(1-(difluoromethyl)cyclopropyl)benzaldehyde (0.55 g, 2.385 mmol) in t-BuOH (10 mL) at room temperature. Then sodium dihydrogenphosphate (0.515 g, 4.29 mmol) in H₂O (3 mL) and sodium chlorite (0.324 g, 3.58 mmol) in H₂O (2 mL) was added. The mixture was stirred at room temperature for 18 h, diluted with ethyl acetate (20 mL) and hydrochloric acid (1 M, 3 mL). The mixture was extracted with ethyl acetate (4×15 mL), washed with brine (20 mL), dried over Na₂SO₄, filtered and the solvent was evaporated under reduced pressure. The residue was purified by preparative HPLC (reverse phase C-18 column), eluting with Acetonitrile/Water+0.1% HCOOH to give the title compound. ¹H NMR (400 MHz, CDCl₃) δ 7.29-7.72 (m, 3H), 5.96-6.32 (m, 1H), 1.30 (brs, 2H), 1.02 (brs, 2H).

Intermediate i-7

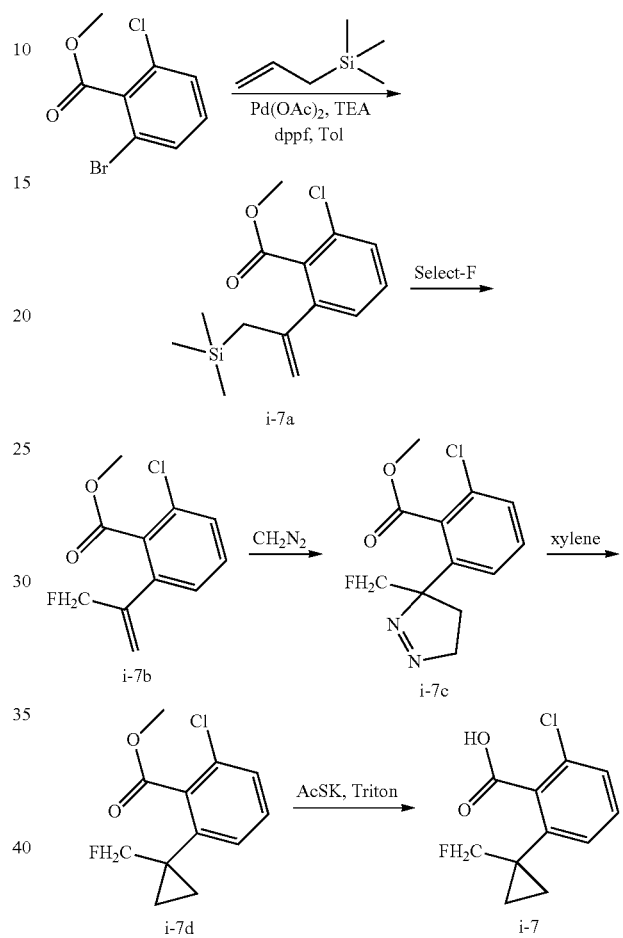

2-chloro-6-(1-(fluoromethyl)cyclopropyl)benzoic acid

Step 1. Preparation of methyl 2-chloro-6-(3-(trimethylsilyl)prop-1-en-2-yl)benzoate (i-7a)

To a mixture of methyl 2-bromo-6-chlorobenzoate (4.6 g, 18.44 mmol), TEA (7.71 mL, 55.3 mmol) and allyltrimethylsilane (2.74 g, 23.97 mmol) in toluene (150 mL) was added Pd(OAc)₂ (0.207 g, 0.922 mmol) and DPPF (1.022 g, 1.844 mmol). The mixture was stirred at 130° C. for 18 h under N₂. TLC showed most of starting material was remained. Allyltrimethylsilane (2.74 g, 23.97 mmol), TEA (7.71 mL, 55.3 mmol), Pd(OAc)₂ (0.207 g, 0.922 mmol) and DPPF (1.022 g, 1.844 mmol) was added and the mixture was stirred for an additional 18 h. Then the above operation was repeated after another 18 h. The mixture was cooled, diluted with water (100 mL) and extracted with EtOAc (3*150 mL). The organic layers were concentrated in vacuo. The residue was purified by column chromatography on silica gel, eluting with petroleum ether to give the title compound. ¹H NMR (400 MHz, CDCl$_3$) δ 7.30 (brs, 1H), 7.22 (s, 1H), 7.13 (d, J=3.5 Hz, 1H), 4.97 (d, J=7.8 Hz, 2H), 3.89 (s, 3H), 1.90 (s, 2H), −0.07 (s, 9H).

Step 2. Preparation of methyl 2-chloro-6-(3-fluoro-prop-1-en-2-yl)benzoate (i-7b)

To a solution of methyl 2-chloro-6-(3-(trimethylsilyl)prop-1-en-2-yl)benzoate (4.5 g, 15.91 mmol) in MeCN (100 mL) was added Selectfluor (14.09 g, 39.8 mmol). The mixture was stirred at room temperature for 24 h. The mixture was concentrated in vacuo. The residue was purified by flash column chromatography on silica gel (100% petroleum ether) to give the title compound. $^1$H NMR (400 MHz, CDCl$_3$) δ 7.31-7.43 (m, 2H), 7.20 (d, J=7.4 Hz, 1H), 5.52 (s, 1H), 5.29 (s, 1H), 5.09 (s, 1H), 4.98 (s, 1H), 3.81-3.92 (m, 3H).

Step 3. Preparation of methyl 2-chloro-6-(3-(fluoromethyl)-4,5-dihydro-3H-pyrazol-3-yl)benzoate (i-7c)

To a solution of methyl 2-chloro-6-(3-fluoroprop-1-en-2-yl)benzoate (1 g, 4.37 mmol) in Et$_2$O (10 mL) was added diazomethane (43.7 mL, 21.87 mmol) (~0.5 M in Et$_2$O) at 0-5° C. The mixture was stand at room temperature for 18 h, then the mixture was concentrated in vacuo. The residue was purified by flash column chromatography on silica gel (petroleum ether: EtOAc=4:1) to give the title compound. MS: 271 (M+1).

Step 4. Preparation of methyl 2-chloro-6-(1-(fluoromethyl)cyclopropyl)benzoate (i-7d)

A solution of methyl 2-chloro-6-(3-(fluoromethyl)-4,5-dihydro-3H-pyrazol-3-yl)benzoate (700 mg, 2.59 mmol) in xylene (50 mL) was stirred at 150° C. for 18 h. The mixture was cooled to room temperature and concentrated in vacuo. The residue was purified by Prep-TLC on silica gel (petroleum ether: EtOAc=1:20) to give the title compound. $^1$H NMR (400 MHz, CDCl$_3$) δ 7.39 (d, J=6.6 Hz, 1H), 7.29-7.36 (m, 2H), 4.45 (s, 1H), 4.33 (s, 1H), 3.95 (s, 3H), 0.95 (s, 4H).

Step 5. Preparation of 2-chloro-6-(1-(fluoromethyl)cyclopropyl)benzoic acid (i-7)

Potassium thioacetate (424 mg, 3.71 mmol) was added to a stirred mixture of methyl 2-chloro-6-(1-(fluoromethyl)cyclopropyl)benzoate (300 mg, 1.236 mmol) and TRITON®X-114 (63 mg, 0.122 mmol) in DMF (20 mL) and the mixture was stirred at 130° C. for 2 h. The mixture was cooled, hydrochloric acid (1 M, 8 mL) was added and the mixture was extracted with ethyl acetate (3×50 mL). The combined organics were evaporated under reduced pressure and purified by preparative HPLC (reverse phase C-18 column), eluting with Acetonitrile/Water+0.1% TFA to give the title compound. $^1$H NMR (400 MHz, CDCl$_3$) δ 7.44 (d, J=6.8 Hz, 1H), 7.31-7.41 (m, 2H), 4.50 (s, 1H), 4.38 (s, 1H), 1.04 (d, J=7.3 Hz, 4H).

Intermediate i-8

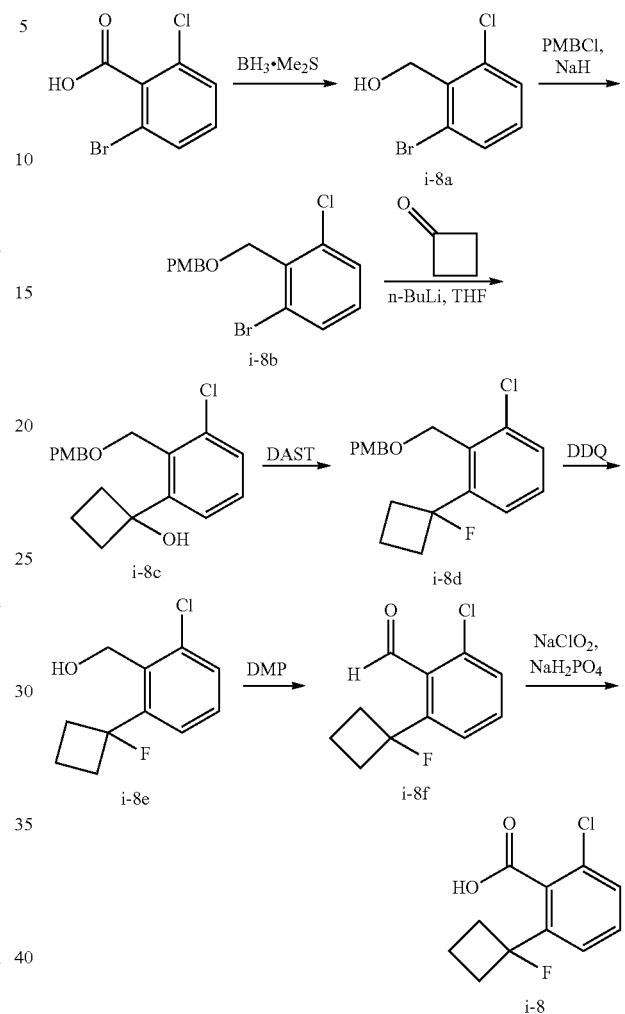

2-chloro-6-(1-fluorocyclobutyl)benzoic acid

Step 1. Preparation of (2-bromo-6-chlorophenyl)methanol (i-8a)

BH$_3$.Me$_2$S (31.9 mL, 10 mol/L) was added dropwise to a stirred solution of 2-bromo-6-chlorobenzoic acid (15.00 g, 63.7 mmol) in anhydrous THF (60 mL) at 5° C. The resulting mixture was stirred at 5° C. for 2 h, warmed up slowly and stirred at 70° C. for 16 h. The mixture was cooled in ice-water bath, quenched by dropping addition of saturated NH$_4$Cl (50 mL) slowly. The resulting suspension was filtered and the filter cake was washed with EtOAc (100 mL). The filtrate was concentrated in vacuo to give the title compound. $^1$H NMR (400 MHz, CDCl$_3$) δ 7.56 (d, J=7.8 Hz, 1H), 7.44 (d, J=7.8 Hz, 1H), 7.23-7.17 (m, 1H), 5.19 (brs, 1H), 4.67 (s, 2H).

Step 2. Preparation of 1-bromo-3-chloro-2-(((4-methoxybenzyl)oxy)methyl)benzene (i-8b)

Sodium hydride (60%, 3.29 g, 82 mmol) was added in small portions to a stirred solution of (2-bromo-6-chlorophenyl)methanol (14.00 g, 63.2 mmol) in anhydrous DMF (140 mL) at 5° C. After stirring for 30 min, 1-(chloromethyl)-4-methoxybenzene (10.3 mL, 76 mmol) was added dropwise. The resulting mixture was stirred at 5° C. for 30 min, then warmed up and stirred at room temperature for 2 h. The mixture was cooled to 5° C., quenched by slow addition of saturated aqueous NH$_4$Cl (150 mL). The mixture was extracted with EtOAc (200 mL*3), the combined organic phase was washed with brine (100 mL*4), dried over Na$_2$SO$_4$, filtered and concentrated. The residue was purified via column chromatography (EtOAc in petroleum ether: 0 to 10%) to give the title compound. $^1$H NMR (400 MHz, CDCl$_3$) δ 7.50 (d, J=7.9 Hz, 1H), 7.29-7.38 (m, 3H), 7.05-7.13 (m, 1H), 6.88 (d, J=8.6 Hz, 2H), 4.79 (s, 2H), 4.57 (s, 2H), 3.80 (s, 3H).

Step 3. Preparation of 1-(3-chloro-2-(((4-methoxybenzyl)oxy)methyl)phenyl)cyclobutanol (i-8c)

n-Butyllithium (9.2 mL, 23.00 mmol) (2.5 M in hexane) was added dropwise to a stirred solution of 1-bromo-3-chloro-2-(((4-methoxybenzyl)oxy)methyl)benzene (6.00 g, 17.56 mmol) in anhydrous THF (40 mL) at −65° C. under nitrogen atmosphere. After stirring at −65° C. for 1 h, cyclobutanone (2.0 mL, 26.8 mmol) was added dropwise. The resulting mixture was stirred at −65° C. for another 2 h, then warmed up slowly and stirred at room temperature for 15 h. The mixture was diluted with EtOAc (50 mL), quenched by slow addition of saturated NH$_4$Cl (30 mL) and brine (30 mL). The organic phase was separated and the aqueous phase was extracted with EtOAc (50 mL*2). The combined organic phase was washed with brine (20 mL), dried over Na$_2$SO$_4$, filtered and concentrated. The residue was purified via column chromatography (EtOAc in petroleum ether: 0 to 15%) to give the title compound. $^1$H NMR (400 MHz, CDCl$_3$) δ 7.31-7.33 (m, 1H), 7.22-7.29 (m, 4H), 6.86 (d, J=8.2 Hz, 2H), 4.85 (s, 2H), 4.49-4.56 (m, 2H), 4.43 (brs, 1H), 3.78 (s, 3H), 2.50-2.61 (m, 2H), 2.33-2.43 (m, 2H), 2.15-2.27 (m, 1H), 1.67-1.75 (m, 1H).

Step 4. Preparation of 1-chloro-3-(1-fluorocyclobutyl)-2-(((4-methoxybenzyl)oxy)methyl)-benzene (i-8d)

DAST (0.50 mL, 3.78 mmol) was added in small drops to a stirred solution of 1-(3-chloro-2-(((4-methoxybenzyl)oxy) methyl)phenyl)cyclobutanol (1.00 g, 3.00 mmol) in anhydrous DCM (20 mL) at 5° C. under N$_2$. The resulting mixture was stirred at 5° C. for 1 h. The reaction was quenched by dropping addition of saturated aqueous NaHCO$_3$ (10 mL) with vigorous stirring. The organic phase was separated and concentrated, the residue was purified via column chromatography (EtOAc in petroleum ether: 0 to 6%) to give the title compound.
$^1$H NMR (400 MHz, CDCl$_3$) δ 7.34 (d, J=7.5 Hz, 1H), 7.20-7.28 (m, 3H), 7.14-7.19 (m, 1H), 6.80 (d, J=8.5 Hz, 2H), 4.56 (s, 2H), 4.49 (s, 2H), 3.73 (s, 3H), 2.65-2.79 (m, 2H), 2.47-2.62 (m, 2H), 1.95-2.08 (m, 1H), 1.53-1.63 (m, 1H).

Step 5. Preparation of (2-chloro-6-(1-fluorocyclobutyl)phenyl)methanol (i-8e)

The mixture of 1-chloro-3-(1-fluorocyclobutyl)-2-(((4-methoxybenzyl)oxy)methyl)benzene (1.25 g, 3.73 mmol) and 4,5-dichloro-3,6-dioxocyclohexa-1,4-diene-1,2-dicarbonitrile (1.70 g, 7.49 mmol) in DCM (10 mL) and water (1 mL) was stirred at room temperature for 3 h. The suspension was filtered and washed with DCM (10 mL). The filtrate was washed with saturated aqueous NaHCO$_3$ (5 mL) and then concentrated. The residue was purified via column chromatography (EtOAc in petroleum ether: 0 to 20%) to give a mixture of (2-chloro-6-(1-fluorocyclobutyl)phenyl)methanol and 4-methoxybenzaldehyde. This mixture was dissolved in MeOH (5 mL), NaBH$_4$ (130 mg, 3.44 mmol) was added. The resulting mixture was stirred at room temperature for 1 h. The mixture was concentrated and the residue was purified via column chromatography (EtOAc in petroleum ether: 0 to 35%) to give the title compound. $^1$H NMR (400 MHz, CDCl$_3$) δ 7.43 (d, J=7.8 Hz, 1H), 7.30-7.36 (m, 1H), 7.22-7.30 (m, 1H), 4.83 (d, J=5.9 Hz, 2H), 2.63-2.81 (m, 4H), 2.28 (d, J=4.3 Hz, 1H), 2.05-2.15 (m, 1H), 1.62-1.72 (m, 1H).

Step 6. Preparation of 2-chloro-6-(1-fluorocyclobutyl)benzaldehyde (i-8f)

The mixture of (2-chloro-6-(1-fluorocyclobutyl)phenyl) methanol (200 mg, 0.932 mmol) and Dess-Martin periodinane (593 mg, 1.40 mmol) in DCM (5 mL) was stirred at room temperature for 2 h. The reaction suspension was filtered and the filter cake was washed with DCM (5 mL), the filtrate was concentrated. The residue was purified via column chromatography (EtOAc in petroleum ether: 0 to 15%) to give the title compound. $^1$H NMR (400 MHz, CDCl$_3$) δ 10.47 (d, J=3.9 Hz, 1H), 7.36-7.48 (m, 3H), 2.60-2.74 (m, 4H), 2.05-2.15 (m, 1H), 1.67-1.78 (m, 1H).

Step 7. Preparation of 2-chloro-6-(1-fluorocyclobutyl)benzoic acid (i-8)

A mixture of 2-chloro-6-(1-fluorocyclobutyl)benzaldehyde (200 mg, 0.941 mmol), sodium dihydrogen phosphate (226 mg, 1.881 mmol), 2-methylbut-2-ene (1.0 mL, 9.44 mmol) in t-BuOH (5 mL) was stirred at room temperature for 30 min. A solution of sodium chlorite (128 mg, 1.411 mmol) in water (1 mL) was added dropwise at 5° C., and then the reaction mixture was stirred at room temperature for 16 h. The mixture was concentrated and diluted with water (5 mL), extracted with EtOAc (10 mL*5). The combined organic phase was dried over Na$_2$SO$_4$, filtered and concentrated to give the title compound. $^1$H NMR (400 MHz, CDCl$_3$) δ 7.32-7.46 (m, 3H), 4.87 (brs, 1H), 2.60-2.78 (m, 4H), 2.08-2.19 (m, 1H), 1.73-1.84 (m, 1H).

Intermediate i-9

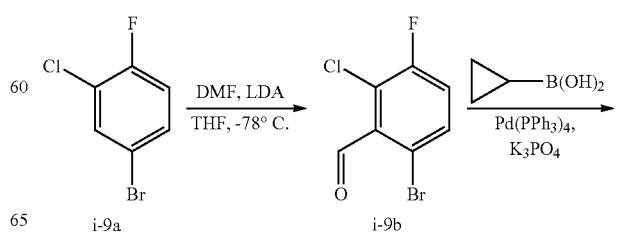

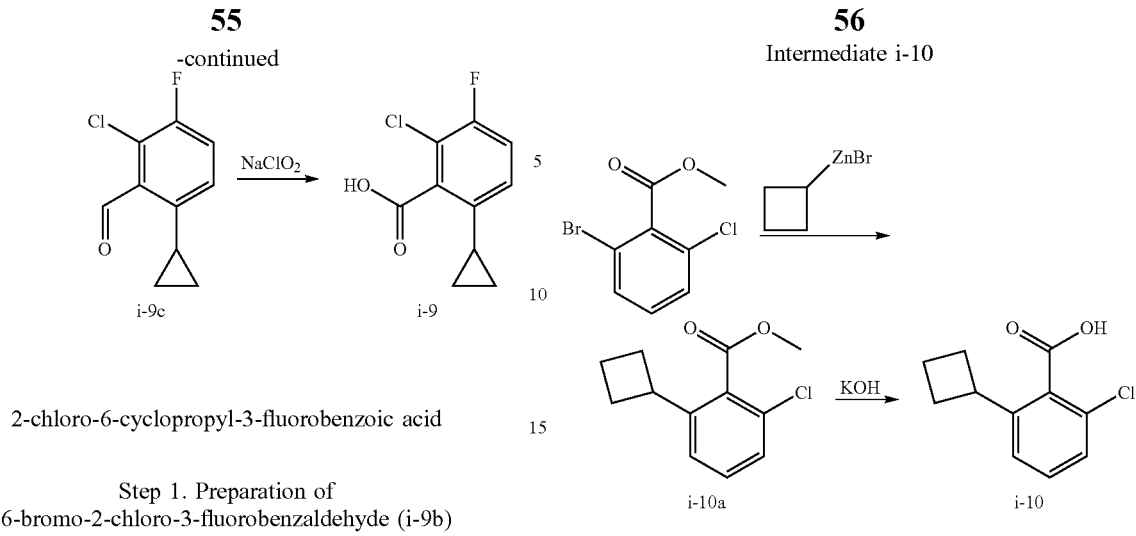

2-chloro-6-cyclopropyl-3-fluorobenzoic acid

Step 1. Preparation of 6-bromo-2-chloro-3-fluorobenzaldehyde (i-9b)

To a solution of 4-bromo-2-chloro-1-fluorobenzene (5.00 g, 23.9 mmol) in THF (40 mL) was added lithium diisopropylamide (14.3 mL, 28.6 mmol) dropwise at −78° C. The resultant mixture was stirred at −78° C. for 2 h and then DMF (2.70 mL, 35.8 mmol) was added. The reaction mixture was warmed to room temperature, quenched with aq. NH$_4$Cl, and extracted with EtOAc (3×100 mL). The combined organic layers were concentrated and purified by chromatography (0-10% EtOAc in petroleum ether) to give the title compound. $^1$H NMR (400 MHz, CDCl$_3$) δ 10.27-10.33 (m, 1H), 7.56 (dd, J=8.6 Hz, 4.3 Hz, 1H), 7.18-7.26 (m, 1H).

Step 2. Preparation of 2-chloro-6-cyclopropyl-3-fluorobenzaldehyde (i-9c)

To a mixture of 6-bromo-2-chloro-3-fluorobenzaldehyde (2.00 g, 8.42 mmol) and cyclopropylboronic acid (1.09 g, 12.7 mmol) in toluene (20 mL) and water (2 mL) was added K$_3$PO$_4$ (3.58 g, 16.8 mmol) and tetrakis(triphenylphosphine)palladium (0.97 g, 0.84 mmol). The resultant mixture was stirred at 100° C. for 3 h under N$_2$. The reaction mixture was cooled to room temperature and concentrated in vacuo. The residue was purified by chromatography (0-10% EtOAc in petroleum ether) to give the title compound. $^1$H NMR (400 MHz, CDCl$_3$) δ 10.63-10.74 (m, 1H), 7.23 (t, J=8.4 Hz, 1H), 7.00 (dd, J=8.6 Hz, 4.7 Hz, 1H), 2.53-2.65 (m, 1H), 1.02-1.09 (m, 3H), 0.66 (q, J=5.5 Hz, 3H).

Step 3. Preparation of 2-chloro-6-cyclopropyl-3-fluorobenzoic acid (i-9)

2-Methylbut-2-ene (2.54 g, 36.2 mmol) was added to the solution of 2-chloro-6-cyclopropyl-3-fluorobenzaldehyde (800 mg, 4.03 mmol) in t-BuOH (3 mL). Then an aqueous solution of sodium chlorite (474 mg, 5.24 mmol) and sodium dihydrogen phosphate (628 mg, 5.24 mmol) was added slowly to the reaction mixture. The resultant mixture was stirred at room temperature for 16 h. The solution was concentrated in vacuo and acidified to pH 2 with 1 M HCl aq., and extracted with EtOAc (3×20 mL). The combined organic layers were concentrated to give the title compound. $^1$H NMR (400 MHz, MeOD) δ 7.16 (t, J=8.8 Hz, 1H), 6.98 (dd, J=8.6 Hz, 4.7 Hz, 1H), 1.89-1.96 (m, 1H), 0.91-0.97 (m, 2H), 0.68 (q, J=5.2 Hz, 2H).

Intermediate i-10

Step 1. Preparation of methyl 2-chloro-6-cyclobutylbenzoate (i-10a)

A mixture of methyl 2-bromo-6-chlorobenzoate (750 mg, 3 mmol), (PPh$_3$)$_4$Pd (345 mg, 0.3 mmol) and cyclobutylzinc bromide (0.5M in THF, 12 mL) were mixed under N$_2$ protection. The mixture was stirred at 70° C. for 12 h under N$_2$. The mixture was extracted with EtOAc and water. The organic phase was washed with brine, dried over Na$_2$SO$_4$, filtered, and concentrated. The residue was purified with flash chromatography (PE: EtOAc=50:1) to give the title compound. MS: 225 (M+1).

Step 2. Preparation of 2-chloro-6-cyclobutylbenzoic acid (i-10)

To a solution of methyl 2-chloro-6-cyclobutylbenzoate (350 mg, 1 mmol) in EtOH (2 mL), was added 0.2M KOH (1.5 mL, 3 mmol). The mixture was stirred at 100° C. for 12 h, acidified with 3N HCl and extracted with EtOAc. The organic phase was washed with brine, dried over Na$_2$SO$_4$, filtered and concentrated. The residue was purified with prep-HPLC (ACN: H$_2$O) to give the title compound. MS: 211 (M+1).

Intermediate i-11

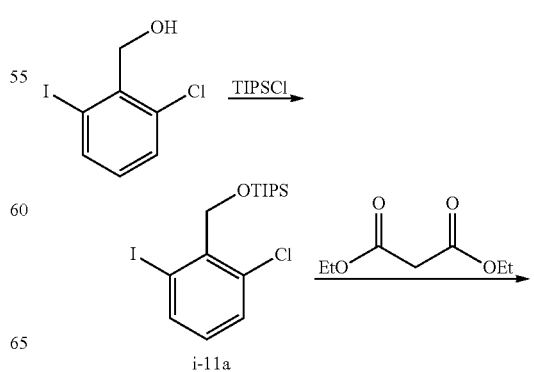

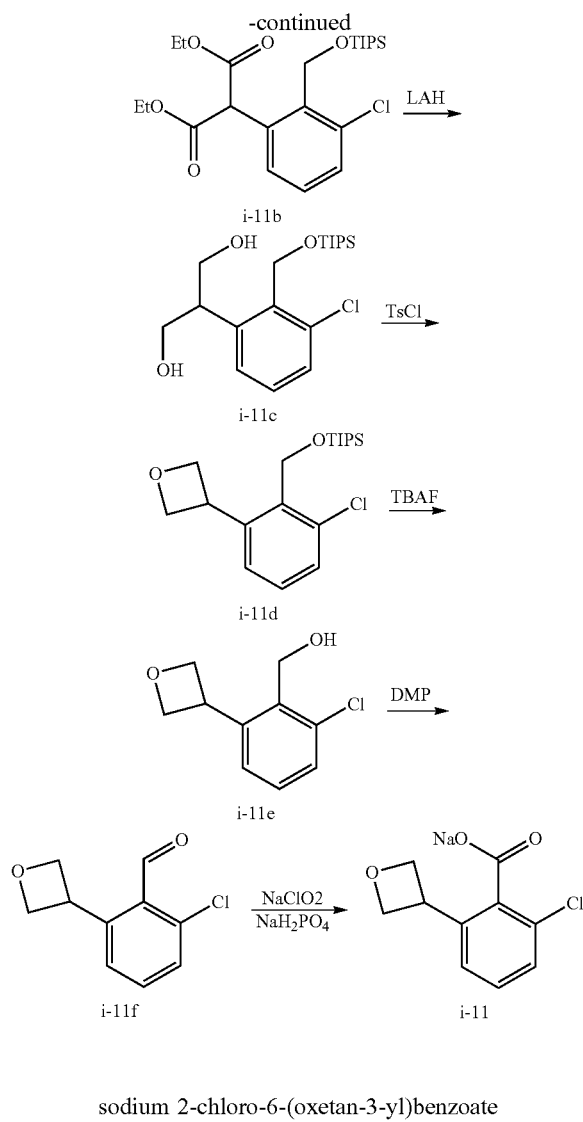

sodium 2-chloro-6-(oxetan-3-yl)benzoate

Step 1. Preparation of ((2-chloro-6-iodobenzyl)oxy)triisopropylsilane (i-11a)

Into a 10 L flask, was charged (2-chloro-6-iodophenyl)methanol (610 g, 2272 mmol), 1H-imidazole (351 g, 5156 mmol) and DMF (3050 mL). Chlorotriisopropylsilane (498 g, 2583 mmol) was added dropwise at r.t over 1 h. The mixture was stirred overnight at r.t. TLC showed that the reaction was completed. Water (7000 mL) was added. The solution was extracted with EA (5 L×3). The combined organic layers were washed with brine, dried with Na₂SO₄, filtered and concentrated to obtain title compound.

Step 2. Preparation of diethyl 2-(3-chloro-2-(((triisopropylsilyl)oxy)methyl)phenyl)malonate (i-11b)

Into a 20 L flask, was charged ((2-chloro-6-iodobenzyl)oxy)triisopropylsilane (1000 g, 2354 mmol), diethyl malonate (754 g, 4708 mmol), cesium carbonate (1153 g, 3539 mmol) and THF (5 L). The mixture was degassed for 15 min. copper(I) iodide (68 g, 357 mmol) and [1,1'-biphenyl]-2-ol (80 g, 471 mmol) was added. The resulting mixture was heated to reflux overnight. LCMS showed reaction completed. The suspension was cooled to r.t. H₂O (10 L) was added. The mixture was extracted with EA (3000 mL×2). The combined organic layers were dried with Na₂SO₄, filtered and concentrated to obtain the crude product, which was purified on silica gel eluting with PE/EA gradient from 100:0 to 30:1 to afford title compound.

Step 3. Preparation of 2-(3-chloro-2-(((triisopropylsilyl)oxy)methyl)phenyl)propane-1,3-diol (i-11c)

To a solution of LAH (56.1 g, 1477 mmol) in THF (1500 mL) at −10° C. was added dropwise diethyl 2-(3-chloro-2-(((triisopropylsilyl)oxy)methyl)phenyl)malonate (300 g, 492 mmol) in THF (1500 mL). The mixture was stirred at r.t for 3 h, then water (500 mL) was dropwise at −10° C. and extracted with EtOAc. The organic layer was separated, dried over Na₂SO₄, filtered and concentrated. The residue was applied onto a silica gel column with ethyl acetate/petroleum ether (1:1) to give title compound.

Step 4. Preparation of ((2-chloro-6-(oxetan-3-yl)benzyl)oxy)triisopropylsilane (i-11d)

Into a 10 L flask, was charged 2-(3-chloro-2-(((triisopropylsilyl)oxy)methyl)phenyl) propane-1,3-diol (190 g, 509 mmol), THF (1900 mL). The solution was cooled to −78° C., butyllithium (224 mL, 560 mmol) was added dropwise at −78° C. over 15 min. The solution was slowly warmed to 10° C. and stirred for 30 min. The mixture was cooled to −20° C., a solution of 4-methylbenzene-1-sulfonyl chloride (97 g, 509 mmol) in THF (200 mL) was added by batch wise at 0° C. over 5 min. The solution was stirred for a further 30 min at 0° C. LCMS showed the reaction completed conversion. The solution was cooled to −60° C., other butyllithium (224 mL, 560 mmol) was added. The reaction mixture was warmed to 35° C. for 30 min. NH₄Cl (1000 mL) was added slowly at 0° C. The mixture was extracted with EA (1000 mL×3). The combined organic layers were washed with brine and dried with Na₂SO₄, filtered and concentrated to obtain crude product which was purified on silica gel eluting with PE/EA (50:1 to 20:1) to afford title compound.

Step 5. Preparation of (2-chloro-6-(oxetan-3-yl)phenyl)methanol (i-11e)

To a flask containing ((2-chloro-6-(oxetan-3-yl)benzyl)oxy)triisopropylsilane (36 g, 101 mmol) in THF (360 mL) at 25° C. was added tetrabutylammonium fluoride (29.2 g, 112 mmol). The mixture was stirred at r.t for 1 h. TLC showed the reaction completed. The mixture was diluted with sat. NaHCO₃ and extracted with EtOAc. The organic layer was separated, washed with brine, dried over Na₂SO₄. The residue was used for next step without purification.

Step 6. Preparation of 2-chloro-6-(oxetan-3-yl)benzaldehyde (i-11f)

To a solution of (2-chloro-6-(oxetan-3-yl)phenyl)methanol (35 g, 88 mmol, crude) in CH₂Cl₂ (350 mL) at 15° C. was added Sodium Bicarbonate (22.20 g, 264 mmol) and Dess-Martin Periodinane (74.7 g, 176 mmol). The mixture was stirred at r.t for 1 h. TLC showed no SM left. The mixture was diluted with sat NaHCO₃ and extracted with EtOAc. The organic layer was dried over Na₂SO₄, concentrated. The residue was purified by flash chromatography (0-30% EtOAc/hexanes) to afford title compound.

Step 7. Preparation of sodium 2-chloro-6-(oxetan-3-yl)benzoate (i-11)

To a solution of 2-chloro-6-(oxetan-3-yl)benzaldehyde (20 g, 102 mmol) in t-Butanol (200 mL) at room temperature was added 2-methylbut-2-ene (35.7 g, 509 mmol). This was followed by the addition of a pre-mixed solution of sodium chlorite (18.40 g, 203 mmol) and sodium dihydrogen phosphate (24.41 g, 203 mmol) in water (100 mL). The mixture was stirred at r.t for 1 h. LCMS showed product formation as major and no SM left. The mixture was acidified with 4 N HCl to PH=1-2, extracted with MTBE. Then the combined organic layers were re-extracted with a solution of 10% $Na_2CO_3$ (100 mL). The aqueous layer was lyophilized to give sodium 2-chloro-6-(oxetan-3-yl)benzoate. MS: 213 (M+1). $^1H$ NMR (400 MHz, $D_2O$) δ 7.54 (1H, d), 7.36 (2H, m), 5.10 (2H, m), 4.77 (2H, m), 4.28 (1H, m).

Intermediate i-12a

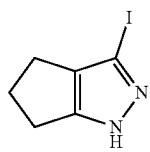

3-iodo-1,4,5,6-tetrahydrocyclopenta[c]pyrazole

A mixture of 1,4,5,6-tetrahydrocyclopenta[c]pyrazole (200 mg, 1.85 mmol) and NIS (416 mg, 1.85 mmol) in DMF (2.3 mL) was stirred at room temperature overnight. The reaction mixture was diluted with water and EtOAc. The organic layer was separated and washed twice with aqueous $NaHCO_3$ and once with brine. Aqueous layers were back extracted once with EtOAc, combined organic layers were dried with $Na_2SO_4$, filtered and the solvent was evaporated under reduced pressure. The residue was purified by silica gel chromatography (EtOAc/Hexane 25-90%) to afford the title compound. MS: 235 (M+1).

The following examples shown in Table 1 were prepared following similar procedures described can be achieved by those of ordinary skill in the art of organic synthesis.

TABLE 1

| Intermediate | Structure | IUPAC Name | MS (M + 1) |
| --- | --- | --- | --- |
| i-12b | 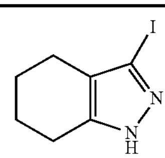 | 3-iodo-4,5,6,7-tetrahydro-1H-indazole | 249 |
| i-12c | 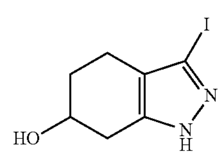 [SMILES: OC1CCc2c(I)n[nH]c2C1] | 3-iodo-4,5,6,7-tetrahydro-1H-indazol-6-ol | 264 |
| i-12d | 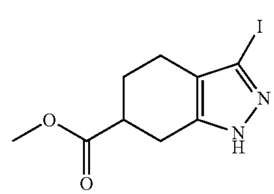 | methyl 3-iodo-4,5,6,7-tetrahydro-1H-indazole-6-carboxylate | 307 |
| i-12e | 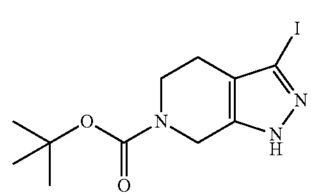 [SMILES: CC(C)(C)OC(=O)N1CCc2c(I)n[nH]c2C1] | tert-butyl 3-iodo-1,4,5,7-tetrahydro-6H-pyrazolo[3,4-c]pyridine-6-carboxylate | 350 |
| i-12f | 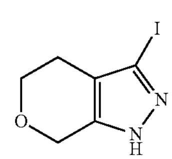 | 3-iodo-1,4,5,7-tetrahydropyrano[3,4-c]pyrazole | 251 |

TABLE 1-continued

| Intermediate | Structure | IUPAC Name | MS (M + 1) |
|---|---|---|---|
| i-12g | 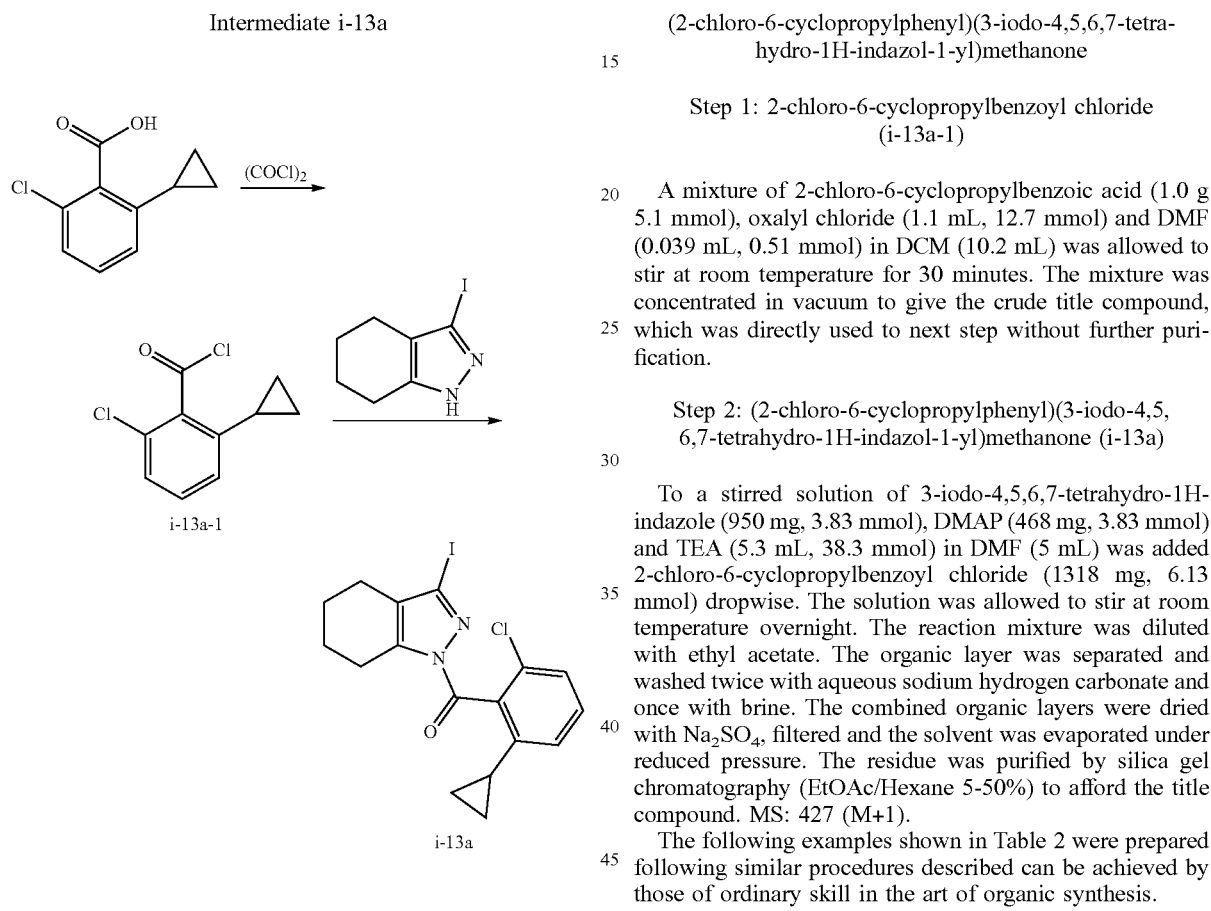 | tert-butyl 3-iodo-1,5,6,7-tetrahydro-4H-pyrazolo[4,3-b]pyridine-4-carboxylate | 350 |

Intermediate i-13a (2-chloro-6-cyclopropylphenyl)(3-iodo-4,5,6,7-tetrahydro-1H-indazol-1-yl)methanone Step 1: 2-chloro-6-cyclopropylbenzoyl chloride (i-13a-1)

A mixture of 2-chloro-6-cyclopropylbenzoic acid (1.0 g 5.1 mmol), oxalyl chloride (1.1 mL, 12.7 mmol) and DMF (0.039 mL, 0.51 mmol) in DCM (10.2 mL) was allowed to stir at room temperature for 30 minutes. The mixture was concentrated in vacuum to give the crude title compound, which was directly used to next step without further purification.

Step 2: (2-chloro-6-cyclopropylphenyl)(3-iodo-4,5,6,7-tetrahydro-1H-indazol-1-yl)methanone (i-13a)

To a stirred solution of 3-iodo-4,5,6,7-tetrahydro-1H-indazole (950 mg, 3.83 mmol), DMAP (468 mg, 3.83 mmol) and TEA (5.3 mL, 38.3 mmol) in DMF (5 mL) was added 2-chloro-6-cyclopropylbenzoyl chloride (1318 mg, 6.13 mmol) dropwise. The solution was allowed to stir at room temperature overnight. The reaction mixture was diluted with ethyl acetate. The organic layer was separated and washed twice with aqueous sodium hydrogen carbonate and once with brine. The combined organic layers were dried with $Na_2SO_4$, filtered and the solvent was evaporated under reduced pressure. The residue was purified by silica gel chromatography (EtOAc/Hexane 5-50%) to afford the title compound. MS: 427 (M+1).

The following examples shown in Table 2 were prepared following similar procedures described can be achieved by those of ordinary skill in the art of organic synthesis.

TABLE 2

| Intermediate | Structure | IUPAC Name | MS (M + 1) |
|---|---|---|---|
| i-13b | 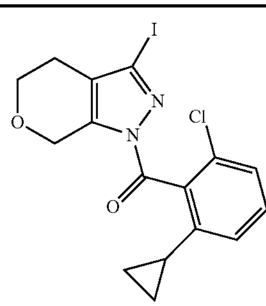 | (2-chloro-6-cyclopropylphenyl)(3-iodo-4,7-dihydropyrano[3,4-c]pyrazol-1(5H)-yl)methanone | 429 |

TABLE 2-continued

| Intermediate | Structure | IUPAC Name | MS (M + 1) |
|---|---|---|---|
| i-13c | 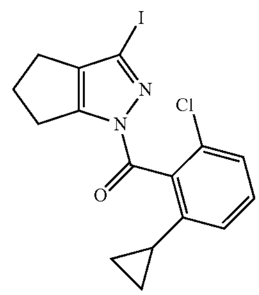 [SMILES: O=C(c1c(Cl)cccc1C1CC1)n1nc(I)c2c1CCC2] | (2-chloro-6-cyclopropylphenyl)(3-iodo-5,6-dihydrocyclopenta[c]pyrazol-1(4H)-yl)methanone | 412.9 |
| i-13g | 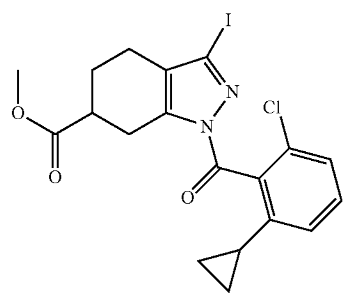 [SMILES: COC(=O)C1CCc2c(I)nn(C(=O)c3c(Cl)cccc3C3CC3)c2C1] | methyl 1-(2-chloro-6-cyclopropylbenzoyl)-3-iodo-4,5,6,7-tetrahydro-1H-indazole-6-carboxylate | 485 |
| i-13h | 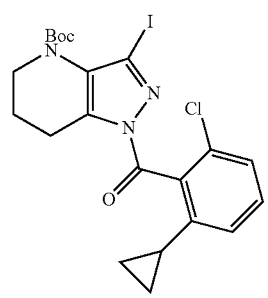 [SMILES: CC(C)(C)OC(=O)N1CCCc2c1c(I)nn2C(=O)c1c(Cl)cccc1C1CC1] | tert-butyl 1-(2-chloro-6-cyclopropylbenzoyl)-3-iodo-1,5,6,7-tetrahydro-4H-pyrazolo[4,3-b]pyridine-4-carboxylate | 528 |
| i-13j | 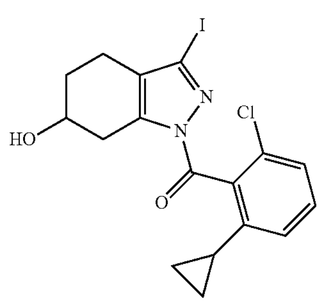 [SMILES: O=C(c1c(Cl)cccc1C1CC1)n1nc(I)c2c1CC(O)CC2] | (2-chloro-6-cyclopropylphenyl)(6-hydroxy-3-iodo-4,5,6,7-tetrahydro-1H-indazol-1-yl)methanone | 443 |
| i-13k | 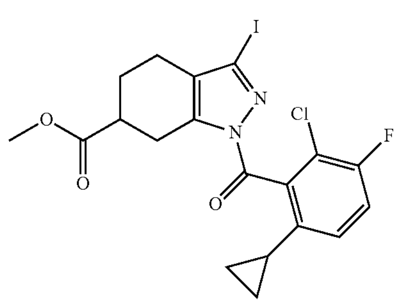 [SMILES: COC(=O)C1CCc2c(I)nn(C(=O)c3c(C4CC4)ccc(F)c3Cl)c2C1] | methyl 1-(2-chloro-6-cyclopropyl-3-fluorobenzoyl)-3-iodo-4,5,6,7-tetrahydro-1H-indazole-6-carboxylate | 503 |

TABLE 2-continued

| Intermediate | Structure | IUPAC Name | MS (M + 1) |
|---|---|---|---|
| i-131 | 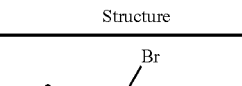 | (2-chloro-6-(1-(trifluoromethyl)cyclopropyl)phenyl)(3-iodo-4,5,6,7-tetrahydro-1H-indazol-1-yl)methanone | 447 |

Intermediate i-14A and i-14B

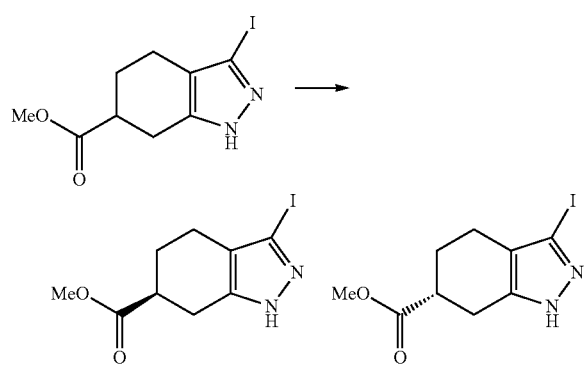

methyl (6R)-3-iodo-4,5,6,7-tetrahydro-1H-indazole-6-carboxylate and methyl (6S)-3-iodo-4,5,6,7-tetrahydro-1H-indazole-6-carboxylate The mixture of the two stereoisomers was purified by chiral SFC (AD-H column, 30%/70% Methanol/CO$_2$) to afford i-14A (faster eluting): MS: 307 (M+1). i-14B (slower eluting): MS: 307 (M+1).

The following examples shown in Table 3 were prepared using i-14A and following similar procedures described in i-13a can be achieved by those of ordinary skill in the art of organic synthesis.

TABLE 3

| Intermediate | Structure | IUPAC Name | MS (M + 1) |
|---|---|---|---|
| i-15A | 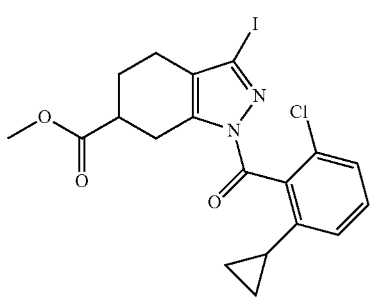 [SMILES: COC(=O)C1CCc2c(I)nn(C(=O)c3c(Cl)cccc3C3CC3)c2C1] | methyl (R or S)-1-(2-chloro-6-cyclopropylbenzoyl)-3-iodo-4,5,6,7-tetrahydro-1H-indazole-6-carboxylate | 485 |
| i-16A | 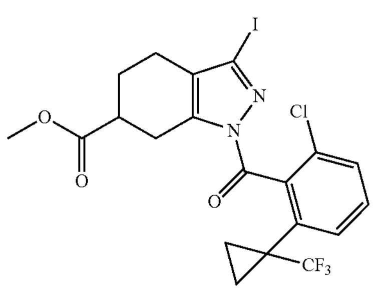 [SMILES: COC(=O)C1CCc2c(I)nn(C(=O)c3c(Cl)cccc3C3(C(F)(F)F)CC3)c2C1] | methyl (R or S)-1-(2-chloro-6-(1-(trifluoromethyl)cyclopropyl)benzoyl)-3-iodo-4,5,6,7-tetrahydro-1H-indazole-6-carboxylate | 553 |

The following examples shown in Table 4 were prepared using i-14B and following similar procedures described in i-13a can be achieved by those of ordinary skill in the art of organic synthesis.

TABLE 4

| Intermediate | Structure | IUPAC Name | Spectral Data |
|---|---|---|---|
| i-15B | 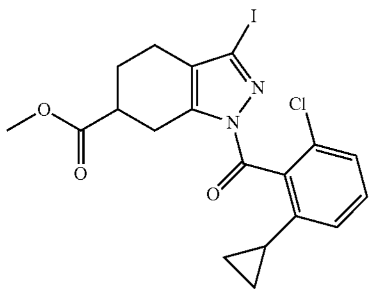 [SMILES: COC(=O)C1CCc2c(I)nn(C(=O)c3c(Cl)cccc3C3CC3)c2C1] | methyl (R or S)-1-(2-chloro-6-cyclopropylbenzoyl)-3-iodo-4,5,6,7-tetrahydro-1H-indazole-6-carboxylate | MS: 485 (M + 1) |
| i-19B | 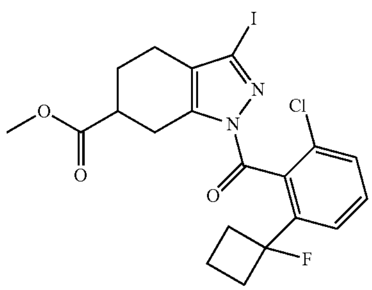 [SMILES: COC(=O)C1CCc2c(I)nn(C(=O)c3c(Cl)cccc3C3(F)CCC3)c2C1] | methyl (R or S)-1-(2-chloro-6-(1-fluorocyclobutyl)benzoyl)-3-iodo-4,5,6,7-tetrahydro-1H-indazole-6-carboxylate | $^1$H NMR (400 MHz, CDCl$_3$) δ 7.35-7.48 (m, 3H), 3.76 (s, 3H), 3.50-3.61 (m, 1H), 3.24-3.36 (m, 1H), 2.79-2.89 (m, 1H), 2.52-2.70 (m, 4H), 2.35-2.49 (m, 3H), 2.20-2.29 (m, 1H), 1.88-1.99 (m, 1H), 1.75-1.84 (m, 1H). |

Intermediate i-20A and i-20B

Intermediate i-21A and i-21B

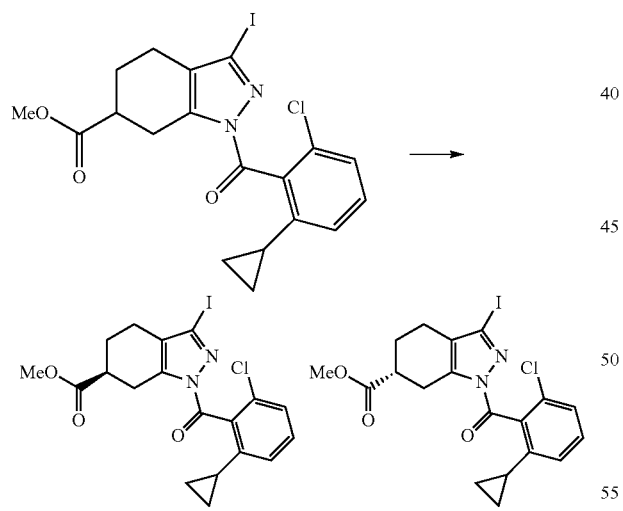

methyl (S)-1-(2-chloro-6-cyclopropylbenzoyl)-3-iodo-4,5,6,7-tetrahydro-1H-indazole-6-carboxylate and methyl (R)-1-(2-chloro-6-cyclopropylbenzoyl)-3-iodo-4,5,6,7-tetrahydro-1H-indazole-6-carboxylate The mixture of the two stereoisomers was purified by chiral SFC (OJ-H column, 20%/80% Methanol with 0.25% DME/CO$_2$) to afford i-20A (faster eluting): MS: 485 (M+1). i-20B (slower eluting): MS: 485 (M+1).

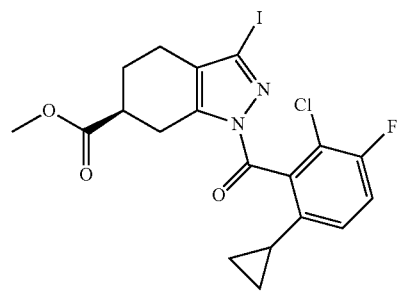

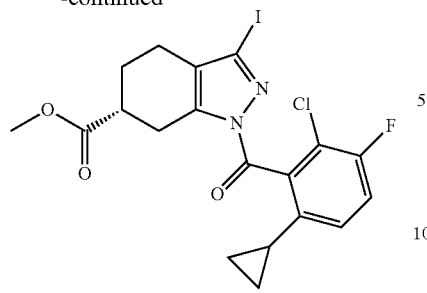

methyl (R)-1-(2-chloro-6-cyclopropyl-3-fluorobenzoyl)-3-iodo-4,5,6,7-tetrahydro-1H-indazole-6-carboxylate and methyl (S)-1-(2-chloro-6-cyclopropyl-3-fluorobenzoyl)-3-iodo-4,5,6,7-tetrahydro-1H-indazole-6-carboxylate The mixture of the two stereoisomers was purified by chiral SFC (OJ-H column, 15%/85% Methanol with 0.25% DMEA/CO$_2$) to afford i-21A (faster eluting): MS: 503 (M+1). i-21B (slower eluting): MS: 503 (M+1).

Intermediate i-22a

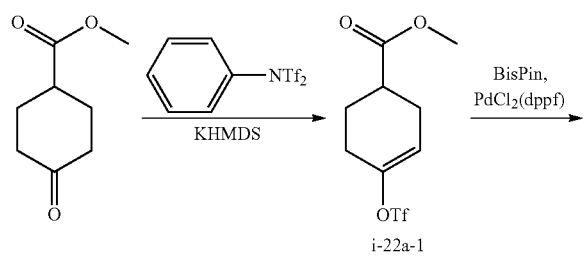

methyl 4-(4,4,5,5-tetramethyl-1,3,2-dioxaborolan-2-yl)cyclohex-3-ene-1-carboxylate Step 1. Preparation of methyl 4-(((trifluoromethyl)sulfonyl)oxy)cyclohex-3-ene-1-carboxylate (i-22a-1)

Into a 100 mL 3-necked, round bottomed flask, purged and maintained with an inert atmosphere of nitrogen was placed KHMDS (9.1 g, 21%), followed by the addition of a solution of methyl 4-oxocyclohexanecarboxylate (1 g, 6.40 mmol, 1.00 equiv) in THF (10 mL) dropwise with stirring, while cooling to a temperature of −70~−80° C. The resulting solution was stirred for 2 hours at −70~−78° C., then added a solution of PhN(Tf)$_2$ (2.75 g, 7.70 mmol, 1.20 equiv) in THF (10 mL) dropwise with stirring at −70~−80° C. The resulting solution was stirred for 2 hours at −70~−78° C. The reaction progress was monitored by TLC (EtOAc/PE=1:2). The reaction mixture was then quenched by adding 10 mL of H$_2$O, followed by extraction three times with 50 mL of EtOAc. The organic layers were combined, washed 3 times with 50 mL of 10% NaHCO$_3$ solution, dried over MgSO$_4$ and concentrated under vacuum. The residue was purified by eluting through a silica gel column with a 1:100 EtOAc/PE solvent system to afford methyl 4-(trifluoromethylsulfonyloxy)cyclohex-3-enecarboxylate.

Step 1. Preparation of methyl 4-(4,4,5,5-tetramethyl-1,3,2-dioxaborolan-2-yl)cyclohex-3-ene-1-carboxylate (i-22a)

Into a 1000 mL 3-necked, round bottomed flask, purged and maintained with an inert atmosphere of nitrogen, were placed a solution of methyl 4-(trifluoromethylsulfonyloxy)cyclohex-3-enecarboxylate (76.3 g, 264.93 mmol, 1.00 equiv) in 1,4-dioxane (800 mL), 4,4,5,5-tetramethyl-2-(4,4,5,5-tetramethyl-1,3,2-dioxaborolan-2-yl)-1,3,2-dioxaborolane (74 g, 308.46 mmol, 1.10 equiv), PdCl$_2$(dppf) (8.5 g, 10.41 mmol, 0.04 equiv) and AcOK (76.3 g, 777.46 mmol, 3.00 equiv). The resulting solution was stirred overnight at 80-90° C. in an oil bath. The reaction progress was monitored by TLC (EtOAc/PE=1:5). After cooled to room temperature, the reaction mixture was filtered. The filtrate was diluted with 800 mL of water, then extracted three times with 800 mL of EtOAc. The organic layers were combined, washed with brine, dried over MgSO$_4$ and concentrated under vacuum. This resulted in 36 g (51%) of methyl 4-(4,4,5,5-tetramethyl-1,3,2-dioxaborolan-2-yl)cyclohex-3-enecarboxylate. MS: 267 (M+1). $^1$H NMR (400 MHz, CDCl$_3$) δ 1.41 (12H, m), 1.58 (1H, m), 2.04 (1H, m), 2.14 (1H, m), 2.30 (3H, m), 2.53 (1H, m), 3.68 (3H, s), 6.5 (1H, s)

The following examples shown in Table 5 were prepared following similar procedures described can be achieved by those of ordinary skill in the art of organic synthesis.

TABLE 5
| Intermediate | Structure | IUPAC Name | NMR |
|---|---|---|---|
| i-22b | 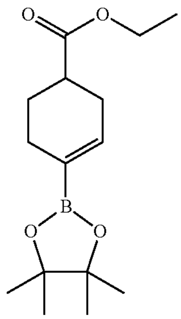 [SMILES: CCOC(=O)C1CC=C(B2OC(C)(C)C(C)(C)O2)CC1] | ethyl 4-(4,4,5,5-tetramethyl-1,3,2-dioxaborolan-2-yl)cyclohex-3-ene-1-carboxylate | $^1$HNMR (400 MHz, CDCl$_3$, ppm): δ 6.55-6.56 (1H, s), 4.18-4.16 (2H, m), 2.49-2.54 (1H, s), 2.26-2.37 (3H, m), 2.01-2.17 (2H, m), 1.59-1.67 (1H, m), 1.25-1.29 (15H, m). |
| i-22c | 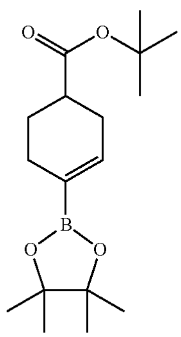 [SMILES: CC(C)(C)OC(=O)C1CC=C(B2OC(C)(C)C(C)(C)O2)CC1] | tert-butyl 4-(4,4,5,5-tetramethyl-1,3,2-dioxaborolan-2-yl)cyclohex-3-ene-1-carboxylate | $^1$HNMR (400 MHz, CDCl$_3$, ppm): δ 6.56 (m, 1H), 2.41 (m, 1H), 2.28 (m, 3H), 2.12 (m, 1H), 1.98 (m, 1H), 1.58 (m, 1H), 1.45 (s, 9H), 1.25 (s, 12H). |
Intermediate i-23
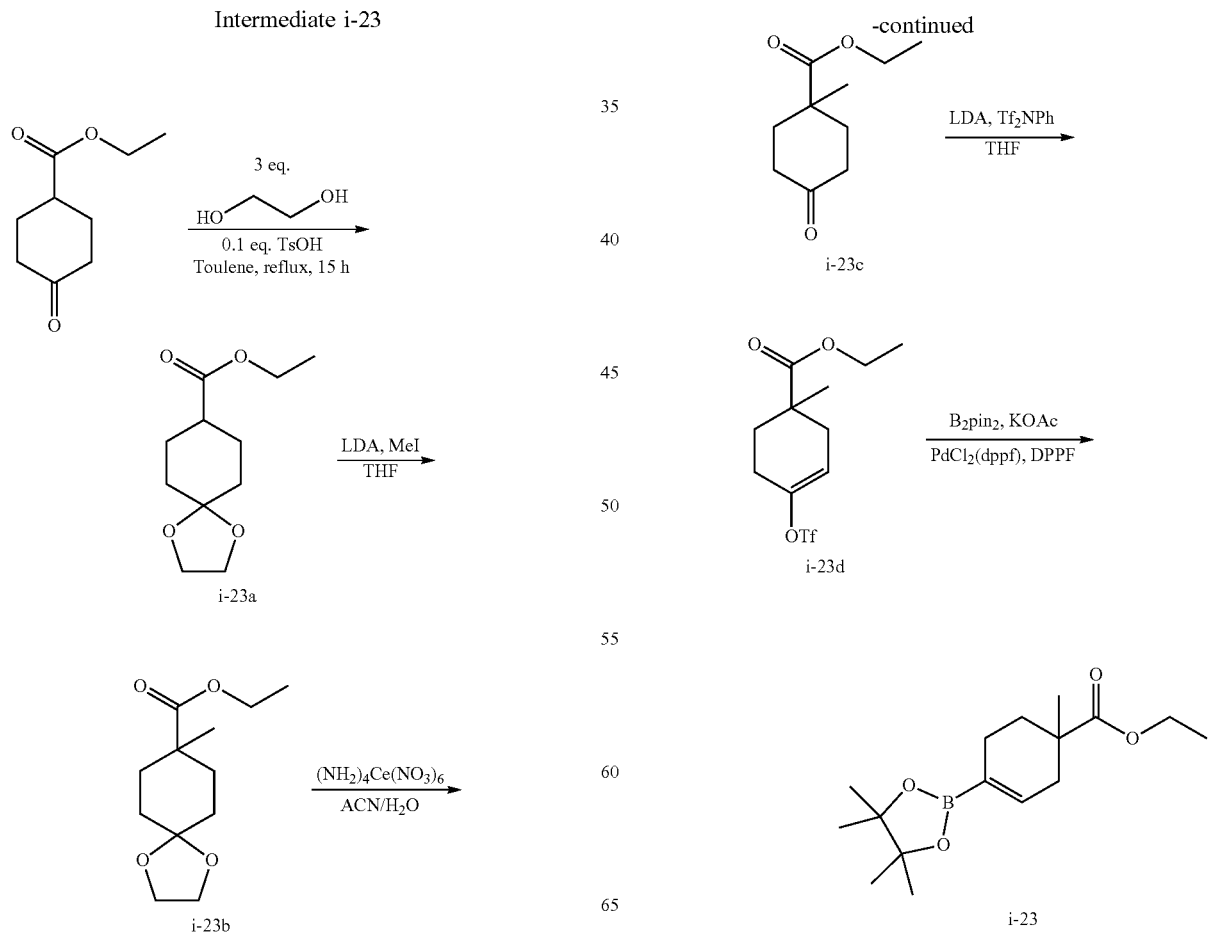

ethyl 1-methyl-4-(4,4,5,5-tetramethyl-1,3,2-dioxaborolan-2-yl)cyclohex-3-enecarboxylate

Step 1. Preparation of ethyl 1,4-dioxaspiro[4.5]decane-8-carboxylate (i-23a)

To a solution of ethyl 4-oxocyclohexanecarboxylate (25 g, 147 mmol) in toluene (300 mL) were added p-toluenesulfonic acid (2.53 g, 14.69 mmol) and ethylene glycol (27.3 g, 441 mmol). The mixture was stirred at 120° C. and refluxed with water knockout trap for 16 h. The reaction mixture was concentrated under reduced pressure and the residue was diluted in EtOAc (100 mL), washed with NaHCO$_3$ (aq.) (200 mL) and brine (200 mL), dried over Na$_2$SO$_4$, filtered and concentrated. The residue was purified by column chromatography on silica gel (Petro. Ether:EtOAc=100: 1-50:1) to afford the title compound. $^1$H NMR (CD$_3$OD, 400 MHz) δ 4.10 (q, J=7.2 Hz, 2H), 3.92 (s, 4H), 2.23-2.35 (m, 1H), 1.89-1.93 (m, 2H), 1.70-1.84 (m, 4H), 1.47-1.58 (m, 2H), 1.22 (t, J=7.2 Hz, 3H).

Step 2. Preparation of ethyl 8-methyl-1,4-dioxaspiro[4.5]decane-8-carboxylate (i-23b)

To a solution of ethyl 1,4-dioxaspiro[4.5]decane-8-carboxylate (11 g, 51.3 mmol) in THF (200 mL) cooled at −78° C. was added LDA (38.5 mL, 2.0 M in THF, 77 mmol) dropwise. The resultant yellow mixture was stirred at −78° C. for 20 min. MeI (9.6 mL, 154 mmol) was added at this temperature. The mixture was stirred at −78° C. for 2 h. The mixture was quenched with NH$_4$Cl (aq.) (50 mL), extracted with EtOAc (50 mL*3), washed with brine (100 mL*2), dried over Na$_2$SO$_4$, filtered and concentrated. The residue was purified by column chromatography on silica gel (Petro. ether:EtOAc=100:1~50:1) to afford the title compound.
$^1$H NMR (CD$_3$OD, 400 MHz) δ 4.14 (q, J=7.2 Hz, 2H), 3.93 (s, 4H), 2.13 (d, J=12.8 Hz, 2H), 1.58-1.64 (m, 4H), 1.45-1.54 (m, 2H), 1.25 (t, J=7.2 Hz, 3H), 1.18 (s, 3H).

Step 3. Preparation of ethyl 1-methyl-4-oxocyclohexanecarboxylate (i-23c)

To a solution of ethyl 8-methyl-1,4-dioxaspiro[4.5]decane-8-carboxylate (7.3 g, 32.0 mmol) in MeCN (50 mL) and water (50 mL) was added ceric ammonium nitrate (2.11 g, 3.85 mmol). The mixture was heated to 70° C. and stirred for 2 h. The reaction mixture was cooled to room temperature, and partitioned between water (50 mL) and EtOAc (50 mL). The aqueous layer was extracted with EtOAc (50 mL*2). The combined organic layers were washed with brine (50 mL*2), dried over Na$_2$SO$_4$, filtered and concentrated under reduced pressure to afford the title compound (5 g, 85%) as yellow oil, which was used for next step without further purification.

Step 4. Preparation of ethyl 1-methyl-4-(((trifluoromethyl)sulfonyl)oxy)cyclohex-3-enecarboxylate (i-23d)

To a solution of LDA (20.4 mL, 2.0 M in THF, 40.8 mmol) in THF (30 mL) cooled at −78° C. was added ethyl 1-methyl-4-oxocyclohexanecarboxylate (5.00 g, 27.1 mmol) in THF (10 mL) dropwise. After stirring at this temperature for 30 min, N,N-bis(trifluoromethylsulfonyl)aniline (10.67 g, 29.9 mmol) in THF (20 mL) was added. The mixture was warmed to room temperature and stirred for 16 h. The mixture was quenched with NH$_4$Cl (aq.) (30 mL), extracted with EtOAc (30 mL*3). The combined organic layers were washed with brine (40 mL*2), dried over Na$_2$SO$_4$, filtered and concentrated. The residue was purified by column chromatography on silica gel (Petro. ether:EtOAc=100: 1~50:1) to afford the title compound. $^1$H NMR (CD$_3$OD, 400 MHz) δ 5.71 (s, 1H), 4.04-4.21 (m, 2H), 2.62-2.75 (m, 1H), 2.27-2.48 (m, 2H), 2.01-2.19 (m, 2H), 1.68-1.75 (m, 1H), 1.14-1.25 (m, 6H).

Step 5. Preparation of ethyl 1-methyl-4-(4,4,5,5-tetramethyl-1,3,2-dioxaborolan-2-yl)cyclohex-3-enecarboxylate (i-23)

To a solution of ethyl 1-methyl-4-(((trifluoromethyl)sulfonyl)oxy)cyclohex-3-enecarboxylate (3.6 g, 11.38 mmol), bis(pinacolato)diboron (3.47 g, 13.66 mmol), potassium acetate (3.35 g, 34.1 mmol) in dioxane (40 mL) were added DPPF (0.631 g, 1.138 mmol) and PdCl$_2$(dppf) (0.833 g, 1.138 mmol). The mixture was stirred at 80° C. for 18 h under N$_2$, cooled to room temperature, diluted with water (20 mL), and extracted with EtOAc (20 mL*3). The combined organic layers were washed with brine (20 mL*2), dried over Na$_2$SO$_4$, filtered and concentrated. The residue was purified by column chromgraphy on silica gel (Petro. ether:EtOAc=100:1~30:1) to afford the title compound. $^1$H NMR (CDCl$_3$, 400 MHz) δ 6.47-6.55 (m, 1H), 4.08-4.15 (m, 2H), 2.59-2.65 (m, 1H), 2.14-2.19 (m, 2H), 1.95-2.00 (m, 1H), 1.86-1.92 (m, 1H), 1.53-1.58 (m, 1H), 1.21-1.26 (m, 15H), 1.18 (s, 3H). MS: 295 (M+1).

Intermediate i-24A

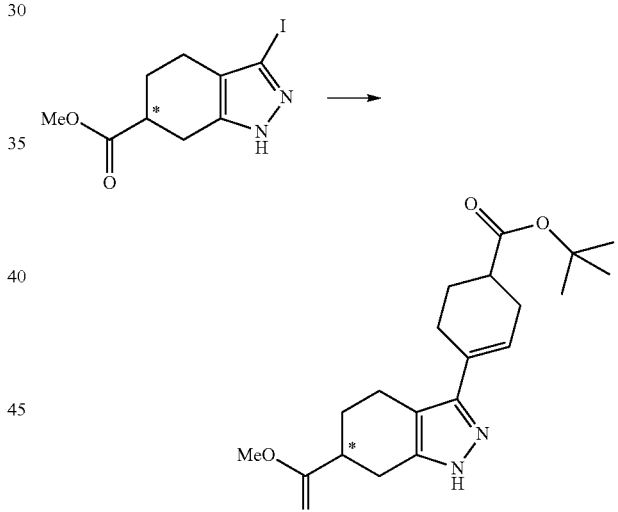

methyl (6R or S)-3-(4-(tert-butoxycarbonyl)cyclohex-1-en-1-yl)-4,5,6,7-tetrahydro-1H-indazole-6-carboxylate

Step 1. Preparation of methyl (6R or S)-3-(4-(tert-butoxycarbonyl)cyclohex-1-en-1-yl)-4,5,6,7-tetrahydro-1H-indazole-6-carboxylate (i-24A)

A mixture of tert-butyl 4-(4,4,5,5-tetramethyl-1,3,2-dioxaborolan-2-yl)cyclohex-3-enecarboxylate (6.04 g, 19.60 mmol), (R or S)-methyl 3-iodo-4,5,6,7-tetrahydro-1H-indazole-6-carboxylate i-14A (3 g, 9.80 mmol), 1,1'-bis(diphenylphosphino)ferrocene-palladium(ii)dichloride dichloromethane complex (1.601 g, 1.960 mmol), and potassium acetate (2.89 g, 29.4 mmol) in dioxane (16.33 mL) was thoroughly degassed with argon. Water (3.27 mL) was then added and the reaction mixture was stirred at 90° C. overnight. The reaction was cooled and diluted with EtOAc. The organic layer was washed twice with aqueous NaHCO₃ and once with brine, dried with Na₂SO₄, filtered, and concentrated under reduced pressure. The residue was purified by silica gel chromatography (0-100% EtOAc/Hexane) to afford the title compound. MS: 361 (M+1).

Intermediate i-24B

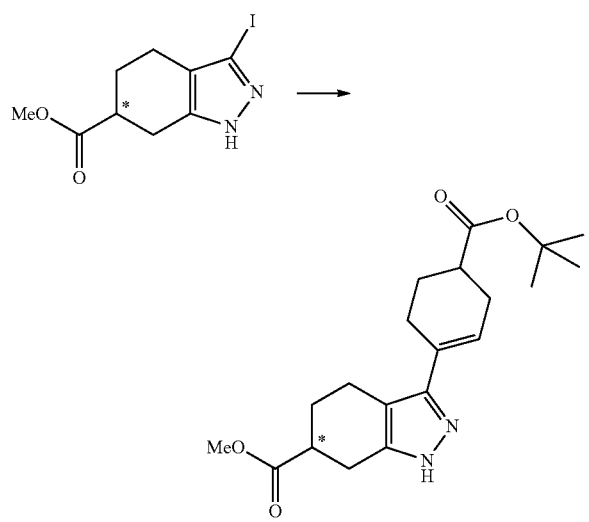

methyl (6R or S)-3-(4-(tert-butoxycarbonyl)cyclohex-1-en-1-yl)-4,5,6,7-tetrahydro-1H-indazole-6-carboxylate Step 1. Preparation of methyl (6R or S)-3-(4-(tert-butoxycarbonyl)cyclohex-1-en-1-yl)-4,5,6,7-tetrahydro-1H-indazole-6-carboxylate (i-24B)

A mixture of tert-butyl 4-(4,4,5,5-tetramethyl-1,3,2-dioxaborolan-2-yl)cyclohex-3-enecarboxylate (201 mg, 0.653 mmol), (R or S)-methyl 3-iodo-4,5,6,7-tetrahydro-1H-indazole-6-carboxylate i-14B (100 mg, 0.33 mmol), potassium carbonate (135 mg, 0.980 mmol), and 1,1'-bis(diphenylphosphino)ferrocene-palladium(ii)dichloride dichloromethane complex (40.0 mg, 0.049 mmol) in dioxane (907 µL) and water (181 µL) was thoroughly degassed under argon. The reaction mixture was stirred at 90° C. overnight. The reaction was cooled and diluted with EtOAc. The organic layer was washed twice with aqueous NaHCO₃ and once with brine, dried with Na₂SO₄, filtered, and concentrated under reduced pressure. The residue was purified by silica gel chromatography (0-100% EtOAc/Hexane) to afford the title compound. MS: 361 (M+1).

The following examples shown in Table 6 were prepared following similar procedures described can be achieved by those of ordinary skill in the art of organic synthesis.

TABLE 6

| Intermediate | Structure | IUPAC Name | MS (M + 1) |
| --- | --- | --- | --- |
| i-25A | 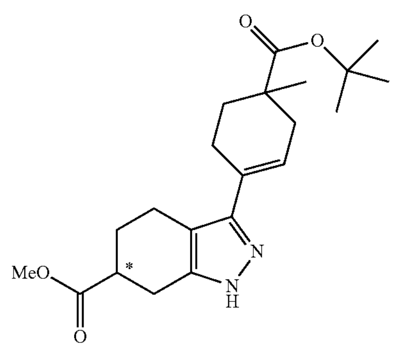 [SMILES: COC(=O)C1CCc2c(C3=CCC(C)(C(=O)OC(C)(C)C)CC3)n[nH]c2C1] | methyl (6R or S)-3-(4-(tert-butoxycarbonyl)-4-methylcyclohex-1-en-1-yl)-4,5,6,7-tetrahydro-1H-indazole-6-carboxylate | 375 |
| i-25B | 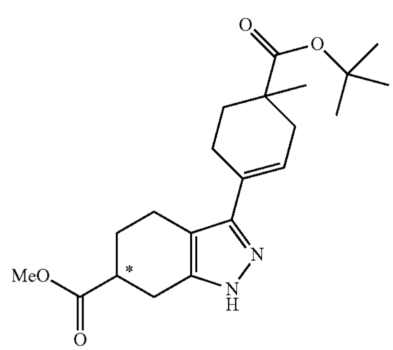 [SMILES: COC(=O)C1CCc2c(C3=CCC(C)(C(=O)OC(C)(C)C)CC3)n[nH]c2C1] | methyl (6R or S)-3-(4-(tert-butoxycarbonyl)-4-methylcyclohex-1-en-1-yl)-4,5,6,7-tetrahydro-1H-indazole-6-carboxylate | 375 |

Intermediate i-26A and i-26B

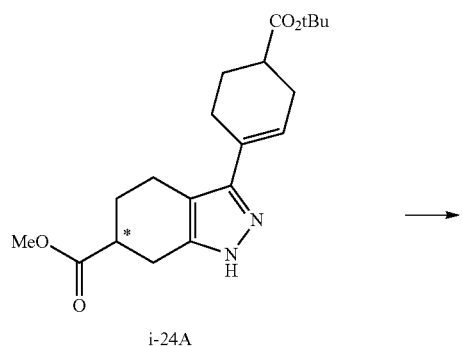

i-24A

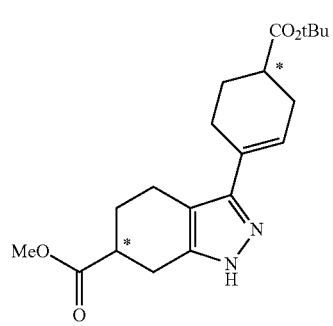

methyl (R or S)-3-((R or S)-4-(tert-butoxycarbonyl)cyclohex-1-en-1-yl)-4,5,6,7-tetrahydro-1H-indazole-6-carboxylate and methyl (R or S)-3-((R or S)-4-(tert-butoxycarbonyl)cyclohex-1-en-1-yl)-4,5,6,7-tetrahydro-H-indazole-6-carboxylate The mixture of the two stereoisomers of i-24A was purified by chiral SFC (AD-H column, 40%/60% EtOH+ DEA/$CO_2$) to afford i-26A (faster eluting): MS: 361 (M+1). i-26B (slower eluting): MS: 361 (M+1).

Intermediate i-27A and i-27B

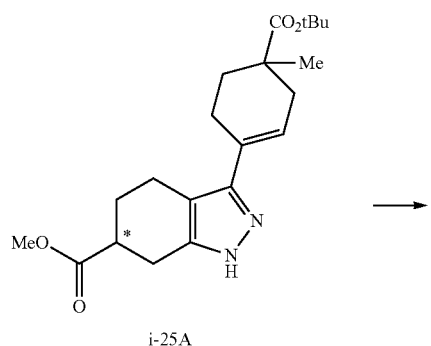

i-25A

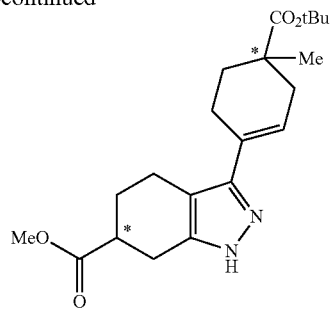

methyl (R or S)-3-((R or S)-4-(tert-butoxycarbonyl)-4-methylcyclohex-1-en-1-yl)-4,5,6,7-tetrahydro-1H-indazole-6-carboxylate and methyl (R or S)-3-((R or S)-4-(tert-butoxycarbonyl)-4-methylcyclohex-1-en-1-yl)-4,5,6,7-tetrahydro-1H-indazole-6-carboxylate The mixture of the two stereoisomers of i-25A were purified by chiral SFC (OJ-H column, 7.5%/92.5% MeOH+ 0.25% DMEA/$CO_2$) to afford i-27A (faster eluting): MS: 375 (M+1). i-27B (slower eluting): MS: 375 (M+1).

Intermediate i-28

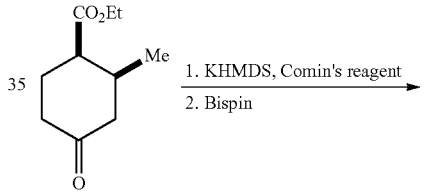

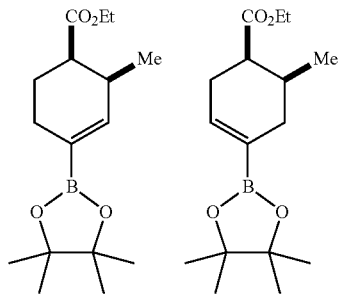

racemic ethyl (cis)-2-methyl-4-(4,4,5,5-tetramethyl-1,3,2-dioxaborolan-2-yl)cyclohex-3-ene-1-carboxylate and racemic ethyl (cis)-6-methyl-4-(4,4,5,5-tetramethyl-1,3,2-dioxaborolan-2-yl)cyclohex-3-ene-1-carboxylate Step 1. Preparation of racemic ethyl (cis)-2-methyl-4-(4,4,5,5-tetramethyl-1,3,2-dioxaborolan-2-yl)cyclohex-3-ene-1-carboxylate and racemic ethyl (cis)-6-methyl-4-(4,4,5,5-tetramethyl-1,3,2-dioxaborolan-2-yl)cyclohex-3-ene-1-carboxylate To a solution of racemic ethyl (cis)-2-methyl-4-oxocyclohexane-1-carboxylate (1 g, 5.43 mmol) in THF (11 mL) at −78° C. was added KHMDS (6.5 mL, 1.0M in THF, 6.5 mmol. The mixture was stirred for 15 min, followed by the addition of 2-[N,N-bis(trifluoromethanesulfonyl)amino]-5-chloropyridine (2.35 g, 5.97 mmol) (dissolved in 3 mL THF). The mixture was kept stirring at −78° C. for 30 min, and then warmed up and stirred at room temperature for 2 h. The mixture was quenched with H$_2$O, and extracted with EtOAc. The combined organics were washed with brine, dried over Na$_2$SO$_4$, filtered and concentrated in vacuo. The residue was purified by flash chromatography (0-40% EtOAc/hexanes) to give the desired vinyl triflate as a mixture of two double bond regio-isomers (ratio ~1:1).

To a solution of the triflate (a mixture of two regio-isomers) from previous step in dioxane (16 mL) were added bis(pinacolato)diboron (1.51 g, 5.9 mmol), potassium acetate (1.16 g, 11.9 mmol). The mixture was degassed for 5 min, followed by the addition of Chloro(2-dicyclohexylphosphino-2',4',6'-triisopropyl-1,1'-biphenyl)[2-(2'-amino-1,1'-biphenyl)]palladium(II) (0.16 g, 0.20 mmol). The mixture was heated at 90° C. for 14 h, cooled down, filtered through celite, concentrated. The residue was purified by flash chromatography (0-40% EtOAc/hexanes) to give final product as a mixture of two inseparable regio-isomers, ethyl (1R,2S or 1S, 2R)-2-methyl-4-(4,4,5,5-tetramethyl-1,3,2-dioxaborolan-2-yl)cyclohex-3-ene-1-carboxylate and ethyl (1R,6S or 1S, 6R)-6-methyl-4-(4,4,5,5-tetramethyl-1,3,2-dioxaborolan-2-yl)cyclohex-3-ene-1-carboxylate. MS: 295 (M+1)

Intermediate i-29A, i-29B, i-29C, and i-29D

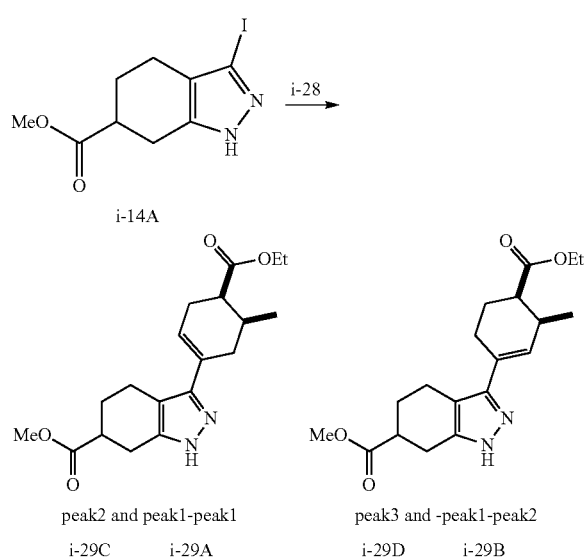

peak2 and peak1-peak1
i-29C    i-29A peak3 and -peak1-peak2
i-29D    i-29B

Step 1. Preparation of methyl (R or S)-3-((3S,4R or 3R, 4S)-4-(ethoxycarbonyl)-3-methylcyclohex-1-en-1-yl)-4,5,6,7-tetrahydro-1H-indazole-6-carboxylate i-29D (peak3)/i-29B (peak1-peak2) and methyl (R or S)-3-((4R,5S or 4S,5R)-4-(ethoxycarbonyl)-5-methylcyclohex-1-en-1-yl)-4,5,6,7-tetrahydro-1H-indazole-6-carboxylate i-29C (peak2)/i-29A (peak1-peak1)

To a microwave reaction vial containing a ~1:1 mixture of methyl ethyl (cis)-2-methyl-4-(4,4,5,5-tetramethyl-1,3,2-dioxaborolan-2-yl)cyclohex-3-ene-1-carboxylate and ethyl (cis)-6-methyl-4-(4,4,5,5-tetramethyl-1,3,2-dioxaborolan-2-yl)cyclohex-3-ene-1-carboxylate (i-28) (1.48 g, 5.03 mmol) were added methyl (R or S)-3-iodo-4,5,6,7-tetrahydro-1H-indazole-6-carboxylate i-14A (1.4 g, 4.57 mmol), dioxane (15 mL), and sodium carbonate (3.43 mL, 6.86 mmol). The mixture was degassed for 5 min, followed by the addition of 1,1'-bis(diphenylphosphino) ferrocene-palladium(ii)dichloride dichloromethane complex (0.37 g, 0.46 mmol). The vial was sealed and heated at 90° C. for 14 h. The reaction mixture was cooled down, diluted with H$_2$O, and extracted with EtOAc. The organic layer was separated, washed with brine, dried over MgSO$_4$, and concentrated. The residue was purified by flash chromatography (50-100% EtOAc/hexanes) to give 1.1 g of final compound as a mixture of four diastereomers.

The mixture of the isomers was purified by chiral SFC (OJ-H column, 10%/90% Methanol +0.25% Dimethyl Ethyl Amine/CO$_2$) to afford three separate peaks. Peaks two and three each contain a single diastereomer, peak 2 yielding i-29C and peak 3 yielding i-29D. The first peak contains two diastereomers and was resubmitted through chiral SFC (Phenomenex, Lux-2 column, 25%/75% Methanol +0.25% Dimethyl Ethyl Amine/CO$_2$) to afford i-29A (faster eluting peak) and i-29B (slower eluting peak)

NMR confirmed that i-29D (peak3) and i-29B (peak1-peak2) possess the same regio-chemistry for cyclohexenyl moiety (Methyl at allyic position), while i-29C (peak2) and i-29A (peak1-peak1) also possess the same regio-chemistry for cyclohexenyl moiety (Methyl at homoallyic position)

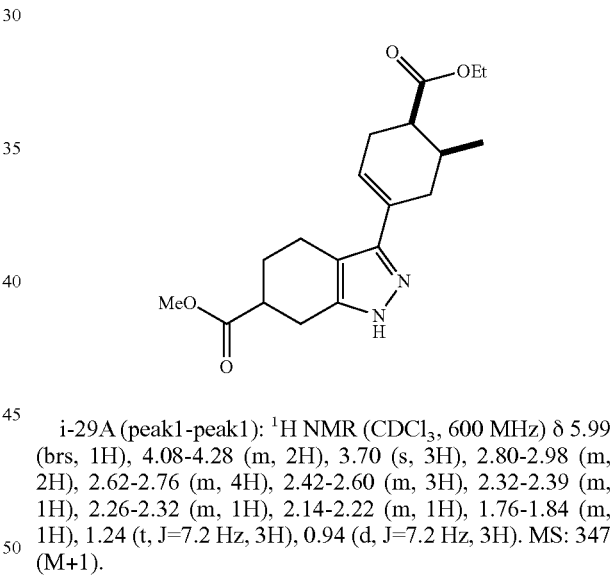

i-29A (peak1-peak1): $^1$H NMR (CDCl$_3$, 600 MHz) δ 5.99 (brs, 1H), 4.08-4.28 (m, 2H), 3.70 (s, 3H), 2.80-2.98 (m, 2H), 2.62-2.76 (m, 4H), 2.42-2.60 (m, 3H), 2.32-2.39 (m, 1H), 2.26-2.32 (m, 1H), 2.14-2.22 (m, 1H), 1.76-1.84 (m, 1H), 1.24 (t, J=7.2 Hz, 3H), 0.94 (d, J=7.2 Hz, 3H). MS: 347 (M+1).

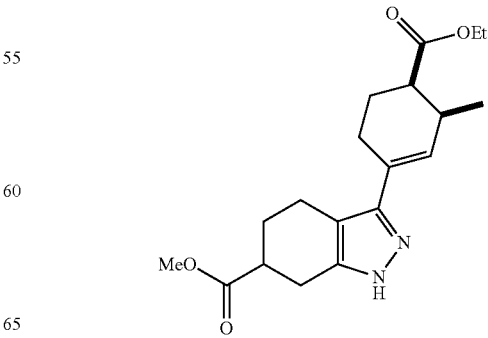

i-29B (peak1-peak2): $^1$H NMR (CDCl$_3$, 600 MHz) δ 5.94-5.98 (m, 1H), 4.08-4.22 (m, 2H), 3.73 (s, 3H), 2.90-2.96 (m, 1H), 2.77-2.87 (m, 2H), 2.66-2.76 (m, 3H), 2.54-2.64 (m, 2H), 2.26-2.33 (m, 1H), 2.16-2.22 (m, 1H), 1.94-1.99 (m, 1H), 1.76-1.88 (m, 2H), 1.26 (t, J=7.2 Hz, 3H), 0.95 (d, J=7.2 Hz, 3H). MS: 347 (M+1).
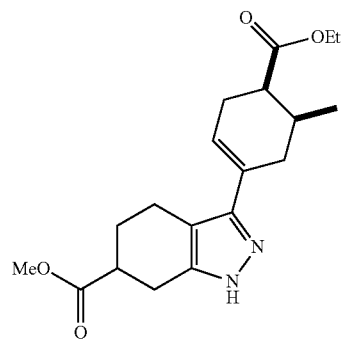 [SMILES: CCOC(=O)[C@@H]1CC=C(c2n[nH]c3c2CCC(C(=O)OC)C3)C[C@@H]1C]
i-29C (peak2): $^1$H NMR (CDCl$_3$, 600 MHz) δ 5.98 (brs, 1H), 4.04-4.28 (m, 2H), 3.70 (s, 3H), 2.86-2.94 (m, 1H), 2.62-2.84 (m, 5H), 2.42-2.60 (m, 2H), 2.30-2.40 (m, 1H), 2.14-2.20 (m, 1H), 1.90-2.00 (m, 1H), 1.74-1.86 (m, 2H), 1.24 (t, J=7.2 Hz, 3H), 0.94 (d, J=7.2 Hz, 3H). MS: 347 (M+1).
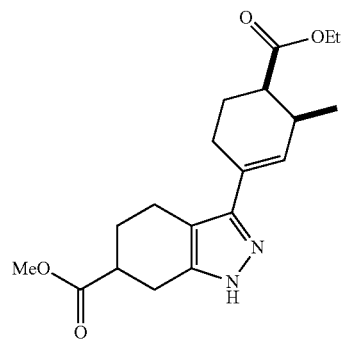 [SMILES: CCOC(=O)[C@@H]1CCC(c2n[nH]c3c2CCC(C(=O)OC)C3)=C[C@@H]1C]
i-29D (peak3): $^1$H NMR (CDCl$_3$, 600 MHz) δ 5.97 (brs, 1H), 4.04-4.20 (m, 2H), 3.70 (s, 3H), 2.86-2.94 (m, 2H), 2.62-2.84 (m, 3H), 2.30-2.60 (m, 6H), 2.10-2.20 (m, 1H), 1.70-1.84 (m, 1H), 1.24 (t, J=7.2 Hz, 3H), 0.94 (d, J=7.2 Hz, 3H). MS: 347 (M+1).
Example 1A
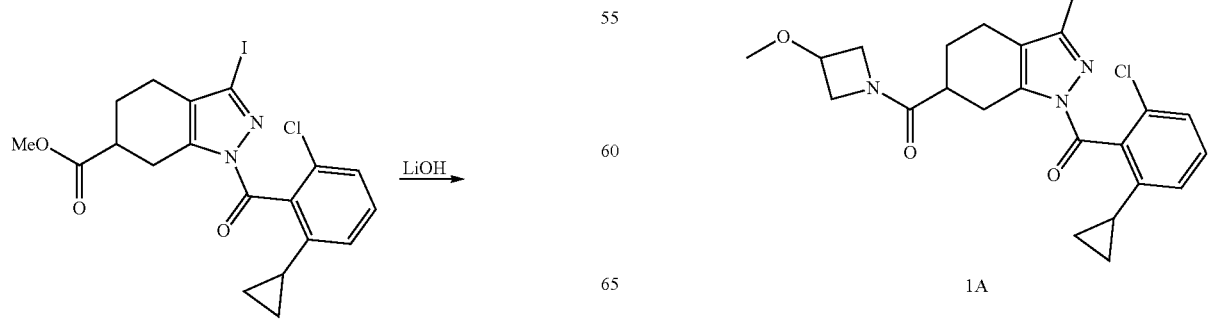
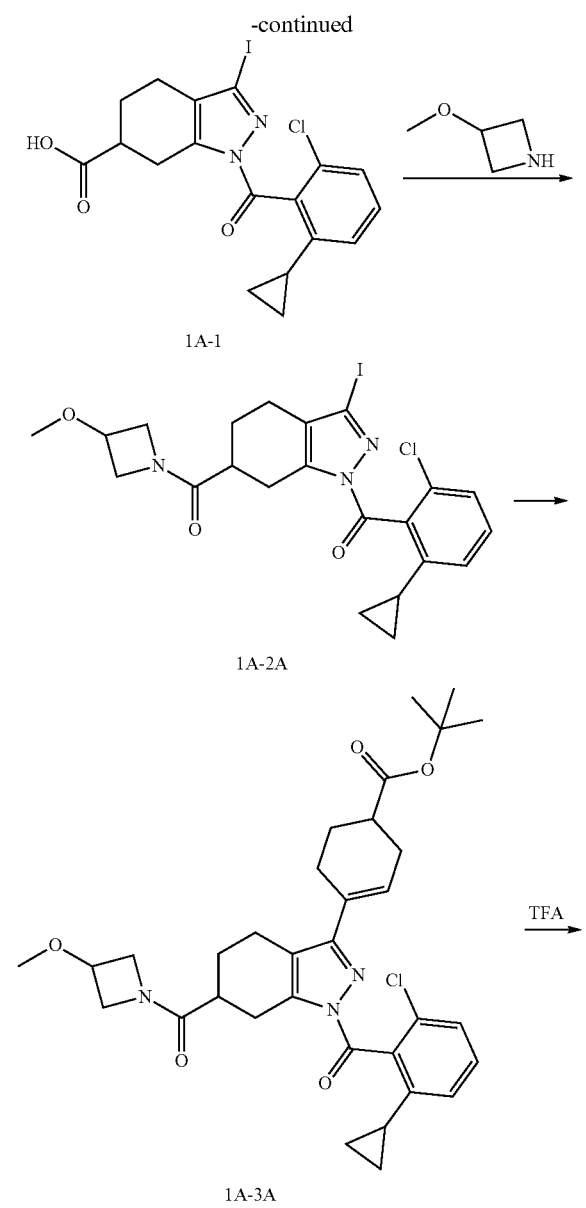

4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylic acid

Step 1. Preparation of 1-(2-chloro-6-cyclopropyl-benzoyl)-3-iodo-4,5,6,7-tetrahydro-1H-indazole-6-carboxylic acid (1A-1)

To an oven dried round bottom flask equipped with magnetic stir bar under an atmosphere of $N_2$ were added racemic methyl 1-(2-chloro-6-cyclopropylbenzoyl)-3-iodo-4,5,6,7-tetrahydro-1H-indazole-6-carboxylate (600 mg, 1.24 mmol, 1 equiv), THF (7.2 mL, 0.1 M), and $H_2O$ (7.2 mL). The reaction mixture was stirred at room temperature for 5 minutes, before lithium hydroxide (89 mg, 3.7 mmol, 3 equiv) was added. The reaction was stirred at room temperature for 6 h, and then quenched with saturated $NH_4Cl$ and diluted with EtOAc (25 mL). The layers were separated, and the aqueous layer was extracted with EtOAc (3×25 mL). The combined organic layers were washed with brine, dried over $Na_2SO_4$, and concentrated in vacuo to afford the title compound. MS: 471 (M+1).

Step 2. Preparation of (R or S)-(1-(2-chloro-6-cyclopropylbenzoyl)-3-iodo-4,5,6,7-tetrahydro-1H-indazol-6-yl)(3-methoxyazetidin-1-yl)methanone (1A-2A)

To an oven dried round bottom flask equipped with magnetic stir bar under an atmosphere of $N_2$ were added 1-(2-chloro-6-cyclopropylbenzoyl)-3-iodo-4,5,6,7-tetrahydro-1H-indazole-6-carboxylic acid (200 mg, 0.425 mmol, 1 equiv), 1-[bis(dimethylamino)methylene]-1H-1,2,3-triazolo[4,5-b]pyridinium 3-oxide hexafluorophosphate (HATU; 242 mg, 0.64 mmol, 1.5 equiv), ethyldiisopropylamine (297 µL, 1.7 mmol, 4 equiv), and DMF (1.4 mL, 0.3 M). The reaction was stirred at room temperature for 15 minutes, followed by the addition of 3-methoxyazetidin-1-ium chloride (79 mg, 0.64 mmol, 1.5 equiv). The reaction mixture was stirred at room temperature for 30 minutes, and then purified using $SiO_2$ gel chromatography to yield racemic-(1-(2-chloro-6-cyclopropylbenzoyl)-3-iodo-4,5,6,7-tetrahydro-1H-indazol-6-yl)(3-methoxyazetidin-1-yl)methanone (1A-2). MS: 540 (M+1).

The mixture of the enantiomers was purified by chiral SFC (OJ-H column, 20%/80% MeOH+0.25% DEA/$CO_2$) to afford 1A-2A (faster eluting): MS: 540 (M+1). 1A-2B (slower eluting): MS: 540 (M+1).

Step 3. Preparation of tert-butyl 4-((S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylate (1A-3A)

To an oven dried microwave vial equipped with magnetic stir bar under an atmosphere of $N_2$ were added (R or S)-(1-(2-chloro-6-cyclopropylbenzoyl)-3-iodo-4,5,6,7-tetrahydro-1H-indazol-6-yl)(3-methoxyazetidin-1-yl)methanone 1A-2A (30 mg, 0.06 mmol, 1 equiv), $2^{nd}$ Gen Sphos Precatalyst (4 mg, 5.56 µmol, 0.1 equiv), racemic tert-butyl 4-(4,4,5,5-tetramethyl-1,3,2-dioxaborolan-2-yl)cyclohex-3-enecarboxylate (25 mg, 0.08 mmol, 1.5 equiv), and dioxane (278 µL, 0.2 M), followed by potassium phosphate tribasic (167 µL, 1M, 3 equiv). The reaction mixture was heated at 80° C. for 24 h, and then cooled to room temperature. The crude reaction mixture was purified using $SiO_2$ gel chromatography to afford the title compound. MS: 594 (M+1).

Step 4. Preparation of 4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylic acid (1A)

To an oven dried microwave vial equipped with magnetic stir bar under an atmosphere of $N_2$ were added tert-butyl 4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylate (22 mg, 0.04 mmol, 1 equiv), and DCM (550 µL, 0.1 M), followed by trifluoroacetic acid (125 µL, 0.1 M). The reaction mixture was stirred at room temperature for 1 h, and then concentrated in vacuo. The resulting oil was purified using mass directed reverse phase chromatography to afford the title compound. MS: 538 (M+1). $^1$H NMR (DMSO-d6) δ (ppm): 7.36-7.31 (m, 2H), 6.99 (m, 1H), 6.15 (m, 1H), 4.40 (m, 1H), 4.33 (m, 1H), 4.19 (m, 1H), 4.05 (m, 1H), 4.00 (m, 1H), 3.66 (m, 1H), 3.19 (s, 3H), 3.00 (m, 1H), 2.72 (m, 1H), 2.59-2.53 (m, 2H), 2.45-2.41 (m, 3H), 2.34 (m, 1H), 2.26 (m, 1H), 2.12 (m, 1H), 1.89 (m, 1H), 1.59-1.55 (m, 2H), 1.49 (m, 1H), 0.81 (m, 1H), 0.70 (m, 1H), 0.62 (m, 1H), 0.54 (m, 1H).

Example 1B

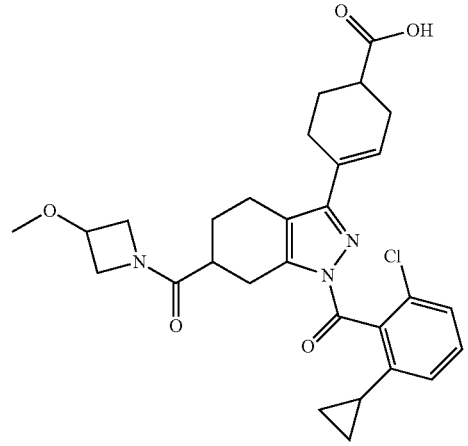 [SMILES: COC1CN(C(=O)C2CCc3c(C4=CCC(C(=O)O)CC4)nn(C(=O)c4c(Cl)cccc4C4CC4)c3C2)C1]

4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylic acid

Step 1. Preparation tert-butyl 4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylate (1B-3B)

To an oven dried microwave vial equipped with magnetic stir bar under an atmosphere of $N_2$ were added (R or S)-(1-(2-chloro-6-cyclopropylbenzoyl)-3-iodo-4,5,6,7-tetrahydro-1H-indazol-6-yl)(3-methoxyazetidin-1-yl)methanone 1A-2B (30 mg, 0.06 mmol, 1 equiv), $2^{nd}$ Gen Sphos Precatalyst (4 mg, 5.56 µmol, 0.1 equiv), racemic tert-butyl 4-(4,4,5,5-tetramethyl-1,3,2-dioxaborolan-2-yl)cyclohex-3-enecarboxylate (25 mg, 0.08 mmol, 1.5 equiv), and dioxane (278 µL, 0.2 M), followed by potassium phosphate tribasic (167 μL, 1M, 3 equiv). The reaction mixture was heated at 80° C. for 24 h, and then cooled to room temperature. The crude reaction mixture was purified using SiO₂ gel chromatography to afford the title compound. MS: 594 (M+1).

Step 2. Preparation 4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylic acid (1B)

To an oven dried microwave vial equipped with magnetic stir bar under an atmosphere of N₂ were added tert-butyl 4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylate (22 mg, 0.04 mmol, 1 equiv), and DCM (550 μL, 0.1 M), followed by trifluoroacetic acid (125 μL, 0.1 M). The reaction mixture was stirred at room temperature for 1 h, and then concentrated in vacuo. The resulting oil was purified using mass directed reverse phase chromatography to afford desired product. MS: 538 (M+1). ¹H NMR (DMSO-d6) δ (ppm): 7.36-7.31 (m, 2H), 6.99 (m, 1H), 6.15 (m, 1H), 4.40 (m, 1H), 4.33 (m, 1H), 4.19 (m, 1H), 4.05 (m, 1H), 4.00 (m, 1H), 3.66 (m, 1H), 3.19 (s, 3H), 3.00 (m, 1H), 2.72 (m, 1H), 2.59-2.53 (m, 2H), 2.45-2.41 (m, 3H), 2.34 (m, 1H), 2.26 (m, 1H), 2.12 (m, 1H), 1.89 (m, 1H), 1.59-1.55 (m, 2H), 1.49 (m, 1H), 0.81 (m, 1H), 0.70 (m, 1H), 0.62 (m, 1H), 0.54 (m, 1H).

Example 2A

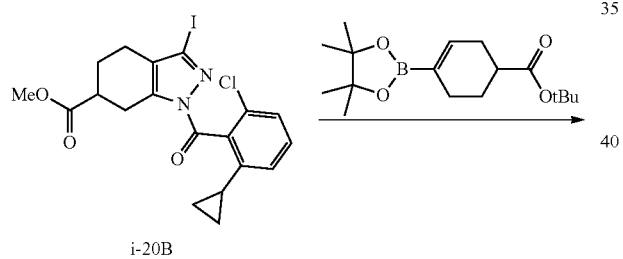

i-20B

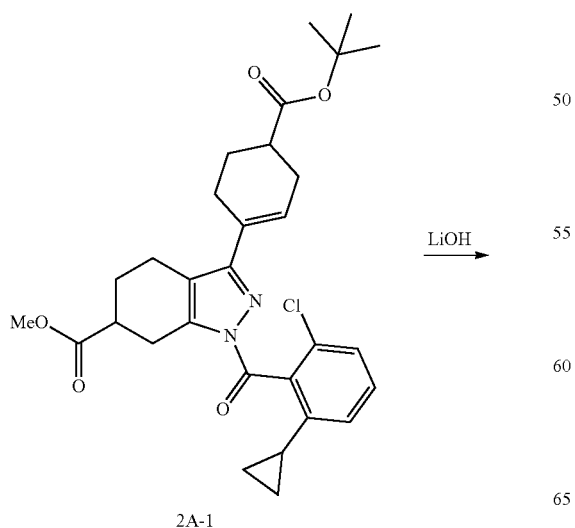

2A-1

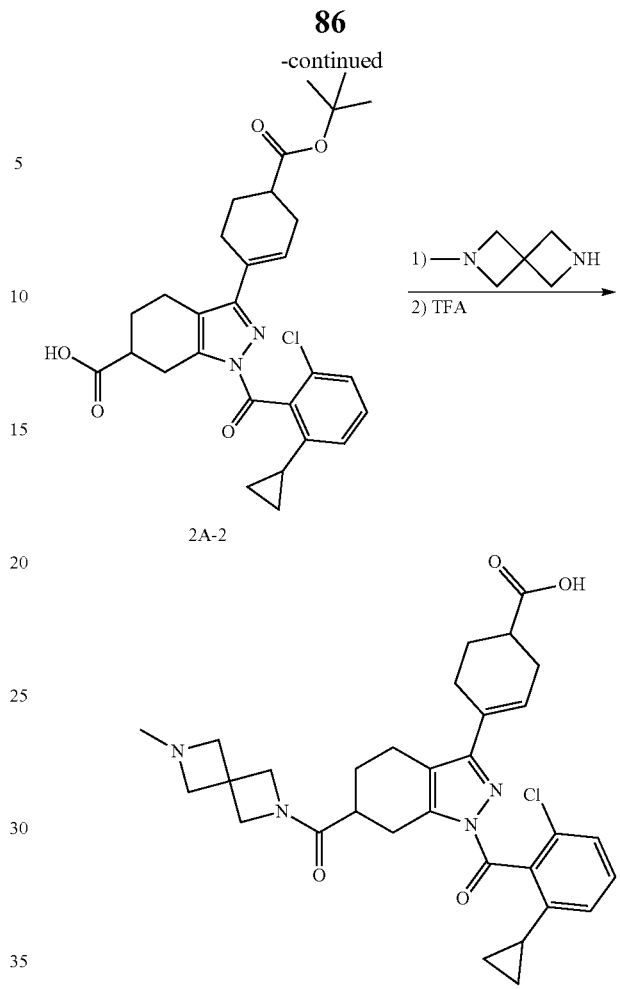

4-((R or S)-1-(2-chloro-6-cyclopropylbenzoyl)-6-(6-methyl-2,6-diazaspiro[3.3]heptane-2-carbonyl)-4,5,6,7-tetrahydro-1H-indazol-3-yl)cyclohex-3-ene-1-carboxylic acid Step 1. Preparation of methyl (6R or S)-3-(4-(tert-butoxycarbonyl)cyclohex-1-en-1-yl)-1-(2-chloro-6-cyclopropylbenzoyl)-4,5,6,7-tetrahydro-1H-indazole-6-carboxylate (2A-1)

A mixture of methyl (R or S)-1-(2-chloro-6-cyclopropylbenzoyl)-3-iodo-4,5,6,7-tetrahydro-1H-indazole-6-carboxylate i-20B (1.04 g, 2.146 mmol), tert-butyl 4-(4,4,5,5-tetramethyl-1,3,2-dioxaborolan-2-yl)cyclohex-3-enecarboxylate (1.058 g, 3.43 mmol), PdCl₂(dppf)-CH₂Cl₂ (0.350 g, 0.429 mmol), potassium acetate (0.632 g, 6.44 mmol), and THF (8.58 mL) was thoroughly degassed with argon for 5 minutes. Water (2.146 mL) was then added and the reaction was heated at 80° C. overnight. The reaction was cooled and diluted with EtOAc. The organic layer was separated and washed twice with aqueous NaHCO₃ and once with brine. The combined organic layers were dried with Na₂SO₄, filtered, and concentrated in vacuo. The residue was purified by silica gel chromatography (0-100% EtOAc/Hexane) to afford the title compound. MS: 539 (M+1).

Step 2. Preparation of (6R or S)-3-(4-(tert-butoxycarbonyl)cyclohex-1-en-1-yl)-1-(2-chloro-6-cyclopropylbenzoyl)-4,5,6,7-tetrahydro-1H-indazole-6-carboxylic acid (2A-2)

A mixture of methyl 3-(4-(tert-butoxycarbonyl)cyclohex-1-en-1-yl)-1-(2-chloro-6-cyclopropylbenzoyl)-4,5,6,7-tetrahydro-1H-indazole-6-carboxylate (747 mg, 1.386 mmol) and LiOH (498 mg, 20.79 mmol) in THF (4619 μL) and water (2310 μL) was stirred overnight at room temperature. The reaction was diluted with EtOAc and the organic layer was washed twice with saturated ammonium chloride. The organic layer was dried with Na$_2$SO$_4$, filtered, and concentrated in vacuo. The crude product thus obtained was used in the next step without further purification. MS: 525 (M+1).

Step 3. Preparation of 4-((R or S)-1-(2-chloro-6-cyclopropylbenzoyl)-6-(6-methyl-2,6-diazaspiro[3.3]heptane-2-carbonyl)-4,5,6,7-tetrahydro-1H-indazol-3-yl)cyclohex-3-ene-1-carboxylic acid (2A)

To a mixture of 3-(4-(tert-butoxycarbonyl)cyclohex-1-en-1-yl)-1-(2-chloro-6-cyclopropylbenzoyl)-4,5,6,7-tetrahydro-1H-indazole-6-carboxylic acid (70 mg, 0.133 mmol), HATU (71.0 mg, 0.187 mmol), Hunig's base (116 μL, 0.667 mmol) and DCM (1333 μL) was added 2-methyl-2,6-diazaspiro[3.3]heptane dihydrochloride (34.5 mg, 0.187 mmol). The resulting solution was stirred at room temperature for 3 hours.

The reaction was concentrated and the residue was diluted with DCM (1333 μL) and TFA (205 μL, 2.67 mmol). The resulting solution was allowed to stir at room temperature overnight.

The reaction was concentrated and the residue was brought up in dimethylsulfoxide. The mixture was filtered and purified by mass triggered reverse phase HPLC (ACN/water with 0.1% TFA modifier) to afford the title compound. MS: 563 (M+1). $^1$H NMR (600 MHz, DMSO-d6) δ 12.18 (s, 1H), 9.72 (s, 1H), 7.38-7.33 (m, 1H), 7.33-7.28 (m, 1H), 7.11-6.92 (m, 1H), 6.15 (s, 1H), 4.47-4.26 (m, 4H), 4.13-3.95 (m, 4H), 3.24-3.15 (m, 1H), 3.03-2.92 (m, 1H), 2.76 (s, 3H), 2.70-2.51 (m, 3H), 2.44-2.19 (m, 3H), 2.18-2.05 (m, 1H), 1.94-1.81 (m, 2H), 1.63-1.43 (m, 3H), 0.80 (s, 1H), 0.74-0.48 (m, 3H).

The following examples shown in Table 7 were prepared following similar procedures described above.

TABLE 7

| Example No. | Structure | IUPAC Name | Exact Mass [M + H]+ |
|---|---|---|---|
| 2B | 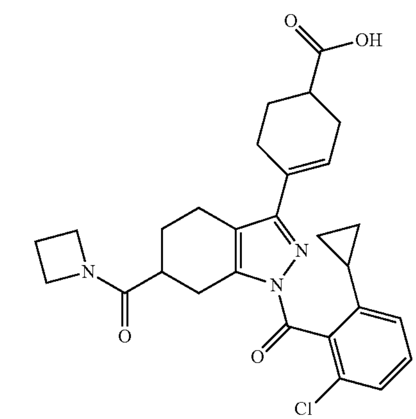 [SMILES: O=C(O)C1CC=C(c2nn(C(=O)c3c(Cl)cccc3C3CC3)c3c2CCC(C(=O)N2CCC2)C3)CC1] | 4-((R or S)-6-(azetidine-1-carbonyl)-1-(2-chloro-6-cyclopropylbenzoyl)-4,5,6,7-tetrahydro-1H-indazol-3-yl)cyclohex-3-ene-1-carboxylic acid | 508 |
| 2C | 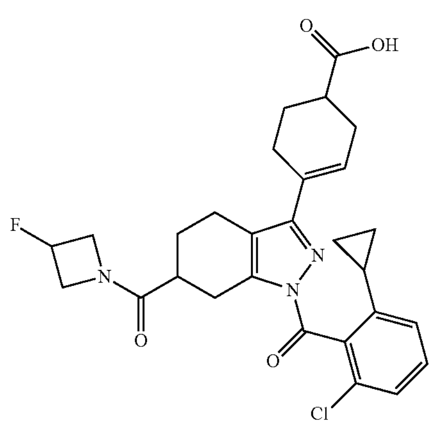 [SMILES: O=C(O)C1CC=C(c2nn(C(=O)c3c(Cl)cccc3C3CC3)c3c2CCC(C(=O)N2CC(F)C2)C3)CC1] | 4-((R or S)-1-(2-chloro-6-cyclopropylbenzoyl)-6-(3-fluoroazetidine-1-carbonyl)-4,5,6,7-tetrahydro-1H-indazol-3-yl)cyclohex-3-ene-1-carboxylic acid | 526 |

TABLE 7-continued

| Example No. | Structure | IUPAC Name | Exact Mass [M + H]+ |
|---|---|---|---|
| 2D | 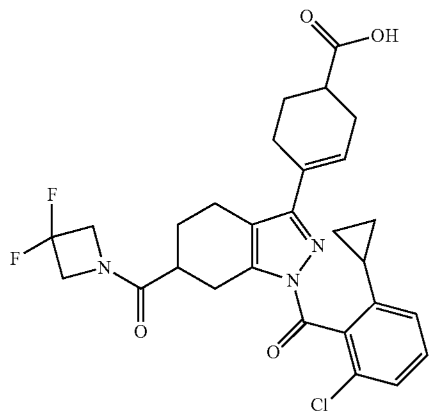 [SMILES: O=C(O)C1CC=C(c2nn(C(=O)c3c(Cl)cccc3C3CC3)c3c2CCC(C(=O)N2CC(F)(F)C2)C3)CC1] | 4-((R or S)-1-(2-chloro-6-cyclopropylbenzoyl)-6-(3,3-difluoroazetidine-1-carbonyl)-4,5,6,7-tetrahydro-1H-indazol-3-yl)cyclohex-3-ene-1-carboxylic acid | 544 |
| 2E | 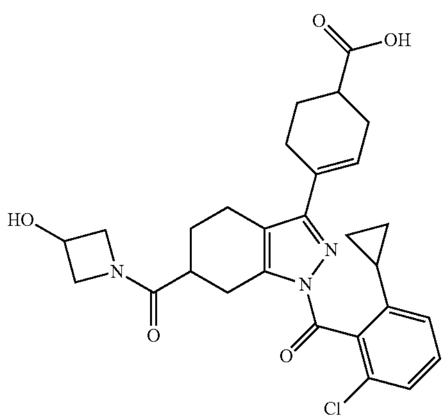 [SMILES: O=C(O)C1CC=C(c2nn(C(=O)c3c(Cl)cccc3C3CC3)c3c2CCC(C(=O)N2CC(O)C2)C3)CC1] | 4-((R or S)-1-(2-chloro-6-cyclopropylbenzoyl)-6-(3-hydroxyazetidine-1-carbonyl)-4,5,6,7-tetrahydro-1H-indazol-3-yl)cyclohex-3-ene-1-carboxylic acid | 524 |
| 2F | 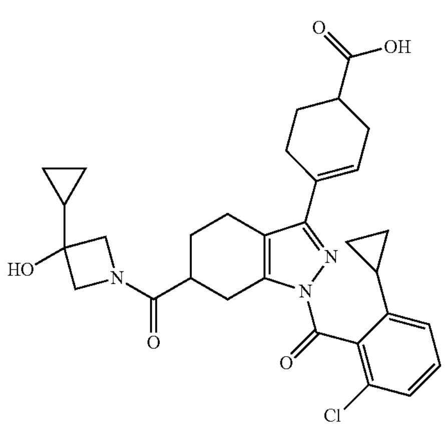 [SMILES: O=C(O)C1CC=C(c2nn(C(=O)c3c(Cl)cccc3C3CC3)c3c2CCC(C(=O)N2CC(O)(C4CC4)C2)C3)CC1] | 4-((R or S)-1-(2-chloro-6-cyclopropylbenzoyl)-6-(3-cyclopropyl-3-hydroxyazetidine-1-carbonyl)-4,5,6,7-tetrahydro-1H-indazol-3-yl)cyclohex-3-ene-1-carboxylic acid | 564 |

TABLE 7-continued

| Example No. | Structure | IUPAC Name | Exact Mass [M + H]+ |
|---|---|---|---|
| 2G | 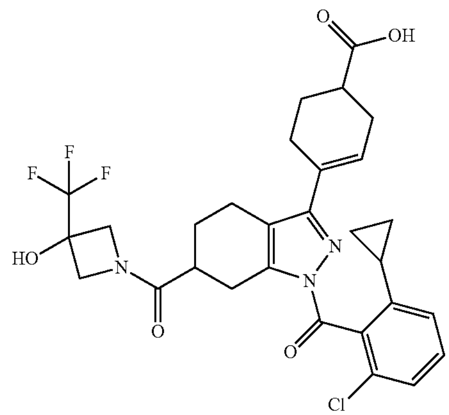 [SMILES: O=C(O)C1CC=C(c2nn(C(=O)c3c(Cl)cccc3C3CC3)c3c2CCC(C(=O)N2CC(O)(C(F)(F)F)C2)C3)CC1] | 4-((R or S)-1-(2-chloro-6-cyclopropylbenzoyl)-6-(3-hydroxy-3-(trifluoromethyl)azetidine-1-carbonyl)-4,5,6,7-tetrahydro-1H-indazol-3-yl)cyclohex-3-ene-1-carboxylic acid | 592 |
| 2H | 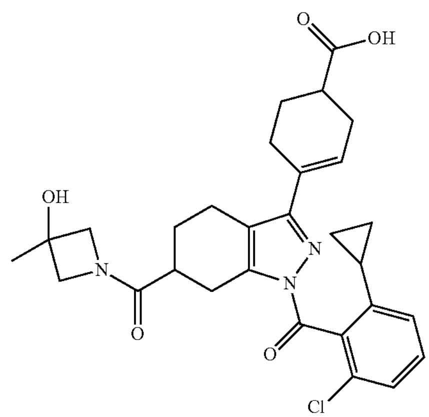 [SMILES: CC1(O)CN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-(3-hydroxy-3-methylazetidine-1-carbonyl)-4,5,6,7-tetrahydro-1H-indazol-3-yl)cyclohex-3-ene-1-carboxylic acid | 538 |
| 2I | 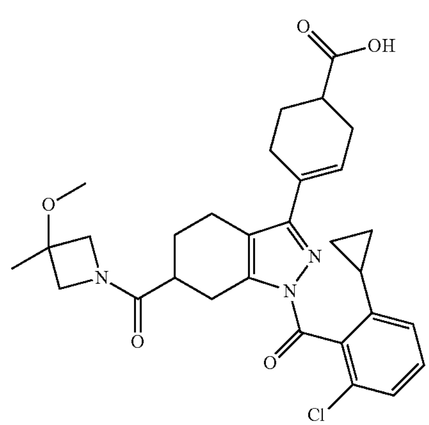 [SMILES: COC1(C)CN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-(3-methoxy-3-methylazetidine-1-carbonyl)-4,5,6,7-tetrahydro-1H-indazol-3-yl)cyclohex-3-ene-1-carboxylic acid | 552 |

TABLE 7-continued

| Example No. | Structure | IUPAC Name | Exact Mass [M + H]+ |
|---|---|---|---|
| 2J | 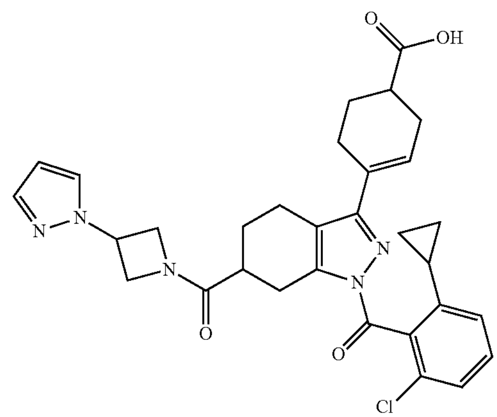 [SMILES: O=C(O)C1CC=C(c2nn(C(=O)c3c(Cl)cccc3C3CC3)c3c2CCC(C(=O)N2CC(n4cccn4)C2)C3)CC1] | 4-((R or S)-6-(3-(1H-pyrazol-1-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid | 574 |
| 2K | 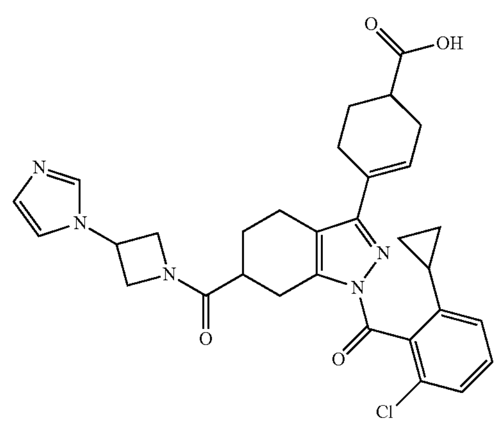 [SMILES: O=C(O)C1CC=C(c2nn(C(=O)c3c(Cl)cccc3C3CC3)c3c2CCC(C(=O)N2CC(n4ccnc4)C2)C3)CC1] | 4-((R or S)-6-(3-(1H-imidazol-1-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid | 574 |
| 2L | 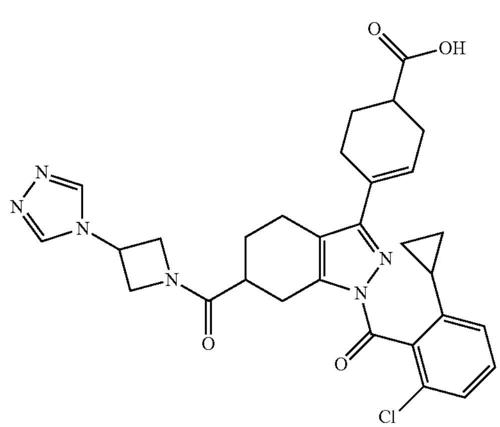 [SMILES: O=C(O)C1CC=C(c2nn(C(=O)c3c(Cl)cccc3C3CC3)c3c2CCC(C(=O)N2CC(n4cnnc4)C2)C3)CC1] | 4-((R or S)-6-(3-(4H-1,2,4-triazol-4-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid | 575 |

TABLE 7-continued

| Example No. | Structure | IUPAC Name | Exact Mass [M + H]+ |
|---|---|---|---|
| 2M | 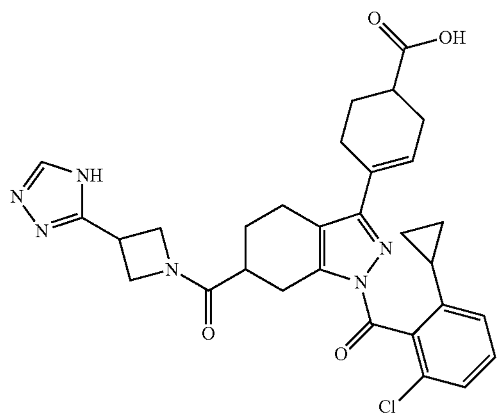 [SMILES: O=C(O)C1CC=C(c2nn(C(=O)c3c(Cl)cccc3C3CC3)c3c2CCC(C(=O)N2CC(c4nnc[nH]4)C2)C3)CC1] | 4-((R or S)-6-(3-(4H-1,2,4-triazol-3-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid | 575 |
| 2N | 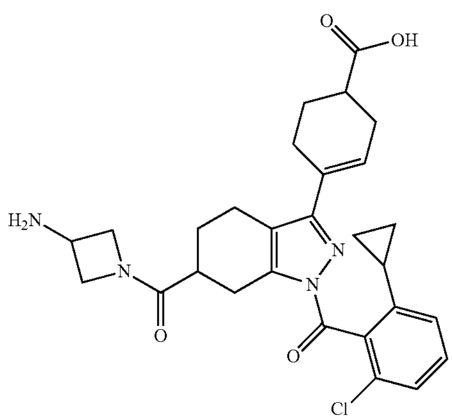 [SMILES: NC1CN(C(=O)C2CCc3c(C4=CCC(C(=O)O)CC4)nn(C(=O)c4c(Cl)cccc4C4CC4)c3C2)C1] | 4-((R or S)-6-(3-aminoazetidine-1-carbonyl)-1-(2-chloro-6-cyclopropylbenzoyl)-4,5,6,7-tetrahydro-1H-indazol-3-yl)cyclohex-3-ene-1-carboxylic acid | 523 |
| 2O | 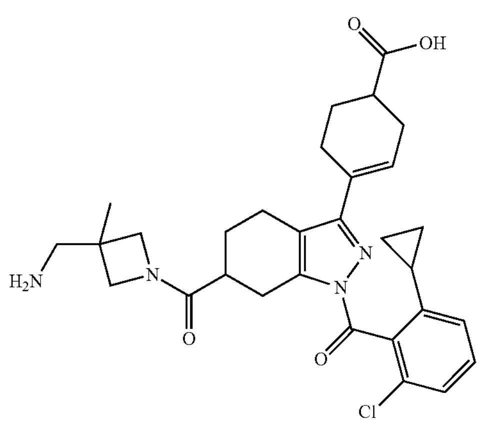 [SMILES: CC1(CN)CN(C(=O)C2CCc3c(C4=CCC(C(=O)O)CC4)nn(C(=O)c4c(Cl)cccc4C4CC4)c3C2)C1] | 4-((R or S)-6-(3-(aminomethyl)-3-methylazetidine-1-carbonyl)-1-(2-chloro-6-cyclopropylbenzoyl)-4,5,6,7-tetrahydro-1H-indazol-3-yl)cyclohex-3-ene-1-carboxylic acid | 551 |

TABLE 7-continued

| Example No. | Structure | IUPAC Name | Exact Mass [M + H]+ |
|---|---|---|---|
| 2P | 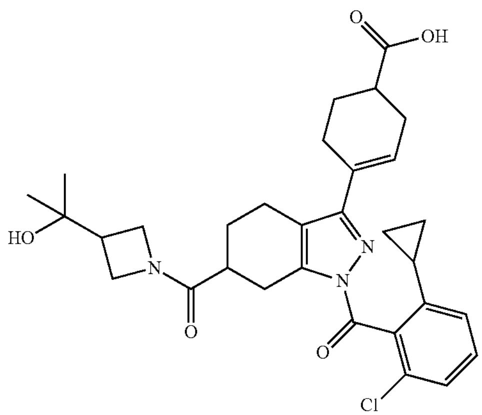 [SMILES: CC(C)(O)C1CN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-(3-(2-hydroxypropan-2-yl)azetidine-1-carbonyl)-4,5,6,7-tetrahydro-1H-indazol-3-yl)cyclohex-3-ene-1-carboxylic acid | 566 |
| 2Q | 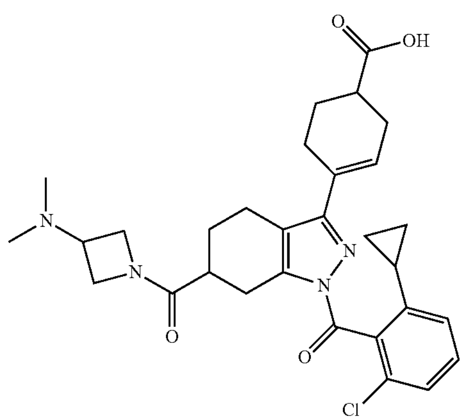 [SMILES: CN(C)C1CN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-(3-(dimethylamino)azetidine-1-carbonyl)-4,5,6,7-tetrahydro-1H-indazol-3-yl)cyclohex-3-ene-1-carboxylic acid | 551 |
| 2R | 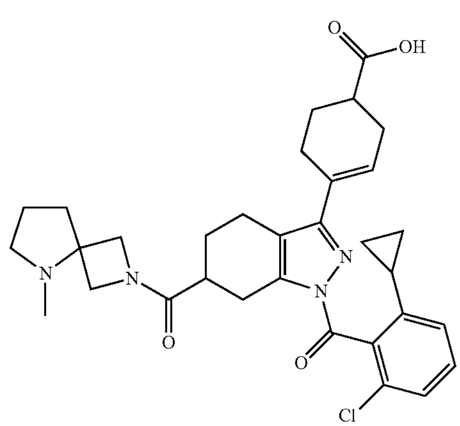 [SMILES: CN1CCCC12CN(C(=O)C1CCc3c(C4=CCC(C(=O)O)CC4)nn(C(=O)c4c(Cl)cccc4C4CC4)c3C1)C2] | 4-((R or S)-1-(2-chloro-6-cyclopropylbenzoyl)-6-(5-methyl-2,5-diazaspiro[3.4]octane-2-carbonyl)-4,5,6,7-tetrahydro-1H-indazol-3-yl)cyclohex-3-ene-1-carboxylic acid | 577 |

TABLE 7-continued

| Example No. | Structure | IUPAC Name | Exact Mass [M + H]+ |
|---|---|---|---|
| 2S | 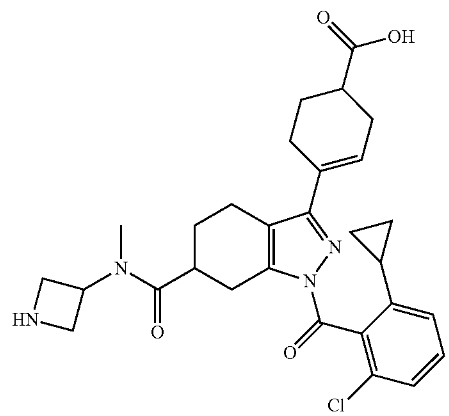 [SMILES: CN(C(=O)C1CCc2c(C3=CCC(C(=O)O)CC3)nn(C(=O)c3c(Cl)cccc3C3CC3)c2C1)C1CNC1] | 4-((R or S)-6-(azetidin-3-yl(methyl)carbamoyl)-1-(2-chloro-6-cyclopropylbenzoyl)-4,5,6,7-tetrahydro-1H-indazol-3-yl)cyclohex-3-ene-1-carboxylic acid | 537 |
| 2T | 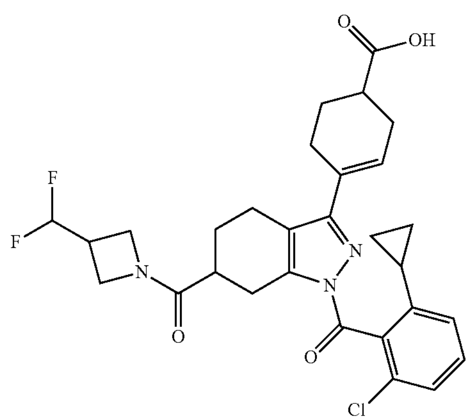 [SMILES: O=C(O)C1CC=C(c2nn(C(=O)c3c(Cl)cccc3C3CC3)c3c2CCC(C(=O)N2CC(C(F)F)C2)C3)CC1] | 4-((R or S)-1-(2-chloro-6-cyclopropylbenzoyl)-6-(3-(difluoromethyl)azetidine-1-carbonyl)-4,5,6,7-tetrahydro-1H-indazol-3-yl)cyclohex-3-ene-1-carboxylic acid | 558 |
| 2U | 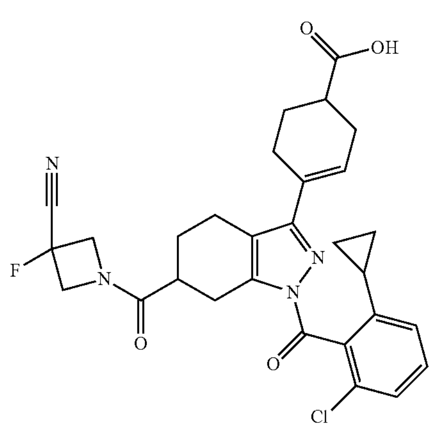 [SMILES: N#CC1(F)CN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-(3-cyano-3-fluoroazetidine-1-carbonyl)-4,5,6,7-tetrahydro-1H-indazol-3-yl)cyclohex-3-ene-1-carboxylic acid | 551 |

TABLE 7-continued

| Example No. | Structure | IUPAC Name | Exact Mass [M + H]+ |
|---|---|---|---|
| 2V | 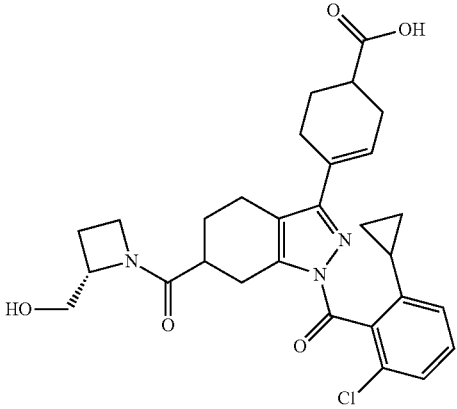 [SMILES: O=C(O)C1CC=C(c2nn(C(=O)c3c(Cl)cccc3C3CC3)c3c2CCC(C(=O)N2CC[C@H]2CO)C3)CC1] | 4-((R or S)-1-(2-chloro-6-cyclopropylbenzoyl)-6-((S)-2-(hydroxymethyl)azetidine-1-carbonyl)-4,5,6,7-tetrahydro-1H-indazol-3-yl)cyclohex-3-ene-1-carboxylic acid | 538 |
| 2W | 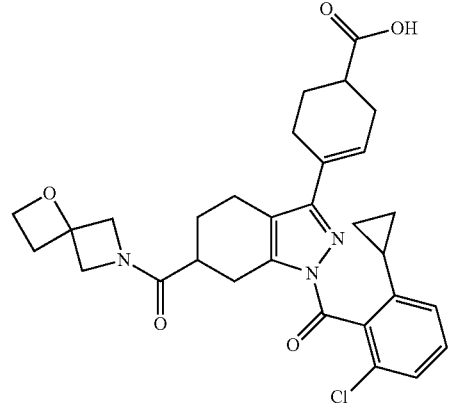 [SMILES: O=C(O)C1CC=C(c2nn(C(=O)c3c(Cl)cccc3C3CC3)c3c2CCC(C(=O)N2CC4(CCO4)C2)C3)CC1] | 4-((R or S)-1-(2-chloro-6-cyclopropylbenzoyl)-6-(1-oxa-6-azaspiro[3.3]heptane-6-carbonyl)-4,5,6,7-tetrahydro-1H-indazol-3-yl)cyclohex-3-ene-1-carboxylic acid | 550 |
| 2X | 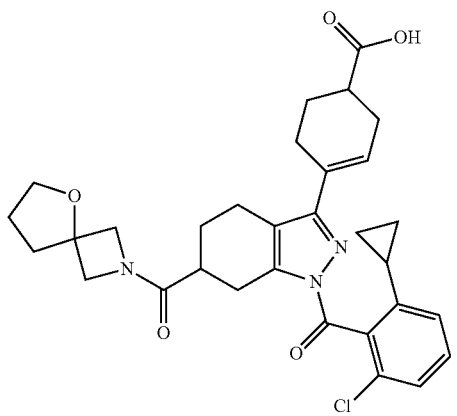 [SMILES: O=C(O)C1CC=C(c2nn(C(=O)c3c(Cl)cccc3C3CC3)c3c2CCC(C(=O)N2CC4(CCCO4)C2)C3)CC1] | 4-((R or S)-1-(2-chloro-6-cyclopropylbenzoyl)-6-(5-oxa-2-azaspiro[3.4]octane-2-carbonyl)-4,5,6,7-tetrahydro-1H-indazol-3-yl)cyclohex-3-ene-1-carboxylic acid | 564 |

TABLE 7-continued

| Example No. | Structure | IUPAC Name | Exact Mass [M + H]+ |
|---|---|---|---|
| 2Y | 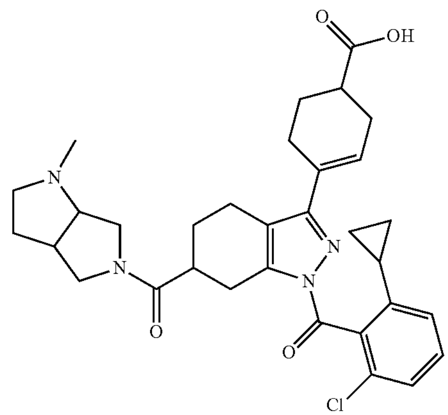 [SMILES: CN1CCC2CN(C(=O)C3CCc4c(C5=CCC(C(=O)O)CC5)nn(C(=O)c5c(Cl)cccc5C5CC5)c4C3)CC21] | 4-((6R or S)-1-(2-chloro-6-cyclopropylbenzoyl)-6-(1-methyloctahydropyrrolo[3,4-b]pyrrole-5-carbonyl)-4,5,6,7-tetrahydro-1H-indazol-3-yl)cyclohex-3-ene-1-carboxylic acid | 577 |
| 2Z | 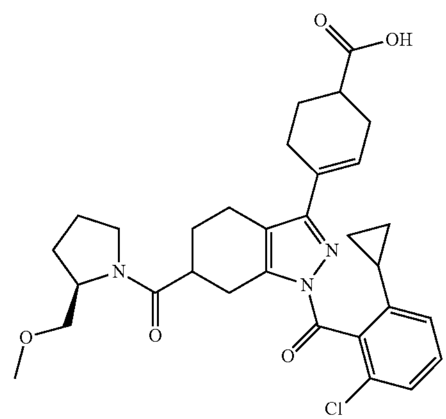 [SMILES: COC[C@H]1CCCN1C(=O)C1CCc2c(C3=CCC(C(=O)O)CC3)nn(C(=O)c3c(Cl)cccc3C3CC3)c2C1] | 4-((R or S)-1-(2-chloro-6-cyclopropylbenzoyl)-6-((R)-2-(methoxymethyl)pyrrolidine-1-carbonyl)-4,5,6,7-tetrahydro-1H-indazol-3-yl)cyclohex-3-ene-1-carboxylic acid | 566 |
| 2AA | 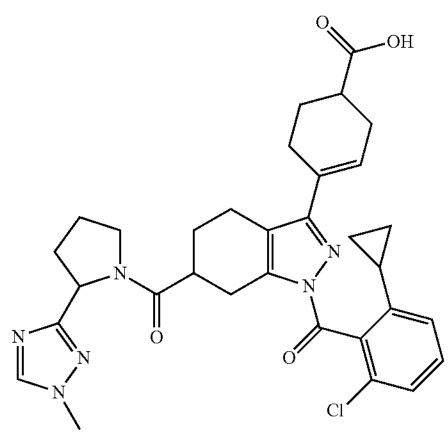 [SMILES: Cn1cnc(C2CCCN2C(=O)C2CCc3c(C4=CCC(C(=O)O)CC4)nn(C(=O)c4c(Cl)cccc4C4CC4)c3C2)n1] | 4-((6R or S)-1-(2-chloro-6-cyclopropylbenzoyl)-6-(2-(1-methyl-1H-1,2,4-triazol-3-yl)pyrrolidine-1-carbonyl)-4,5,6,7-tetrahydro-1H-indazol-3-yl)cyclohex-3-ene-1-carboxylic acid | 603 |

TABLE 7-continued

| Example No. | Structure | IUPAC Name | Exact Mass [M + H]+ |
|---|---|---|---|
| 2BB | 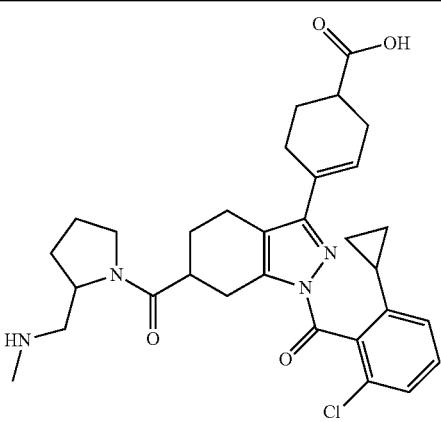 | 4-((6R or S)-1-(2-chloro-6-cyclopropylbenzoyl)-6-(2-((methylamino)methyl)pyrrolidine-1-carbonyl)-4,5,6,7-tetrahydro-1H-indazol-3-yl)cyclohex-3-ene-1-carboxylic acid | 565 |
| 2CC | 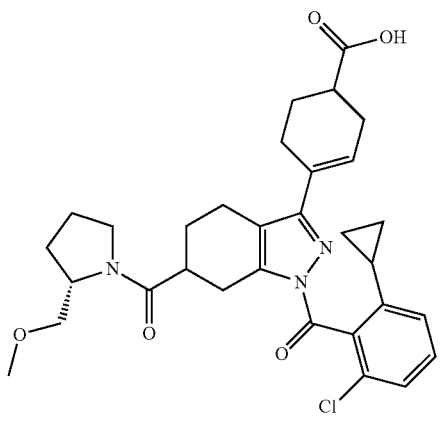 [SMILES: COC[C@@H]1CCCN1C(=O)C1CCc2c(C3=CCC(C(=O)O)CC3)nn(C(=O)c3c(Cl)cccc3C3CC3)c2C1] | 4-((R or S)-1-(2-chloro-6-cyclopropylbenzoyl)-6-((S)-2-(methoxymethyl)pyrrolidine-1-carbonyl)-4,5,6,7-tetrahydro-1H-indazol-3-yl)cyclohex-3-ene-1-carboxylic acid | 566 |
| 2DD | 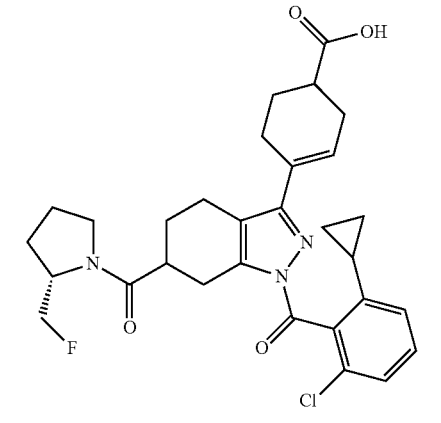 [SMILES: O=C(O)C1CC=C(c2nn(C(=O)c3c(Cl)cccc3C3CC3)c3c2CCC(C(=O)N2CCC[C@H]2CF)C3)CC1] | 4-((R or S)-1-(2-chloro-6-cyclopropylbenzoyl)-6-((S)-2-(fluoromethyl)pyrrolidine-1-carbonyl)-4,5,6,7-tetrahydro-1H-indazol-3-yl)cyclohex-3-ene-1-carboxylic acid | 554 |

TABLE 7-continued

| Example No. | Structure | IUPAC Name | Exact Mass [M + H]+ |
|---|---|---|---|
| 2EE | 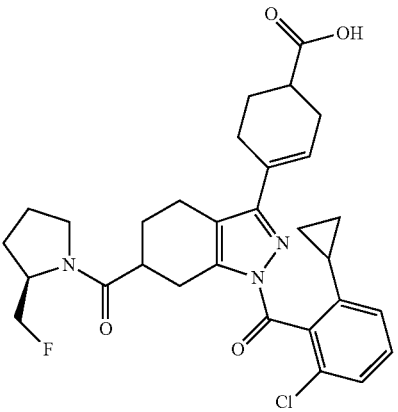 [SMILES: O=C(O)C1CC=C(c2nn(C(=O)c3c(Cl)cccc3C3CC3)c3c2CCC(C(=O)N2CCC[C@@H]2CF)C3)CC1] | 4-((R or S)-1-(2-chloro-6-cyclopropylbenzoyl)-6-((R)-2-(fluoromethyl)pyrrolidine-1-carbonyl)-4,5,6,7-tetrahydro-1H-indazol-3-yl)cyclohex-3-ene-1-carboxylic acid | 554 |
| 2FF | 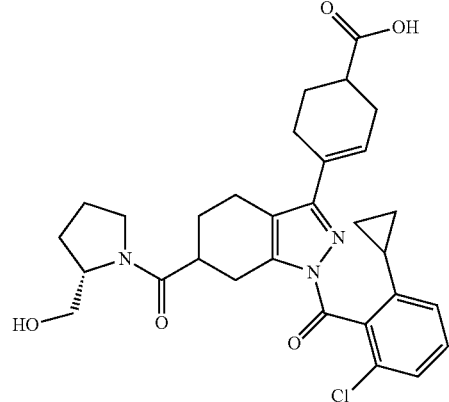 [SMILES: O=C(O)C1CC=C(c2nn(C(=O)c3c(Cl)cccc3C3CC3)c3c2CCC(C(=O)N2CCC[C@H]2CO)C3)CC1] | 4-((R or S)-1-(2-chloro-6-cyclopropylbenzoyl)-6-((S)-2-(hydroxymethyy)pyrrolidine-1-carbonyl)-4,5,6,7-tetrahydro-1H-indazol-3-yl)cyclohex-3-ene-1-carboxylic acid | 552 |
| 2GG | 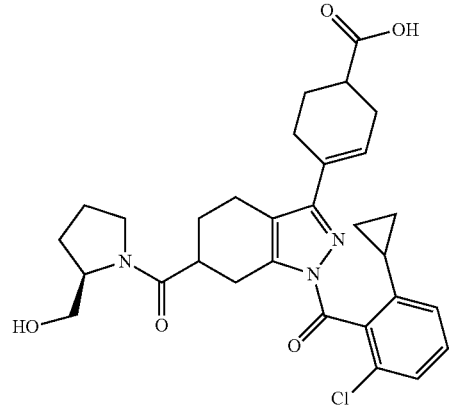 [SMILES: O=C(O)C1CC=C(c2nn(C(=O)c3c(Cl)cccc3C3CC3)c3c2CCC(C(=O)N2CCC[C@@H]2CO)C3)CC1] | 4-((R or S)-1-(2-chloro-6-cyclopropylbenzoyl)-6-((R)-2-(hydroxymethyl)pyrrolidine-1-carbonyl)-4,5,6,7-tetrahydro-1H-indazol-3-yl)cyclohex-3-ene-1-carboxylic acid | 552 |

TABLE 7-continued

| Example No. | Structure | IUPAC Name | Exact Mass [M + H]+ |
|---|---|---|---|
| 2HH | 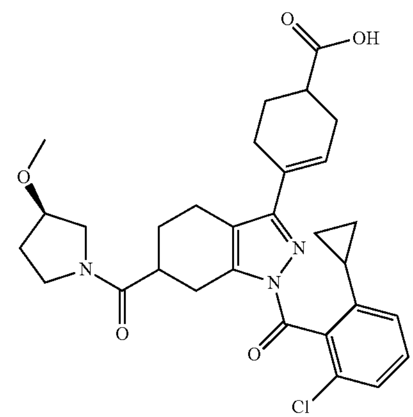 [SMILES: CO[C@@H]1CCN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-((R)-3-methoxypyrrolidine-1-carbonyl)-4,5,6,7-tetrahydro-1H-indazol-3-yl)cyclohex-3-ene-1-carboxylic acid | 552 |
| 2II | 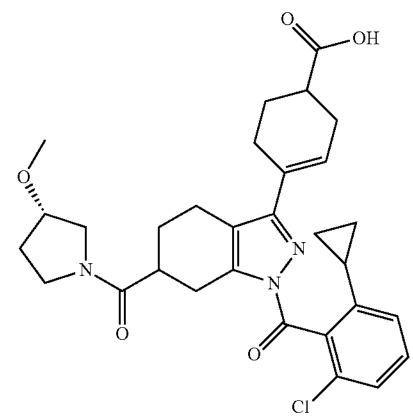 [SMILES: CO[C@H]1CCN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-((S)-3-methoxypyrrolidine-1-carbonyl)-4,5,6,7-tetrahydro-1H-indazol-3-yl)cyclohex-3-ene-1-carboxylic acid | 552 |
| 2JJ | 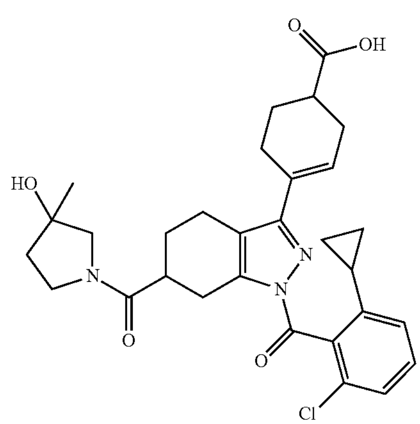 [SMILES: CC1(O)CCN(C(=O)C2CCc3c(C4=CCC(C(=O)O)CC4)nn(C(=O)c4c(Cl)cccc4C4CC4)c3C2)C1] | 4-((6R or S)-1-(2-chloro-6-cyclopropylbenzoyl)-6-(3-hydroxy-3-methylpyrrolidine-1-carbonyl)-4,5,6,7-tetrahydro-1H-indazol-3-yl)cyclohex-3-ene-1-carboxylic acid | 552 |

TABLE 7-continued

| Example No. | Structure | IUPAC Name | Exact Mass [M + H]+ |
|---|---|---|---|
| 2KK | 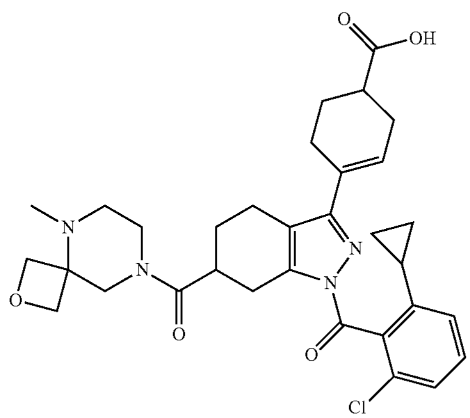 [SMILES: CN1CCN(C(=O)C2CCc3c(C4=CCC(C(=O)O)CC4)nn(C(=O)c4c(Cl)cccc4C4CC4)c3C2)CC12COC2] | 4-((R or S)-1-(2-chloro-6-cyclopropylbenzoyl)-6-(5-methyl-2-oxa-5,8-diazaspiro[3.5]nonane-8-carbonyl)-4,5,6,7-tetrahydro-1H-indazol-3-yl)cyclohex-3-ene-1-carboxylic acid | 593 |
| 2LL | 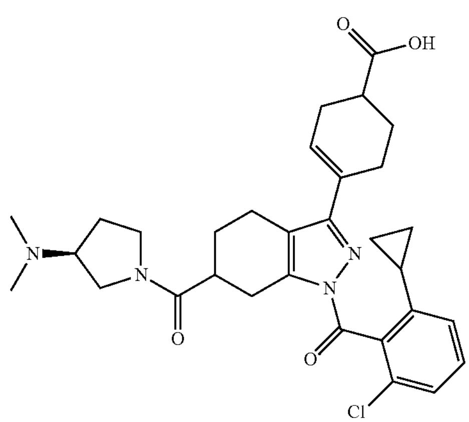 [SMILES: CN(C)[C@H]1CCN(C(=O)C2CCc3c(C4=CCC(C(=O)O)CC4)nn(C(=O)c4c(Cl)cccc4C4CC4)c3C2)C1] | 4-((R or S)-1-chloro-6-cyclopropylbenzoyl)-6-((S)-3-(dimethylamino)pyrrolidine-1-carbonyl)-4,5,6,7-tetrahydro-1H-indazol-3-yl)cyclohex-3-ene-1-carboxylic acid | 565 |
| 2MM | 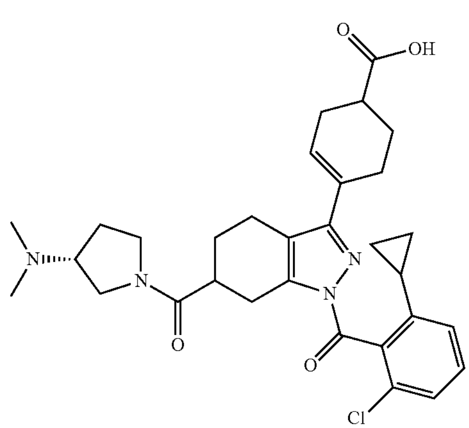 [SMILES: CN(C)[C@@H]1CCN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-((R)-3-(dimethylamino)pyrrolidine-1-carbonyl)-4,5,6,7-tetrahydro-1H-indazol-3-yl)cyclohex-3-ene-1-carboxylic acid | 565 |

TABLE 7-continued

| Example No. | Structure | IUPAC Name | Exact Mass [M + H]+ |
|---|---|---|---|
| 2NN | 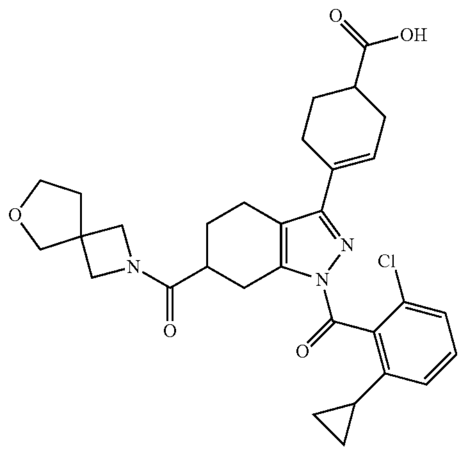 [SMILES: O=C(O)C1CC=C(c2nn(C(=O)c3c(Cl)cccc3C3CC3)c3c2CCC(C(=O)N2CC4(CCOC4)C2)C3)CC1] | 4-((R or S)-2-chloro-6-cyclopropylbenzoyl)-6-(6-oxa-2-azaspiro[3.4]octane-2-carbonyl)-4,5,6,7-tetrahydro-1H-indazol-3-yl)cyclohex-3-ene-1-carboxylic acid | 564 |
| 2OO | 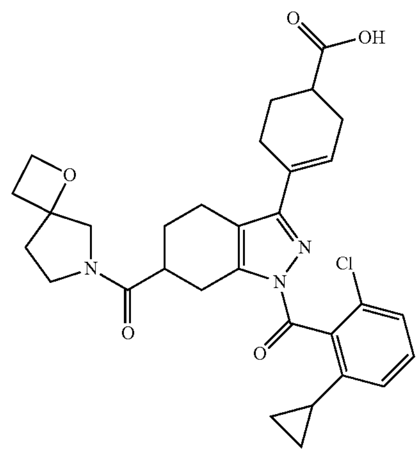 [SMILES: O=C(O)C1CC=C(c2nn(C(=O)c3c(Cl)cccc3C3CC3)c3c2CCC(C(=O)N2CCC4(CCO4)C2)C3)CC1] | 4-((6R or S)-1-(2-chloro-6-cyclopropylbenzoyl)-6-(1-oxa-6-azaspiro[3.4]octane-6-carbonyl)-4,5,6,7-tetrahydro-1H-indazol-3-yl)cyclohex-3-ene-1-carboxylic acid | 564 |
| 2PP | 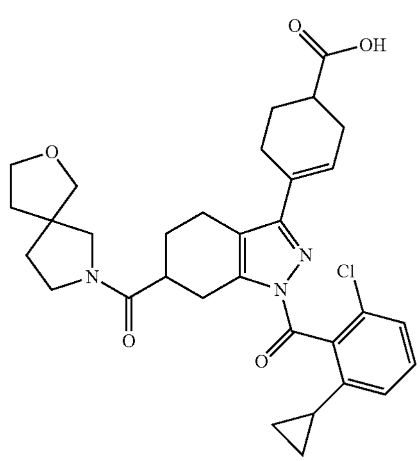 [SMILES: O=C(O)C1CC=C(c2nn(C(=O)c3c(Cl)cccc3C3CC3)c3c2CCC(C(=O)N2CCC4(CCOC4)C2)C3)CC1] | 4-((6R or S)-1-(2-chloro-6-cyclopropylbenzoyl)-6-(2-oxa-7-azaspiro[4.4]nonane-7-carbonyl)-4,5,6,7-tetrahydro-1H-indazol-3-yl)cyclohex-3-ene-1-carboxylic acid | 578 |

TABLE 7-continued

| Example No. | Structure | IUPAC Name | Exact Mass [M + H]+ |
|---|---|---|---|
| 2QQ | 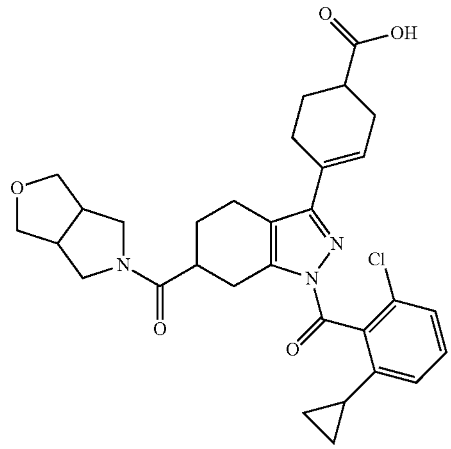 [SMILES: O=C(O)C1CC=C(c2nn(C(=O)c3c(Cl)cccc3C3CC3)c3c2CCC(C(=O)N2CC4COCC4C2)C3)CC1] | 4-((6R or S)-1-(2-chloro-6-cyclopropylbenzoyl)-6-(hexahydro-1H-furo[3,4-c]pyrrole-5-carbonyl)-4,5,6,7-tetrahydro-1H-indazol-3-yl)cyclohex-3-ene-1-carboxylic acid | 564 |
| 2RR | 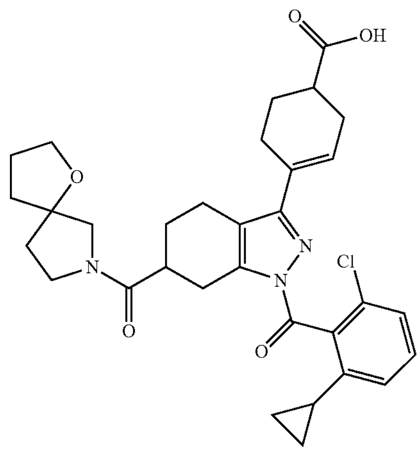 [SMILES: O=C(O)C1CC=C(c2nn(C(=O)c3c(Cl)cccc3C3CC3)c3c2CCC(C(=O)N2CCC4(CCCO4)C2)C3)CC1] | 4-((6R or S)-1-(2-chloro-6-cyclopropylbenzoyl)-6-(1-oxa-7-azaspiro[4.4]nonane-7-carbonyl)-4,5,6,7-tetrahydro-1H-indazol-3-yl)cyclohex-3-ene-1-carboxylic acid | 578 |
| 2SS | 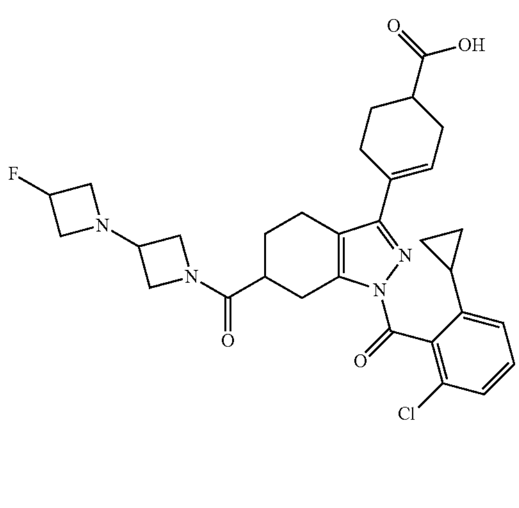 [SMILES: O=C(O)C1CC=C(c2nn(C(=O)c3c(Cl)cccc3C3CC3)c3c2CCC(C(=O)N2CC(N4CC(F)C4)C2)C3)CC1] | 4-((R or S)-1-(2-chloro-6-cyclopropylbenzoyl)-6-(3-fluoro-[1,3'-biazetidine]-1'-carbonyl)-4,5,6,7-tetrahydro-1H-indazol-3-yl)cyclohex-3-ene-1-carboxylic acid | 581 |

TABLE 7-continued

| Example No. | Structure | IUPAC Name | Exact Mass [M + H]+ |
|---|---|---|---|
| 2TT | 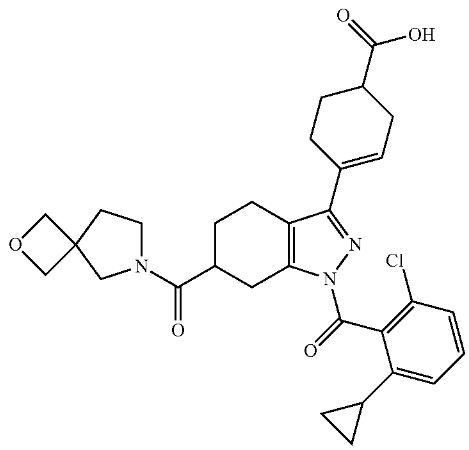 [SMILES: O=C(O)C1CC=C(c2nn(C(=O)c3c(Cl)cccc3C3CC3)c3c2CCC(C(=O)N2CCC4(COC4)C2)C3)CC1] | 4-((R or S)-1-(2-chloro-6-cyclopropylbenzoyl)-6-(2-oxa-6-azaspiro[3.4]octane-6-carbonyl)-4,5,6,7-tetrahydro-1H-indazol-3-yl)cyclohex-3-ene-1-carboxylic acid | 564 |
| 2UU | 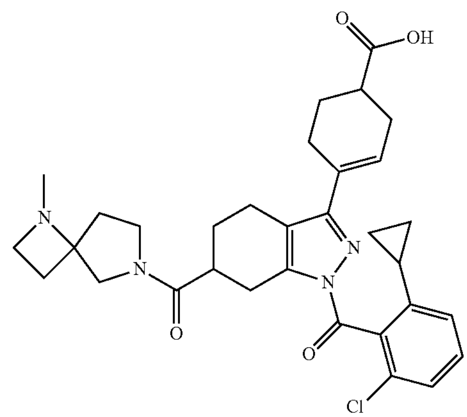 [SMILES: CN1CCC12CCN(C(=O)C1CCc3c(C4=CCC(C(=O)O)CC4)nn(C(=O)c4c(Cl)cccc4C4CC4)c3C1)C2] | 4-((6R or S)-1-(2-chloro-6-cyclopropylbenzoyl)-6-(1-methyl-1,6-diazaspiro[3.4]octane-6-carbonyl)-4,5,6,7-tetrahydro-1H-indazol-3-yl)cyclohex-3-ene-1-carboxylic acid | 577 |
| 2VV | 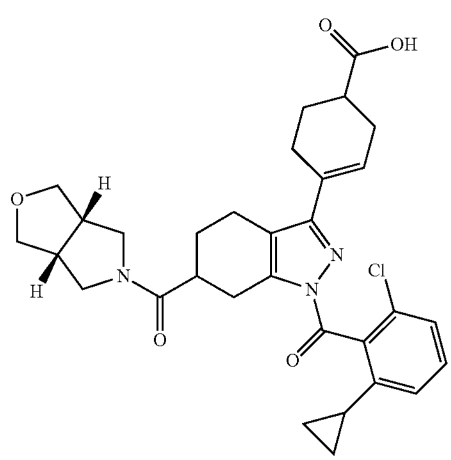 [SMILES: O=C(O)C1CC=C(c2nn(C(=O)c3c(Cl)cccc3C3CC3)c3c2CCC(C(=O)N2C[C@H]4COC[C@H]4C2)C3)CC1] | 4-((R or S)-1-(2-chloro-6-cyclopropylbenzoyl)-6-((3aR,6aS)-hexahydro-1H-furo[3,4-c]pyrrole-5-carbonyl)-4,5,6,7-tetrahydro-1H-indazol-3-yl)cyclohex-3-ene-1-carboxylic acid | 564 |

TABLE 7-continued

| Example No. | Structure | IUPAC Name | Exact Mass [M + H]+ |
|---|---|---|---|
| 2WW | 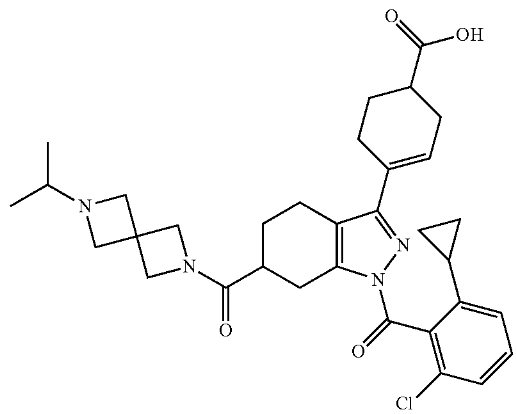 [SMILES: CC(C)N1CC2(CN(C(=O)C3CCc4c(C5=CCC(C(=O)O)CC5)nn(C(=O)c5c(Cl)cccc5C5CC5)c4C3)C2)C1] | 4-[(6R or S)-1-[(2-chloro-6-cyclopropylphenyl)carbonyl]-6-{[6-(1-methylethyl)-2,6-diazaspiro[3.3]hept-2-yl]carbonyl}-4,5,6,7-tetrahydro-1H-indazol-3-yl]cyclohex-3-ene-1-carboxylic acid | 591 |
| 2XX | 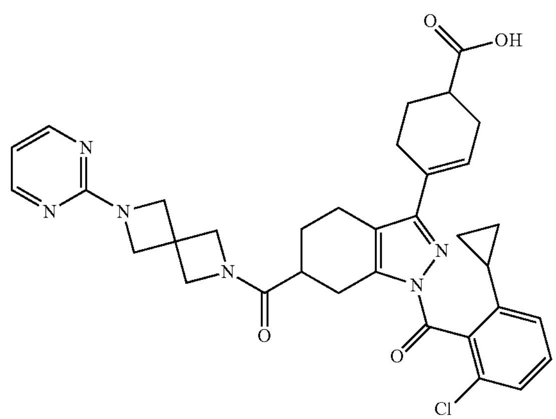 [SMILES: O=C(O)C1CC=C(c2nn(C(=O)c3c(Cl)cccc3C3CC3)c3c2CCC(C(=O)N2CC4(C2)CN(c2ncccn2)C4)C3)CC1] | 4-{(6R or S)-1-[(2-chloro-6-cyclopropylphenyl)carbonyl]-6-[(6-pyrimidin-2-yl-2,6-diazaspiro[3.3]hept-2-yl)carbonyl]-4,5,6,7-tetrahydro-1H-indazol-3-yl}cyclohex-3-ene-1-carboxylic acid | 627 |
| 2YY | 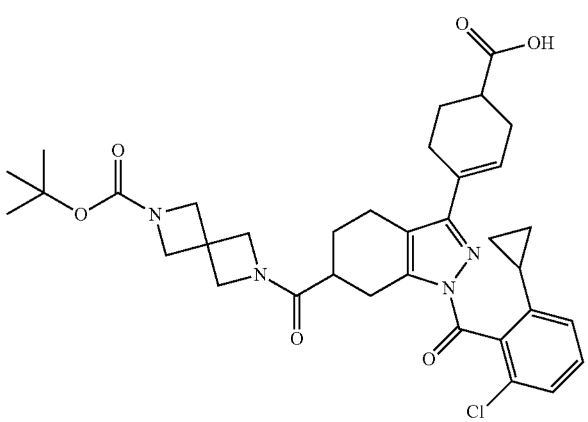 [SMILES: CC(C)(C)OC(=O)N1CC2(C1)CN(C(=O)C1CCc3c(C4=CCC(C(=O)O)CC4)nn(C(=O)c4c(Cl)cccc4C4CC4)c3C1)C2] | 4-{(6R or S)-6-{[6-(tert-butoxycarbonyl)-2,6-diazaspiro[3.3]hept-2-yl]carbonyl}-1-[(2-chloro-6-cyclopropylphenyl)carbonyl]-4,5,6,7-tetrahydro-1H-indazol-3-yl}cyclohex-3-ene-1-carboxylic acid | 649 |

TABLE 7-continued

| Example No. | Structure | IUPAC Name | Exact Mass [M + H]+ |
|---|---|---|---|
| 2ZZ | 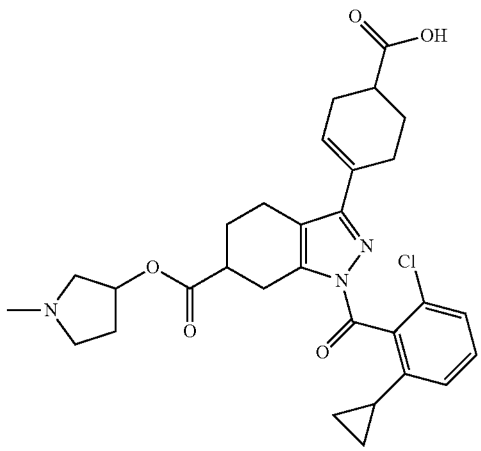 [SMILES: CN1CCC(OC(=O)C2CCc3c(C4=CCC(C(=O)O)CC4)nn(C(=O)c4c(Cl)cccc4C4CC4)c3C2)C1] | 4-((6R or S)-1-(2-chloro-6-cyclopropylbenzoyl)-6-(((1-methylpyrrolidin-3-yl)oxy)carbonyl)-4,5,6,7-tetrahydro-1H-indazol-3-yl)cyclohex-3-ene-1-carboxylic acid | 552 |
| 2AAA | 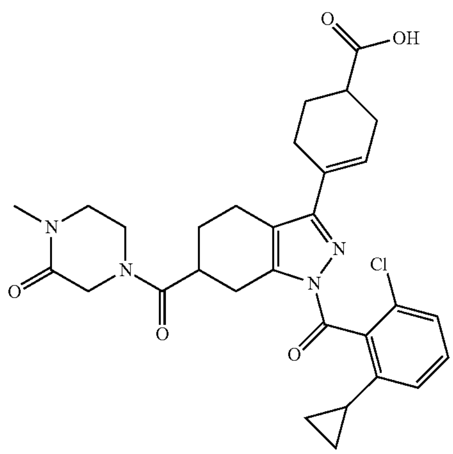 [SMILES: CN1CCN(C(=O)C2CCc3c(C4=CCC(C(=O)O)CC4)nn(C(=O)c4c(Cl)cccc4C4CC4)c3C2)CC1=O] | 4-((R or S)-1-(2-chloro-6-cyclopropylbenzoyl)-6-(4-methyl-3-oxopiperazine-1-carbonyl)-4,5,6,7-tetrahydro-1H-indazol-3-yl)cyclohex-3-ene-1-carboxylic acid | 565 |
| 2BBB | 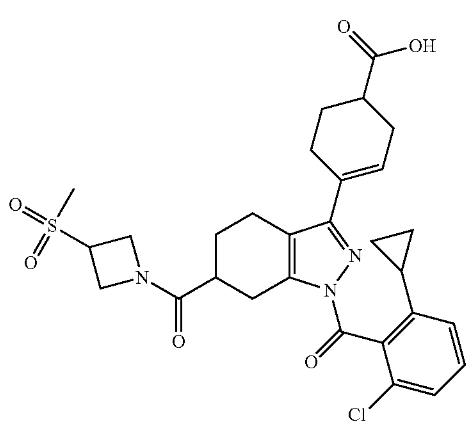 [SMILES: CS(=O)(=O)C1CN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-(3-(methylsulfonyl)azetidine-1-carbonyl)-4,5,6,7-tetrahydro-1H-indazol-3-yl)cyclohex-3-ene-1-carboxylic acid | 586 |

TABLE 7-continued

| Example No. | Structure | IUPAC Name | Exact Mass [M + H]+ |
|---|---|---|---|
| 2CCC | 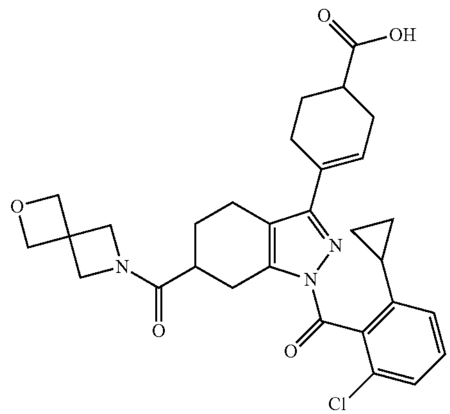 [SMILES: O=C(O)C1CC=C(c2nn(C(=O)c3c(Cl)cccc3C3CC3)c3c2CCC(C(=O)N2CC4(COC4)C2)C3)CC1] | 4-((R or S)-1-(2-chloro-6-cyclopropylbenzoyl)-6-(2-oxa-6-azaspiro[3.3]heptane-6-carbonyl)-4,5,6,7-tetrahydro-1H-indazol-3-yl)cyclohex-3-ene-1-carboxylic acid | 550 |

The following examples shown in Table 8 were prepared using i-20A and following similar procedures described in Example 2 above.

TABLE 8

| Example No. | Structure | IUPAC Name | Exact Mass [M + H]+ |
|---|---|---|---|
| 3A | 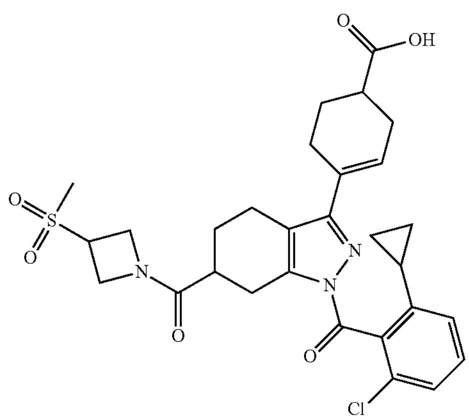 [SMILES: CS(=O)(=O)C1CN(C(=O)C2CCc3c(C4=CCC(C(=O)O)CC4)nn(C(=O)c4c(Cl)cccc4C4CC4)c3C2)C1] | 4-((R or S)-1-(2-chloro-6-cyclopropylbenzoyl)-6-(3-(methylsulfonyl)azetidine-1-carbonyl)-4,5,6,7-tetrahydro-1H-indazol-3-yl)cyclohex-3-ene-1-carboxylic acid | 586 |
| 3B | 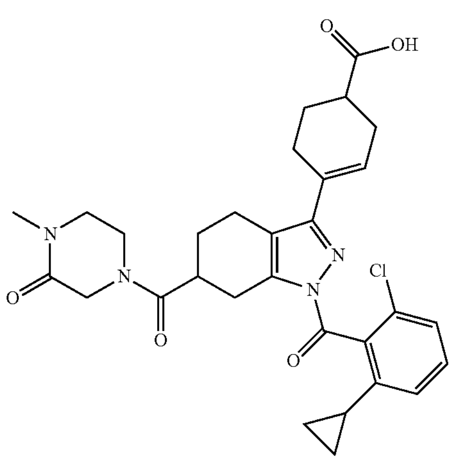 [SMILES: CN1CCN(C(=O)C2CCc3c(C4=CCC(C(=O)O)CC4)nn(C(=O)c4c(Cl)cccc4C4CC4)c3C2)CC1=O] | 4-((R or S)-1-(2-chloro-6-cyclopropylbenzoyl)-6-(4-methyl-3-oxopiperazine-1-carbonyl)-4,5,6,7-tetrahydro-1H-indazol-3-yl)cyclohex-3-ene-1-carboxylic acid | 565 |

TABLE 8-continued

| Example No. | Structure | IUPAC Name | Exact Mass [M + H]+ |
|---|---|---|---|
| 3C | 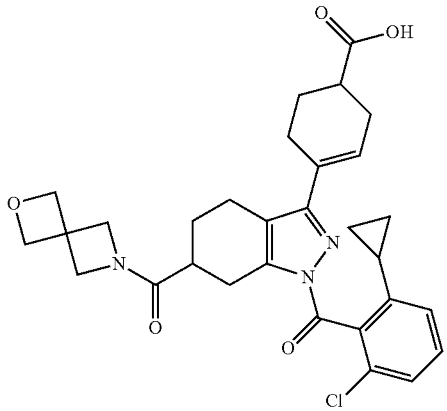 [SMILES: O=C(O)C1CC=C(c2nn(C(=O)c3c(Cl)cccc3C3CC3)c3c2CCC(C(=O)N2CC4(COC4)C2)C3)CC1] | 4-((R or S)-1-(2-chloro-6-cyclopropylbenzoyl)-6-(2-oxa-6-azaspiro[3.3]heptane-6-carbonyl)-4,5,6,7-tetrahydro-1H-indazol-3-yl)cyclohex-3-ene-1-carboxylic acid | 550 |

The following examples shown in Table 9 were prepared using i-21B and following similar procedures described in Example 2 above.

TABLE 9

| Example No. | Structure | IUPAC Name | Exact Mass [M + H]+ |
|---|---|---|---|
| 4A | 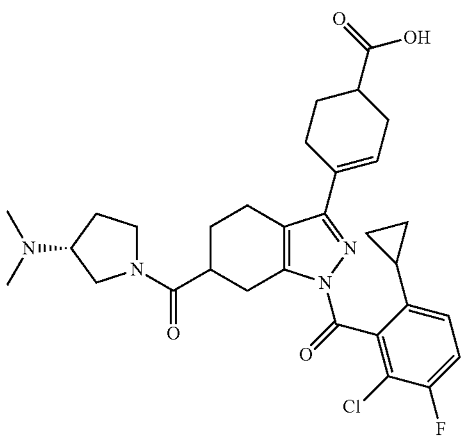 [SMILES: CN(C)[C@@H]1CCN(C(=O)C2CCc3c(C4=CCC(C(=O)O)CC4)nn(C(=O)c4c(C5CC5)ccc(F)c4Cl)c3C2)C1] | 4-((R or S)-1-(2-chloro-6-cyclopropyl-3-fluorobenzoyl)-6-((R)-3-(dimethylamino)pyrrolidine-1-carbonyl)-4,5,6,7-tetrahydro-1H-indazol-3-yl)cyclohex-3-ene-1-carboxylic acid | 583 |
| 4B | 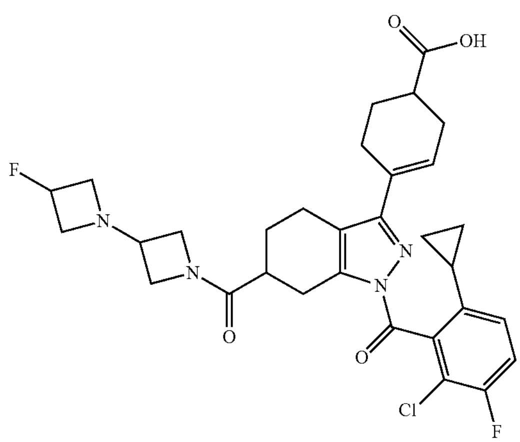 [SMILES: O=C(O)C1CC=C(c2nn(C(=O)c3c(C4CC4)ccc(F)c3Cl)c3c2CCC(C(=O)N2CC(N4CC(F)C4)C2)C3)CC1] | 4-((R or S)-1-(2-chloro-6-cyclopropyl-3-fluorobenzoyl)-6-(3-fluoro-[1,3'-biazetidine]-1'-carbonyl)-4,5,6,7-tetrahydro-1H-indazol-3-yl)cyclohex-3-ene-1-carboxylic acid | 599 |

TABLE 9-continued

| Example No. | Structure | IUPAC Name | Exact Mass [M + H]+ |
|---|---|---|---|
| 4C | 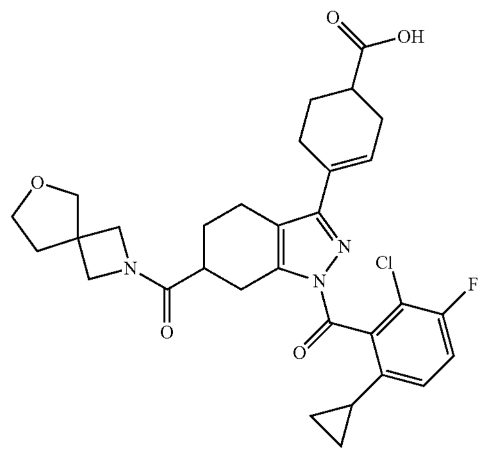 [SMILES: O=C(O)C1CC=C(c2nn(C(=O)c3c(C4CC4)ccc(F)c3Cl)c3c2CCC(C(=O)N2CC4(CCOC4)C2)C3)CC1] | 4-((R or S)-1-(2-chloro-6-cyclopropyl-3-fluorobenzoyl)-6-(6-oxa-2-azaspiro[3.4]octane-1-carbonyl)-4,5,6,7-tetrahydro-1H-indazol-3-yl)cyclohex-3-ene-1-carboxylic acid | 582 |
| 4D | 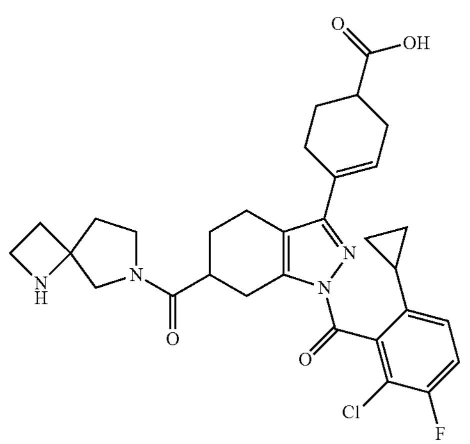 [SMILES: O=C(O)C1CC=C(c2nn(C(=O)c3c(C4CC4)ccc(F)c3Cl)c3c2CCC(C(=O)N2CCC4(CCN4)C2)C3)CC1] | 4-((6R or S)-1-(2-chloro-6-cyclopropyl-3-fluorobenzoyl)-6-(1,6-diazaspiro[3.4]octane-6-carbonyl)-4,5,6,7-tetrahydro-1H-indazol-3-yl)cyclohex-3-ene-1-carboxylic acid | 581 |
| 4E | 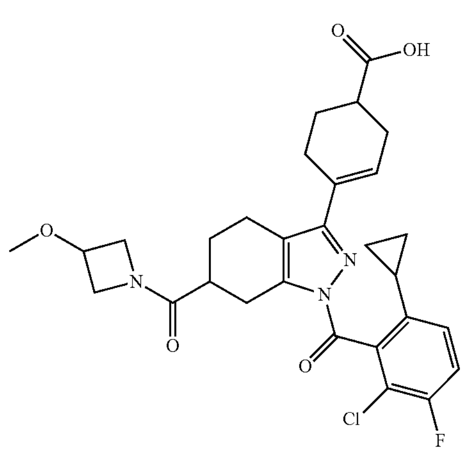 [SMILES: COC1CN(C(=O)C2CCc3c(C4=CCC(C(=O)O)CC4)nn(C(=O)c4c(C5CC5)ccc(F)c4Cl)c3C2)C1] | 4-((R or S)-1-(2-chloro-6-cyclopropyl-3-fluorobenzoyl)-6-(3-methoxyazetidine-1-carbonyl)-4,5,6,7-tetrahydro-1H-indazol-3-yl)cyclohex-3-ene-1-carboxylic acid | 556 |

TABLE 9-continued
| Example No. | Structure | IUPAC Name | Exact Mass [M + H]+ |
| --- | --- | --- | --- |
| 4F | 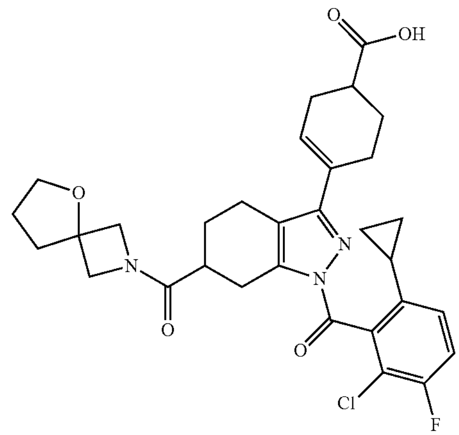 [SMILES: O=C(O)C1CC=C(c2nn(C(=O)c3c(C4CC4)ccc(F)c3Cl)c3c2CCC(C(=O)N2CC4(CCCO4)C2)C3)CC1] | 4-((R or S)-1-(2-chloro-6-cyclopropyl-3-fluorobenzoyl)-6-(5-oxa-2-azaspiro[3.4]octane-2-carbonyl)-4,5,6,7-tetrahydro-1H-indazol-3-yl)cyclohex-3-ene-1-carboxylic acid | 582 |
Example 5A
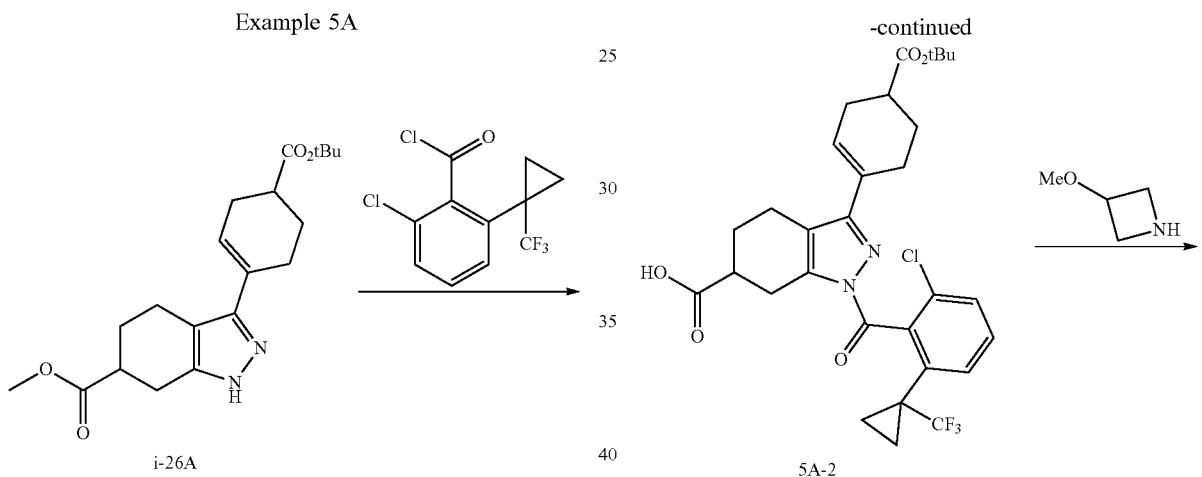
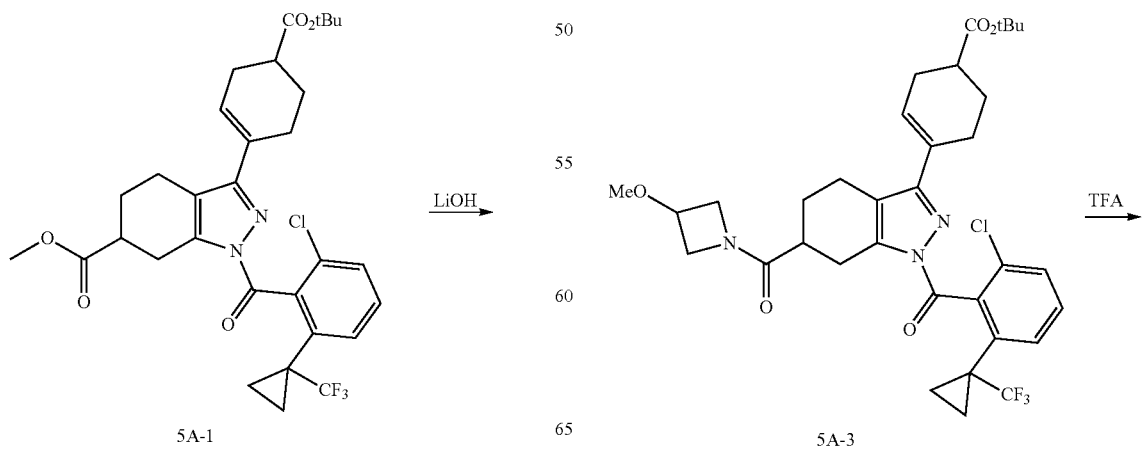

131

-continued

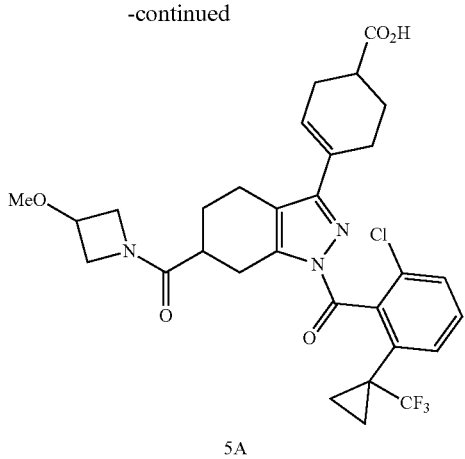

5A (R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-H-indazol-3-yl)cyclohex-3-ene-1-carboxylic acid Step 1. Preparation of methyl (R or S)-3-((R or S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylate (5A-1)

To an oven dried microwave vial equipped with magnetic stir bar under an atmosphere of $N_2$, methyl (R or S)-3-((R or S)-4-(tert-butoxycarbonyl)cyclohex-1-en-1-yl)-4,5,6,7-tetrahydro-1H-indazole-6-carboxylate i-26A (500 mg, 1.39 mmol, 1 equiv), and pyridine (3.47 mL, 0.4 M) were added, followed by 2-chloro-6-(1-(trifluoromethyl)cyclopropyl)benzoyl chloride (750 mg, 2.65 mmol, 1.9 equiv). The reaction mixture was stirred at 70° C. for 24 h. The resulting crude material was cooled to room temperature, diluted with DCM (3 mL), and then purified using $SiO_2$ gel chromatography to afford the title compound. MS: 607 (M+1).

Step 2. Preparation of (R or S)-3-((R or S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylic acid (5A-2)

To an oven dried microwave vial equipped with magnetic stir bar under an atmosphere of $N_2$, methyl (R or S)-3-((R or S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylate (145 mg, 0.24 mmol, 1 equiv), THF (1.9 mL, 0.1 M), and water (478 µL, 0.1 M) were added, followed by lithium hydroxide (17 mg, 0.72 mmol, 3.0 equiv). The reaction mixture was stirred at room temperature for 6 h. The reaction was quenched with saturated aqueous $NH_4Cl$ (10 mL), and diluted with EtOAc (20 mL). The layers were separated, and the aqueous layer was extracted with EtOAc (3×20 mL). The combined organic layers were washed with brine (25 mL), dried over solid

132

$Na_2SO_4$, and concentrated in vacuo to afford desired product, used without further purification. MS: 593 (M+1).

Step 3. Preparation of tert-butyl (R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)cyclohex-3-ene-1-carboxylate (5A-3)

To an oven dried microwave vial equipped with magnetic stir bar under an atmosphere of $N_2$, (R or S)-3-((R or S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylic acid 5A-2 (142 mg, 0.24 mmol, 1 equiv), 1-[Bis(dimethylamino)methylene]-1H-1,2,3-triazolo[4,5-b]pyridinium 3-oxide hexafluorophosphate (HATU; 137 mg, 0.36 mmol, 1.5 equiv), ethyldiisopropylamine (167 µL, 0.96 mmol, 6 equiv), and DMF (1.2 mL, 0.2 M) were added. The reaction was stirred at room temperature for 15 minutes, followed by the addition of 3-methoxyazetidin-1-ium chloride (44.4 mg, 0.36 mmol, 1.5 equiv). The reaction mixture was stirred at room temperature for 30 minutes, and then purified using $SiO_2$ gel chromatography to afford the desired product. MS: 662 (M+1).

Step 4. Preparation of (R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid (5A)

To an oven dried microwave vial equipped with magnetic stir bar under an atmosphere of $N_2$, tert-butyl (R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)cyclohex-3-ene-1-carboxylate (90 mg, 0.14 mmol, 1 equiv), and DCM (1.1 mL, 0.1 M) were added, followed by trifluoroacetic acid (272 µL, 0.1 M). The reaction mixture was stirred at room temperature for 1 h, and then concentrated in vacuo. The resulting oil was purified using mass directed reverse phase chromatography to yield (R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid. MS: 606 (M+1). $^1$H NMR (DMSO-d6) δ (ppm): 12.14 (s, 1H), 7.57-7.52 (m, 3H), 6.16 (d, J=12.43 Hz, 1H), 4.37 (m, 1H), 4.19 (m, 1H), 4.04-4.00 (m, 2H), 3.66 (t, J=12.35 Hz, 1H), 3.15 (m, 4H), 3.02 (m, 1H), 2.73 (m, 1H), 2.59-2.52 (m, 2H), 2.42 (m, 1H), 2.31 (m, 1H), 2.27 (m, 1H), 2.07 (m, 1H), 2.04 (m, 1H), 1.99 (m, 1H), 1.91 (m, 1H), 1.84 (m, 1H), 1.58 (m, 1H), 1.50 (m, 1H), 1.30 (m, 1H), 1.14 (m, 1H), 0.66 (m, 1H).

The following examples shown in Table 10 were prepared following similar procedures described above.

TABLE 10

| Example No. | Structure | IUPAC Name | Exact Mass [M + H]+ |
|---|---|---|---|
| 5B | 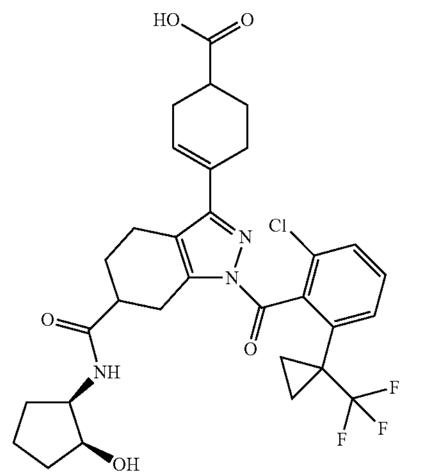 [SMILES: O=C(O)C1CC=C(c2nn(C(=O)c3c(Cl)cccc3C3(C(F)(F)F)CC3)c3c2CCC(C(=O)N[C@@H]2CCC[C@@H]2O)C3)CC1] | (R or S)-4-((R or S)-1-(2-chloro-6-(1-(trifluoromethyl)cyclopropyl)benzoyl)-6-(((1R,2S)-2-hydroxycyclopentyl)carbamoyl)-4,5,6,7-tetrahydro-1H-indazol-3-yl)cyclohex-3-ene-1-carboxylic acid | 620 |
| 5C | 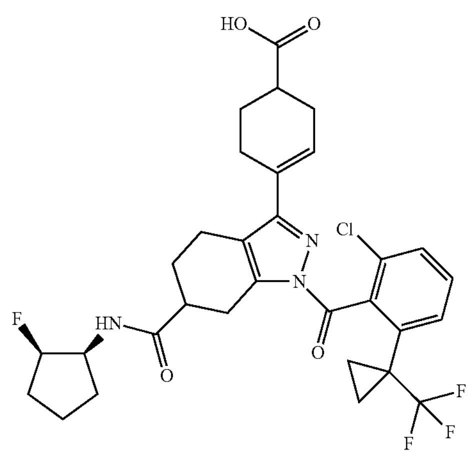 [SMILES: O=C(O)C1CC=C(c2nn(C(=O)c3c(Cl)cccc3C3(C(F)(F)F)CC3)c3c2CCC(C(=O)N[C@H]2CCC[C@H]2F)C3)CC1] | (R or S)-4-((R or S)-1-(2-chloro-6-(1-(trifluoromethyl)cyclopropyl)benzoyl)-6-(((1S,2R)-2-fluorocyclopentyl)carbamoyl)-4,5,6,7-tetrahydro-1H-indazol-3-yl)cyclohex-3-ene-1-carboxylic acid | 622 |
| 5D | 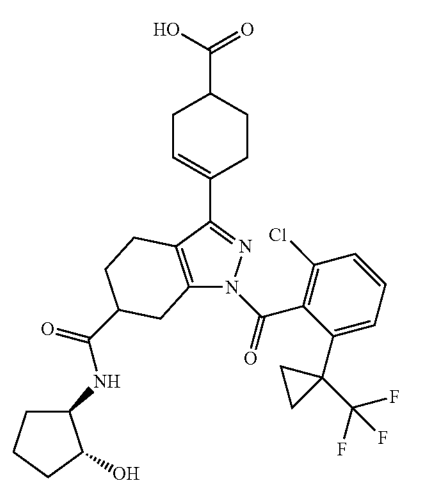 [SMILES: O=C(O)C1CC=C(c2nn(C(=O)c3c(Cl)cccc3C3(C(F)(F)F)CC3)c3c2CCC(C(=O)N[C@@H]2CCC[C@H]2O)C3)CC1] | (R or S)-4-((R or S)-1-(2-chloro-6-(1-(trifluoromethyl)cyclopropyl)benzoyl)-6-(((1R,2R)-2-hydroxycyclopentyl)carbamoyl)-4,5,6,7-tetrahydro-1H-indazol-3-yl)cyclohex-3-ene-1-carboxylic acid | 620 |

TABLE 10-continued

| Example No. | Structure | IUPAC Name | Exact Mass [M + H]+ |
|---|---|---|---|
| 5E | 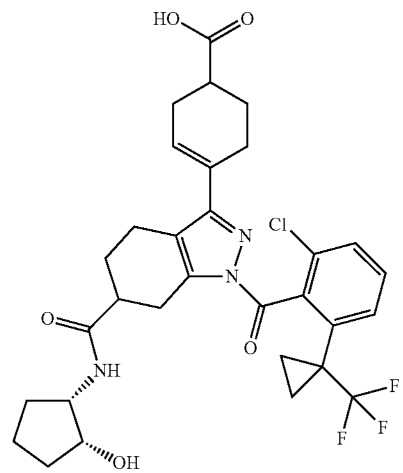 [SMILES: O=C(O)C1CC=C(c2nn(C(=O)c3c(Cl)cccc3C3(C(F)(F)F)CC3)c3c2CCC(C(=O)N[C@H]2CCC[C@H]2O)C3)CC1] | (R or S)-4-((R or S)-1-(2-chloro-6-(1-(trifluoromethyl)cyclopropyl)benzoyl)-6-((((1S,2R)-2-hydroxycyclopentyl)carbamoyl)-4,5,6,7-tetrahydro-1H-indazol-3-yl)cyclohex-3-ene-1-carboxylic acid | 620 |
| 5F | 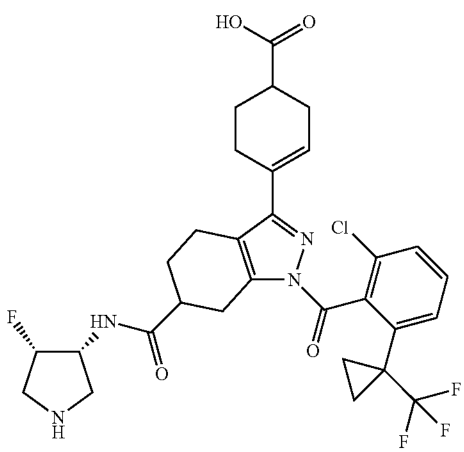 [SMILES: O=C(O)C1CC=C(c2nn(C(=O)c3c(Cl)cccc3C3(C(F)(F)F)CC3)c3c2CCC(C(=O)N[C@@H]2CNC[C@@H]2F)C3)CC1] | (R or S)-4-((R or S)-1-(2-chloro-6-(1-(trifluoromethyl)cyclopropyl)benzoyl)-6-((((3R,4S)-4-fluoropyrrolidin-3-yl)carbamoyl)-4,5,6,7-tetrahydro-1H-indazol-3-yl)cyclohex-3-ene-1-carboxylic acid | 623 |
| 5G | 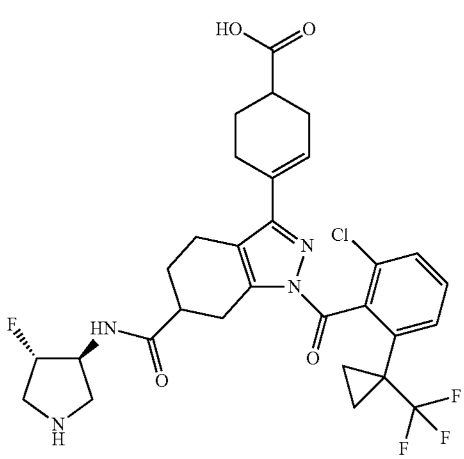 [SMILES: O=C(O)C1CC=C(c2nn(C(=O)c3c(Cl)cccc3C3(C(F)(F)F)CC3)c3c2CCC(C(=O)N[C@H]2CNC[C@@H]2F)C3)CC1] | (R or S)-4-((R or S)-1-(2-chloro-6-(1-(trifluoromethyl)cyclopropyl)benzoyl)-6-((((3S,4S)-4-fluoropyrrolidin-3-yl)carbamoyl)-4,5,6,7-tetrahydro-1H-indazol-3-yl)cyclohex-3-ene-1-carboxylic acid | 623 |

TABLE 10-continued

| Example No. | Structure | IUPAC Name | Exact Mass [M + H]+ |
|---|---|---|---|
| 5H | 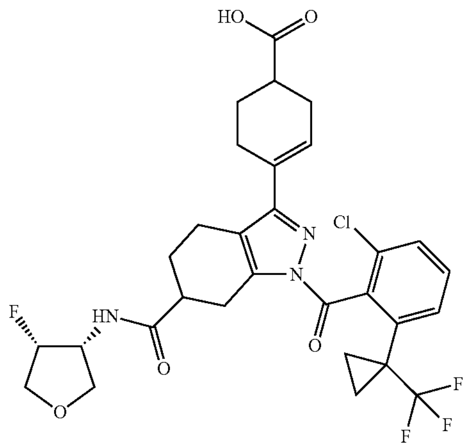 [SMILES: O=C(O)C1CC=C(c2nn(C(=O)c3c(Cl)cccc3C3(C(F)(F)F)CC3)c3c2CCC(C(=O)N[C@@H]2COC[C@@H]2F)C3)CC1] | (R or S)-4-((R or S)-1-(2-chloro-6-(1-(trifluoromethyl)cyclopropyl)benzoyl)-6-(((3R,4R)-4-fluorotetrahydrofuran-3-yl)carbamoyl)-4,5,6,7-tetrahydro-1H-indazol-3-yl)cyclohex-3-ene-1-carboxylic acid | 624 |
| 5I | 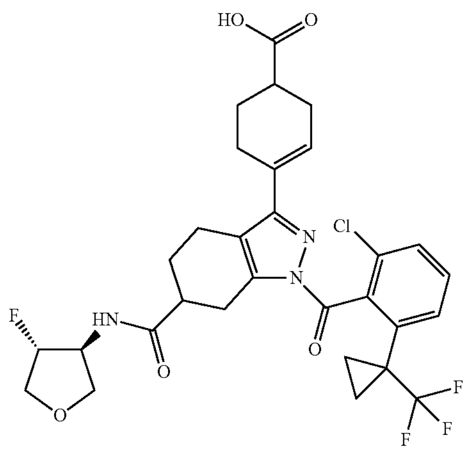 [SMILES: O=C(O)C1CC=C(c2nn(C(=O)c3c(Cl)cccc3C3(C(F)(F)F)CC3)c3c2CCC(C(=O)N[C@H]2COC[C@@H]2F)C3)CC1] | (R or S)-4-((R or S)-1-(2-chloro-6-(1-(trifluoromethyl)cyclopropyl)benzoyl)-6-(((3S,4R)-4-fluorotetrahydrofuran-3-yl)carbamoyl)-4,5,6,7-tetrahydro-1H-indazol-3-yl)cyclohex-3-ene-1-carboxylic acid | 624 |
| 5J | 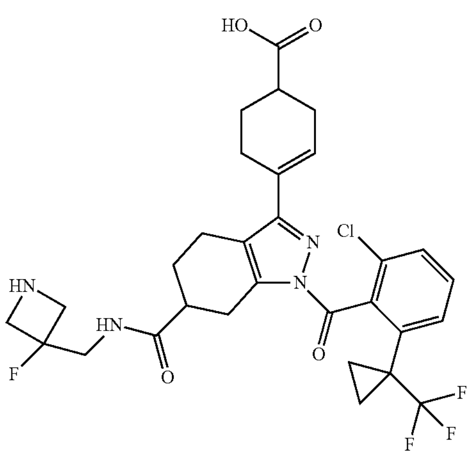 [SMILES: O=C(O)C1CC=C(c2nn(C(=O)c3c(Cl)cccc3C3(C(F)(F)F)CC3)c3c2CCC(C(=O)NCC2(F)CNC2)C3)CC1] | (R or S)-4-((R or S)-1-(2-chloro-6-(1-(trifluoromethyl)cyclopropyl)benzoyl)-6-(((3-fluoroazetidin-3-yl)methyl)carbamoyl)-4,5,6,7-tetrahydro-1H-indazol-3-yl)cyclohex-3-ene-1-carboxylic acid | 623 |

TABLE 10-continued

| Example No. | Structure | IUPAC Name | Exact Mass [M + H]+ |
|---|---|---|---|
| 5K | 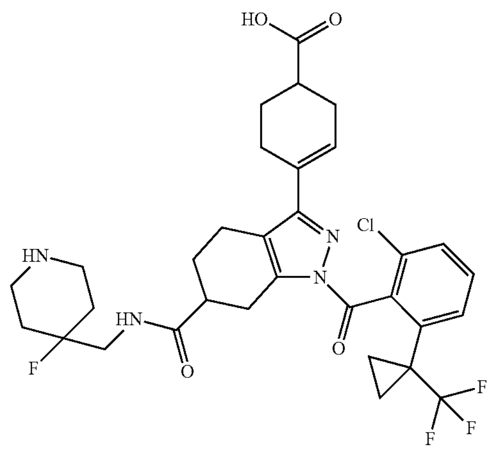 [SMILES: O=C(O)C1CC=C(c2nn(C(=O)c3c(Cl)cccc3C3(C(F)(F)F)CC3)c3c2CCC(C(=O)NCC2(F)CCNCC2)C3)CC1] | (R or S)-4-((R or S)-1-(2-chloro-6-(1-(trifluoromethyl)cyclopropyl)benzoyl)-6-(((4-fluoropiperidin-4-yl)methyl)carbamoyl)-4,5,6,7-tetrahydro-1H-indazol-3-yl)cyclohex-3-ene-1-carboxylic acid | 651 |
| 5L | 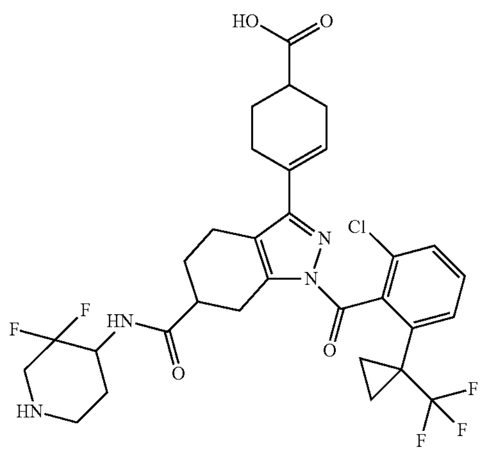 [SMILES: O=C(O)C1CC=C(c2nn(C(=O)c3c(Cl)cccc3C3(C(F)(F)F)CC3)c3c2CCC(C(=O)NC2CCNCC2(F)F)C3)CC1] | (1R or S)-4-((6R or S)-1-(2-chloro-6-(1-(trifluoromethyl)cyclopropyl)benzoyl)-6-((3,3-difluoropiperidin-4-yl)carbamoyl)-4,5,6,7-tetrahydro-1H-indazol-3-yl)cyclohex-3-ene-1-carboxylic acid | 655 |
| 5M | 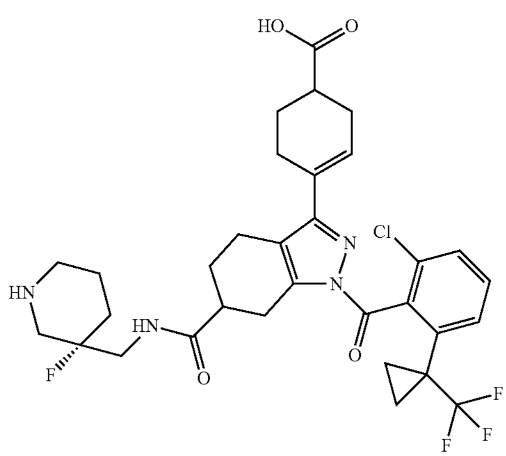 [SMILES: O=C(O)C1CC=C(c2nn(C(=O)c3c(Cl)cccc3C3(C(F)(F)F)CC3)c3c2CCC(C(=O)NC[C@]2(F)CCCNC2)C3)CC1] | (R or S)-4-((R or S)-1-(2-chloro-6-(1-(trifluoromethyl)cyclopropyl)benzoyl)-6-((((S)-3-fluoropiperidin-3-yl)methyl)carbamoyl)-4,5,6,7-tetrahydro-1H-indazol-3-yl)cyclohex-3-ene-1-carboxylic acid | 651 |

TABLE 10-continued

| Example No. | Structure | IUPAC Name | Exact Mass [M + H]+ |
|---|---|---|---|
| 5N | 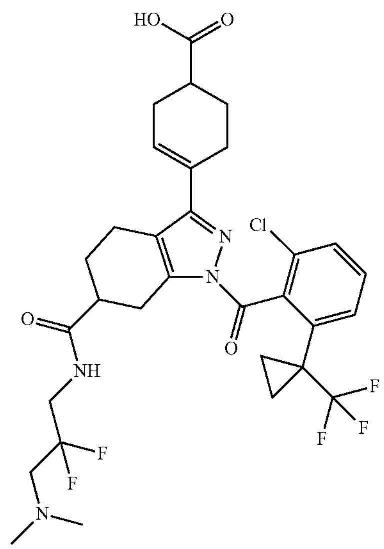 [SMILES: CN(C)CC(F)(F)CNC(=O)C1CCc2c(C3=CCC(C(=O)O)CC3)nn(C(=O)c3c(Cl)cccc3C3(C(F)(F)F)CC3)c2C1] | (R or S)-4-((R or S)-1-(2-chloro-6-(1-(trifluoromethyl)cyclopropyl)benzoyl)-6-((3-(dimethylamino)-2,2-difluoropropyl)carbamoyl)-4,5,6,7-tetrahydro-1H-indazol-3-yl)cyclohex-3-ene-1-carboxylic acid | 657 |
| 5O | 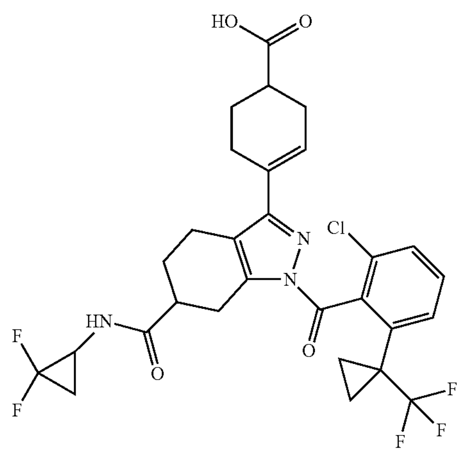 [SMILES: O=C(O)C1CC=C(c2nn(C(=O)c3c(Cl)cccc3C3(C(F)(F)F)CC3)c3c2CCC(C(=O)NC2CC2(F)F)C3)CC1] | (1R or S)-4-((6R or S)-1-(2-chloro-6-(1-(trifluoromethyl)cyclopropyl)benzoyl)-6-((2,2-difluorocyclopropyl)carbamoyl)-4,5,6,7-tetrahydro-1H-indazol-3-yl)cyclohex-3-ene-1-carboxylic acid | 612 |
| 5P | 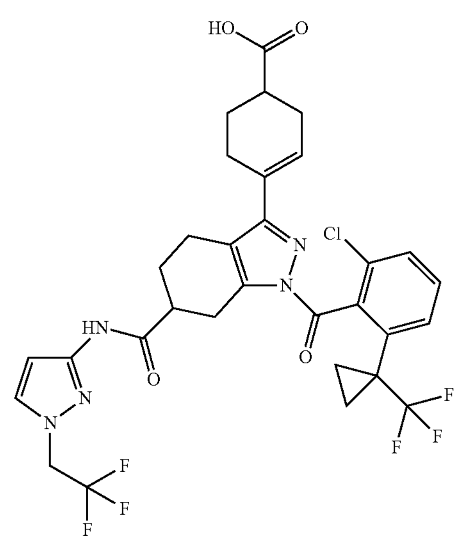 [SMILES: O=C(O)C1CC=C(c2nn(C(=O)c3c(Cl)cccc3C3(C(F)(F)F)CC3)c3c2CCC(C(=O)Nc2ccn(CC(F)(F)F)n2)C3)CC1] | (R or S)-4-((R or S)-1-(2-chloro-6-(1-(trifluoromethyl)cyclopropyl)benzoyl)-6-((1-(2,2,2-trifluoroethyl)-1H-pyrazol-3-yl)carbamoyl)-4,5,6,7-tetrahydro-1H-indazol-3-yl)cyclohex-3-ene-1-carboxylic acid | 684 |

TABLE 10-continued

| Example No. | Structure | IUPAC Name | Exact Mass [M + H]+ |
|---|---|---|---|
| 5Q | 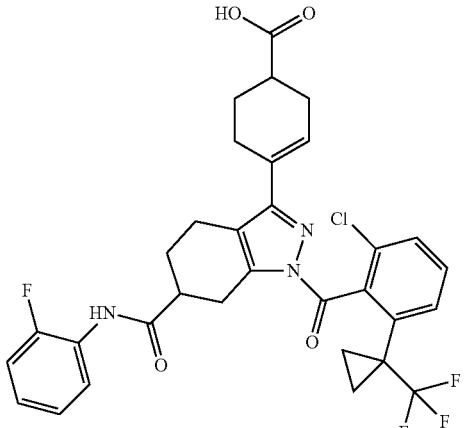 | (R or S)-4-((R or S)-1-(2-chloro-6-(1-(trifluoromethyl)cyclopropyl)benzoyl)-6-((2-fluorophenyl)carbamoyl)-4,5,6,7-tetrahydro-1H-indazol-3-yl)cyclohex-3-ene-1-carboxylic acid | 630 |
| 5R | 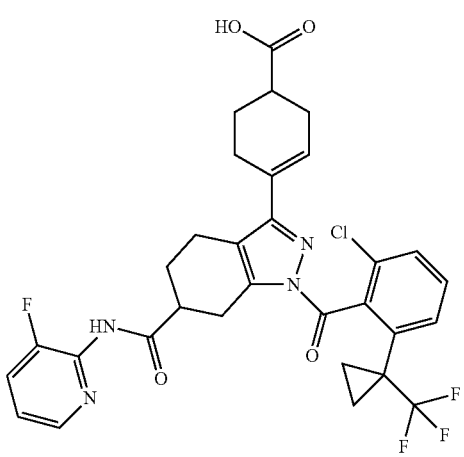 [SMILES: O=C(O)C1CC=C(c2nn(C(=O)c3c(Cl)cccc3C3(C(F)(F)F)CC3)c3c2CCC(C(=O)Nc2ncccc2F)C3)CC1] | (R or S)-4-((R or S)-1-(2-chloro-6-(1-(trifluoromethyl)cyclopropyl)benzoyl)-6-((3-fluoropyridin-2-yl)carbamoyl)-4,5,6,7-tetrahydro-1H-indazol-3-yl)cyclohex-3-ene-1-carboxylic acid | 631 |
| 5S | 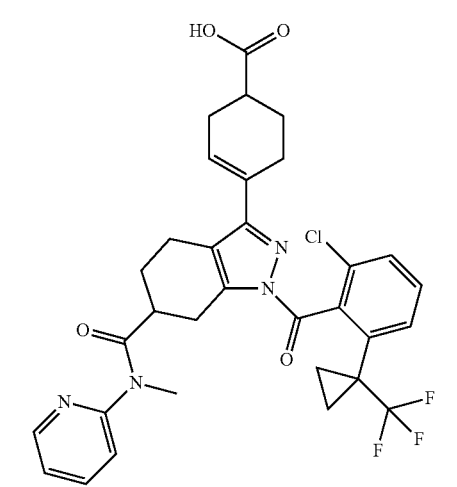 [SMILES: CN(C(=O)C1CCc2c(C3=CCC(C(=O)O)CC3)nn(C(=O)c3c(Cl)cccc3C3(C(F)(F)F)CC3)c2C1)c1ccccn1] | (R or S)-4-((R or S)-1-(2-chloro-6-(1-(trifluoromethyl)cyclopropyl)benzoyl)-6-(methyl(pyridin-2-yl)carbamoyl)-4,5,6,7-tetrahydro-1H-indazol-3-yl)cyclohex-3-ene-1-carboxylic acid | 627 |

TABLE 10-continued

| Example No. | Structure | IUPAC Name | Exact Mass [M + H]+ |
|---|---|---|---|
| 5T | 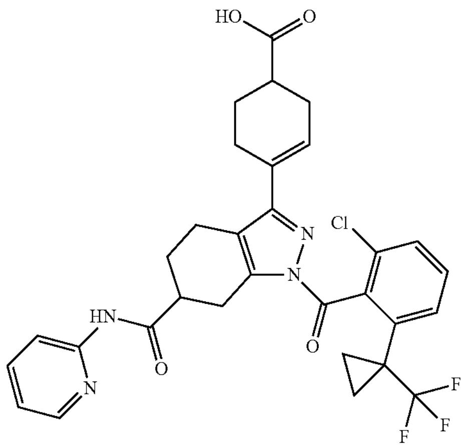 [SMILES: O=C(O)C1CC=C(c2nn(C(=O)c3c(Cl)cccc3C3(C(F)(F)F)CC3)c3c2CCC(C(=O)Nc2ccccn2)C3)CC1] | (R or S)-4-((R or S)-1-(2-chloro-6-(1-(trifluoromethyl)cyclopropyl)benzoyl)-6-(pyridin-2-ylcarbamoyl)-4,5,6,7-tetrahydro-1H-indazol-3-yl)cyclohex-3-ene-1-carboxylic acid | 613 |
| 5U | 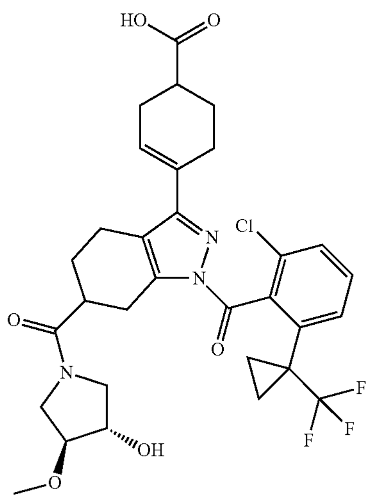 [SMILES: CO[C@H]1CN(C(=O)C2CCc3c(C4=CCC(C(=O)O)CC4)nn(C(=O)c4c(Cl)cccc4C4(C(F)(F)F)CC4)c3C2)C[C@@H]1O] | (R or S)-4-((R or S)-1-(2-chloro-6-(1-(trifluoromethyl)cyclopropyl)benzoyl)-6-((3S,4S)-3-hydroxy-4-methoxypyrrolidine-1-carbonyl)-4,5,6,7-tetrahydro-1H-indazol-3-yl)cyclohex-3-ene-1-carboxylic acid | 636 |
| 5V | 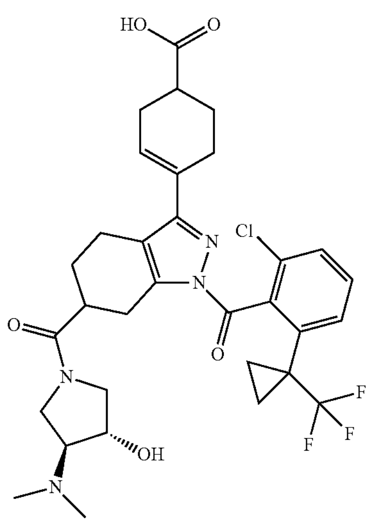 [SMILES: CN(C)[C@H]1CN(C(=O)C2CCc3c(C4=CCC(C(=O)O)CC4)nn(C(=O)c4c(Cl)cccc4C4(C(F)(F)F)CC4)c3C2)C[C@@H]1O] | (R or S)-4-((R or 5)-1-(2-chloro-6-(1-(trifluoromethyl)cyclopropyl)benzoyl)-6-((3S,4S)-3-(dimethylamino)-4-hydroxypyrrolidine-1-carbonyl)-4,5,6,7-tetrahydro-1H-indazol-3-yl)cyclohex-3-ene-1-carboxylic acid | 649 |

TABLE 10-continued

| Example No. | Structure | IUPAC Name | Exact Mass [M + H]+ |
|---|---|---|---|
| 5W | 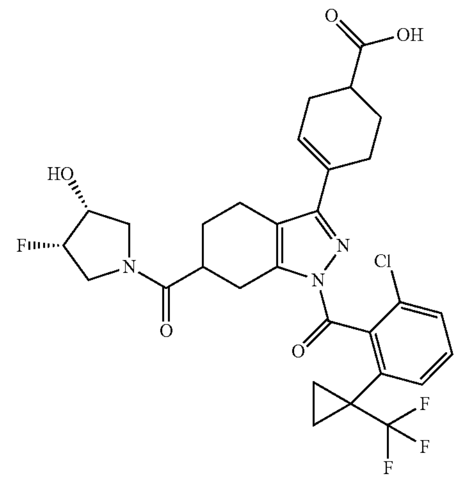 [SMILES: O=C(O)C1CC=C(c2nn(C(=O)c3c(Cl)cccc3C3(C(F)(F)F)CC3)c3c2CCC(C(=O)N2C[C@@H](O)[C@@H](F)C2)C3)CC1] | (R or S)-4-((R or S)-1-(2-chloro-6-(1-(trifluoromethyl)cyclopropyl)benzoyl)-6-((3S,4R)-3-fluoro-4-hydroxypyrrolidine-1-carbonyl)-4,5,6,7-tetrahydro-1H-indazol-3-yl)cyclohex-3-ene-1-carboxylic acid | 624 |
| 5X | 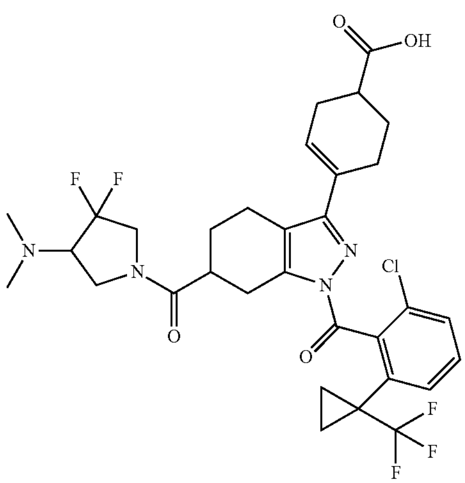 [SMILES: CN(C)C1CN(C(=O)C2CCc3c(C4=CCC(C(=O)O)CC4)nn(C(=O)c4c(Cl)cccc4C4(C(F)(F)F)CC4)c3C2)CC1(F)F] | (1R or S)-4-((6R or S)-1-(2-chloro-6-(1-(trifluoromethyl)cyclopropyl)benzoyl)-6-(4-(dimethylamino)-3,3-difluoropyrrolidine-1-carbonyl)-4,5,6,7-tetrahydro-1H-indazol-3-yl)cyclohex-3-ene-1-carboxylic acid | 669 |
| 5Y | 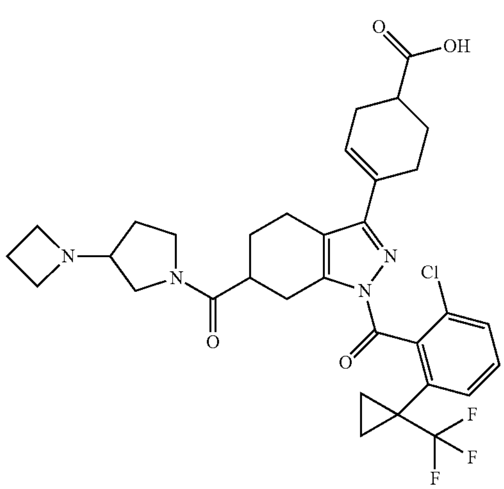 [SMILES: O=C(O)C1CC=C(c2nn(C(=O)c3c(Cl)cccc3C3(C(F)(F)F)CC3)c3c2CCC(C(=O)N2CCC(N4CCC4)C2)C3)CC1] | (R or S)-4-((6R or S)-6-(3-(azetidin-1-yl)pyrrolidine-1-carbonyl)-1-(2-chloro-6-(1-(trifluoromethyl)cyclopropyl)benzoyl)-4,5,6,7-tetrahydro-1H-indazol-3-yl)cyclohex-3-ene-1-carboxylic acid | 645 |

TABLE 10-continued

| Example No. | Structure | IUPAC Name | Exact Mass [M + H]+ |
|---|---|---|---|
| 5Z | 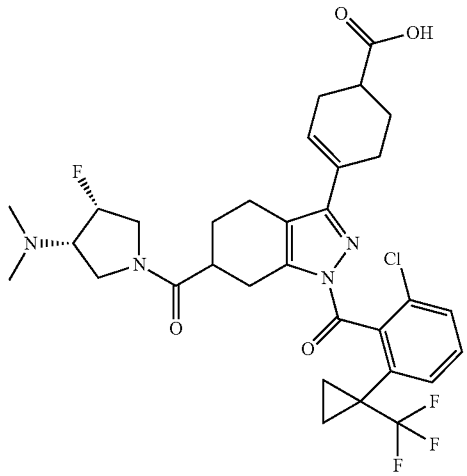 [SMILES: CN(C)[C@H]1CN(C(=O)C2CCc3c(C4=CCC(C(=O)O)CC4)nn(C(=O)c4c(Cl)cccc4C4(C(F)(F)F)CC4)c3C2)C[C@H]1F] | (R or S)-4-((R or S)-1-(2-chloro-6-(1-(trifluoromethyl)cyclopropyl)benzoyl)-6-((3S,4R)-3-(dimethylamino)-4-fluoropyrrolidine-1-carbonyl)-4,5,6,7-tetrahydro-1H-indazol-3-yl)cyclohex-3-ene-1-carboxylic acid | 651 |
| 5AA | 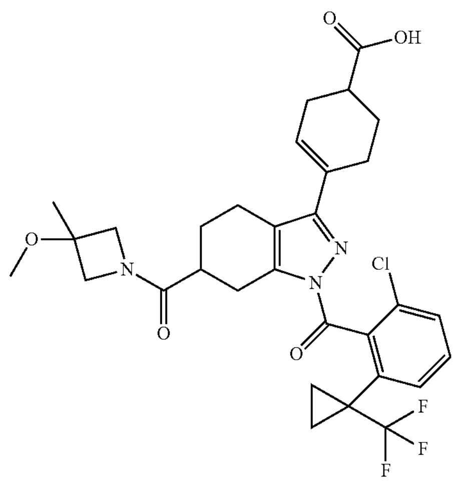 [SMILES: COC1(C)CN(C(=O)C2CCc3c(C4=CCC(C(=O)O)CC4)nn(C(=O)c4c(Cl)cccc4C4(C(F)(F)F)CC4)c3C2)C1] | (R or S)-4-((R or S)-1-(2-chloro-6-(1-(trifluoromethyl)cyclopropyl)benzoyl)-6-(3-methoxy-3-methylazetidine-1-carbonyl)-4,5,6,7-tetrahydro-1H-indazol-3-yl)cyclohex-3-ene-1-carboxylic acid | 620 |
| 5BB | 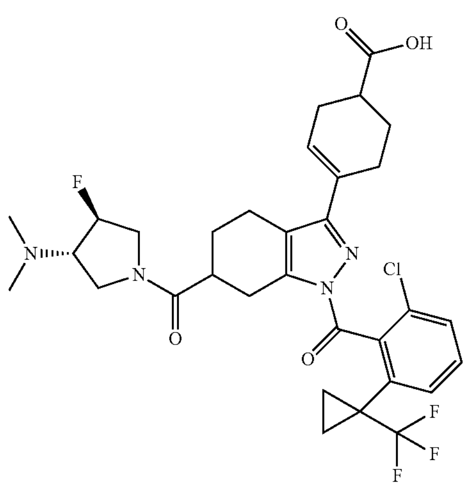 [SMILES: CN(C)[C@H]1CN(C(=O)C2CCc3c(C4=CCC(C(=O)O)CC4)nn(C(=O)c4c(Cl)cccc4C4(C(F)(F)F)CC4)c3C2)C[C@@H]1F] | (R or S)-4-((R or S)-1-(2-chloro-6-(1-(trifluoromethyl)cyclopropyl)benzoyl)-6-((3S,4S)-3-(dimethylamino)-4-fluoropyrrolidine-1-carbonyl)-4,5,6,7-tetrahydro-1H-indazol-3-yl)cyclohex-3-ene-1-carboxylic acid | 651 |

TABLE 10-continued

| Example No. | Structure | IUPAC Name | Exact Mass [M + H]+ |
|---|---|---|---|
| 5CC | 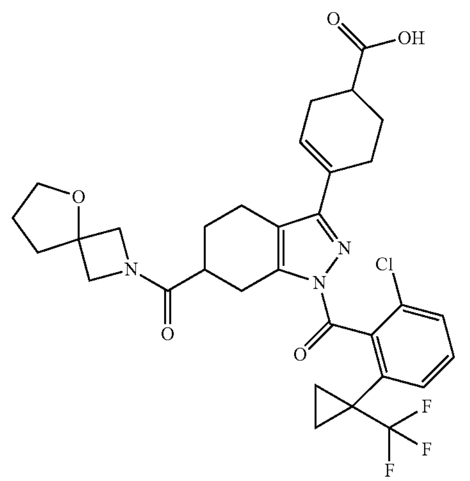 [SMILES: O=C(O)C1CC=C(c2nn(C(=O)c3c(Cl)cccc3C3(C(F)(F)F)CC3)c3c2CCC(C(=O)N2CC4(CCCO4)C2)C3)CC1] | (R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)cyclohex-3-ene-1-carboxylic acid | 632 |
| 5DD | 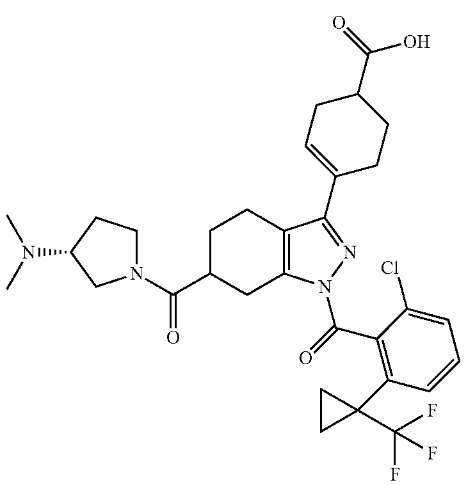 [SMILES: CN(C)[C@@H]1CCN(C(=O)C2CCc3c(C4=CCC(C(=O)O)CC4)nn(C(=O)c4c(Cl)cccc4C4(C(F)(F)F)CC4)c3C2)C1] | (R o rS)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid | 633 |
| 5EE | 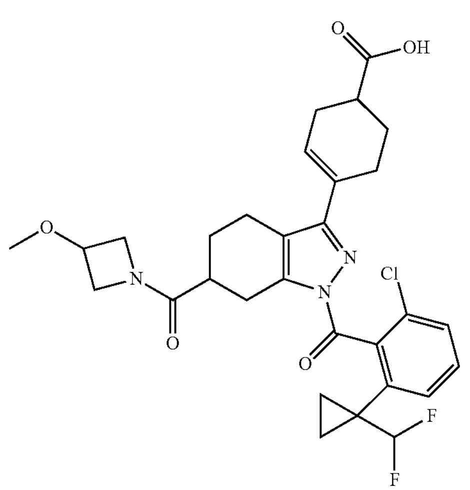 [SMILES: COC1CN(C(=O)C2CCc3c(C4=CCC(C(=O)O)CC4)nn(C(=O)c4c(Cl)cccc4C4(C(F)F)CC4)c3C2)C1] | (R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid | 588 |

TABLE 10-continued

| Example No. | Structure | IUPAC Name | Exact Mass [M + H]+ |
|---|---|---|---|
| 5FF | 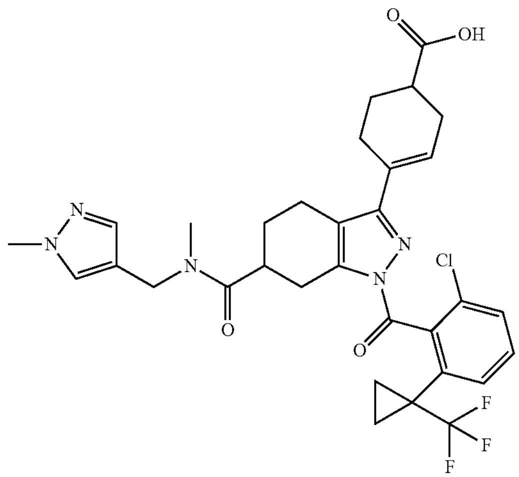 [SMILES: CN(Cc1cnn(C)c1)C(=O)C1CCc2c(C3=CCC(C(=O)O)CC3)nn(C(=O)c3c(Cl)cccc3C3(C(F)(F)F)CC3)c2C1] | (R or S)-4-((R or S)-1-(2-chloro-6-(1-(trifluoromethyl)cyclopropyl)benzoyl)-6-(methyl((1-methyl-1H-pyrazol-4-yl)methyl)carbamoyl)-4,5,6,7-tetrahydro-1H-indazol-3-yl)cyclohex-3-ene-1-carboxylic acid | 644 |
| 5GG | 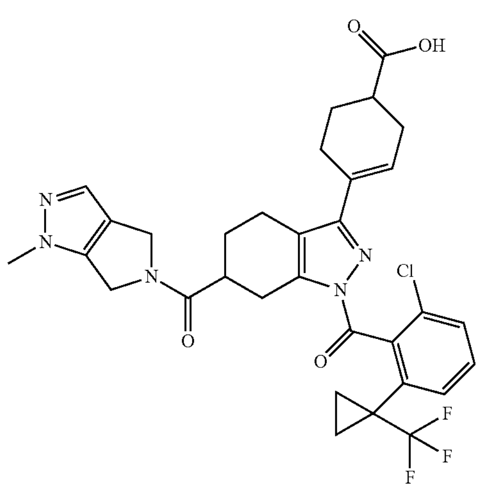 [SMILES: Cn1ncc2c1CN(C(=O)C1CCc3c(C4=CCC(C(=O)O)CC4)nn(C(=O)c4c(Cl)cccc4C4(C(F)(F)F)CC4)c3C1)C2] | (R or S)-4-((R or S)-1-(2-chloro-6-(1-(trifluoromethyl)cyclopropyl)benzoyl)-6-(1-methyl-1,4,5,6-tetrahydropyrrolo[3,4-c]pyrazole-5-carbonyl)-4,5,6,7-tetrahydro-1H-indazol-3-yl)cyclohex-3-ene-1-carboxylic acid | 642 |

TABLE 10-continued

| Example No. | Structure | IUPAC Name | Exact Mass [M + H]+ |
|---|---|---|---|
| 5HH | 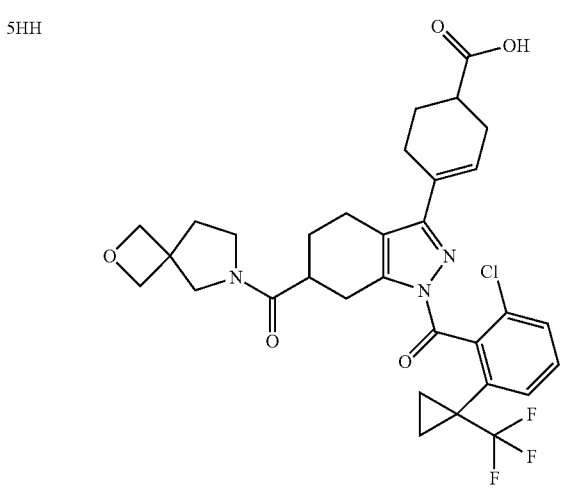 | (R or S)-4-((R or S)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid | 632 |
| 5II | 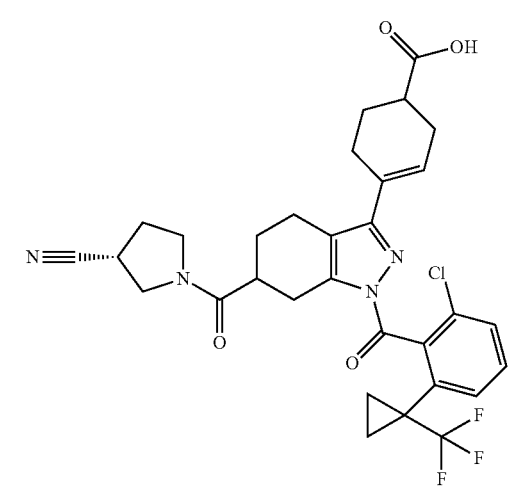 [SMILES: N#C[C@@H]1CCN(C(=O)C2CCc3c(C4=CCC(C(=O)O)CC4)nn(C(=O)c4c(Cl)cccc4C4(C(F)(F)F)CC4)c3C2)C1] | 4-((R or S)-1-(2-chloro-6-(1-(trifluoromethyl)cyclopropyl)benzoyl)-6-((R)-3-cyanopyrrolidine-1-carbonyl)-4,5,6,7-tetrahydro-1H-indazol-3-yl)cyclohex-3-ene-1-carboxylic acid | 615 |

The following examples shown in Table 11 were prepared using i-26B and following similar procedures described in Example 5A above.

TABLE 11

| Example No. | Structure | IUPAC Name | Exact Mass [M + H]+ |
| --- | --- | --- | --- |
| 6A | 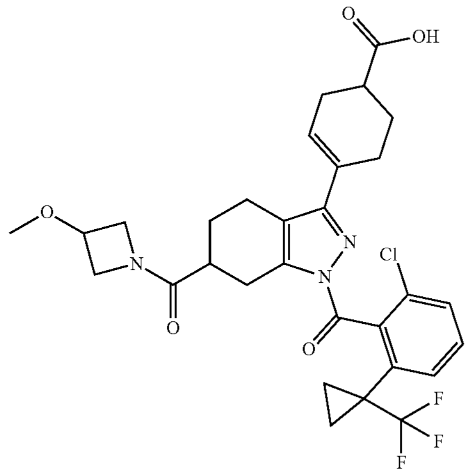 [SMILES: COC1CN(C(=O)C2CCc3c(C4=CCC(C(=O)O)CC4)nn(C(=O)c4c(Cl)cccc4C4(C(F)(F)F)CC4)c3C2)C1] | (R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid | 606 |
| 6B | 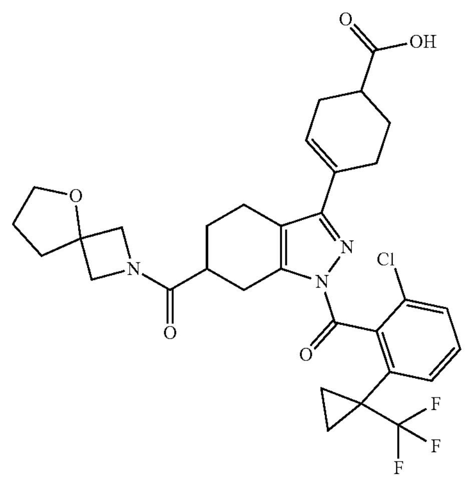 [SMILES: O=C(O)C1CC=C(c2nn(C(=O)c3c(Cl)cccc3C3(C(F)(F)F)CC3)c3c2CCC(C(=O)N2CC4(CCCO4)C2)C3)CC1] | (R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)cyclohex-3-ene-1-carboxylic acid | 632 |
| 6C | 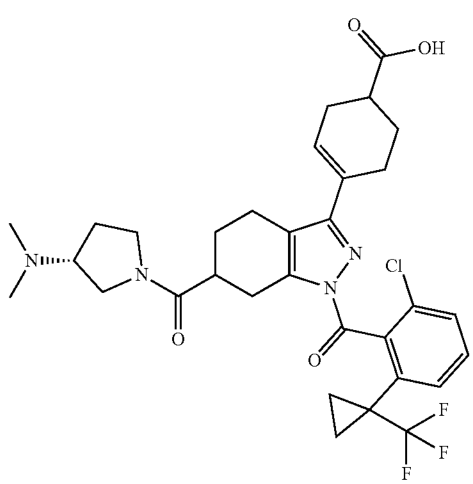 [SMILES: CN(C)[C@@H]1CCN(C(=O)C2CCc3c(C4=CCC(C(=O)O)CC4)nn(C(=O)c4c(Cl)cccc4C4(C(F)(F)F)CC4)c3C2)C1] | (R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid | 633 |

TABLE 11-continued

| Example No. | Structure | IUPAC Name | Exact Mass [M + H]+ |
|---|---|---|---|
| 6D | 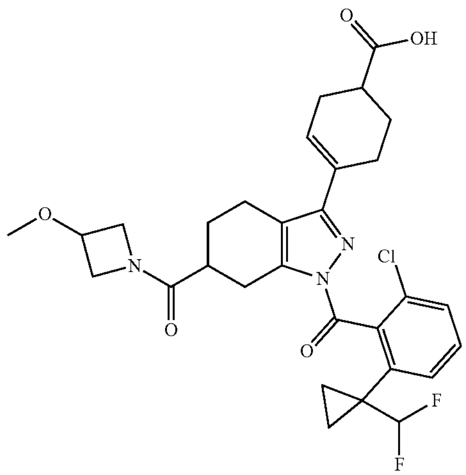 [SMILES: COC1CN(C(=O)C2CCc3c(C4=CCC(C(=O)O)CC4)nn(C(=O)c4c(Cl)cccc4C4(C(F)F)CC4)c3C2)C1] | (R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid | 588 |
| 6E | 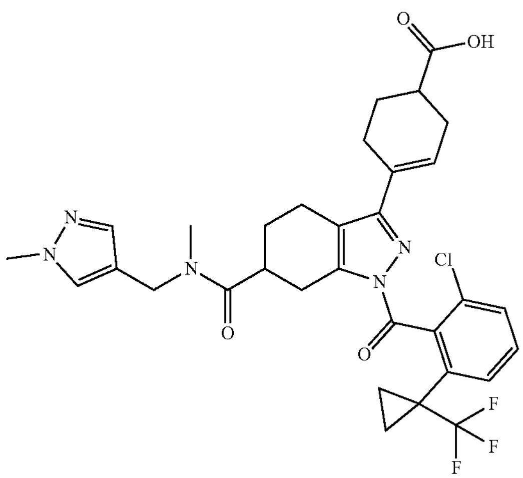 [SMILES: CN(Cc1cnn(C)c1)C(=O)C1CCc2c(C3=CCC(C(=O)O)CC3)nn(C(=O)c3c(Cl)cccc3C3(C(F)(F)F)CC3)c2C1] | (R or S)-4-((R or S)-1-(2-chloro-6-(1-(trifluoromethyl)cyclopropyl)benzoyl)-6-(methyl((1-methyl-1H-pyrazol-4-yl)methyl)carbamoyl)-4,5,6,7-tetrahydro-1H-indazol-3-yl)cyclohex-3-ene-1-carboxylic acid | 644 |
| 6F | 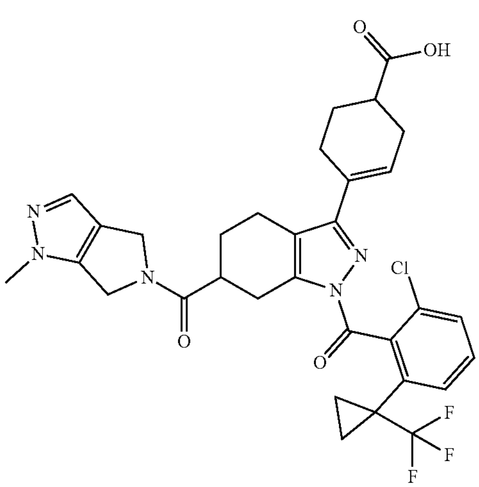 [SMILES: Cn1ncc2c1CN(C(=O)C1CCc3c(C4=CCC(C(=O)O)CC4)nn(C(=O)c4c(Cl)cccc4C4(C(F)(F)F)CC4)c3C1)C2] | (R or S)-4-((R or S)-1-(2-chloro-6-(1-(trifluoromethyl)cyclopropyl)benzoyl)-6-(1-methyl-1,4,5,6-tetrahydropyrrolo[3,4-c]pyrazole-5-carbonyl)-4,5,6,7-tetrahydro-1H-indazol-3-yl)(cyclohex-3-ene-1-carboxylic acid | 642 |

TABLE 11-continued

| Example No. | Structure | IUPAC Name | Exact Mass [M + H]+ |
|---|---|---|---|
| 6G | 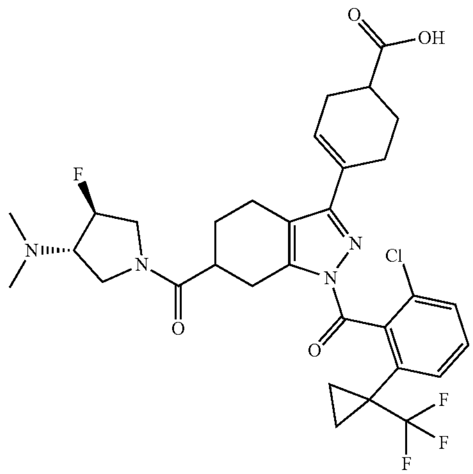 [SMILES: CN(C)[C@H]1CN(C(=O)C2CCc3c(C4=CCC(C(=O)O)CC4)nn(C(=O)c4c(Cl)cccc4C4(C(F)(F)F)CC4)c3C2)C[C@@H]1F] | (R or S)-4-((R or S)-1-(2-chloro-6-(1-(trifluoromethyl)cyclopropyl)benzoyl)-6-((3S,4S)-3-(dimethylamino)-4-fluoropyrrolidine-1-carbonyl)-4,5,6,7-tetrahydro-1H-indazol-3-yl)cyclohex-3-ene-1-carboxylic acid | 651 |
| 6H | 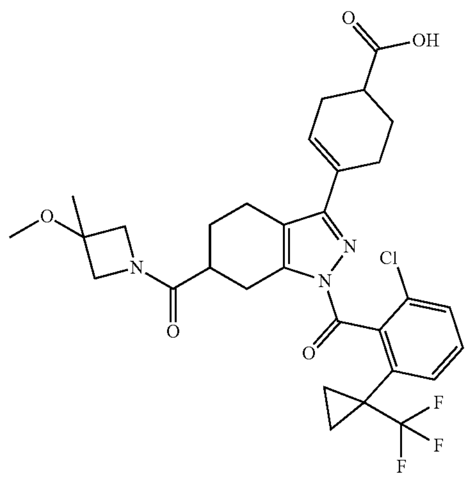 [SMILES: COC1(C)CN(C(=O)C2CCc3c(C4=CCC(C(=O)O)CC4)nn(C(=O)c4c(Cl)cccc4C4(C(F)(F)F)CC4)c3C2)C1] | (R or S)-4-((R or S)-1-(2-chloro-6-(1-(trifluoromethyl)cyclopropyl)benzoyl)-6-(3-methoxy-3-methylazelidine-1-carbonyl)-4,5,6,7-tetrahydro-1H-indazol-3-yl)cyclohex-3-ene-1-carboxylic acid | 620 |
| 6I | 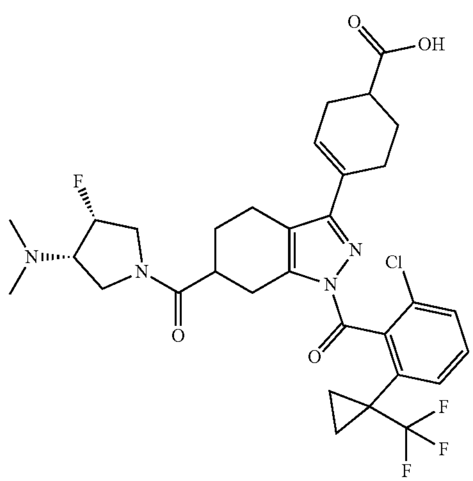 [SMILES: CN(C)[C@H]1CN(C(=O)C2CCc3c(C4=CCC(C(=O)O)CC4)nn(C(=O)c4c(Cl)cccc4C4(C(F)(F)F)CC4)c3C2)C[C@H]1F] | (R or S)-4-((R or S)-1-(2-chloro-6-(1-(trifluoromethyl)cyclopropyl)benzoyl)-6-((3S,4R)-3-(dimethylamino)-4-fluoropyrrolidine-1-carbonyl)-4,5,6,7-tetrahydro-1H-indazol-3-yl)cyclohex-3-ene-1-carboxylic acid | 651 |

TABLE 11-continued

| Example No. | Structure | IUPAC Name | Exact Mass [M + H]+ |
|---|---|---|---|
| 6J | 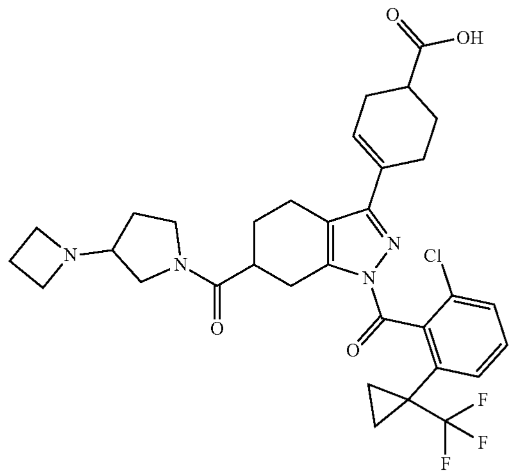 [SMILES: O=C(O)C1CC=C(c2nn(C(=O)c3c(Cl)cccc3C3(C(F)(F)F)CC3)c3c2CCC(C(=O)N2CCC(N4CCC4)C2)C3)CC1] | (1R or S)-4-((6R or S)-6-(3-(azetidin-1-yl)pyrrolidine-1-carbonyl)-1-(2-chloro-6-(1-(trifluoromethyl)cyclopropyl)benzoyl)-4,5,6,7-tetrahydro-1H-indazol-3-yl)cyclohex-3-ene-1-carboxylic acid | 645 |
| 6K | 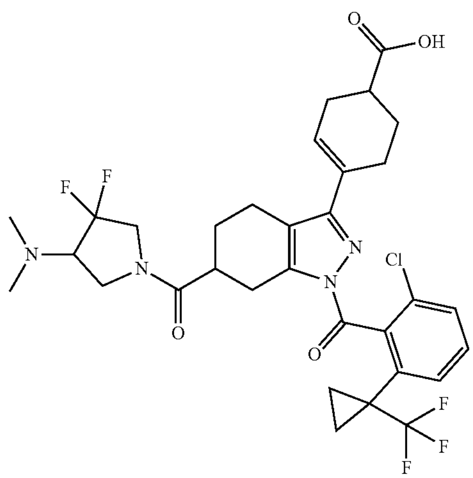 [SMILES: CN(C)C1CN(C(=O)C2CCc3c(C4=CCC(C(=O)O)CC4)nn(C(=O)c4c(Cl)cccc4C4(C(F)(F)F)CC4)c3C2)CC1(F)F] | (1R or S)-4-((6R or S)-1-(2-chloro-6-(1-(trifluoromethyl)cyclopropyl)benzoyl)-6-(4-(dimethylamino)-3,3-difluoropyrrolidine-1-carbonyl)-4,5,6,7-tetrahydro-1H-indazol-3-yl)cyclohex-3-ene-1-carboxylic acid | 669 |
| 6L | 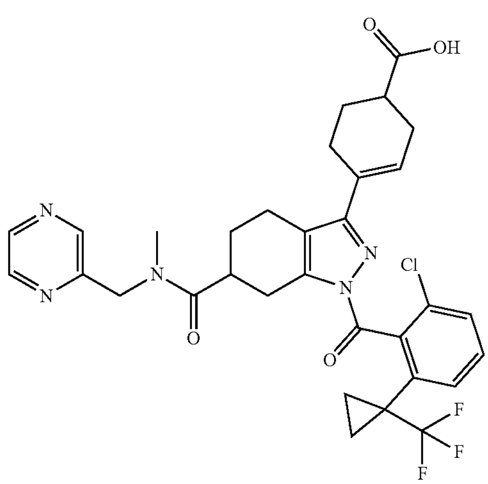 [SMILES: CN(Cc1cnccn1)C(=O)C1CCc2c(C3=CCC(C(=O)O)CC3)nn(C(=O)c3c(Cl)cccc3C3(C(F)(F)F)CC3)c2C1] | (R or S)-4-((R or S)-1-(2-chloro-6-(1-(trifluoromethyl)cyclopropyl)benzoyl)-6-(methyl(pyrazin-2-ylmethyl)carbamoyl)-4,5,6,7-tetrahydro-1H-indazol-3-yl)cyclohex-3-ene-1-carboxylic acid | 642 |

TABLE 11-continued

| Example No. | Structure | IUPAC Name | Exact Mass [M + H]+ |
|---|---|---|---|
| 6M | 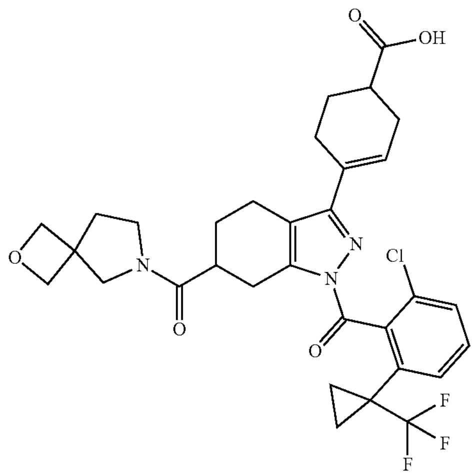 [SMILES: O=C(O)C1CC=C(c2nn(C(=O)c3c(Cl)cccc3C3(C(F)(F)F)CC3)c3c2CCC(C(=O)N2CCC4(COC4)C2)C3)CC1] | (R or S)-4-((R or S)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid | 632 |
| 6N | 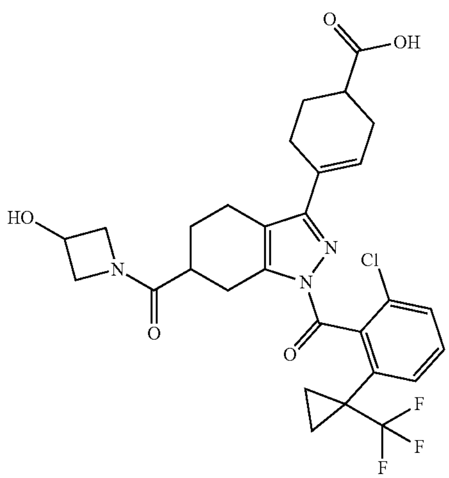 [SMILES: O=C(O)C1CC=C(c2nn(C(=O)c3c(Cl)cccc3C3(C(F)(F)F)CC3)c3c2CCC(C(=O)N2CC(O)C2)C3)CC1] | (R or S)-4-((R or S)-1-(2-chloro-6-(1-(trifluoromethyl)cyclopropyl)benzoyl)-6-(3-hydroxyazetidine-1-carbonyl)-4,5,6,7-tetrahydro-1H-indazol-3-yl)cyclohex-3-ene-1-carboxylic acid | 592 |
| 6O | 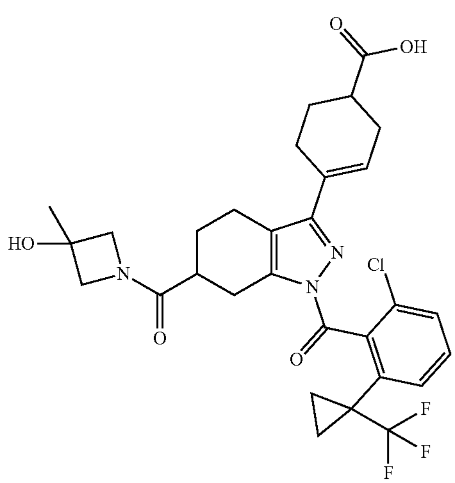 [SMILES: CC1(O)CN(C(=O)C2CCc3c(C4=CCC(C(=O)O)CC4)nn(C(=O)c4c(Cl)cccc4C4(C(F)(F)F)CC4)c3C2)C1] | (R or S)-4-((R or S)-1-(2-chloro-6-(1-(trifluoromethyl)cyclopropyl)benzoyl)-6-(3-hydroxy-3-methylazetidine-1-carbonyl)-4,5,6,7-tetrahydro-1H-indazol-3-yl)cyclohex-3-ene-1-carboxylic acid | 606 |

TABLE 11-continued

| Example No. | Structure | IUPAC Name | Exact Mass [M + H]+ |
|---|---|---|---|
| 6P | 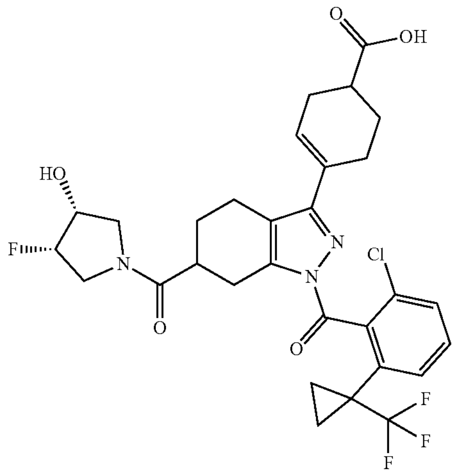 [SMILES: O=C(O)C1CC=C(c2nn(C(=O)c3c(Cl)cccc3C3(C(F)(F)F)CC3)c3c2CCC(C(=O)N2C[C@@H](O)[C@@H](F)C2)C3)CC1] | (R or S)-4-((R or S)-1-(2-chloro-6-(1-(trifluoromethyl)cyclopropyl)benzoyl)-6-((3S,4R)-3-fluoro-4-hydroxypyrrolidine-1-carbonyl)-4,5,6,7-tetrahydro-1H-indazol-3-yl)cyclohex-3-ene-1-carboxylic acid | 624 |
| 6Q | 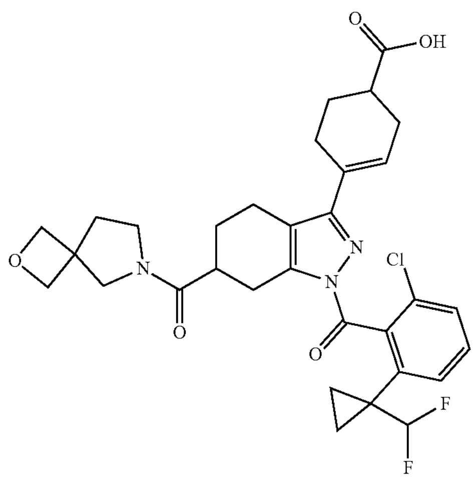 [SMILES: O=C(O)C1CC=C(c2nn(C(=O)c3c(Cl)cccc3C3(C(F)F)CC3)c3c2CCC(C(=O)N2CCC4(COC4)C2)C3)CC1] | 4-((R or S)-1-(2-chloro-6-(1-(difluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid | 614 |
| 6R | 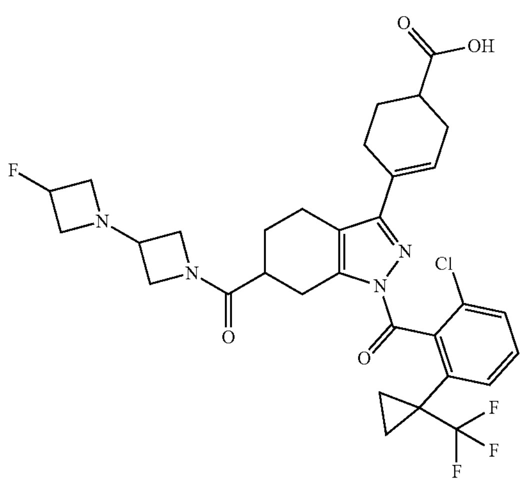 [SMILES: O=C(O)C1CC=C(c2nn(C(=O)c3c(Cl)cccc3C3(C(F)(F)F)CC3)c3c2CCC(C(=O)N2CC(N4CC(F)C4)C2)C3)CC1] | 4-((R or S)-1-(2-chloro-6-(1-(trifluoromethyl)cyclopropyl)benzoyl)-6-(3-fluoro-[1,3'-biazetidine]-1'-carbonyl)-4,5,6,7-tetrahydro-1H-indazol-3-yl)cyclohex-3-ene-1-carboxylic acid | 649 |

The following examples shown in Table 12 were prepared using i-27A and following similar procedures described in Example 5A above.

TABLE 12

| Example No. | Structure | IUPAC Name | Exact Mass [M + H]+ |
|---|---|---|---|
| 7A | 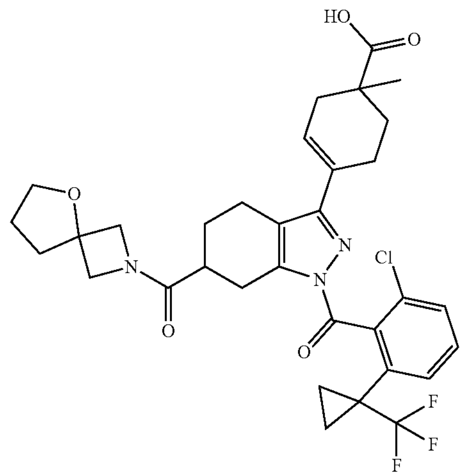 [SMILES: CC1(C(=O)O)CC=C(c2nn(C(=O)c3c(Cl)cccc3C3(C(F)(F)F)CC3)c3c2CCC(C(=O)N2CC4(CCCO4)C2)C3)CC1] | (R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)-1-methylcyclohex-3-ene-1-carboxylic acid | 646 |
| 7B | 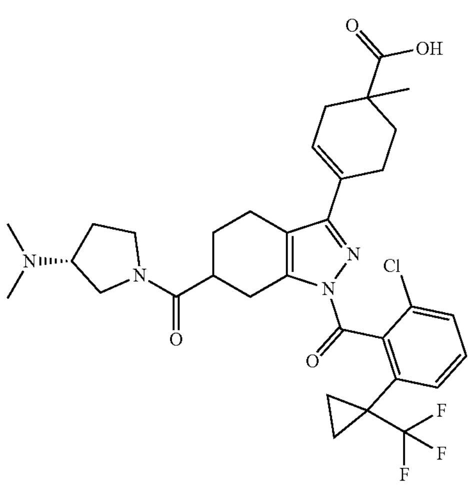 [SMILES: CN(C)[C@@H]1CCN(C(=O)C2CCc3c(C4=CCC(C)(C(=O)O)CC4)nn(C(=O)c4c(Cl)cccc4C4(C(F)(F)F)CC4)c3C2)C1] | (R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)-1-methylcyclohex-3-ene-1-carboxylic acid | 647 |

TABLE 12-continued

| Example No. | Structure | IUPAC Name | Exact Mass [M + H]+ |
|---|---|---|---|
| 7C | 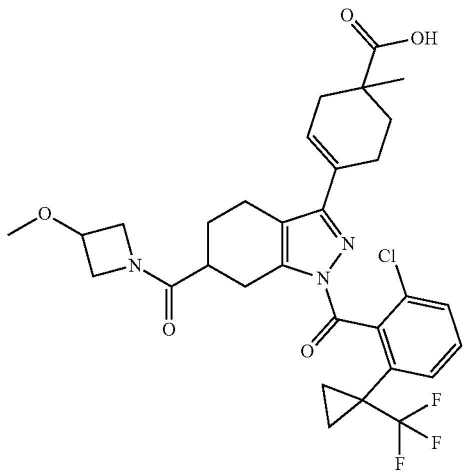 [SMILES: COC1CN(C(=O)C2CCc3c(C4=CCC(C)(C(=O)O)CC4)nn(C(=O)c4c(Cl)cccc4C4(C(F)(F)F)CC4)c3C2)C1] | (R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid | 620 |
| 7D | 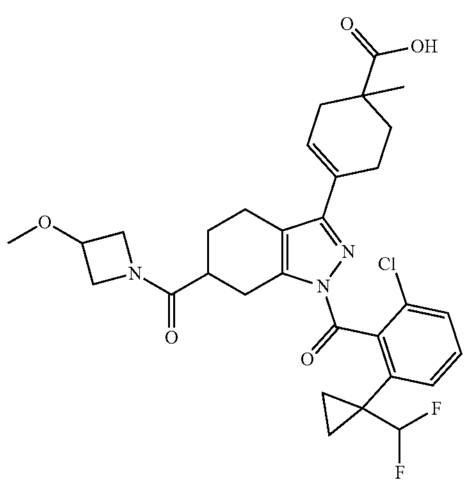 [SMILES: COC1CN(C(=O)C2CCc3c(C4=CCC(C)(C(=O)O)CC4)nn(C(=O)c4c(Cl)cccc4C4(C(F)F)CC4)c3C2)C1] | (R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid | 602 |

The following examples shown in Table 13 were prepared using i-27B and following similar procedures described in Example 5A above.

TABLE 13

| Example No. | Structure | IUPAC Name | Exact Mass [M + H]+ |
|---|---|---|---|
| 8A | 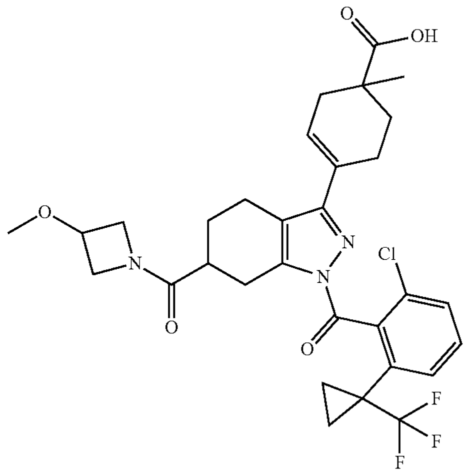 [SMILES: COC1CN(C(=O)C2CCc3c(C4=CCC(C)(C(=O)O)CC4)nn(C(=O)c4c(Cl)cccc4C4(C(F)(F)F)CC4)c3C2)C1] | (R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid | 620 |
| 8B | 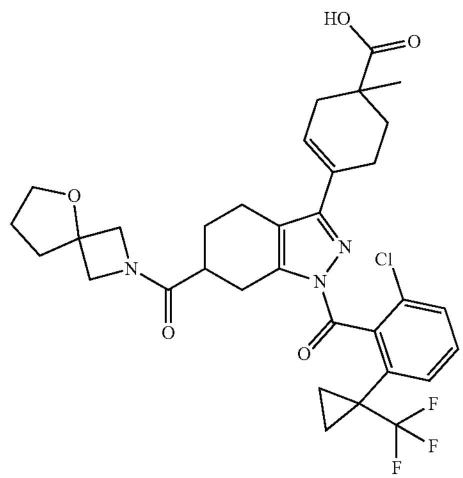 [SMILES: CC1(C(=O)O)CC=C(c2nn(C(=O)c3c(Cl)cccc3C3(C(F)(F)F)CC3)c3c2CCC(C(=O)N2CC4(CCCO4)C2)C3)CC1] | (R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)-1-methylcyclohex-3-ene-1-carboxylic acid | 646 |
| 8C | 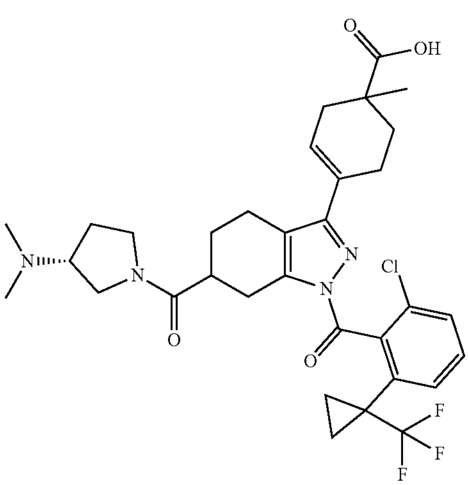 [SMILES: CN(C)[C@@H]1CCN(C(=O)C2CCc3c(C4=CCC(C)(C(=O)O)CC4)nn(C(=O)c4c(Cl)cccc4C4(C(F)(F)F)CC4)c3C2)C1] | (R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)-1-methylcyclohex-3-ene-1-carboxylic acid | 647 |

TABLE 13-continued
| Example No. | Structure | IUPAC Name | Exact Mass [M + H]+ |
|---|---|---|---|
| 8D | 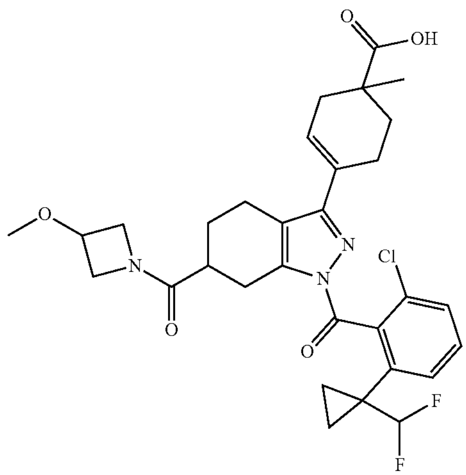 [SMILES: COC1CN(C(=O)C2CCc3c(C4=CCC(C)(C(=O)O)CC4)nn(C(=O)c4c(Cl)cccc4C4(C(F)F)CC4)c3C2)C1] | (R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid | 602 |
Examples 9A
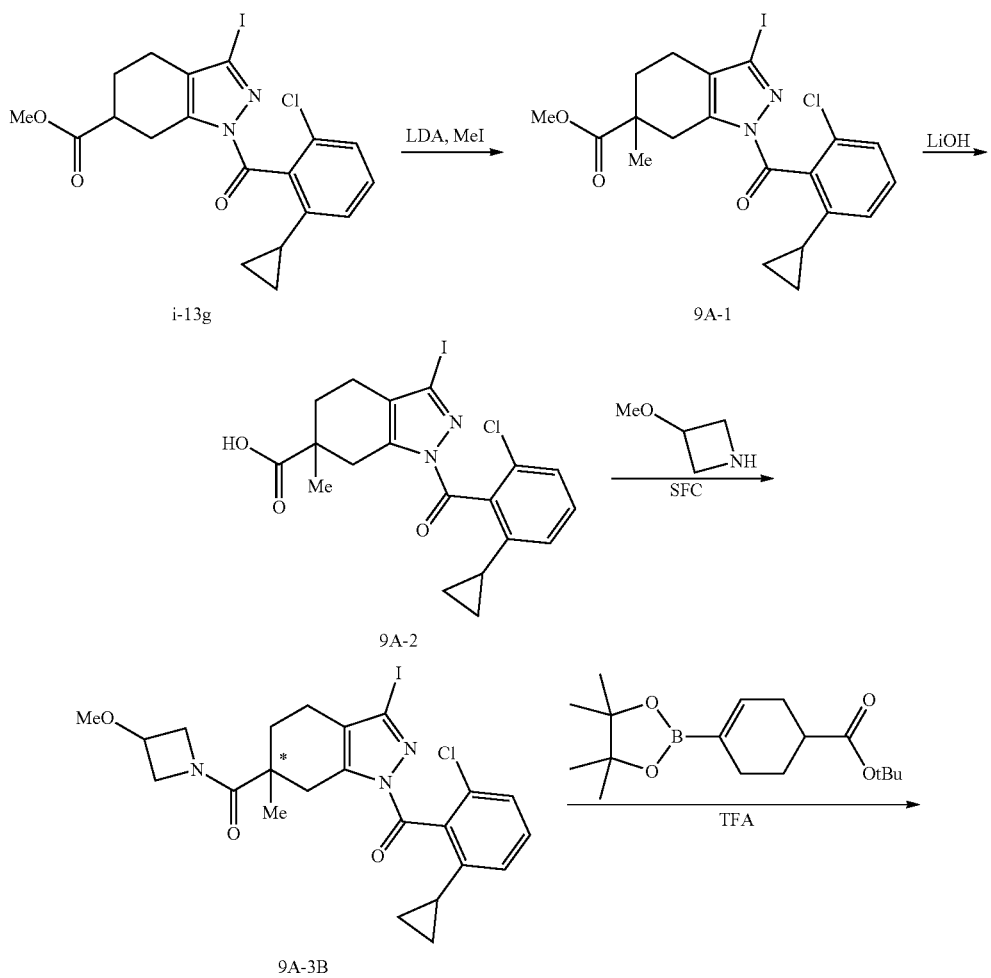

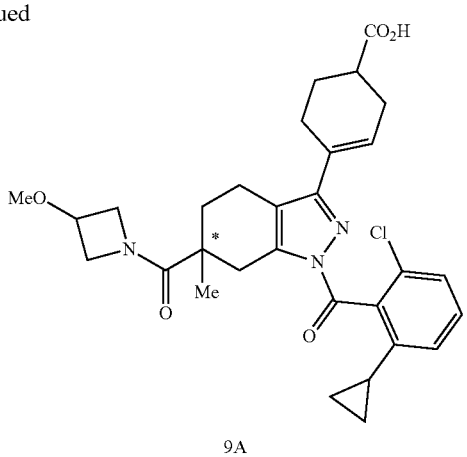

9A

4-((R or S)-1-(2-chloro-6-cyclopropylbenzoyl)-6-(3-methoxyazetidine-1-carbonyl)-6-methyl-4,5,6,7-tetrahydro-1H-indazol-3-yl)cyclohex-3-ene-1-carboxylic acid

Step 1. Preparation of methyl-1-(2-chloro-6-cyclopropylbenzoyl)-3-iodo-6-methyl-4,5,6,7-tetrahydro-1H-indazole-6-carboxylate (9A-1)

To an oven dried round bottom flask equipped with magnetic stir bar under an atmosphere of $N_2$, methyl 1-(2-chloro-6-cyclopropylbenzoyl)-3-iodo-4,5,6,7-tetrahydro-1H-indazole-6-carboxylate (240 mg, 0.495 mmol, 1 equiv), and THF (2.48 mL, 0.2 M) were added. The reaction flask was cooled to −78° C., followed by the addition of lithium diisopropyl amide (0.5 mL, 2 M in THF, 0.99 mmol, 2.00 equiv). The reaction mixture was stirred for 30 minutes followed by the addition of methyl iodide (281 mg, 1.98 mmol, 4 equiv). The reaction mixture was slowly warmed to room temperature over 16 h, and then quenched with saturated $NH_4Cl$ (25 mL) and diluted with EtOAc (25 mL). The layers were separated, and the resulting aqueous layer was extracted with EtOAc (3×25 mL). The combined organic layers were washed with brine, dried over $Na_2SO_4$, and concentrated in vacuo. The crude oil was purified using $SiO_2$ gel chromatography to yield racemic methyl-1-(2-chloro-6-cyclopropylbenzoyl)-3-iodo-6-methyl-4,5,6,7-tetrahydro-1H-indazole-6-carboxylate. MS: 499 (M+1).

Step 2. Preparation of 1-(2-chloro-6-cyclopropylbenzoyl)-3-iodo-6-methyl-4,5,6,7-tetrahydro-1H-indazole-6-carboxylic acid (9A-2)

To an oven dried round bottom flask equipped with magnetic stir bar under an atmosphere of $N_2$, racemic methyl-1-(2-chloro-6-cyclopropylbenzoyl)-3-iodo-6-methyl-4,5,6,7-tetrahydro-1H-indazole-6-carboxylate (240 mg, 0.495 mmol, 1 equiv), THF (2.5 mL), and $H_2O$ (2.5 mL, 0.1 M combined) were added. The reaction mixture was stirred at room temperature for 5 minutes, and then lithium hydroxide (36 mg, 1.5 mmol, 3 equiv) was added. The reaction was stirred at room temperature for 12 h, and then quenched with saturated $NH_4Cl$ and diluted with EtOAc (25 mL). The layers were separated, and the aqueous layer was extracted with EtOAc (3×25 mL), washed with brine, dried over $Na_2SO_4$, and concentrated in vacuo to afford the title compound. MS: 485 (M+1).

Step 3. Preparation of (R or S)-(1-(2-chloro-6-cyclopropylbenzoyl)-3-iodo-6-methyl-4,5,6,7-tetrahydro-1H-indazol-6-yl)(3-methoxyazetidin-1-yl)methanone (9A-3B)

To an oven dried round bottom flask equipped with magnetic stir bar under an atmosphere of $N_2$, racemic 1-(2-chloro-6-cyclopropylbenzoyl)-3-iodo-6-methyl-4,5,6,7-tetrahydro-1H-indazole-6-carboxylic acid (240 mg, 0.499 mmol, 1 equiv), 1-[Bis(dimethylamino)methylene]-1H-1,2,3-triazolo[4,5-b]pyridinium 3-oxid hexafluorophosphate (HATU; 380 mg, 0.99 mmol, 2 equiv), ethyldiisopropylamine (0.43 mL, 2.47 mmol, 5 equiv), and DMF (1.6 mL, 0.3 M) were added. The reaction was stirred at room temperature for 15 minutes, followed by the addition of 3-methoxyazetidin-1-ium chloride (123 mg, 1.0 mmol, 2 equiv). The reaction mixture was stirred at room temperature for 30 minutes, and then purified using $SiO_2$ gel chromatography to yield racemic (1-(2-chloro-6-cyclopropylbenzoyl)-3-iodo-6-methyl-4,5,6,7-tetrahydro-1H-indazol-6-yl)(3-methoxyazetidin-1-yl)methanone. MS: 554 (M+1).

The mixture of stereoisomers were purified by chiral SFC (OJ-H column, 20%/80% MeOH+0.25% DEA/$CO_2$) to afford Isomer 9A-3A (faster eluting): MS: 554 (M+1). Isomer 9A-3B (slower eluting): MS: 554 (M+1).

Step 4. Preparation of 4-((R or S)-1-(2-chloro-6-cyclopropylbenzoyl)-6-(3-methoxyazetidine-1-carbonyl)-6-methyl-4,5,6,7-tetrahydro-1H-indazol-3-yl)cyclohex-3-ene-1-carboxylic acid (9A)

To an oven dried microwave vial equipped with magnetic stir bar under an atmosphere of $N_2$, (R or S)-(1-(2-chloro-6-cyclopropylbenzoyl)-3-iodo-6-methyl-4,5,6,7-tetrahydro-1H-indazol-6-yl)(3-methoxyazetidin-1-yl)methanone Isomer 9A-3B (40 mg, 0.07 mmol, 1 equiv), $2^{nd}$ Gen Sphos Precatalyst (5.2 mg, 7.22 μmol, 0.1 equiv), racemic tert-butyl 4-(4,4,5,5-tetramethyl-1,3,2-dioxaborolan-2-yl)cyclohex-3-enecarboxylate (44 mg, 0.144 mmol, 2 equiv), and dioxane (361 μL, 0.2 M) were added, followed by potassium phosphate tribasic (217 μL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was taken up in DCM (1 mL), and trifluoroacetic acid (1 mL). After stirring for 3 h at room temperature, the solution was concentrated in vacuo, and purified using mass directed reverse phase chromatography to afford the title compound. MS: 553 (M+1). ¹H NMR (DMSO-d6) δ (ppm): 12.15 (s, 1H), 7.36-7.32 (m, 1H), 7.03-6.98 (m, 2H), 6.20 (s, 1H), 4.57 (m, 1H), 4.13 (m, 1H), 3.97 (m, 1H), 3.71 (m, 1H), 3.59 (m, 1H), 3.17 (s, 3H), 2.70 (m, 1H), 2.62-2.46 (m, 3H) 2.40-2.32 (m, 2H), 2.30-2.23 (m, 3H), 2.04 (m, 1H), 1.85 (m, 1H), 1.69 (m, 1H), 1.56 (m, 1H), 1.49 (m, 1H), 1.24 (s, 3H), 0.82 (m, 1H), 0.69 (m, 1H), 0.62 (m, 1H), 0.53 (m, 1H).
Examples 10A
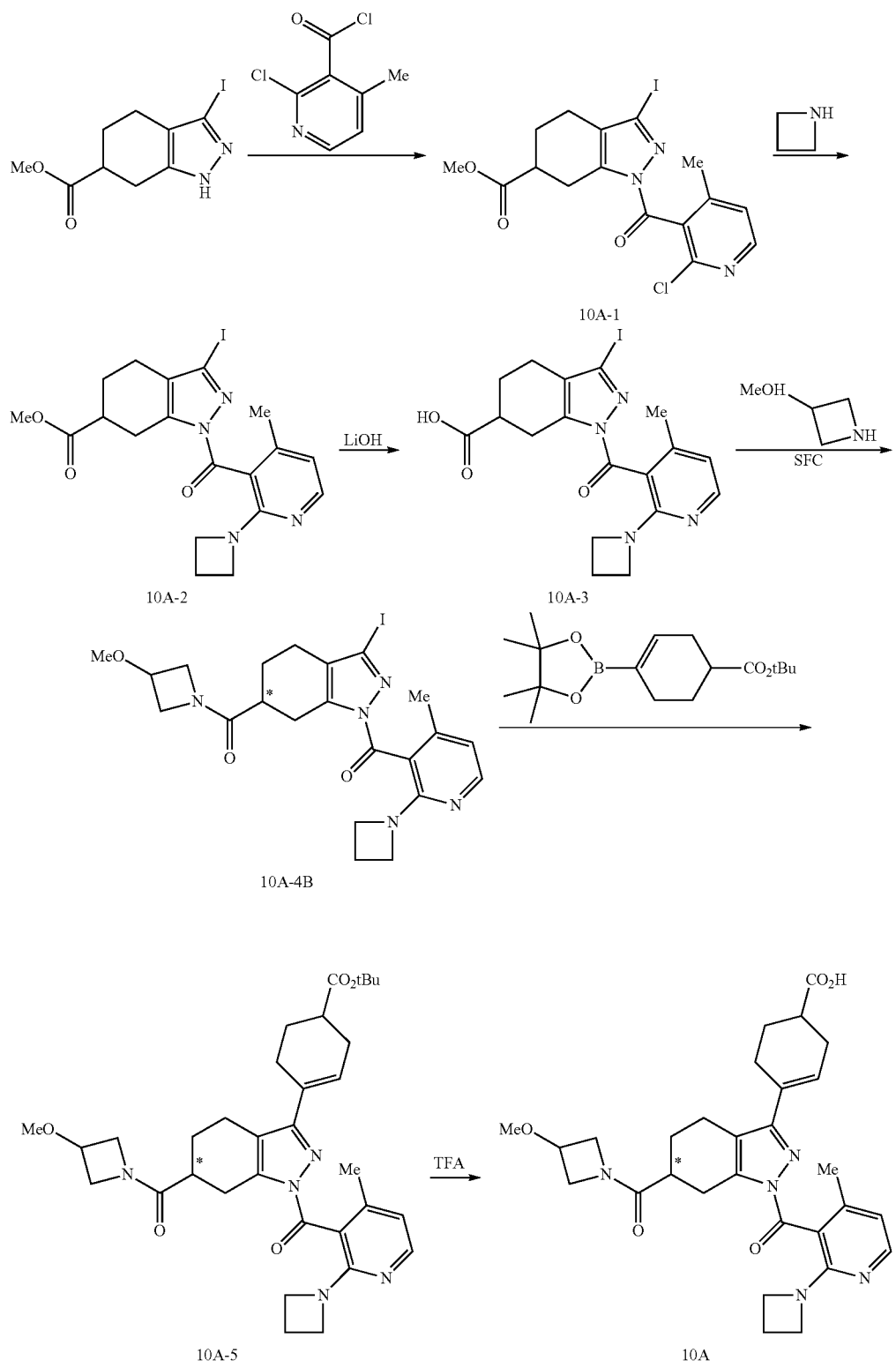

4-((R or S)-1-(2-(azetidin-1-yl)-4-methylnicotinoyl)-6-(3-methoxyazetidine-1-carbonyl)-4,5,6,7-tetrahydro-1H-indazol-3-yl)cyclohex-3-ene-1-carboxylic acid Step 1. Preparation of methyl 1-(2-chloro-4-methylnicotinoyl)-3-iodo-4,5,6,7-tetrahydro-1H-indazole-6-carboxylate (10A-1)

To an oven dried round bottom flask equipped with magnetic stir bar under an atmosphere of $N_2$, racemic methyl 3-iodo-4,5,6,7-tetrahydro-1H-indazole-6-carboxylate (650 mg, 2.12 mmol, 1 equiv), DCM (5.4 mL, 0.4 M), triethylamine (1.77 mL, 12.74 mmol, 6 equiv), and DMAP (259 mg, 2.12 mmol, 1.0 equiv) were added. The reaction was stirred at room temperature for 5 minutes followed by the addition of 2-chloro-4-methylnicotinoyl chloride (600 mg, 3.16 mmol, 1.5 equiv). After 12 h, the reaction was concentrated in vacuo, and purified using $SiO_2$ gel chromatography to afford the title compound. MS: 460 (M+1).

Step 2. Preparation of methyl 1-(2-(azetidin-1-yl)-4-methylnicotinoyl)-3-iodo-4,5,6,7-tetrahydro-1H-indazole-6-carboxylate (10A-2)

To an oven dried round bottom flask equipped with magnetic stir bar under an atmosphere of $N_2$, racemic methyl 1-(2-chloro-4-methylnicotinoyl)-3-iodo-4,5,6,7-tetrahydro-1H-indazole-6-carboxylate (300 mg, 0.653 mmol, 1 equiv), dioxane (2.18 mL, 0.3 M), ethyldiisopropylamine (800 µL, 4.57 mmol, 7 equiv), and azetidine (264 µL, 3.92 mmol, 6 equiv) were added. The reaction mixture was heated to 110° C. for 4 h, and then cooled to room temperature. The crude material was purified using $SiO_2$ gel chromatography to afford the title compound. MS: 481 (M+1).

Step 3. Preparation of 1-(2-(azetidin-1-yl)-4-methylnicotinoyl)-3-iodo-4,5,6,7-tetrahydro-1H-indazole-6-carboxylic acid (10A-3)

To an oven dried round bottom flask equipped with magnetic stir bar under an atmosphere of $N_2$, racemic methyl 1-(2-(azetidin-1-yl)-4-methylnicotinoyl)-3-iodo-4,5,6,7-tetrahydro-1H-indazole-6-carboxylate (286 mg, 0.595 mmol, 1 equiv), THF (2.38 mL, 0.1 M), and water (0.6 mL) were added, followed by lithium hydroxide (42.8 mg, 1.78 mmol, 3 equiv). The reaction mixture was stirred at room temperature for 6 h, and then quenched with saturated $NH_4Cl$ (25 mL) and diluted with EtOAc (25 mL). The layers were separated, and the aqueous layer was extracted with EtOAc (3×25 mL), washed with brine (25 mL), dried over $Na_2SO_4$, and concentrated in vacuo to afford the title compound. MS: 467 (M+1).

Step 4. Preparation of (R or S)-(1-(2-(azetidin-1-yl)-4-methylnicotinoyl)-3-iodo-4,5,6,7-tetrahydro-1H-indazol-6-yl)(3-methoxyazetidin-1-yl)methanone (10A-4B)

To an oven dried round bottom flask equipped with magnetic stir bar under an atmosphere of $N_2$, racemic 1-(2-(azetidin-1-yl)-4-methylnicotinoyl)-3-iodo-4,5,6,7-tetrahydro-1H-indazole-6-carboxylic acid (278 mg, 0.596 mmol, 1 equiv), 1-[Bis(dimethylamino)methylene]-1H-1,2,3-triazolo[4,5-b]pyridinium 3-oxid hexafluorophosphate (HATU; 453 mg, 1.192 mmol, 2 equiv), ethyldiisopropylamine (0.625 mL, 3.58 mmol, 6 equiv), and DMF (2.98 mL, 0.3 M) were added. The reaction was stirred at room temperature for 15 minutes, followed by the addition of 3-methoxyazetidin-1-ium chloride (147 mg, 1.192 mmol, 2 equiv). The reaction mixture was stirred at room temperature for 30 minutes, and then purified using $SiO_2$ gel chromatography to yield mixture of isomers. MS: 536 (M+1).

The mixture of stereoisomers was purified by chiral SFC (OJ-H column, 20%/80% MeOH+0.25% Dimethyl ethylamine/$CO_2$) to afford Isomer 10A-4A (faster eluting): MS: 536 (M+1). Isomer 10A-4B (slower eluting): MS: 536 (M+1).

Step 5. Preparation of tert-butyl 4-((R or S)-1-(2-(azetidin-1-yl)-4-methylnicotinoyl)-6-(3-methoxyazetidine-1-carbonyl)-4,5,6,7-tetrahydro-1H-indazol-3-yl)cyclohex-3-ene-1-carboxylate (10A-5)

To an oven dried microwave vial equipped with magnetic stir bar under an atmosphere of $N_2$, (R or S)-(1-(2-(azetidin-1-yl)-4-methylnicotinoyl)-3-iodo-4,5,6,7-tetrahydro-1H-indazol-6-yl)(3-methoxyazetidin-1-yl)methanone Isomer 10A-4B (45 mg, 0.08 mmol, 1 equiv), $2^{nd}$ Gen Sphos Precatalyst (6 mg, 8.41 µmol, 0.1 equiv), racemic tert-butyl 4-(4,4,5,5-tetramethyl-1,3,2-dioxaborolan-2-yl)cyclohex-3-enecarboxylate (52 mg, 0.17 mmol, 2 equiv), and dioxane (420 µL, 0.2 M) were added, followed by potassium phosphate tribasic (252 µL, 1M, 3 equiv). The reaction mixture was heated to 80° C. for 24 h, and then cooled to room temperature. The crude reaction mixture was diluted with EtOAc (50 mL), filtered through celite, and concentrated in vacuo. The resulting oil was purified using $SiO_2$ gel chromatography to afford title compound. MS: 590 (M+1).

Step 6. Preparation of 4-((R or S)-1-(2-(azetidin-1-yl)-4-methylnicotinoyl)-6-(3-methoxyazetidine-1-carbonyl)-4,5,6,7-tetrahydro-1H-indazol-3-yl)cyclohex-3-ene-1-carboxylic acid (10A)

To an oven dried microwave vial equipped with magnetic stir bar under an atmosphere of $N_2$. tert-butyl 4-((R or S)-1-(2-(azetidin-1-yl)-4-methylnicotinoyl)-6-(3-methoxyazetidine-1-carbonyl)-4,5,6,7-tetrahydro-1H-indazol-3-yl)cyclohex-3-ene-1-carboxylate (50 mg, 0.085 mmol, 1 equiv, 1:1 mixture of diastereomers), and DCM (636 µL, 0.1 M) were added followed by trifluoroacetic acid (212 µL, 0.1 M). The reaction mixture was stirred at room temperature for 3 h, concentrated in vacuo, and purified using mass directed reverse phase chromatography to afford title compound. MS: 534 (M+1). $^1$H NMR (DMSO-d6) δ (ppm): 7.99 (m, 1H), 6.70 (m, 1H), 6.20 (s, 1H), 4.36 (m, 1H), 4.18 (m, 1H), 4.06-3.93 (m, 3H), 3.74-3.60 (m, 3H), 3.21-3.10 (m, 5H), 3.01 (m, 1H), 2.69 (m, 1H), 2.63-2.52 (m, 2H), 2.49-2.40 (m, 4H), 2.23-2.18 (m, 2H), 2.04 (m, 4H), 1.93-1.85 (m, 2H), 1.57-1.51 (m, 2H).

Example 11A

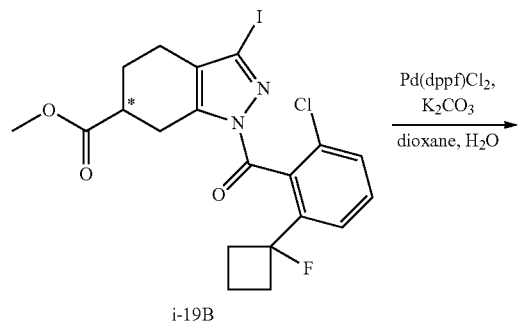

i-19B

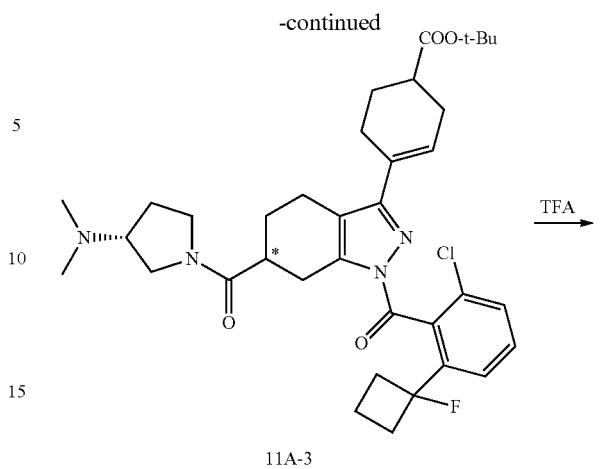

11A-3

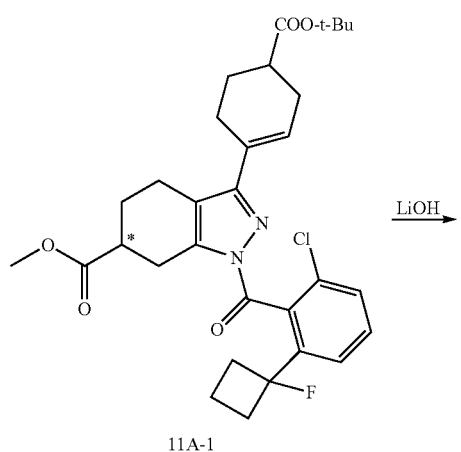

11A-1

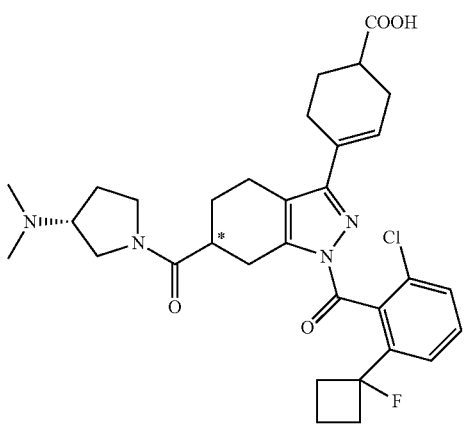

11A 4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid Step 1. Preparation of methyl (6R or S)-3-(4-(tert-butoxycarbonyl)cyclohex-1-en-1-yl)-1-(2-chloro-6-(1-fluorocclobutyl)benzoyl)-4,5,6,7-tetrahydro-1H-indazole-6-carboxylate (11A-1)

To a solution of tert-butyl 4-(4,4,5,5-tetramethyl-1,3,2-dioxaborolan-2-yl)cyclohex-3-enecarboxylate (73 mg, 0.237 mmol), methyl (R or S)-1-(2-chloro-6-(1-fluorocyclobutyl)benzoyl)-3-iodo-4,5,6,7-tetrahydro-1H-indazole-6-carboxylate i-19B (110 mg, 0.213 mmol), and K$_2$CO$_3$ (75 mg, 0.543 mmol) in dioxane (10 mL) and water (1 mL) was added PdCl$_2$(dppf) (10 mg, 0.014 mmol) at room temperature. The reaction mixture was stirred at 80° C. for 15 h under N$_2$. The mixture was cooled, diluted with water (10 mL), extracted with ethyl acetate (3×8 mL), washed with brine (saturated, 15 mL), dried (Na$_2$SO$_4$), filtered and the solvent was evaporated under reduced pressure. The residue was purified by silica gel column flash chromatography, eluting with EtOAc/petroleum ether=0-20% to give the title compound.

$^1$H NMR (400 MHz, CDCl$_3$) δ 7.33-7.44 (m, 3H), 6.14 (brs, 1H), 3.71-3.80 (m, 3H), 3.59 (dt, J=11.5 Hz, 5.1 Hz, 1H), 3.29 (d, J=7.1 Hz, 1H), 2.84 (brs, 1H), 2.56-2.67 (m, 4H), 2.40-2.46 (m, 2H), 1.92-1.99 (m, 1H), 1.78 (d, J=7.1 Hz, 1H), 1.43 (s, 9H).

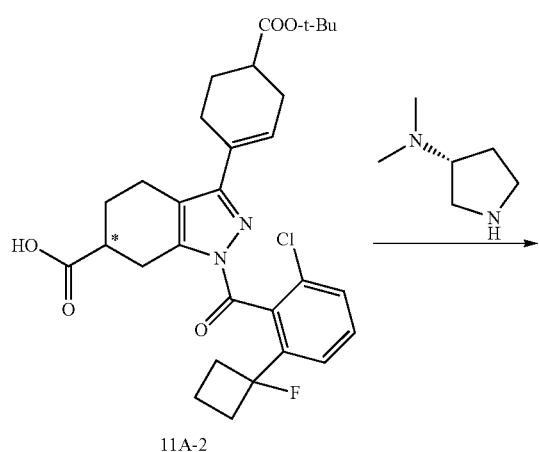

11A-2

Step 2. Preparation of (6R or S)-3-(4-(tert-butoxy-carbonyl)cyclohex-1-en-1-yl)-1-(2-chloro-6-(1-fluorocyclobutyl)benzoyl)-4,5,6,7-tetrahydro-1H-indazole-6-carboxylic acid (11A-2)

To a solution of methyl (6R or S)-3-(4-(tert-butoxycarbonyl)cyclohex-1-en-1-yl)-1-(2-chloro-6-(1-fluorocyclobutyl)benzoyl)-4,5,6,7-tetrahydro-1H-indazole-6-carboxylate (90 mg, 0.158 mmol) in THF (5 mL) was added LiOH·H$_2$O (14 mg, 0.333 mmol) in water (1 mL) at room temperature. The reaction mixture was stirred at room temperature for 3 h and then 45° C. for 12 h. Then LiOH·H$_2$O (14 mg, 0.333 mmol) was added, and the mixture was stirred at 55° C. for 12 h. The mixture was cooled to room temperature, hydrochloric acid (1 M, 1 mL) was added and the mixture was extracted with ethyl acetate (3×8 mL). The combined organic fractions were washed with brine (saturated, 15 mL), dried (Na$_2$SO$_4$), filtered and the solvent was evaporated under reduced pressure. The residue was concentrated to give crude title compound. MS: 557 (M+1).

Step 3. Preparation of tert-butyl 4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylate (11A-3)

To a solution of (R)—N,N-dimethylpyrrolidin-3-amine hydrochloride (10 mg, 0.066 mmol), (6R or S)-3-(4-(tert-butoxycarbonyl)cyclohex-1-en-1-yl)-1-(2-chloro-6-(1-fluorocyclobutyl)benzoyl)-4,5,6,7-tetrahydro-1H-indazole-6-carboxylic acid (30 mg, 0.054 mmol) in DMF (2 mL) was added Et$_3$N (30 μL, 0.215 mmol), HATU (41 mg, 0.108 mmol) at room temperature. The reaction mixture was stirred for 30 min. The mixture was diluted with water (15 mL), extracted with ethyl acetate (3×10 mL), washed with brine (saturated, 20 mL), dried (Na$_2$SO$_4$), filtered and the solvent was evaporated under reduced pressure. The residue was concentrated to give the crude title compound. MS: 675 (M+Na)+.

Step 4. Preparation of 4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid (11A)

To a solution of tert-butyl 4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylate (80 mg, 0.122 mmol) in DCM (5 mL) was added TFA (1 mL, 12.98 mmol) at room temperature. The reaction mixture was stirred at room temperature for 2 h. Aqueous NaHCO$_3$ (saturated, 5 mL) was added, the layers were separated and the organic layer was concentrated. The residue was dissolved in MeCN (3 mL). The residue was purified by preparative HPLC, eluting with Acetonitrile/Water (0.1% TFA buffer), to give the title compound. MS: 597 (M+1). $^1$H NMR (400 MHz, CDCl$_3$) δ 7.39 (brs, 3H), 6.14 (brs, 1H), 3.71-3.98 (m, 3H), 3.21-3.66 (m, 9H), 3.04 (brs, 1H), 2.70-2.88 (m, 3H), 2.46-2.66 (m, 6H), 2.35-2.44 (m, 6H), 2.33 (s, 2H), 1.59-1.96 (m, 3H).

Example 12A

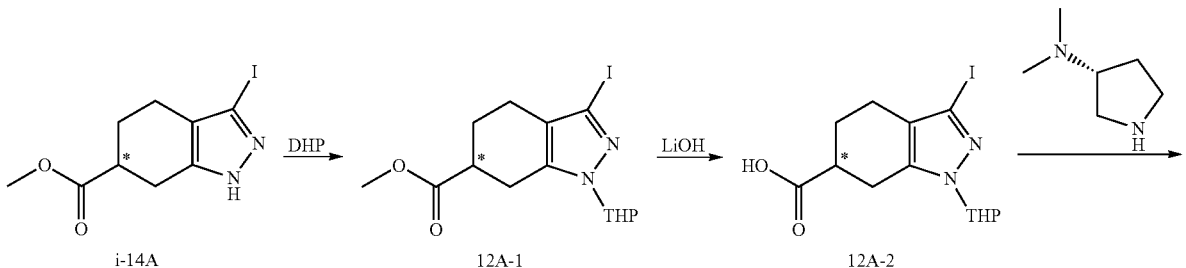

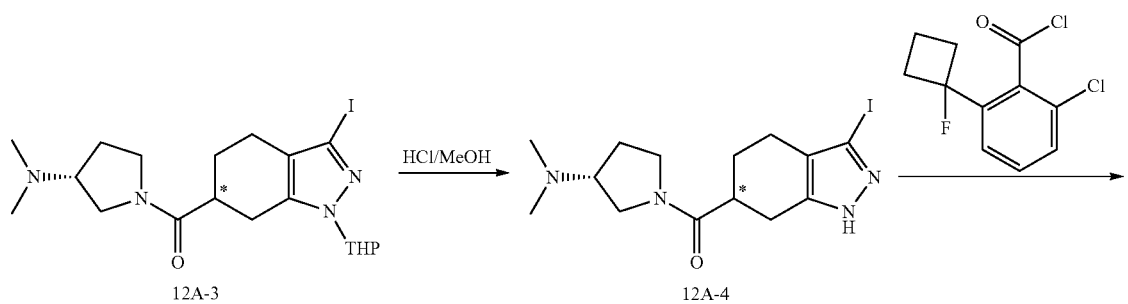

-continued

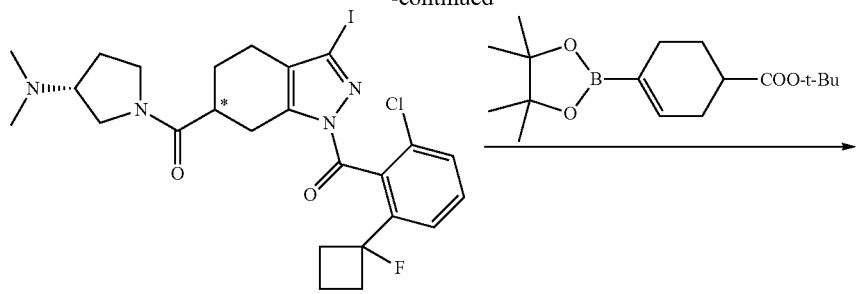

12A-5

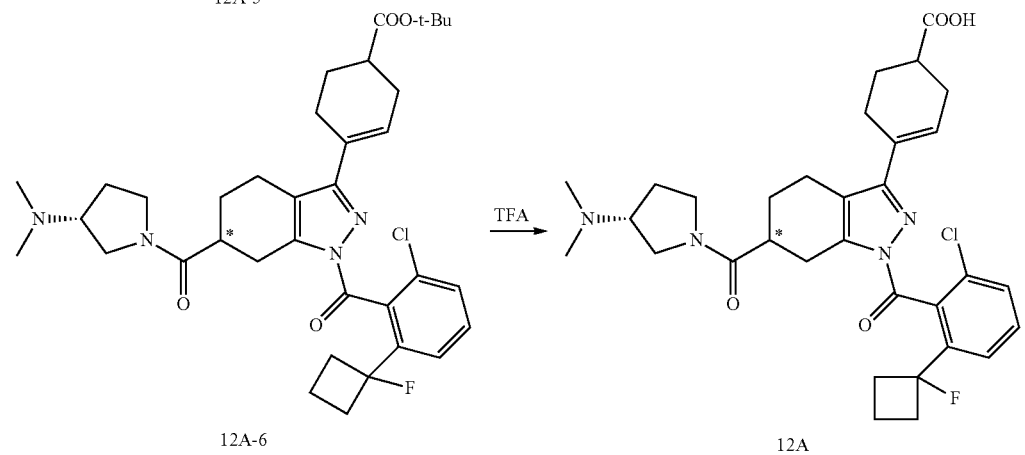

12A-6    12A 4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid Step 1: Preparation of methyl (6R or S)-3-iodo-1-(tetrahydro-2H-pyran-2-yl)-4,5,6,7-tetrahydro-1H-indazole-6-carboxylate (12A-1)

DHP (0.72 mL, 7.87 mmol) was added to a stirred mixture of methyl 3-iodo-4,5,6,7-tetrahydro-1H-indazole-6-carboxylate i-14A (0.8 g, 2.61 mmol) and 4-methylbenzenesulfonic acid (0.14 g, 0.813 mmol) in THF (20 mL) at room temperature and the mixture was stirred at 65° C. for 18 h. The mixture was cooled to room temperature, aqueous sodium hydrogen carbonate (saturated, 10 mL) was added and the mixture was extracted with ethyl acetate (3×20 mL). The combined organic fractions were washed with brine (saturated, 20 mL), dried ($Na_2SO_4$), filtered and the solvent was evaporated under reduced pressure. The residue was purified by silica gel column flash chromatography, eluting with EtOAc/petroleum ether=0-25% to give the title compound. MS: 391 (M+1).

Step 2: Preparation of (6R or S)-3-iodo-1-(tetrahydro-2H-pyran-2-yl)-4,5,6,7-tetrahydro-1H-indazole-6-carboxylic acid (12A-2)

LiOH·$H_2O$ (0.205 g, 4.87 mmol) in water (5 mL) was added to a stirred mixture of methyl (6R or S)-3-iodo-1-(tetrahydro-2H-pyran-2-yl)-4,5,6,7-tetrahydro-1H-indazole-6-carboxylate (0.95 g, 2.435 mmol) in THF (10 mL) at room temperature and the mixture was stirred at room temperature for 18 h. The mixture was concentrated to remove THF, then hydrochloric acid (2 M) was added to pH=4-6 and the mixture was extracted with ethyl acetate (3×15 mL). The combined organic fractions were washed with brine (saturated, 10 mL), dried ($Na_2SO_4$), filtered and the solvent was evaporated under reduced pressure to give the title compound. MS: 377 (M+1).

Step 3: Preparation of ((R)-3-(dimethylamino)pyrrolidin-1-yl)((6R or S)-3-iodo-1-(tetrahydro-2H-pyran-2-yl)-4,5,6,7-tetrahydro-1H-indazol-6-yl)methanone (12A-3)

HATU (0.910 g, 2.392 mmol) and Et3N (0.7 mL, 5.02 mmol) was added to a stirred mixture of (6R or S)-3-iodo-1-(tetrahydro-2H-pyran-2-yl)-4,5,6,7-tetrahydro-1H-indazole-6-carboxylic acid (0.6 g, 1.595 mmol) and (R)—N,N-dimethylpyrrolidin-3-amine hydrochloride (0.360 g, 2.392 mmol) in DMF (6 mL) at room temperature and the mixture was stirred for 18 h. The mixture was concentrated to dryness, diluted with ethyl acetate (30 mL), washed with brine (saturated, 2×15 mL), dried ($Na_2SO_4$), filtered and the solvent was evaporated under reduced pressure. The residue was purified by silica gel column flash chromatography, eluting with MeOH/$CH_2Cl_2$=0-10% to give the title compound. MS: 495 (M+Na)+

Step 4: Preparation of ((R)-3-(dimethylamino)pyrrolidin-1-yl)((R or S)-3-iodo-4,5,6,7-tetrahydro-1H-indazol-6-yl)methanone (12A-4)

4.0 M HCl/MeOH (0.5 mL, 2.00 mmol) was added to a stirred mixture of ((R)-3-(dimethylamino)pyrrolidin-1-yl)((6R or S)-3-iodo-1-(tetrahydro-2H-pyran-2-yl)-4,5,6,7-tetrahydro-1H-indazol-6-yl)methanone (200 mg, 0.423 mmol)

in MeOH (2 mL) at room temperature and the mixture was stirred at 40° C. for 18 h. The mixture was cooled to room temperature, aqueous sodium hydrogen carbonate (saturated, 10 mL) was added and the mixture was extracted with DCM (3×15 mL). The combined organic fractions were washed with brine (saturated, 10 mL), dried (Na₂SO₄), filtered and the solvent was evaporated under reduced pressure. The residue was purified by silica gel column flash chromatography, eluting with MeOH/Et₃N/CH₂Cl₂=1:1:10 to give the title compound. MS: 389 (M+1).

Step 5: Preparation of ((R or S)-1-(2-chloro-6-(1-fluorocyclobutyl)benzoyl)-3-iodo-4,5,6,7-tetrahydro-1H-indazol-6-yl)((R)-3-(dimethylamino)pyrrolidin-1-yl)methanone (12A-5)

Et₃N (0.3 mL, 2.152 mmol) and DMAP (50 mg, 0.409 mmol) were added to a stirred mixture of ((R)-3-(dimethylamino)pyrrolidin-1-yl)((R or S)-3-iodo-4,5,6,7-tetrahydro-1H-indazol-6-yl)methanone (78 mg, 0.201 mmol) in THF (6 mL) at room temperature and 2-chloro-6-(1-fluorocyclobutyl)benzoyl chloride (67 mg, 0.271 mmol) in DCM (1 mL) was added. The mixture was stirred at 70° C. for 48 h. The mixture was concentrated to dryness. The residue was purified by silica gel column flash chromatography, eluting with MeOH/CH₂Cl₂=0-10% to give the title compound. MS: 599 (M+1).

Step 6: Preparation of tert-butyl 4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylate (12A-6)

K₂CO₃ (50 mg, 0.362 mmol) was added to a stirred mixture of tert-butyl 4-(4,4,5,5-tetramethyl-1,3,2-dioxaborolan-2-yl)cyclohex-3-enecarboxylate (50 mg, 0.162 mmol) and ((R or S)-1-(2-chloro-6-(1-fluorocyclobutyl)benzoyl)-3-iodo-4,5,6,7-tetrahydro-1H-indazol-6-yl)((R)-3-(dimethylamino)pyrrolidin-1-yl)methanone (70 mg, 0.117 mmol) in dioxane (12 mL) and water (3 mL) at room temperature. Then Pd(dppf)Cl₂ (10 mg, 0.014 mmol) was added. The mixture was stirred at 80° C. for 12 h under N₂. The mixture was concentrated to dryness. The residue was purified by silica gel column flash chromatography, eluting with MeOH/CH₂Cl₂=0-20% to give the title compound. MS: 653 (M+1).

Step 7: Preparation of 4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid (12A)

TFA (0.5 mL, 6.49 mmol) was added to a stirred mixture of tert-butyl 4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylate (40 mg, 0.061 mmol) in DCM (3 mL) at room temperature and the mixture was stirred for 12 h. The mixture was quenched with aqueous sodium hydrogen carbonate (saturated) to pH=7-8. Then the mixture was concentrated. The residue was purified by preparative HPLC, eluting with Acetonitrile/Water (0.1% TFA buffer), to give the title compound. MS: 597 (M+1). ¹H NMR (400 MHz, CDCl₃) δ 7.31-7.44 (m, 3H), 6.13 (brs, 1H), 3.71-3.94 (m, 3H), 3.38-3.65 (m, 4H), 3.19-3.33 (m, 1H), 3.04 (brs, 1H), 2.71-2.88 (m, 3H), 2.49-2.68 (m, 6H), 2.26-2.45 (m, 10H), 2.07 (brs, 2H), 1.85-1.98 (m, 1H), 1.79 (brs, 1H), 1.65 (brs, 1H).

Example 13A

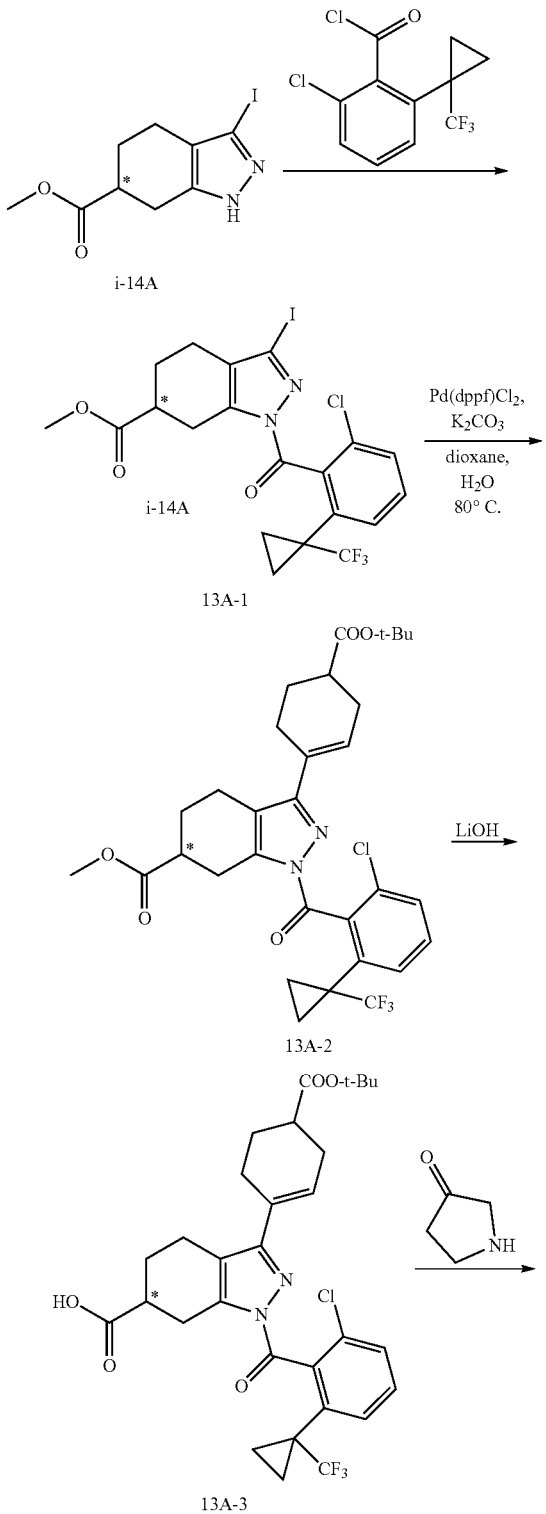

-continued

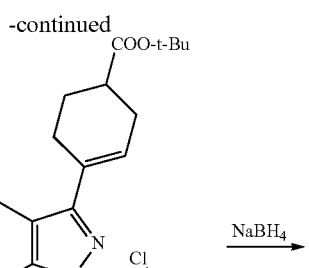

13A-4

13A-5

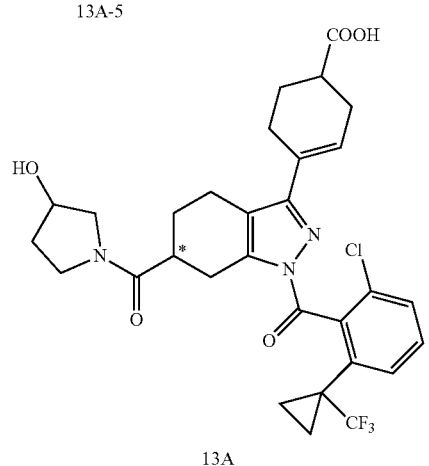

13A 4-((6R or S)-1-(2-chloro-6-(1-(trifluoromethyl)cyclopropyl)benzoyl)-6-(3-hydroxypyrrolidine-1-carbonyl)-4,5,6,7-tetrahydro-1H-indazol-3-yl)cyclohex-3-ene-1-carboxylic acid Step 1: Preparation of methyl (R or S)-1-(2-chloro-6-(1-(trifluoromethyl)cyclopropyl)benzoyl)-3-iodo-4,5,6,7-tetrahydro-1H-indazole-6-carboxylate (13A-1)

2-Chloro-6-(1-(trifluoromethyl)cyclopropyl)benzoyl chloride (800 mg, 2.83 mmol) was added to a stirred mixture of methyl 3-iodo-4,5,6,7-tetrahydro-1H-indazole-6-carboxylate i-14A (800 mg, 2.61 mmol) in THF (40 mL) at 0° C. and the mixture was stirred at 70° C. for 72 h. The mixture was concentrated and the residue was purified by silica gel column flash chromatography, eluting with EtOAc/petroleum ether=1:5 to give the title compound. $^1$H NMR (400 MHz, CDCl$_3$) δ 7.52 (d, J=3.5 Hz, 1H), 7.38-7.43 (m, 2H), 7.26 (s, 1H), 4.12 (q, J=7.1 Hz, 1H), 3.75 (s, 3H), 3.44-3.62 (m, 1H), 3.22-3.40 (m, 1H), 2.77-2.91 (m, 1H), 2.42 (d, J=5.5 Hz, 2H), 2.16-2.30 (m, 1H), 1.88-2.01 (m, 1H), 1.13-1.21 (m, 2H), 0.75-0.86, (m, 2H).

Step 2: Preparation of methyl (6R or S)-3-(4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylate (13A-2)

PdCl$_2$(dppf) (0.119 g, 0.163 mmol) was added to a stirred mixture of K$_2$CO$_3$ (0.900 g, 6.51 mmol), tert-butyl 4-(4,4,5,5-tetramethyl-1,3,2-dioxaborolan-2-yl) cyclohex-3-en-ecarboxylate (0.552 g, 1.791 mmol) and methyl (R or S)-1-(2-chloro-6-(1-(trifluoromethyl)cyclopropyl)benzoyl)-3-iodo-4,5,6,7-tetrahydro-1H-indazole-6-carboxylate (0.9 g, 1.628 mmol) in dioxane (40 mL) and water (4 mL) at room temperature under N$_2$ and the mixture was stirred at 80° C. for 18 h. The mixture was cooled, diluted with EtOAc (50 mL), washed with brine (saturated, 2×20 mL), dried (Na$_2$SO$_4$), filtered and the solvent was evaporated under reduced pressure. The residue was purified by silica gel flash chromatography, eluting with EtOAc/petroleum ether=1:10 to give the title compound. $^1$H NMR (400 MHz, CDCl$_3$) δ 7.50 (d, J=6.4 Hz, 1H), 7.38 (s, 1H), 7.26 (s, 1H), 6.15 (brs, 1H), 3.75 (s, 3H), 2.61-2.78 (m, 2H), 2.37 (brs, 2H), 2.15-2.27 (m, 2H), 1.88-2.00 (m, 3H), 1.55 (s, 1H), 1.47 (s, 2H), 1.42 (d, J=1.8 Hz, 9H), 1.26 (brs, 2H), 0.71-0.85 (m, 2H).

Step 3: Preparation of (6R or S)-3-(4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylic acid (13A-3)

Lithium hydroxide hydrate (111 mg, 2.64 mmol) was added to a stirred mixture of methyl (6R or S)-3-(4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylate (400 mg, 0.659 mmol) in THF (20 mL) and water (4 mL) at 40° C. and the mixture was stirred at 40° C. for 6 h. The mixture was diluted with DCM (50 mL), washed with brine (saturated, 3×20 mL), dried (Na$_2$SO$_4$), filtered and the solvent was evaporated under reduced pressure. The residue was purified by preparative TLC on silica gel, eluting with EtOAc/petroleum ether=1:1 to give the title compound. $^1$H NMR (400 MHz, DMSO-d$_6$) δ 7.33-7.77 (m, 3H), 6.16 (brs, 1H), 2.26-2.37 (m, 2H), 2.23 (brs, 1H), 1.94-2.12 (m, 3H), 1.70-1.89 (m, 2H), 1.48 (d, J=7.1 Hz, 1H), 1.40 (s, 2H), 1.35 (d, J=3.3 Hz, 9H), 1.03-1.16 (m, 3H), 0.68 (brs, 1H).

Step 4: Preparation of tert-butyl 4-((R or S)-1-(2-chloro-6-(1-(trifluoromethyl)cyclopropyl)benzoyl)-6-(3-oxopyrrolidine-1-carbonyl)-4,5,6,7-tetrahydro-1H-indazol-3-yl)cyclohex-3-ene-1-carboxylate (13A-4)

Pyrrolidin-3-one hydrochloride (20 mg, 0.169 mmol) was added to a stirred mixture of (6R or S)-3-(4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylic acid (100 mg, 0.169 mmol), TEA (0.235 mL, 1.686 mmol) and HATU (96 mg, 0.253 mmol) in DMF (3 mL) at room temperature and the mixture was stirred at 40° C. for 30 min. The solvent was evaporated under reduced pressure. The residue was purified by silica gel flash chromatography, eluting with EtOAc/petroleum ether=1:1 to give the title compound. MS: 660 (M+1).

Step 5: Preparation or tert-butyl 4-((6R or S)-1-(2-chloro-6-(1-(trifluoromethyl)cyclopropyl)benzol)-6-(3-hydroxypyrrolidine-1-carbonyl)-4,5,6,7-tetrahydro-1H-indazol-3-yl)cyclohex-3-ene-1-carboxylate (13A-5)

NaBH₄ (2 mg, 0.053 mmol) was added to a stirred mixture of tert-butyl 4-((R or S)-1-(2-chloro-6-(1-(trifluoromethyl)cyclopropyl)benzoyl)-6-(3-oxopyrrolidine-1-carbonyl)-4,5,6,7-tetrahydro-1H-indazol-3-yl)cyclohex-3-ene-1-carboxylate (20 mg, 0.030 mmol) in MeOH (5 mL) at −10° C. and the mixture was stirred at −10° C. for 1 h. The mixture concentrated after adding 1 mL of water to give the crude title compound. MS: 662 (M+1).

Step 6: Preparation of 4-((6R or S)-1-(2-chloro-6-(1-(trifluoromethyl)cyclopropyl)benzoyl)-6-(3-hydroxypyrrolidine-1-carbonyl)-4,5,6,7-tetrahydro-1H-indazol-3-yl)cyclohex-3-ene-1-carboxylic acid (13A)

TFA (2 mL, 26.0 mmol) was added to a stirred mixture of tert-butyl 4-((6R or S)-1-(2-chloro-6-(1-(trifluoromethyl)cyclopropyl)benzoyl)-6-(3-hydroxypyrrolidine-1-carbonyl)-4,5,6,7-tetrahydro-1H-indazol-3-yl)cyclohex-3-ene-1-carboxylate (20 mg, 0.030 mmol) in DCM (2 mL) at 40° C. and the mixture was stirred at 40° C. for 2 h. The mixture was concentrated. The residue was purified by preparative HPLC, eluting with Acetonitrile/Water+0.1% TFA, to give the title compound. MS: 606 (M+1). ¹H NMR (400 MHz, CDCl₃) δ 7.48 (brs, 1H), 7.30-7.41 (m, 2H), 6.13 (brs, 1H), 3.53-3.81 (m, 4H), 3.17-3.36 (1H, m), 2.68-2.92 (m, 2H), 2.57 (brs, 2H), 2.42 (brs, 1H), 2.25 (brs, 6H), 1.92-2.09 (m, 2H), 1.55-1.80 (m, 1H), 1.04-1.31 (m, 3H), 0.72-0.93 (m, 1H).

Example 14A

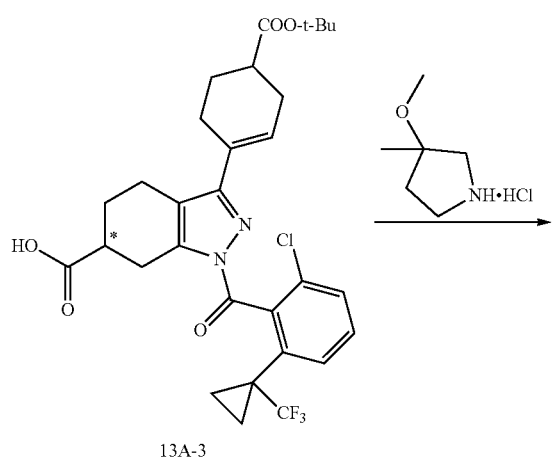

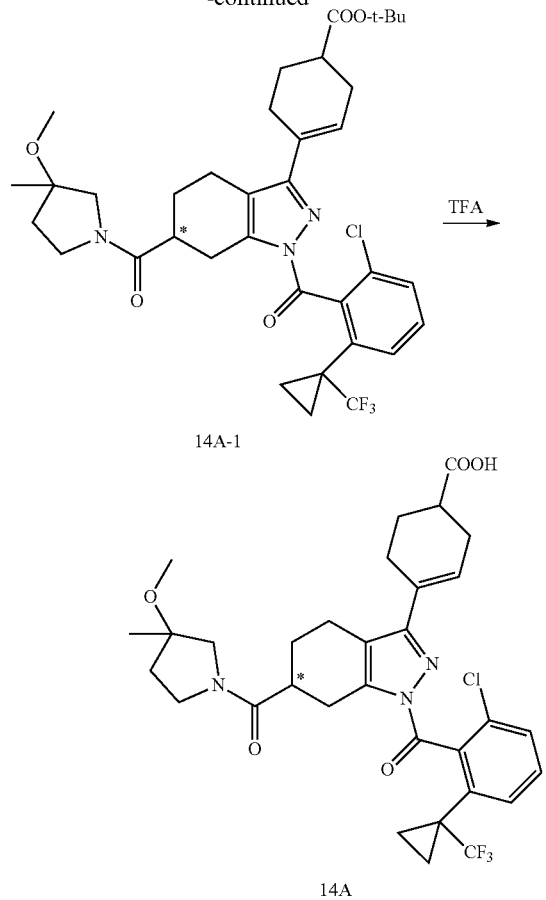

4-((6R or S)-1-(2-chloro-6-(1-(trifluoromethyl)cyclopropyl)benzo)-6-(3-methoxy-3-methylpyrrolidine-1-carbonyl)-4,5,6,7-tetrahydro-1H-indazol-3-yl)cyclohex-3-ene-1-carboxylic acid Step 1: Preparation of tert-butyl 4-((6R or S)-1-(2-chloro-6-(1-(trifluoromethyl)cyclopropyl)benzoyl)-6-(3-methoxy-3-methylpyrrolidine-1-carbonyl)-4,5,6,7-tetrahydro-1H-indazol-3-yl)cyclohex-3-ene-1-carboxylate (14A-1)

TEA (0.2 mL, 1.435 mmol) was added to a stirred mixture of HATU (61 mg, 0.160 mmol), (6R or S)-3-(4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylic acid 13A-3 (50 mg, 0.084 mmol) and 3-methoxy-3-methylpyrrolidine hydrochloride (35 mg, 0.231 mmol) in DMF (3 mL) at room temperature and the mixture was stirred for 2 h. The mixture was concentrated to dryness. The residue was purified by silica gel column flash chromatography, eluting with EtOAc/petroleum ether=20-80% to give the title compound. MS: 690 (M+1).

Step 2: Preparation of 4-((6R or S)-1-(2-chloro-6-(1-(trifluoromethyl)cyclopropyl)benzoyl)-6-(3-methoxy-3-methylpyrrolidine-1-carbonyl)-4,5,6,7-tetrahydro-1H-indazol-3-yl)cyclohex-3-ene-1-carboxylic acid (14A)

TFA (0.5 mL, 6.49 mmol) was added to a stirred mixture of tert-butyl 4-((6R or S)-1-(2-chloro-6-(1-(trifluoromethyl)

cyclopropyl)benzoyl)-6-(3-methoxy-3-methylpyrrolidine-1-carbonyl)-4,5,6,7-tetrahydro-1H-indazol-3-yl)cyclohex-3-ene-1-carboxylate (55 mg, 0.080 mmol) in DCM (3 mL) at room temperature and the mixture was stirred at room temperature for 2 h. The mixture was concentrated to dryness. The residue was diluted with CH$_3$CN (4 mL), and purified by preparative HPLC, eluting with Acetonitrile/Water+0.1% HCOOH, to give the title compound. MS: 634 (M+1). $^1$H NMR (400 MHz, CDCl$_3$) δ 7.51 (brs, 1H), 7.34-7.44 (m, 2H), 6.16 (brs, 1H), 3.83-3.93 (m, 1H), 3.62-3.74 (m, 2H), 3.43-3.52 (m, 1H), 3.25-3.29 (m, 3H), 3.17-3.24 (m, 1H), 2.75-2.89 (m, 2H), 2.61 (brs, 2H), 2.46 (brs, 2H), 2.20 (d, J=13.2 Hz, 2H), 2.06 (d, J=11.9 Hz, 2H), 1.86-1.99 (m, 2H), 1.63-1.80 (m, 2H), 1.40 (brs, 3H), 1.34 (brs, 1H), 1.17 (brs, 1H), 1.10 (brs, 1H), 0.89 (brs, 1H), 0.78 (brs, 1H).

The following examples shown in Table 14 were prepared following similar procedures described above and can be achieved by those of ordinary skill in the art of organic synthesis.

TABLE 14

| Example No. | Structure | IUPAC Name | Exact Mass [M + H]+ |
| --- | --- | --- | --- |
| 14B | 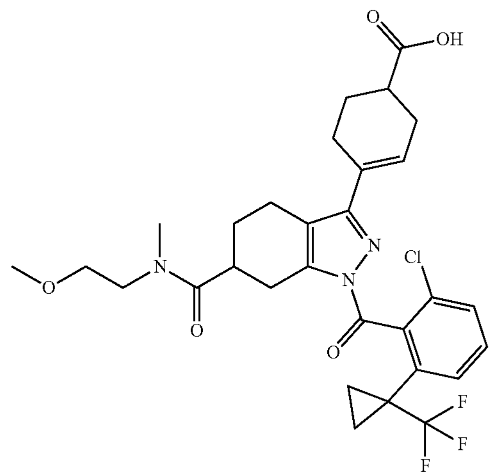 [SMILES: COCCN(C)C(=O)C1CCc2c(C3=CCC(C(=O)O)CC3)nn(C(=O)c3c(Cl)cccc3C3(C(F)(F)F)CC3)c2C1] | 4-((R or S)-1-(2-chloro-6-(1-(trifluoromethyl)cyclopropyl)benzoyl)-6-((2-methoxyethyl)(methyl)carbamoyl)-4,5,6,7-tetrahydro-1H-indazol-3-yl)cyclohex-3-ene-1-carboxylic acid | 608 |
| 14C | 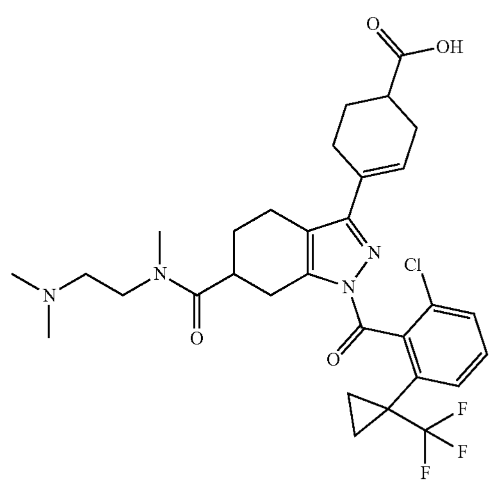 [SMILES: CN(C)CCN(C)C(=O)C1CCc2c(C3=CCC(C(=O)O)CC3)nn(C(=O)c3c(Cl)cccc3C3(C(F)(F)F)CC3)c2C1] | 4-((R or S)-1-(2-chloro-6-(1-(trifluoromethyl)cyclopropyl)benzoyl)-6-((2-(dimethylamino)ethyl)(methyl)carbamoyl)-4,5,6,7-tetrahydro-1H-indazol-3-yl)cyclohex-3-ene-1-carboxylic acid | 621 |

TABLE 14-continued

| Example No. | Structure | IUPAC Name | Exact Mass [M + H]+ |
|---|---|---|---|
| 14D | 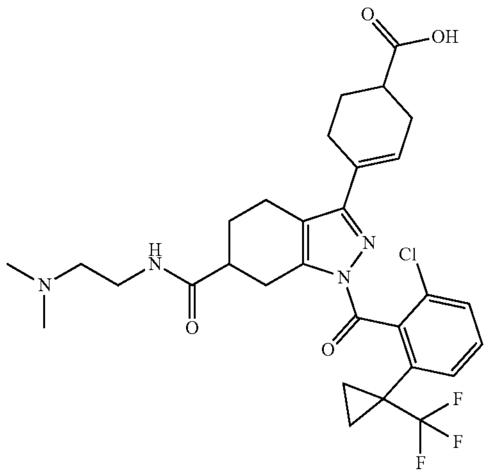 [SMILES: CN(C)CCNC(=O)C1CCc2c(C3=CCC(C(=O)O)CC3)nn(C(=O)c3c(Cl)cccc3C3(C(F)(F)F)CC3)c2C1] | 4-((R or S)-1-(2-chloro-6-(1-(trifluoromethyl)cyclopropyl)benzoyl)-6-((2-(dimethylamino)ethyl)carbamoyl)-4,5,6,7-tetrahydro-1H-indazol-3-yl)cyclohex-3-ene-1-carboxylic acid | 607 |
| 14E | 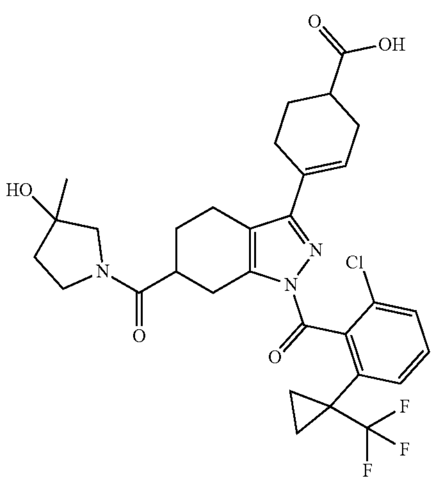 [SMILES: CC1(O)CCN(C(=O)C2CCc3c(C4=CCC(C(=O)O)CC4)nn(C(=O)c4c(Cl)cccc4C4(C(F)(F)F)CC4)c3C2)C1] | 4-((6R or S)-1-(2-chloro-6-(1-(trifluoromethyl)cyclopropyl)benzoyl)-6-(3-hydroxy-3-methylpyrrolidine-1-carbonyl)-4,5,6,7-tetrahydro-1H-indazol-3-yl)cyclohex-3-ene-1-carboxylic acid | 620 |

Example 15A

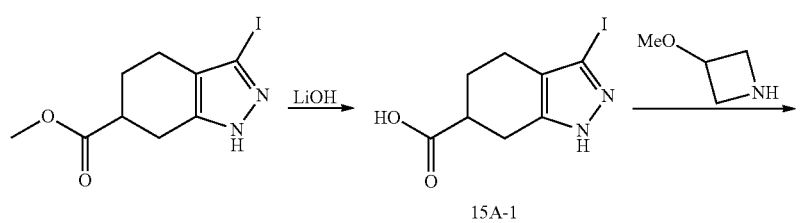

15A-1

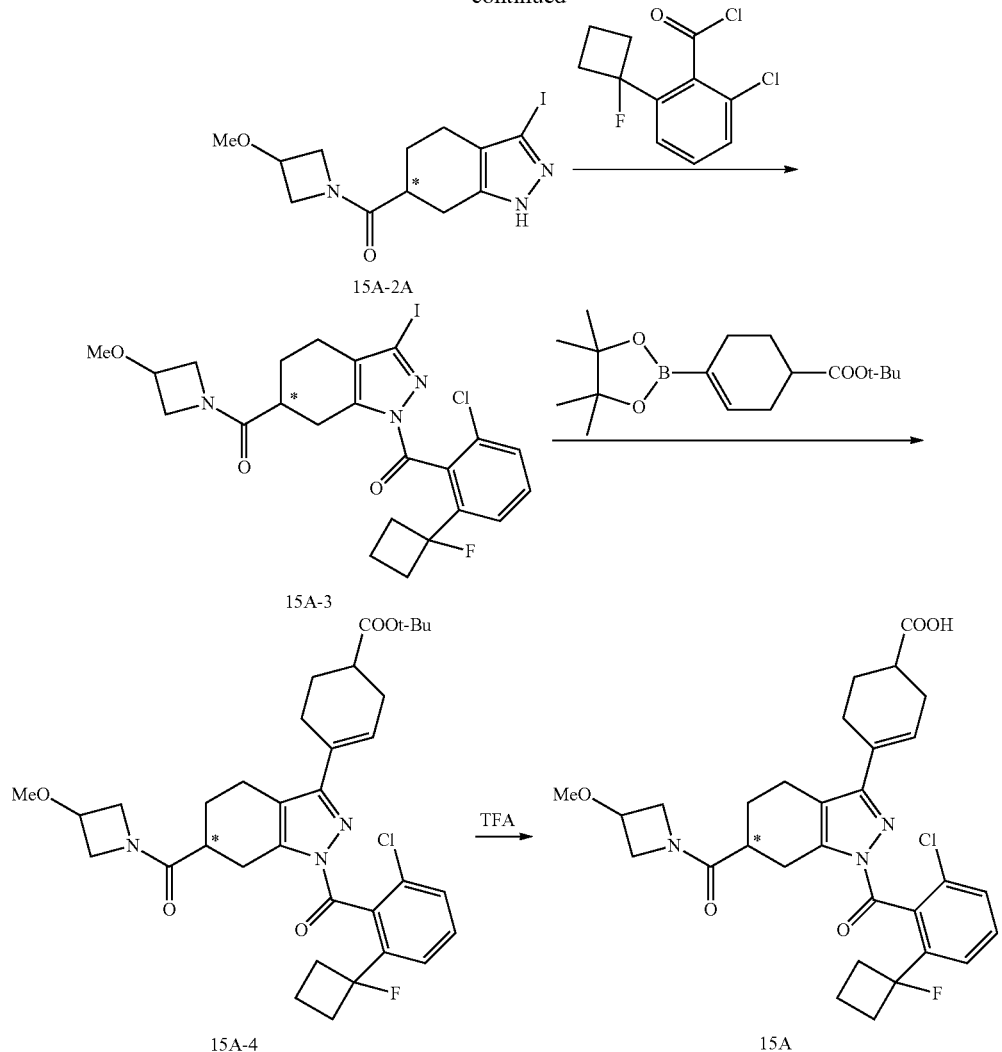

4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylic acid Step 1: Preparation of 3-iodo-4,5,6,7-tetrahydro-1H-indazole-6-carboxylic acid (15A-1)

Lithium hydroxide hydrate (2.74 g, 65.3 mmol) was added to a stirred mixture of methyl 3-iodo-4,5,6,7-tetrahydro-1H-indazole-6-carboxylate (5 g, 16.33 mmol) in MeOH (50 mL) and water (5 mL) at 40° C. and the mixture was stirred at 40° C. for 12 h. The mixture was filtered and the filter cake was washed with ethyl acetate (100 mL). The filtrate was concentrated to give the crude title compound as yellow oil.

Step 2: Preparation of (R or S)-(3-iodo-4,5,6,7-tetrahydro-1H-indazol-6-yl)(3-methoxyazetidin-1-yl)methanone (15A-2A)

To a solution of 3-iodo-4,5,6,7-tetrahydro-1H-indazole-6-carboxylic acid (500 mg, 1.712 mmol) in DMF (10 mL) was added Et$_3$N (800 μL, 5.74 mmol), HATU (976 mg, 2.57 mmol), and 3-methoxyazetidine hydrochloride (233 mg, 1.883 mmol) at room temperature. The reaction mixture was stirred for 12 h. The mixture was cooled, diluted with water (10 mL), extracted with EtOAc (3×10 mL), washed with brine (saturated, 20 mL), dried (Na$_2$SO$_4$), filtered and the solvent was evaporated under reduced pressure. The residue was purified by silica gel column flash chromatography, eluting with MeOH/DCM=0-10% to give the title compound. MS: 362 (M+1).

The mixture of stereoisomers was purified by chiral SFC (OJ-3 column, 40%/60% MeOH/0.05% DEA/CO$_2$) to afford Isomer 15A-2A (faster eluting): MS: 362 (M+1). Isomer 15A-2B (slower eluting): MS: 362 (M+1).

Step 3: Preparation of (R or S)-(1-(2-chloro-6-(1-fluorocyclobutyl)benzoyl)-3-iodo-4,5,6,7-tetrahydro-1H-indazol-6-yl)(3-methoxyazetidin-1-yl)methanone (15A-3)

To a solution of (R or S)-(3-iodo-4,5,6,7-tetrahydro-1H-indazol-6-yl)(3-methoxyazetidin-1-yl)methanone 15A-2A (100 mg, 0.277 mmol) in THF (5 mL) was added 2-chloro-6-(1-fluorocyclobutyl)benzoyl chloride (76 mg, 0.308 mmol) in DCM (1 mL) at room temperature. The reaction mixture was stirred at 70° C. for 24 h. The mixture was cooled, diluted with water (10 mL), extracted with ethyl acetate (3×10 mL), washed with brine (saturated, 10 mL), dried (Na₂SO₄), filtered and the solvent was evaporated under reduced pressure. The residue was purified by silica gel column flash chromatography, eluting with EtOAc/petroleum ether=0-100% to give the title compound. MS: 572 (M+1).

Step 4: Preparation of tert-butyl 4-((S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylate (15A-4)

To a solution of (R or S)-(1-(2-chloro-6-(1-fluorocyclobutyl)benzoyl)-3-iodo-4,5,6,7-tetrahydro-1H-indazol-6-yl)(3-methoxyazetidin-1-yl)methanone (80 mg, 0.140 mmol) in THF (2 mL)/H₂O (0.5 mL) was added PdCl₂(dppf) (7 mg, 9.57 μmol), K₂CO₃ (40 mg, 0.289 mmol) at room temperature. The reaction mixture was stirred under microwave irradiation at 80° C. for 30 min. The mixture was cooled, diluted with water (10 mL), extracted with ethyl acetate (3×10 mL), washed with brine (saturated, 15 mL), dried (Na₂SO₄), filtered and the solvent was evaporated under reduced pressure. The residue was purified by silica gel column flash chromatography, eluting with EtOAc/petroleum ether=0-100% to give the title compound. ¹H NMR (400 MHz, CDCl₃) δ 7.34-7.42 (m, 3H), 6.12 (brs, 1H), 4.32-4.44 (m, 1H), 4.17-4.28 (m, 2H), 4.04-4.15 (m, 2H), 3.88-3.97 (m, 1H), 3.34 (brs, 3H), 2.22-2.81 (m, 13H), 1.94 (brs, 1H), 1.77 (brs, 2H), 1.34-1.53 (m, 9H).

Step 5: Preparation of 4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylic acid (15A)

To a solution of tert-butyl 4-((S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylate (80 mg, 0.128 mmol) in DCM (2.5 mL) was added TFA (0.5 mL, 6.49 mmol) at room temperature. The reaction mixture was stirred for 2 h. Then the reaction mixture was neutralized with sat. aqueous NaHCO₃ (3 mL), and pH was adjusted to 8. Removed most of DCM, and diluted with MeCN (2 mL). The residue was purified by preparative HPLC, eluting with Acetonitrile/Water+0.05% NH₄OH, to give the title compound. MS: 570 (M+1). ¹H NMR (400 MHz, CDCl₃) δ 7.32-7.44 (m, 3H), 6.12 (brs, 1H), 4.33-4.43 (m, 1H), 4.19-4.28 (m, 2H), 4.11 (dd, J=18.7 Hz, 7.9 Hz, 1H), 3.94 (d, J=9.7 Hz, 1H), 3.39-3.49 (m, 1H), 3.34 (s, 3H), 3.22 (dd, J=18.2 Hz, 8.7 Hz, 1H), 2.51-2.80 (m, 8H), 2.26-2.45 (m, 4H), 2.05 (brs, 1H), 1.63-1.94 (m, 3H).

Example 16A

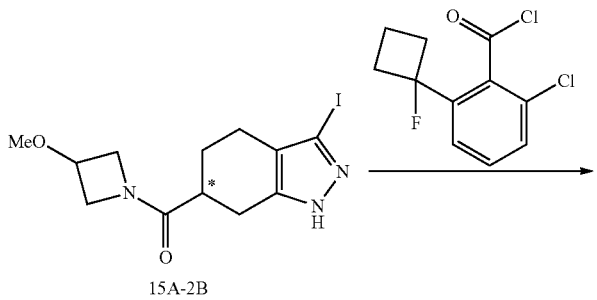

15A-2B

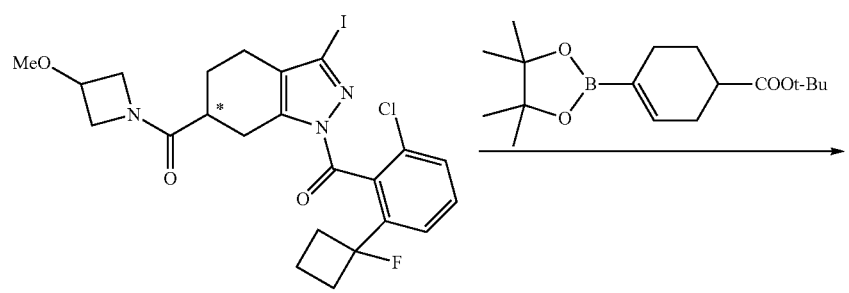

16A-1

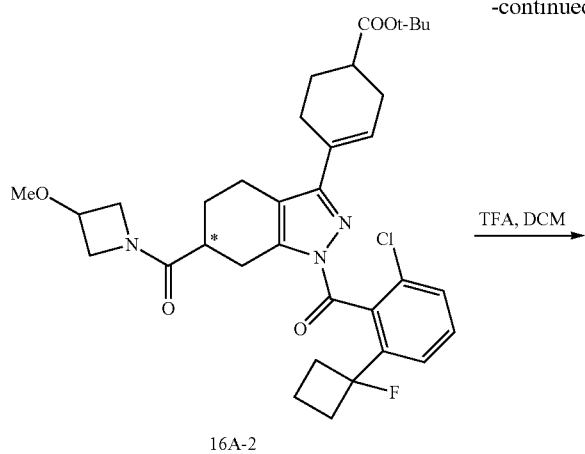

16A-2

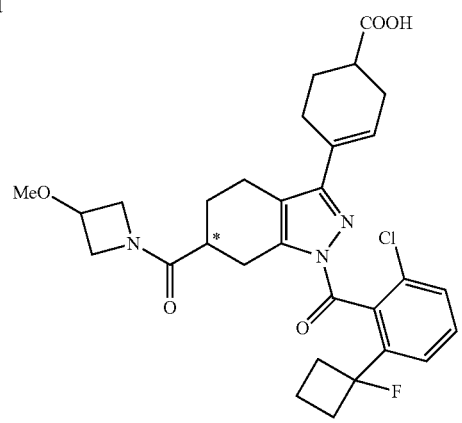

16A

4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylic acid

Step 1: Preparation of (R or S)-(1-(2-chloro-6-(1-fluorocyclobutyl)benzoyl)-3-iodo-4,5,6,7-tetrahydro-1H-indazol-6-yl)(3-methoxyazetidin-1-yl)methanone (16A-1)

To a solution of (3-iodo-4,5,6,7-tetrahydro-1H-indazol-6-yl)(3-methoxyazetidin-1-yl)methanone (chiral peak 2, 100 mg, 0.277 mmol) in THF (5 mL) was added 2-chloro-6-(1-fluorocyclobutyl)benzoyl chloride (76 mg, 0.307 mmol) in DCM (1 mL) at room temperature. The reaction mixture was stirred at 70° C. for 24 h. The mixture was cooled, diluted with ethyl acetate (10 mL), washed with brine (saturated, 2×8 mL), dried ($Na_2SO_4$), filtered and the solvent was evaporated under reduced pressure. The residue was purified by preparative TLC on silica gel, eluting with EtOAc to give the title compound. MS: 572 (M+1).

Step 2: Preparation of tert-butyl 4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylate (16A-2)

To a solution of (R or S)-(1-(2-chloro-6-(1-fluorocyclobutyl)benzoyl)-3-iodo-4,5,6,7-tetrahydro-1H-indazol-6-yl)(3-methoxyazetidin-1-yl)methanone (50 mg, 0.087 mmol) in THF (2 mL)/$H_2O$ (0.5 mL) was added $PdCl_2(dppf)$ (4 mg, 5.47 μmol), $K_2CO_3$ (30 mg, 0.217 mmol) at room temperature. The reaction mixture was stirred under microwave irradiation at 80° C. for 30 min. The mixture was cooled, diluted with ethyl acetate (5 mL), washed with brine (saturated, 10 mL), dried ($Na_2SO_4$), filtered and the solvent was evaporated under reduced pressure. The residue was purified by silica gel column flash chromatography, eluting with EtOAc to give the title compound. MS: 626 (M+1).

Step 3: Preparation of 4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylic acid (16A)

To a solution of tert-butyl 4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylate (25 mg, 0.040 mmol) in DCM (2.5 mL) was added TFA (0.5 mL, 6.49 mmol) at room temperature. The reaction mixture was stirred for 2 h. Then the reaction mixture was neutralized with sat. aqueous $NaHCO_3$ (3 mL), and pH was adjusted to 8. Removed most of DCM, and diluted with MeCN (2 mL). The residue was purified by preparative HPLC, eluting with Acetonitrile/Water+0.05% $NH_4OH$, to give the title compound. MS: 570 (M+1). $^1H$ NMR (400 MHz, $CDCl_3$) δ 7.33-7.48 (m, 3H), 6.14 (brs, 1H), 4.32-4.46 (m, 1H), 4.17-4.31 (m, 2H), 4.05-4.16 (m, 1H), 3.95 (brs, 1H), 3.43 (d, J=16.1 Hz, 1H), 3.34 (s, 3H), 3.23 (brs, 1H), 2.70-2.83 (m, 2H), 2.61 (d, J=9.0 Hz, 5H), 2.45 (brs, 3H), 2.04 (brs, 3H), 1.92 (brs, 1H), 1.77 (brs, 1H).

Example 17A

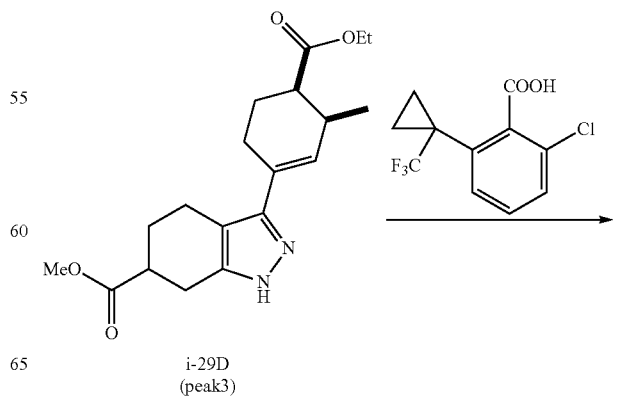

i-29D
(peak3)

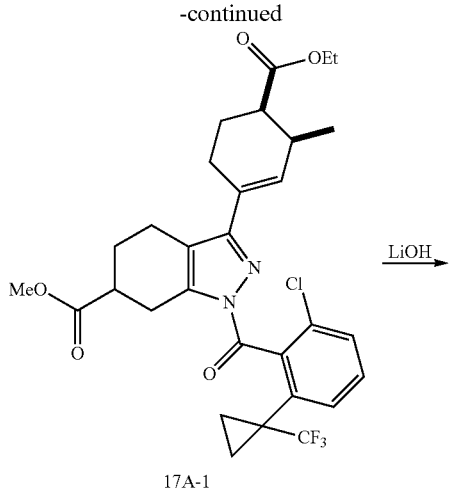

17A-1

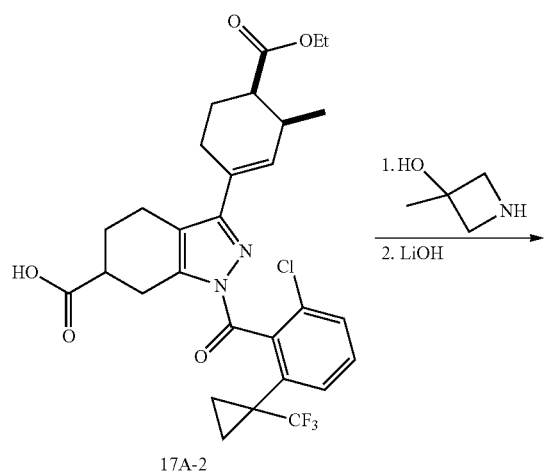

17A-2

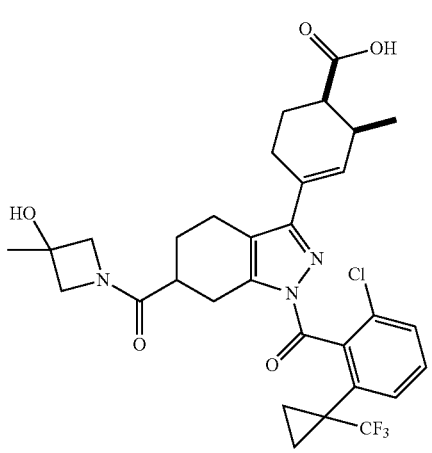

17A (1R,2S or 1S,2R)-4-((R or S)-1-(2-chloro-6-(1-(trifluoromethyl)cyclopropyl)benzoyl)-6-(3-hydroxy-3-methylazetidine-1-carbonyl)-4,5,6,7-tetrahydro-1H-indazol-3-yl)-2-methylcyclohex-3-ene-1-carboxylic acid Step 1. Preparation of methyl (R or S)-1-(2-chloro-6-(1-(trifluoromethyl)cyclopropyl)benzoyl)-3-((3S,4R or 3R,4S)-4-(ethoxycarbonyl)-3-methylcyclohex-1-en-1-yl)-4,5,6,7-tetrahydro-1H-indazole-6-carboxylate (17A-1)

To a flask containing 2-chloro-6-(1-(trifluoromethyl)cyclopropyl)benzoic acid (367 mg, 1.39 mmol) in DCM (1.7 mL) at room temperature was added catalytic amount of DMF and oxalyl chloride (352 uL, 2.77 mmol). The mixture was stirred at room temperature for one hour and then concentrated. The resulting crude containing 2-chloro-6-(1-(trifluoromethyl)cyclopropyl)benzoyl chloride was taken up in pyridine (1.7 mL), followed by the addition of i-29D (peak3) (240 mg, 0.79 mmol. The mixture was heated at 70° C. for 14 h, cooled down, diluted with EtOAc, and washed with 2N HCl, sat. NaHCO₃, H₂O and brine. The organic layer was separated, washed with brine, dried over MgSO₄, and concentrated. The residue was purified by flash chromatography (0-60% EtOAc/hexanes) to give the final compound. MS: 593 (M+1)

Step 2. Preparation of (R, S)-1-(2-chloro-6-(1-(trifluoromethyl)cyclopropyl)benzoyl)-3-((3S,4R or 3R,4S)-4-(ethoxycarbonyl)-3-methylcyclohex-1-en-1-yl)-4,5,6,7-tetrahydro-1H-indazole-6-carboxylic acid (17A-2)

To a solution of bis-ester from previous step (213 mg, 0.359 mmol) in THF (1.8 mL) was added LiOH (1.0 mL, 2.2 mmol). The resulting mixture was stirred at 25° C. for 4 h. LCMS showed desired product formation as major, along with some minor bis-acid byproduct. The mixture was acidified with 2N HCl, and extracted with EtOAc. The organic layer was separated, washed with brine, dried over MgSO₄, and concentrated. Crude product used directly in next step.

Step 3. Preparation of ethyl (1R,2S or 1S,2R)-4-((S or R)-1-(2-chloro-6-(1-(trifluoromethyl)cyclopropyl)benzoyl)-6-(3-hydroxy-3-methylcyclobutane-1-carbonyl)-4,5,6,7-tetrahydro-1H-indazol-3-yl)-2-methylcyclohex-3-ene-1-carboxylate (17A-3)

To a flask containing an aliquot of the crude acid from previous step (70 mg, 0.12 mmol) was added 3-methylazetidin-3-ol hydrochloride (27 mg, 0.22 mmol), Hunig's Base (63 L, 0.36 mmol), and HOBt (33 mg, 0.22 mmol) in DCM (300 μL) was added 1-(3-dimethylaminopropyl)-3-ethylcarbodiimide hydrochloride (42 mg, 0.22 mmol). The resultant mixture was stirred at room temperature for 2 h and then concentrated. The residue was subjected to flash chromatography (50-100% EtOAc/hexanes) to afford the desired product. MS: 648 (M+1)

Step 4. Preparation of (1R,2S)-4-((S)-1-(2-chloro-6-(1-(trifluoromethyl)cyclopropyl)benzoyl)-6-(3-hydroxy-3-methylcyclobutane-1-carbonyl)-4,5,6,7-tetrahydro-1H-indazol-3-yl)-2-methylcyclohex-3-ene-1-carboxylic acid (17A)

To a solution of ethyl ester from previous step (50 mg, 0.077 mmol) in THF (0.5 mL)/MeOH (0.5 mL) was added LiOH (386 µL, 0.77 mmol). The mixture was heated at 50° C. for 2 h. The mixture was cooled down, acidified with 2N HCl, and extracted with EtOAc. The organic layer was separated, washed with brine, and concentrated. The residue was purified by reverse HPLC(H$_2$O/CH$_3$CN containing 0.1% TFA) to give the title compound. $^1$H NMR (DMSO-d6, 600 MHz) δ 12.16 (brs, 1H), 7.54-7.60 (m, 3H), 6.11 (brs, 1H), 5.60 (brs, 1H), 3.94-4.10 (m, 2H), 3.64-3.74 (m, 2H), 3.12-3.22 (m, 1H), 2.94-3.60 (m, 1H), 2.66-2.76 (m, 1H), 2.48-2.64 (m, 3H), 2.10-2.30 (m, 3H), 1.88-2.04 (m, 2H), 1.52-1.62 (m, 1H), 1.36 (brs, 3H), 1.26-1.32 (m, 1H), 0.62-1.16 (m, 7H). MS: 620 (M+1).

The following examples shown in Table 15 were prepared following similar procedures described in Example 17A can be achieved by those of ordinary skill in the art of organic synthesis.

TABLE 15

| Ex. No. | Intermed. used | Structure | IUPAC Name | Exact Mass [M + H]+ |
|---|---|---|---|---|
| 17B | i-29D (peak3) | 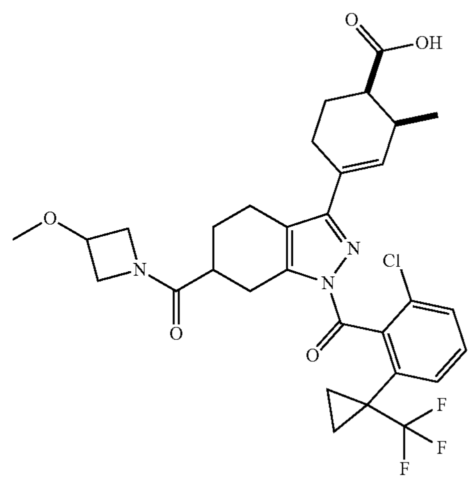 [SMILES: COC1CN(C(=O)C2CCc3c(C4=C[C@H](C)[C@H](C(=O)O)CC4)nn(C(=O)c4c(Cl)cccc4C4(C(F)(F)F)CC4)c3C2)C1] | (1R,2S or 1S,2R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-2-methylcyclohex-3-ene-1-carboxylic acid | 620 |
| 17C | i-29B (peak1-peak2) | 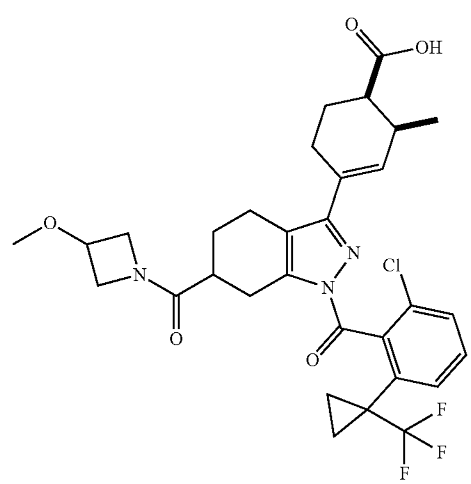 [SMILES: COC1CN(C(=O)C2CCc3c(C4=C[C@H](C)[C@H](C(=O)O)CC4)nn(C(=O)c4c(Cl)cccc4C4(C(F)(F)F)CC4)c3C2)C1] | (1R,2S or 1S,2R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-2-methylcyclohex-3-ene-1-carboxylic acid | 620 |

TABLE 15-continued

| Ex. No. | Intermed. used | Structure | IUPAC Name | Exact Mass [M + H]+ |
|---|---|---|---|---|
| 17D | i-29C (peak2) | 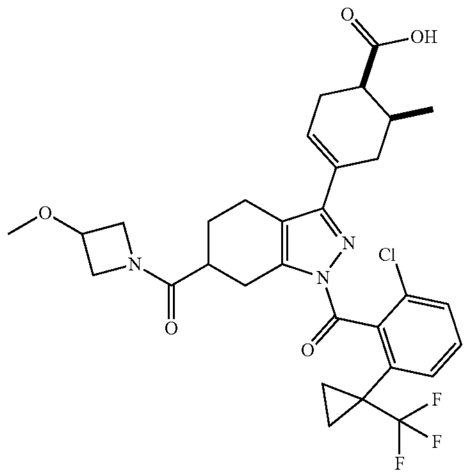 [SMILES: COC1CN(C(=O)C2CCc3c(C4=CC[C@@H](C(=O)O)[C@@H](C)C4)nn(C(=O)c4c(Cl)cccc4C4(C(F)(F)F)CC4)c3C2)C1] | (1R,6S or 1S, 6R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-6-methylcyclohex-3-ene-1-carboxylic acid | 620 |
| 17E | i-29A (peak1-peak1) | 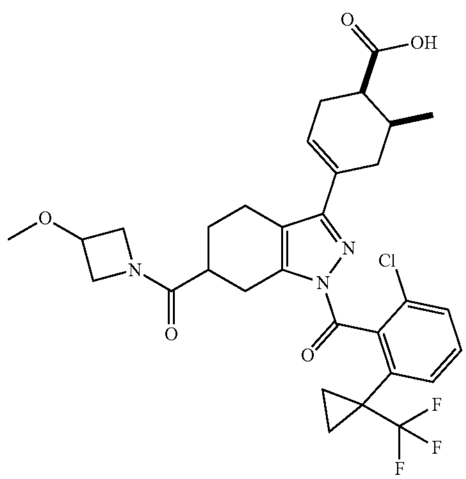 [SMILES: COC1CN(C(=O)C2CCc3c(C4=CC[C@@H](C(=O)O)[C@@H](C)C4)nn(C(=O)c4c(Cl)cccc4C4(C(F)(F)F)CC4)c3C2)C1] | (1R,6S or 1S, 6R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-6-methylcyclohex-3-ene-1-carboxylic acid | 620 |
| 17F | i-29D (peak3) | 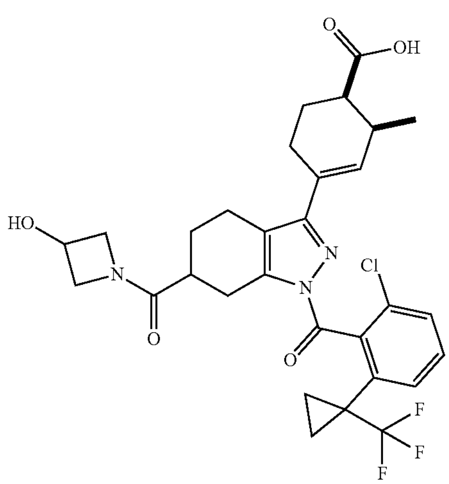 [SMILES: C[C@H]1C=C(c2nn(C(=O)c3c(Cl)cccc3C3(C(F)(F)F)CC3)c3c2CCC(C(=O)N2CC(O)C2)C3)CC[C@H]1C(=O)O] | (1R,2S or 1S,2R)-4-((S or R)-1-(2-chloro-6-(1-(trifluoromethyl)cyclopropyl)benzoyl)-6-(3-hydroxyazetidine-1-carbonyl)-4,5,6,7-tetrahydro-1H-indazol-3-yl)-2-methylcyclohex-3-ene-1-carboxylic acid | 606 |

TABLE 15-continued

| Ex. No. | Intermed. used | Structure | IUPAC Name | Exact Mass [M + H]+ |
|---|---|---|---|---|
| 17G | i-29C (peak2) | 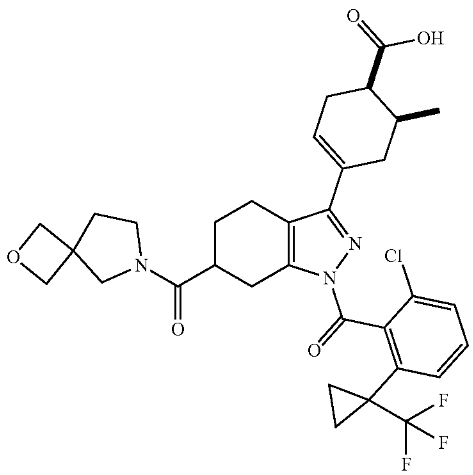 [SMILES: C[C@H]1CC(c2nn(C(=O)c3c(Cl)cccc3C3(C(F)(F)F)CC3)c3c2CCC(C(=O)N2CCC4(COC4)C2)C3)=CC[C@H]1C(=O)O] | (1R,6S or 1S,6R)-4-((S or R)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)-6-methylcyclohex-3-ene-1-carboxylic acid | 646 |
| 17H | i-29C (peak2) | 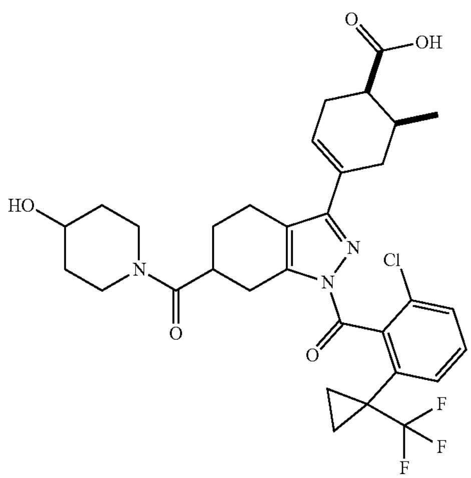 [SMILES: C[C@H]1CC(c2nn(C(=O)c3c(Cl)cccc3C3(C(F)(F)F)CC3)c3c2CCC(C(=O)N2CCC(O)CC2)C3)=CC[C@H]1C(=O)O] | (1R,6S or 1S,6R)-4-((S or R)-1-(2-chloro-6-(1-(trifluoromethyl)cyclopropyl)benzoyl)-6-(4-hydroxypiperidine-1-carbonyl)-4,5,6,7-tetrahydro-1H-indazol-3-yl)-6-methylcyclohex-3-ene-1-carboxylic acid | 634 |

Example 18A

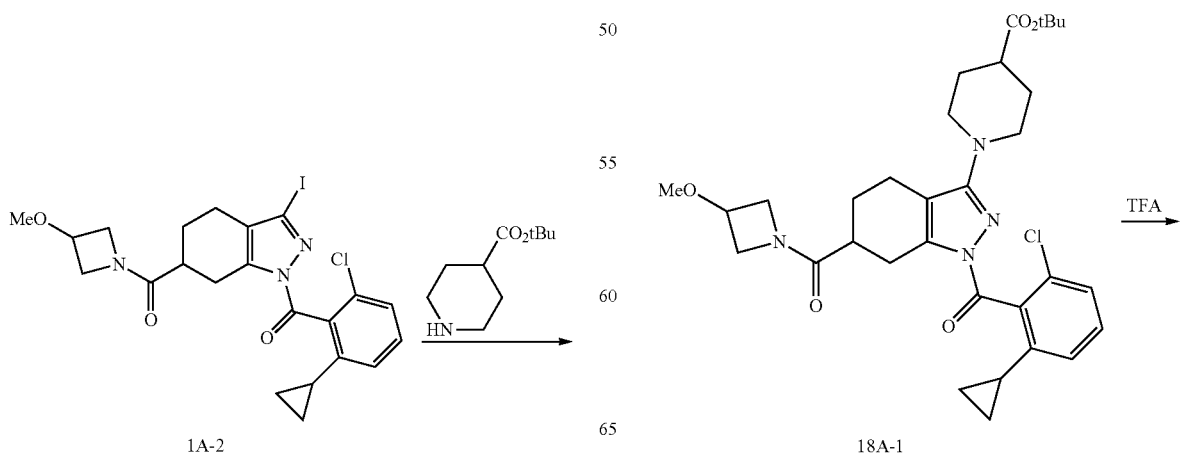

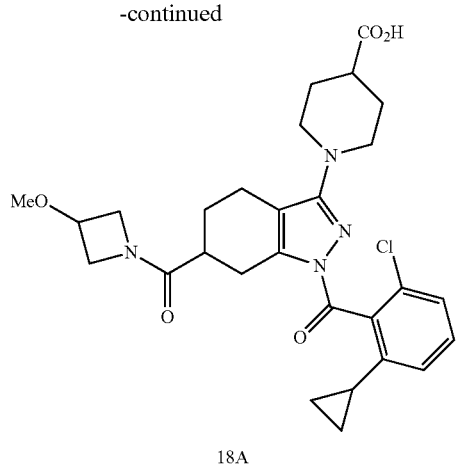

18A (R or S)-1-(1-(2-chloro-6-cyclpropylbenzoyl)-6-(3-methoxyazetidine-1-carbonyl)-4,5,6,7-tetrahydro-1H-indazol-3-yl)piperidine-4-carboxylic acid Step 1. Preparation of tert-butyl (R or S)-1-(1-(2-chloro-6-cyclopropylbenzoyl)-6-(3-methoxyazetidine-1-carbonyl)-4,5,6,7-tetrahydro-1H-indazol-3-yl)piperidine-4-carboxylate (18A-1)

To an oven dried microwave vial equipped with magnetic stir bar under an atmosphere of $N_2$, (R or S)-(1-(2-chloro-6-cyclopropylbenzoyl)-3-iodo-4,5,6,7-tetrahydro-1H-indazol-6-yl)(3-methoxyazetidin-1-yl)methanone 1A-2 (100 mg, 0.19 mmol, 1 equiv), tert-butyl piperidine-4-carboxylate (45 mg, 0.24 mmol, 1.3 equiv), $Cs_2CO_3$ (241 mg, 0.74 mmol, 4 equiv), Chloro(2-dicyclohexylphosphino-2',6'-di-isopropoxy-1,1'-biphenyl)[2-(2'-amino-1,1'-biphenyl)]palladium(II) (RuPhos-Pd G2; 13 mg, 0.02 mmol, 0.1 equiv), and dioxane (0.93 mL, 0.2 M) were added. The reaction mixture was stirred at 80° C. for 24 h, and then concentrated in vacuo. The resulting oil was purified using $SiO_2$ gel chromatography to afford the title compound. MS: 597 (M+1).

Step 2. Preparation of (R or S)-1-(1-(2-chloro-6-cyclopropylbenzoyl)-6-(3-methoxyazetidine-1-carbonyl)-4,5,6,7-tetrahydro-1H-indazol-3-yl)piperidine-4-carboxylic acid (18A)

To an oven dried microwave vial equipped with magnetic stir bar under an atmosphere of $N_2$, tert-butyl (R or S)-1-(1-(2-chloro-6-cyclopropylbenzoyl)-6-(3-methoxyazetidine-1-carbonyl)-4,5,6,7-tetrahydro-1H-indazol-3-yl)piperidine-4-carboxylate (90 mg, 0.15 mmol, 1 equiv), and DCM (1.1 mL, 0.1 M) were added, followed by trifluoroacetic acid (377 µL, 0.1 M). The reaction mixture was stirred at room temperature for 1 h, and then concentrated in vacuo. The resulting oil was purified using mass directed reverse phase chromatography to afford the title compound. MS: 541 (M+1). $^1$H NMR (DMSO-d6) δ (ppm): 7.30 (m, 1H), 7.27 (d, J=8.29 Hz, 1H), 6.94 (m, 1H), 4.39 (m, 1H), 4.33 (m, 1H), 4.19 (m, 1H), 4.04-3.96 (m, 2H), 3.65 (m, 1H), 3.42 (m, 1H), 3.33 (m, 1H), 3.19-3.14 (m, 4H), 2.94 (m, 1H), 2.70 (m, 1H), 2.62-2.56 (m, 2H), 2.48-2.43 (m, 2H), 2.30 (m, 1H), 1.87 (m, 1H), 1.73-1.68 (m, 2H), 1.55-1.50 (m, 2H), 1.42 (m, 1H), 0.81 (m, 1H), 0.72 (m, 1H), 0.63-0.58 (m, 2H).

Example 19A

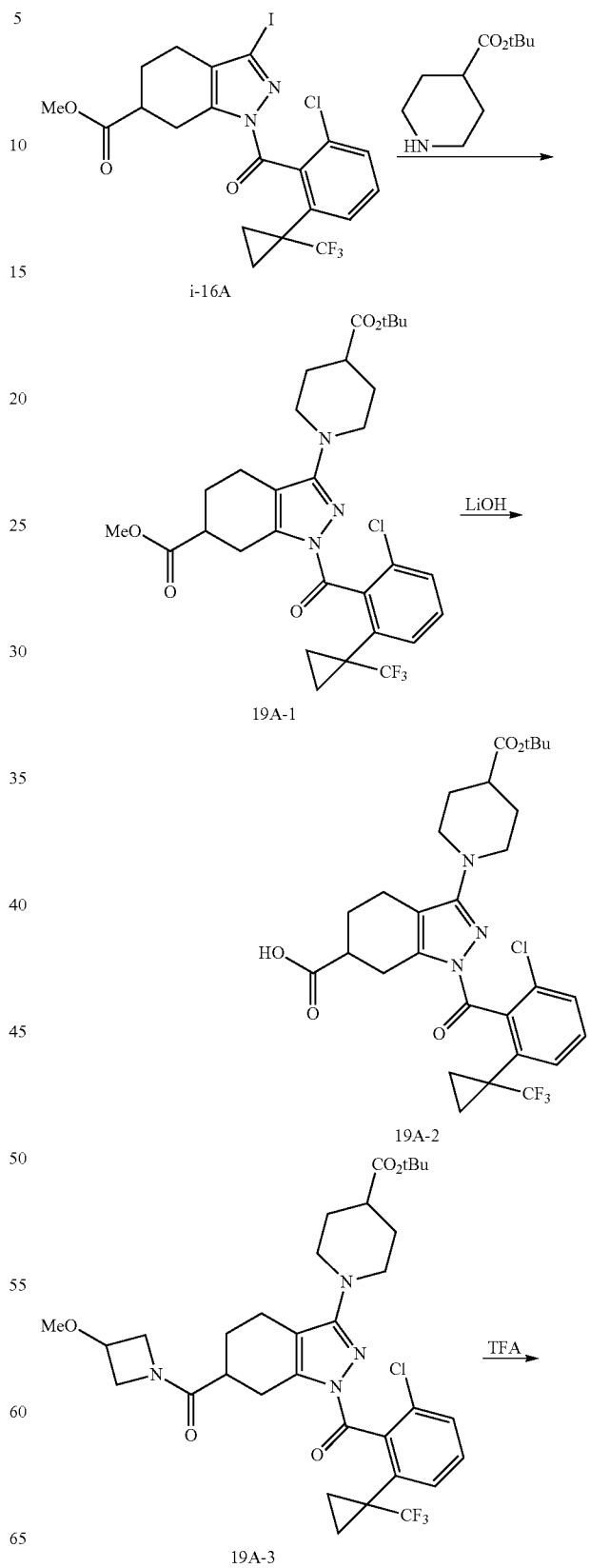

-continued

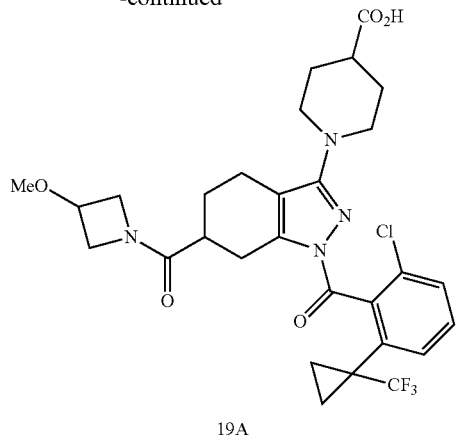

19A (R or S)-1-(1-(2-chloro-6-(1-(trifluoromethyl)cyclopropyl)benzol)-6-(3-methoxyazetidine-1-carbonyl)-4,5,6,7-tetrahydro-1H-indazol-3-yl)piperidine-4-carboxylic acid Step 1. Preparation of methyl (R or S)-3-(4-(tert-butoxycarbonyl)piperidin-1-yl)-1-(2-chloro-6-(1-(trifluoromethyl)cyclopropyl)benzoyl)-4,5,6,7-tetrahydro-1H-indazole-6-carboxylate (19A-1)

To an oven dried microwave vial equipped with magnetic stir bar under an atmosphere of $N_2$, (R or S)-methyl 1-(2-chloro-6-(1-(trifluoromethyl)cyclopropyl)benzoyl)-3-iodo-4,5,6,7-tetrahydro-1H-indazole-6-carboxylate i-16A (200 mg, 0.36 mmol, 1.0 equiv), tert-butyl piperidine-4-carboxylate (100 mg, 0.54 mmol, 1.5 equiv), copper(I) iodide (27 mg, 0.15 mmol, 0.4 equiv), 2-((2,6-dimethoxyphenyl)amino)-2-oxoacetic acid (65 mg, 0.29 mmol, 0.8 equiv), and potassium phosphate tribasic (230 mg, 1.1 mmol, 3 equiv) were added, followed by DMSO (3.6 mL, 0.1 M). The reaction mixture was stirred at 80° C. for 24 h. The resulting solution was purified using $SiO_2$ gel chromatography to afford the title compound. MS: 610 (M+1).

Step 2. Preparation of (R or S)-3-(4-(tert-butoxycarbonyl)piperidin-1-yl)-1-(2-chloro-6-(1-(trifluoromethyl)cyclopropyl)benzoyl)-4,5,6,7-tetrahydro-1H-indazole-6-carboxylic acid (19A-2)

To an oven dried microwave vial equipped with magnetic stir bar under an atmosphere of $N_2$, methyl (R or S)-3-(4-(tert-butoxycarbonyl)piperidin-1-yl)-1-(2-chloro-6-(1-(trifluoromethyl)cyclopropyl)benzoyl)-4,5,6,7-tetrahydro-1H-indazole-6-carboxylate (80 mg, 0.13 mmol, 1.0 equiv), THF (1 mL, 0.1 M), and water (262 µL, 0.1 M) were added, followed by lithium hydroxide (9.4 mg, 0.4 mmol, 3 equiv). The reaction mixture was stirred at room temperature for 6 h. The reaction was quenched with saturated aqueous $NH_4Cl$ and diluted with EtOAc (20 mL). The aqueous layer was extracted with EtOAc (3×20 mL), washed with brine (20 mL), dried over $Na_2SO_4$, filtered through celite, and concentrated in vacuo to yield crude title compound. MS: 596 (M+1), that was used without further purification.

Step 3. Preparation of tert-butyl (R or S)-1-(1-(2-chloro-6-(1-(trifluoromethyl)cyclopropyl)benzoyl)-6-(3-methoxyazetidine-1-carbonyl)-4,5,6,7-tetrahydro-1H-indazol-3-yl)piperidine-4-carboxylate (19A-3)

To an oven dried microwave vial equipped with magnetic stir bar under an atmosphere of $N_2$, crude methyl (R or S)-3-(4-(tert-butoxycarbonyl)piperidin-1-yl)-1-(2-chloro-6-(1-(trifluoromethyl)cyclopropyl)benzoyl)-4,5,6,7-tetrahydro-1H-indazole-6-carboxylate (78 mg, 0.13 mmol, 1.0 equiv), 1-[Bis(dimethylamino)methylene]-1H-1,2,3-triazolo[4,5-b]pyridinium 3-oxid hexafluorophosphate (HATU; 75 mg, 0.2 mmol, 1.5 equiv), ethyldiisopropylamine (69 µL, 0.39 mmol, 3 equiv), and DMF (654 µL, 0.2 M) were added. The reaction was stirred at room temperature for 15 minutes, followed by the addition of 3-methoxyazetidin-1-ium chloride (24 mg, 0.2 mmol, 1.5 equiv). The reaction mixture was stirred at room temperature for 30 minutes, and then purified using $SiO_2$ gel chromatography to afford title compound. MS: 665 (M+1).

Step 4. Preparation of (R or S)-1-(1-(2-chloro-6-(1-(trifluoromethyl)cyclopropyl)benzoyl)-6-(3-methoxyazetidine-1-carbonyl)-4,5,6,7-tetrahydro-1H-indazol-3-yl)piperidine-4-carboxylic acid (19A)

To an oven dried microwave vial equipped with magnetic stir bar under an atmosphere of $N_2$, tert-butyl (R or S)-1-(1-(2-chloro-6-(1-(trifluoromethyl)cyclopropyl)benzoyl)-6-(3-methoxyazetidine-1-carbonyl)-4,5,6,7-tetrahydro-1H-indazol-3-yl)piperidine-4-carboxylate (55 mg, 0.08 mmol, 1 equiv), and DCM (620 µL, 0.1 M) were added, followed by trifluoroacetic acid (207 µL, 0.1 M). The reaction mixture was stirred at room temperature for 1 h, and then concentrated in vacuo. The resulting oil was purified using mass directed reverse phase chromatography to afford the title compound. MS: 609 (M+1). $^1$H NMR (DMSO-d6) δ (ppm): 7.53-7.46 (m, 3H), 4.37 (m, 1H), 4.19 (m, 1H), 4.05-3.97 (m, 2H), 3.65 (m, 1H), 3.38 (m, 1H), 3.29 (m, 1H), 3.16 (s, 3H), 3.14 (m, 1H), 2.95 (m, 1H), 2.71 (m, 1H), 2.62-2.57 (m, 3H), 2.46 (m, 1H), 2.29 (m, 1H), 1.88 (m, 1H), 1.69-1.63 (m, 2H), 1.49 (m, 1H), 1.38 (m, 1H), 1.28 (m, 1H), 1.11 (m, 1H), 1.03 (m, 1H), 0.80 (m, 1H), 0.70 (m, 1H).

Example 20A (S)-4-((R)-1-(2-chloro-6-(1-(trifluoromethyl)cyclopropyl)benzoyl)-6-(2-oxa-6-azaspiro[3,4]octane-6-carbonyl)-4,5,6,7-tetrahydro-1H-indazol-3-yl)cyclohex-3-ene-1-carboxylic acid

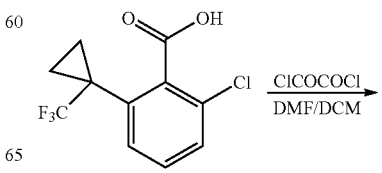

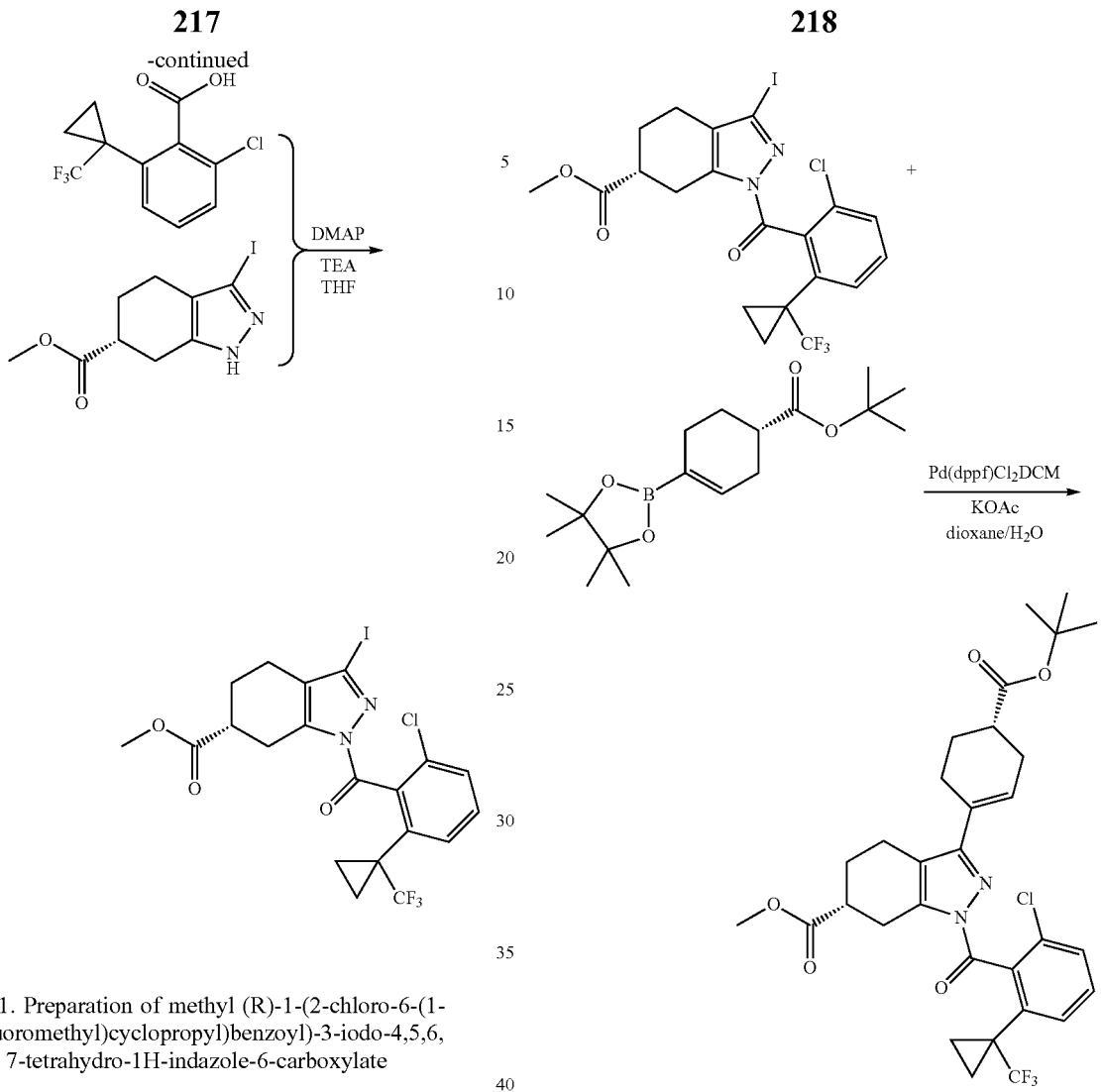

Step 1. Preparation of methyl (R)-1-(2-chloro-6-(1-(trifluoromethyl)cyclopropyl)benzoyl)-3-iodo-4,5,6,7-tetrahydro-1H-indazole-6-carboxylate To a mixture of 2-chloro-6-(1-(trifluoromethyl)cyclopropyl)benzoic acid (449 g, 1.70 mol), DMF (2.6 mL) and DCM (4.6 L) was added under stirring oxalyl chloride (175 mL, 258.7 g, 2.04 mol). The mixture was stirred at room temperature for 2.5 h and then solvents were evaporated. The resulting residue was dried twice more from DCM (2×4.5 L) to afford 2-chloro-6-(1-(trifluoromethyl)cyclopropyl)benzoyl chloride as a light tan oil. The oil was combined with methyl (R)-3-iodo-4,5,6,7-tetrahydro-1H-indazole-6-carboxylate (370 g, 1.21 mol), THF (4 L), DMAP (15.67 g, 128 mmol) and triethyl amine (275 mL, 199.65 g, 1.97 mol). The mixture was protected with nitrogen and stirred at 40° C. for 32 h. Then, the reaction mixture was diluted with MTBE (10 L), 10% citric acid (6.5 L) and brine (6.5 L). The organic layer was separated, washed with brine (6.5 L) and evaporated. The resulting residue was dissolved in DCM (3 L), and the solution was diluted with heptanes (3 L). The solution was loaded on a 6″ glass column prepacked with a slurry of 7.5 kg silica gel and 10:1 (v/v) heptanes/EtOAc. The column was eluted with 10:1 (v/v) heptanes/EtOAc (200 L) into 10 L fractions as monitored by TLC (8:1 heptanes/EtOAc). Fractions containing product (55 L) were combined and evaporated to give methyl (R)-1-(2-chloro-6-(1-(trifluoromethyl)cyclopropyl)benzoyl)-3-iodo-4,5,6,7-tetrahydro-1H-indazole-6-carboxylate as a white solid (500 g, 0.905 mol, 75% yield).

Step 2. Preparation of methyl (R)-3-((S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylate A mixture of methyl (R)-1-(2-chloro-6-(1-(trifluoromethyl)cyclopropyl)benzoyl)-3-iodo-4,5,6,7-tetrahydro-1H-indazole-6-carboxylate (490 g, 0.887 mol), tert-butyl (S)-4-(4,4,5,5-tetramethyl-1,3,2-dioxaborolan-2-yl)cyclohex-3-ene-1-carboxylate (328 g, 1.06 mol), Pd(dppf)Cl$_2$, DCM (97 g, 132 mmol), KOAc (259.7 g, 2.65 mol), 1,4-dioxane (4.9 L) and water (0.98 L) was sparged with nitrogen for 20 min under stirring. The suspension was then stirred at 90° C. under a blanket of nitrogen for 24 h. The mixture was cooled to 45° C., and then diluted with 4:1 (v/v) heptanes/EtOAc (20 L) and water (20 L). Some brown greasy residue (catalyst) formed on the flask walls. The organic layer was separated and stripped. The resulting residue was dissolved in toluene (4 L) at 45° C. and further diluted with heptanes (4 L). The solution was allowed to pass through a 6″ glass column prepacked with a slurry of 7.5 kg silica gel and 10:1 (v/v) heptanes/EtOAc. The column was eluted with 10:1 (v/v) heptanes/EtOAc (200 L) into 10 L fractions as monitored by TLC (8:1 heptanes/EtOAc). Fractions containing product (80 L) were combined and evaporated to give methyl (R)-3-((S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylate as a light tan glass (457 g, 0.753 mol, 85% yield).

the organic layer. The organic layer was separated, washed with brine (2×4.5 L), dried with MgSO$_4$ (400 g) overnight, filtered and evaporated to give (R)-3-((S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylic acid as a white foamy solid (437 g, 737 mmol, 98% crude yield, 41% de).

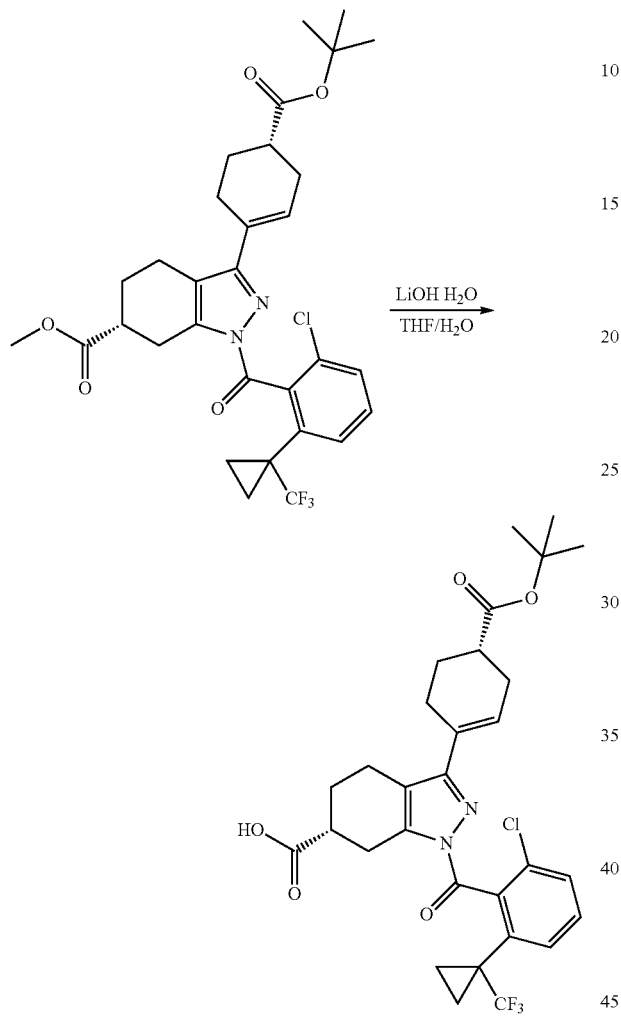

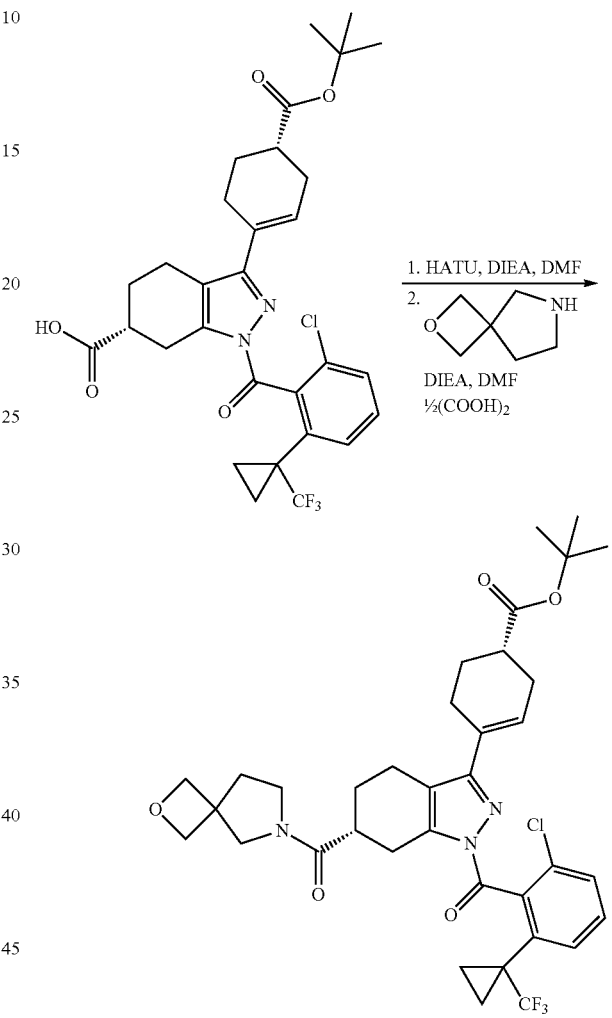

Step 3. Preparation of (R)-3-((S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylic acid A solution of methyl (R)-3-((S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylate (457 g, 753 mmol) in THF (2.74 L) was stirred at 15° C. under nitrogen protection. To it was added a solution of LiOH·H$_2$O (94.7 g, 2.26 mol) in water (913 mL) with stirring to maintain the internal temperature below 25° C. After addition, the mixture was stirred at room temperature under a blanket of nitrogen for 18 h. The mixture was diluted with MTBE (9.15 L) and brine (4.6 L) and stirred at 10° C. To it was added under nitrogen protection 1 N aqueous HCl with stirring to maintain the internal temperature below 25° C. Approximately 2.5 L of 1 N HCl was added, at which point the pH reached 1.5 in the aqueous layer, and 4.5-5 in Step 4. Preparation of tert-butyl (S)-4-((R)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylate A mixture of (R)-3-((S)-4-(tert-butoxycarbonyl)cyclohex-1-en-1-yl)-1-(2-chloro-6-(1-(trifluoromethyl)cyclopropyl)benzoyl)-4,5,6,7-tetrahydro-1H-indazole-6-carboxylic acid (437 g, 737 mmol), HATU (420.6 g, 1.11 mol) and DMF (1.48 L) was stirred under cooling with a water bath. The mixture was sparged with a good stream of nitrogen for 10 min. To it was added DIEA (514 mL, 2.95 mol) to maintain the internal temperature below 30° C. (by adding ice into the water bath as necessary). After complete addition, the mixture was sparged with nitrogen for 2 min and stirred at room temperature under a blanket of nitrogen for 18 min. To it was added 2-oxa-6-azaspiro[3.4]octane hemioxalate (152 g, 959 mmol) in portions under nitrogen protection and stirring to maintain the internal temperature below 30° C., as well as to control the rate of gas evolution. After complete addition, the mixture was stirred at room temperature under a blanket of nitrogen for 30 min. The reaction mixture was partitioned between MTBE (11 L) and water (11 L). The organic layer was separated and washed with 2% brine (7 L). Solid NaCl was added into the mixture to achieve 20% brine concentration to aid phase separation. The organic layer was separated, washed with 20% brine (2×7 L), dried with MgSO$_4$ (500 g) overnight and filtered. The filtrate was evaporated to give tert-butyl (S)-4-((R)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylate as a light tan foamy solid (514 g).

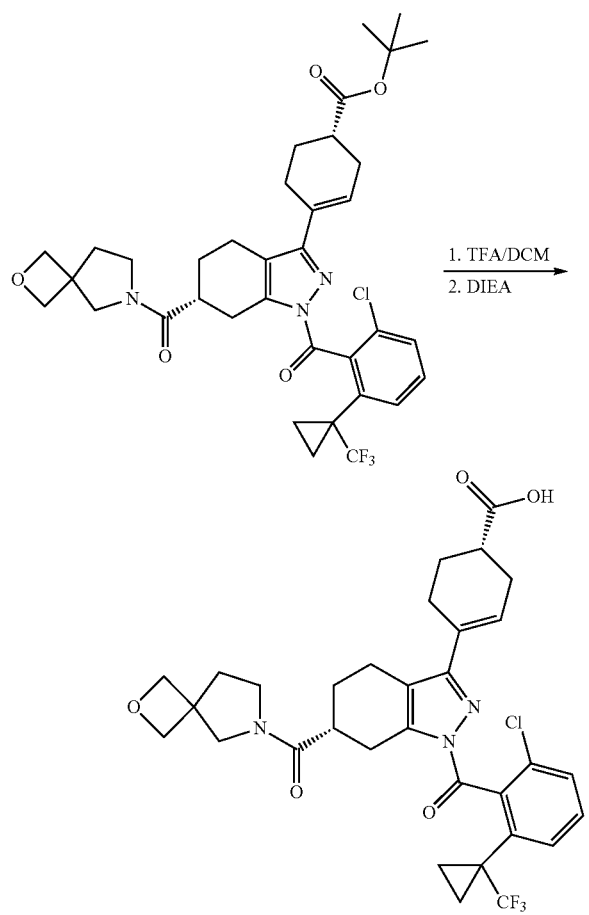

Step 5. Preparation of (S)-4-((R)-1-(2-chloro-6-(1-(trifluoromethyl)cyclopropyl)benzoyl)-6-(2-oxa-6-azaspiro 3.41 octane-6-carbonyl)-4,5,6,7-tetrahydro-1H-indazol-3-yl)cyclohex-3-ene-1-carboxylic acid A solution of tert-butyl (S)-4-((R)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylate (514 g, 737 mmol) in dry DCM (770 mL) was stirred under cooling with a water bath, and sparged with nitrogen for 2 min. To it was added TFA (770 mL) under stirring and cooling to maintain the internal temperature below 25° C. After complete addition, the mixture was stirred at room temperature for 3 h. Then, the mixture was diluted with heptanes (1.5 L) and evaporated at 25° C. The resulting residue was further evaporated under high vacuum to remove residual TFA. The residue was dissolved in dry DCM (2 L), and the solution was titrated with DIEA under cooling to pH 3. A total of 618 g of DIEA was consumed. The resulting slurry was stripped at 28° C. and the residue was taken up in EtOAc (5 L). The slurry was filtered through a polypropylene filter cloth, and the filter cake was rinsed with EtOAc (2×1 L). The combined filtrate was washed with water (2×5 L), dried with anhydrous MgSO$_4$ (500 g) and filtered. The filtrate was evaporated to give crude product (342.6 g). The crude product was dissolved in dry DCM (4 L), treated with HOAc (10 mL) and then loaded onto a 4" glass column prepacked with a slurry of silica gel (3.4 kg) in 1:2 heptanes-EtOAc. The column was eluted with 1:2 heptanes-EtOAc (100 L) into 10 L fractions, followed by elution with EtOAc (100 L) into 20 L fractions as monitored by TLC (EtOAc). Fractions containing product were pooled (100 L) and evaporated. The residue was further dried under high vacuum, and ground to give (S)-4-((R)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid as an off-white solid (154 g, 244 mmol, 33% yield, 91.3% chemical purity and 69% de by HPLC). MS: 630.5 (negative mode). $^1$H NMR (DMSO, 400 MHz) δ 7.42-7.69 (m), 6.18 (br s), 4.51-4.74 (m), 4.47 (dt, J=5.7, 2.8 Hz), 3.70-3.90 (m), 3.44-3.69 (m), 3.34-3.44 (m), 3.14-3.27 (m), 3.06 (br d, J=17.2 Hz), 2.80-2.98 (m), 2.52-2.78 (m), 2.14-2.26 (m), 2.10 (br t, J=6.9 Hz), 1.84-2.03 (m), 1.76 (br d, J=8.8 Hz), 1.46-1.69 (m), 1.22-1.43 (m), 1.00-1.22 (m), 0.72 ppm (br s). $^{19}$F NMR (DMSO, 376 MHz) δ 67.6.

Example 21

Biological Assay for RORgammaT Activity

The compounds of the invention inhibit RORgammaT activity. Activation of RORgammaT activity can be measured using, e.g., biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was recombinantly expressed in *Escherichia coli*. The RORγ-LBD protein was purified by Ni2+-affinity resin. Purified protein was then diluted in assay buffer (50 mM Tris pH 7.0, 50 mM KCl, 1 mM EDTA, 0.1 mM DTT, 100 mg/ml bovine serum albumin, delipidated) to obtain a RORγ-LBD final concentration of 3 nM. Europium tagged anti-HIS antibody was also added to this solution (1.25 nM). Separately, SF9 cells not expressing any recombinant protein were lysed (32,000 cells per ml in 25 mM Tris, 50 mM NaCl) and the previously frozen lysate was added to the diluted RORγ-LBD solution at a ratio of 0.75 ml SF9 lysate per 15 ml of diluted RORγ-LBD.

Compounds to be tested were injected to the 384-well assay plate using Acoustic Droplet Ejection technology by Echo 550 liquid handler (Labcyte, CA).

A stock of biotinylated-LXXLL peptide from coactivator SRC1 (Biotin-SPSSHSSLTERHKILHRLLQEGSP) (SEQ ID NO: 1) and APC-conjugated streptavidin (final concentrations 100 nM and 8 nM respectively) were also added to each well.

The final assay mixture was incubated overnight at 4° C., warmed to room temperature and the fluorescence signal was measured on an Envision plate reader: (Excitation filter=340 nm; APC emission=665 nm; Europium emission=615 nm; dichroic mirror=D400/D630; delay time=100 tis, integration time=200 tis). IC50 values for test compounds were calculated from the quotient of the fluorescence signal at 665 nm divided by the fluorescence signal at 615 nm.

The $IC_{50}$ values for representative compounds of the invention are set forth below in Table 16.

TABLE 16

| Example No. | Fret $IC_{50}$ (nM) |
| --- | --- |
| 1A | 769 |
| 1B | 2 |
| 2A | 2 |
| 2B | 2 |
| 2C | 3 |
| 2D | 3 |
| 2E | 3 |
| 2F | 5 |
| 2G | 8 |
| 2H | 4 |
| 2I | 2 |
| 2J | 2 |
| 2K | 4 |
| 2L | 2 |
| 2M | 2 |
| 2N | 8 |
| 2O | 14 |
| 2P | 7 |
| 2Q | 19 |
| 2R | 35 |
| 2S | 18 |
| 2T | 3 |
| 2U | 3 |
| 2V | 88 |
| 2W | 3 |
| 2X | 2 |
| 2Y | 61 |
| 2Z | 9 |
| 2AA | 137 |
| 2BB | 452 |
| 2CC | 20 |
| 2DD | 12 |
| 2EE | 111 |
| 2FF | 320 |
| 2GG | 21 |
| 2HH | 4 |
| 2II | 2 |
| 2JJ | 6 |
| 2KK | 79 |
| 2LL | 6 |
| 2MM | 3 |
| 2NN | 3 |
| 2OO | 2 |
| 2PP | 2 |
| 2QQ | 1 |
| 2RR | 1 |
| 2SS | 6 |

TABLE 16-continued

| Example No. | Fret $IC_{50}$ (nM) |
| --- | --- |
| 2TT | 3 |
| 2UU | 27 |
| 2VV | 5 |
| 2WW | 6 |
| 2XX | 2 |
| 2YY | 3 |
| 2ZZ | 525 |
| 2AAA | 4 |
| 2BBB | 5 |
| 2CCC | 10 |
| 3A | 61 |
| 3B | 1036 |
| 3C | 586 |
| 4A | 4 |
| 4B | 4 |
| 4C | 2 |
| 4D | 6 |
| 4E | 2 |
| 4F | 3 |
| 5A | 1 |
| 5B | 44 |
| 5C | 20 |
| 5D | 7 |
| 5E | 13 |
| 5F | 6 |
| 5G | 4 |
| 5H | 9 |
| 5I | 6 |
| 5J | 36 |
| 5K | 65 |
| 5L | 36 |
| 5M | 56 |
| 5N | 49 |
| 5O | 5 |
| 5P | 3 |
| 5Q | 8 |
| 5R | 4 |
| 5S | 1 |
| 5T | 2 |
| 5U | 1 |
| 5V | 1 |
| 5W | 1 |
| 5X | 1 |
| 5Y | 4 |
| 5Z | 2 |
| 5AA | 1 |
| 5BB | 1 |
| 5CC | 1 |
| 5DD | 2 |
| 5EE | 1 |
| 5FF | 4 |
| 5GG | 1 |
| 5HH | 2 |
| 5II | 1 |
| 6A | 1 |
| 6B | 1 |
| 6C | 1 |
| 6D | 1 |
| 6E | 4 |
| 6F | 1 |
| 6G | 1 |
| 6H | 1 |
| 6I | 1 |
| 6J | 5 |
| 6K | 1 |
| 6L | 4 |
| 6M | 2 |
| 6N | 1 |
| 6O | 2 |
| 6P | 1 |
| 6Q | 2 |
| 6R | 2 |
| 7A | 2 |
| 7B | 6 |
| 7C | 2 |
| 7D | 1 |
| 8A | 2 |
| 8B | 2 |

TABLE 16-continued

| Example No. | Fret IC$_{50}$ (nM) |
|---|---|
| 8C | 2 |
| 8D | 1 |
| 9A | 446 |
| 10A | 508 |
| 11A | 62 |
| 12A | 3 |
| 13A | 92 |
| 14A | 50 |
| 14B | 55 |
| 14C | 357 |
| 14D | 802 |
| 14E | 45 |
| 15A | 281 |
| 16A | 2 |
| 17A | 2 |
| 17B | 1 |
| 17C | 2 |
| 17D | 1 |
| 17E | 2 |
| 17F | 2 |
| 17G | 1 |
| 17H | 2 |
| 18A | 44 |
| 19A | 20 |

Example 22

TR-FRET RORgammaT Coactivator Recruitment Assay

The compound having the following formula (hereinafter the "Test Compound") was evaluated for inhibitory activity towards RORγ in a TR-FRET RORgammaT coactivator recruitment assay:

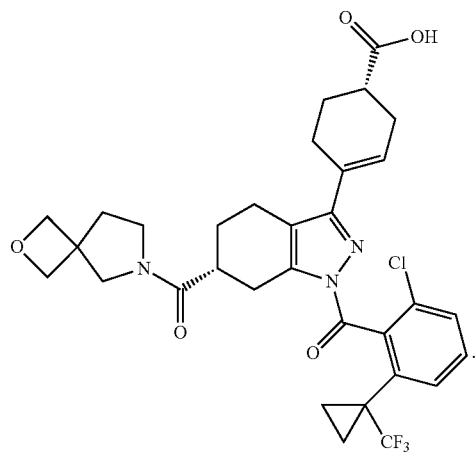 [SMILES: O=C(O)[C@@H]1CC=C(c2nn(C(=O)c3c(Cl)cccc3C3(C(F)(F)F)CC3)c3c2CC[C@@H](C(=O)N2CCC4(COC4)C2)C3)CC1]

Experimental procedures and results are provided below.

Part I—Procedure

Recombinant, HIS-tagged RORγ-LBD protein was expressed in SF9 cells using a baculovirus expression system. Cells were lysed, and the lysate was used as a source for RORγ-LBD for the assay. A 1:80 dilution of RORγ-LBD lysate in assay buffer (25 mM HEPES pH 7.0, 100 mM NaCl, 0.01% Tween 20, 0.1% BSA) was prepared and a 5 μL aliquot was added to each well (RORγ-LBD final concentration 3 nM).

Compound to be tested was diluted to 100× final test concentration in DMSO and further diluted to 4× final test concentration using assay buffer to provide the test compound mixture. An aliquot (5 μL) of the test compound mixture was added to each well.

A 4× stock of biotinylated-LXXLL peptide from SRC1-2 (Biotin-CPSSHSSLTERHKILHRLLQEGSPS) was prepared in assay buffer, and a 5 μL aliquot was added to each well (450 nM final concentration).

A 4× solution of europium-tagged anti-HIS antibody (2 nM final concentration) and APC-conjugated streptavidin (60 nM final concentration) were prepared, and a 5 μL aliquot of the solution added to each well.

The final assay mixture was incubated overnight at 4° C., and the fluorescence signal was measured on an Envision plate reader: (Excitation filter=340 nm; APC emission=665 nm; Europium emission=615 nm; dichroic mirror=D400/D630; delay time=100 μs, integration time=200 μs). The IC$_{50}$ value for the Test Compound was calculated from the quotient of the fluorescence signal at 665 nm divided by the fluorescence signal at 615 nm using GraphPad Prism software.

Part II—Results

Results of the assay for the Test Compound are provided in graphical form in FIG. 1, demonstrating an IC$_{50}$ of 1 nM for the Test Compound.

Example 23

Gal4-RORγ Luciferase Reporter Assay in HEK293 Cells

The compound having the following formula (hereinafter the "Test Compound") was evaluated for inhibitory activity towards RORγ in a Gal4-RORγ Luciferase Reporter assay in HEK293 cells:

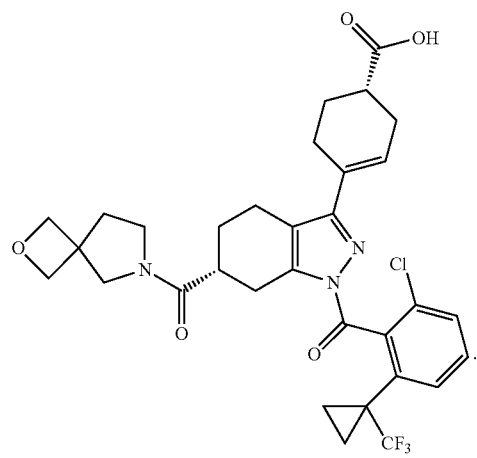 [SMILES: O=C(O)[C@@H]1CC=C(c2nn(C(=O)c3c(Cl)cccc3C3(C(F)(F)F)CC3)c3c2CC[C@@H](C(=O)N2CCC4(COC4)C2)C3)CC1]

Experimental procedures and results are provided below.

Part I—Procedure

The RORγt DNA binding domain (DBD) was replaced with heterologous yeast GAL4 DBD using standard recombinant DNA methods. The resulting GAL4-RORγt-LBD fusion construct was placed under the control of a constitutive cytomegalovirus (CMV) promoter by cloning it into the CMV-driven mammalian expression vector pCDNA3.1+− (Promega Corporation, Madison, Wis.).

HEK293 cells were transfected with the GAL4-RORγt-LBD construct (pcDNA3.1neo) and the pGL4.31 GAL4-luciferase reporter construct (Promega). The transfection protocol used the Mirus Trans-It 293 reagent. A 60 µL aliquot of Trans-IT reagent at room temperature was added drop wise to 1.5 mL of Optimem (Invitrogen). The resulting solution was mixed by inversion and incubated for 5-20 minutes at room temperature. This reagent mixture was added to 10 µg of DNA (5 µg of each expression vector). The resulting transfection mixture was mixed by inversion and incubated at room temperature for 20 minutes.

HEK293 cells were harvested and prepared for transfection while the transfection mixture was incubating. Media was removed from the cell-containing flasks via aspiration, and then an amount of TrypLE Express (stable Trypsin-like reagent, Invitrogen) was added sufficient to cover the bottom of the T75 flask. The mixture was incubated at room temperature until the cells were visibly loose in the flask (approximately 2-5 minutes). An equal volume of complete growth media (DMEM high glucose/10% dialyzed FBS/pen/strep; Invitrogen) was added, and then the mixture was pipetted to achieve a single cell suspension.

A portion ($1 \times 10^7$ cells) of the resulting suspension was spun down and then re-suspended in 10 mL of complete growth media. These cells and the transfection mixture were added to a single T75 flask. The contents of the T75 flask were mixed and incubated overnight at 37° C. and 5% $CO_2$.

After incubation for 16-24 hours, the transfected cells were harvested and plated for screening the Test Compound. The cells were harvested as described above (in preparation for transfection). The cells were counted and an appropriate number of cells were spun down. The cells were aspirated and then re-suspended in complete growth media at a concentration of $0.5 \times 10^6$ cells/mL. An aliquot (20 µL) of the suspension was added to each well in a white, tissue-culture-treated 384 well plate (10,000 cells/well).

Compound to be tested was diluted to 500× final test concentration in DMSO and further diluted to 5× the final test concentration with complete growth medium to provide the test compound solution. An aliquot (5 µL) of the Test Compound was added to each test well in the 384-well plate previously plated with the cell suspension. The plates were spun briefly and then incubated overnight at 37° C. and 5% $CO_2$.

After incubation for 16-24 hours, the luciferase assay was performed. Plates and luciferase reagent (e.g. One-Glo® or Dual Glo®; Promega, Madison, Wis.) were brought to room temperature. An aliquot (25 µL) of luciferase reagent was added to each well. The plates were spun down briefly and then incubated at room temperature for 10 minutes. The luciferase signal was measured on an Envision plate reader (Perkin Elmer) set to the ultra-sensitive luminescence setting. An $IC_{50}$ value for the Test Compound was calculated from the luciferase signal data using GraphPad Prism software.

Part II—Results

Figure 2:
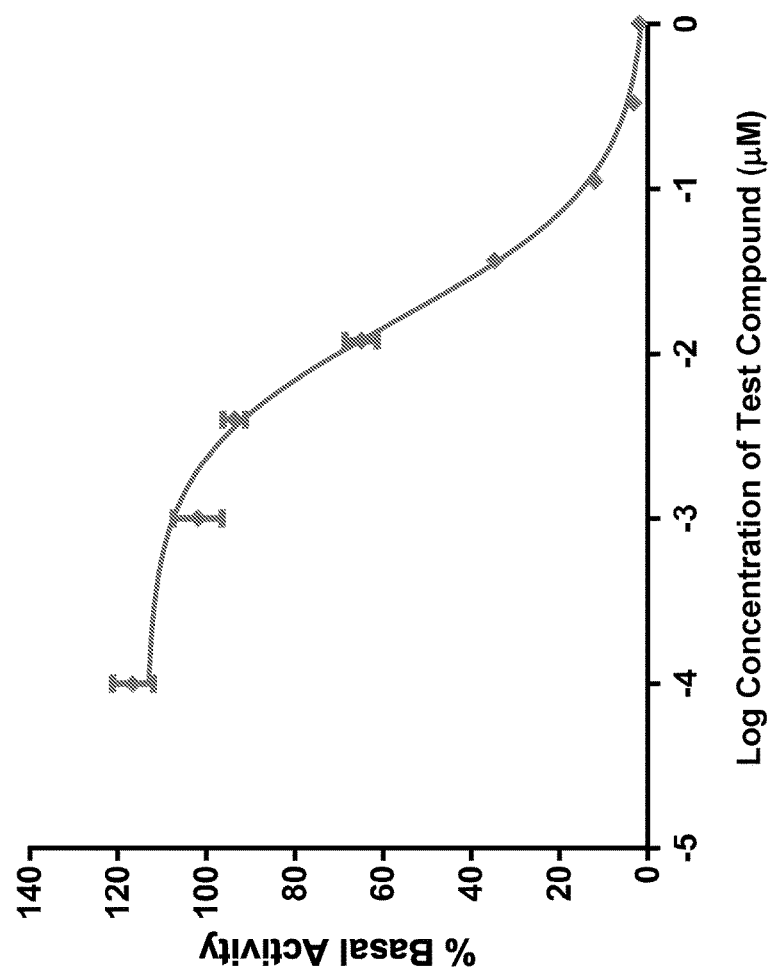
FIG. 2 is a line graph showing assay results, as described in Example 23.

Results of the assay for the Test Compound are provided in graphical form in FIG. 2, demonstrating an $IC_{50}$ of 16 nM for the Test Compound.

Example 24

Nuclear Hormone Receptor Selectivity Assay

The compound having the following formula (hereinafter the "Test Compound") was evaluated for activity towards various nuclear hormone receptors:

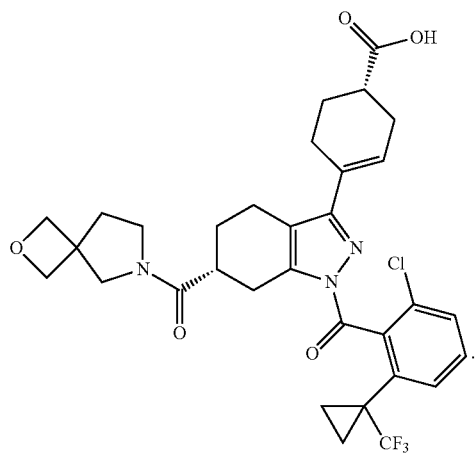 [SMILES: O=C(O)[C@@H]1CC=C(c2nn(C(=O)c3c(Cl)cccc3C3(C(F)(F)F)CC3)c3c2CC[C@@H](C(=O)N2CCC4(COC4)C2)C3)CC1]

In the assay system used, an activated GAL4-nuclear hormone receptor (NHR) fusion construct binds to an upstream activation sequence (UAS) and drives a luciferase reporter gene. In the Selectivity Panel, the Gal4 DNA binding domain (DBD) is expressed as a fusion protein with the ligand binding domain (LBD) of 18 different NHR, permitting the Test Compound to be analyzed for ability to serve as a ligand for these proteins and modulate the expression of luciferase. Experimental procedures and results are provided below.

Part I—Procedure

HEK293 cells were transfected with GAL4-NHR-LBD construct (pcDNA3.1neo) and the pGL4.31 GAL4-luciferase reporter construct (Promega) and incubated overnight at 37° C. and 5% $CO_2$. After 16-24 hours, cells were harvested and plated at 20 µL (10,000 cells)/well in tissue-culture treated 384 well plate. A 10 mM stock solution of Test Compound in dimethylsulfoxide (DMSO) was serially diluted to 5× the final test concentration with complete growth medium. A 5 µL aliquot of Test Compound solution is added to each test well in the 384 well plate previously plated with the cell suspension. Next, plates are spun briefly and incubated overnight at 37° C. and 5% $CO_2$. Test Compound was tested in both agonist mode and antagonist mode on these receptors to assess if it activates or inhibits their transcriptional activities, respectively. In agonist mode, test compound was incubated directly with the cells. For receptors that are not constitutively active, a known agonist is also tested as a positive control. In antagonist mode, a known reference agonist is added at its $EC_{80}$ concentration together with the Test Compound.

After 16-24 hours, luciferase activity was measured. Plates and luciferase reagent (e.g. One-Glo® or Dual Glo®; Promega, Madison, Wis.) were brought to room temperature. Next, a 25 µL aliquot of luciferase reagent was added to each well. Plates were spun down briefly and incubated at room temperature for 10 minutes. The luciferase signal was measured on an Envision plate reader (Perkin Elmer) set to the ultra-sensitive luminescence setting.

The $IC_{50}$ value for the Test compound was calculated from the luciferase signal data using GraphPad Prism software.

Part II—Results

Results of the assay for the Test Compound are provided in Table 1 below, where the abbreviation N/A means no data available.

TABLE 1

| Nuclear Hormone Receptor | Agonist Mode $EC_{50}$ (μM) | Antagonist Mode $IC_{50}$ (μM) |
|---|---|---|
| RORγ | N/A | 0.016 |
| RORα | N/A | >10 |
| RORβ | N/A | >10 |
| TRα | >10 | 16 |
| TRβ | >10 | >10 |
| RARα | >10 | >10 |
| RARβ | >10 | >10 |
| RARγ | >10 | >10 |
| PPARα | >10 | >10 |
| PPARβ | >10 | >10 |
| PPARγ | 5.1 (partial agonist) | >10 |
| LXRα | >10 | >10 |
| LXRβ | >10 | >10 |
| FXR | >10 | >10 |
| VDR | >10 | >10 |
| PXR | 8.2 | N/A |
| RXRα | >10 | >10 |
| CAR | >10 | >10 |

Example 25

Murine Thymic BclxL Gene Expression Assay

The compound having the following formula (hereinafter the "Test Compound") was evaluated for ability to decrease expression in murine thymus of the BclxL gene, the target gene of RORγ:

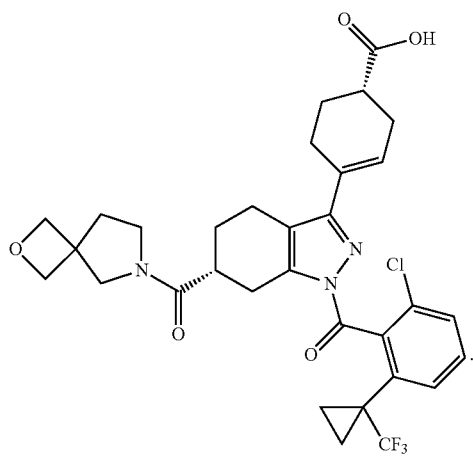 [SMILES: O=C(O)[C@@H]1CC=C(c2nn(C(=O)c3c(Cl)cccc3C3(C(F)(F)F)CC3)c3c2CC[C@@H](C(=O)N2CCC4(COC4)C2)C3)CC1]

Experimental procedures and results are provided below.
Part I—Procedure

Female C57BL/6 mice (18-20 g) were weighed and then dosed orally with either vehicle (1% Tween 80) or escalating doses of Test Compound (0.1-30 mg/kg). Animals were euthanized with carbon dioxide ($CO_2$) at 2 hours after dosing, and thymi were collected and immediately placed on ice before processing. Tween 80 is polyoxyethylene (20) sorbitan monooleate, also known as Polysorbate 80.

Thymus tissue samples were mashed with syringe plungers in a 48-well, flat-bottom tissue culture plate. Cells were suspended in 1 mL phosphate buffered saline (PBS), and passed through a Falcon 70 μM cell strainer into 50-mL centrifuge tubes. A 200 μL aliquot of cells from each sample were transferred into a 96-well, round-bottom plate. The plate was centrifuged at 1200 rpm and 4° C., flicked to remove supernatant, and the cell pellets were frozen at −80° C. until further processing.

Initial further processing consisted of ribonucleic acid (RNA) isolation and complementary deoxyribonucleic acid (cDNA) synthesis. RNA was isolated using the Qiagen RNeasy Mini Kit. cDNA was synthesized with reverse transcription using 20 μL reactions, as dictated in the High-Capacity RNA-to-cDNA Kit (Applied Biosystems). Each cDNA sample was diluted with 30 μL of RNase-free water.

Gene expression of BclxL in the samples was analyzed via real-time quantitative polymerase chain reaction (qPCR) using the StepOnePlus Real-Time PCR system (Applied Biosystems). qPCR was performed in 20 μL reactions according to manufacturer protocol using 4 μL of each cDNA sample and Power SYBR Green PCR master mix with conditions as follows: denaturation and activation at 95° C. for 10 minutes, amplification for 40 cycles (95° C. for 15 seconds, 60° C. for 1 minute), cooling at 25° C. The thresholds for significant amplification were manually set in the StepOne v2.1 software. The threshold cycle ($C_t$) for BclxL gene was automatically calculated in the software based on expression of the housekeeping gene Cyclophilin A. Relative quantification of select genes of interest was calculated using the $\Delta\Delta C_t$ method.

Part II—Results

Figure 3:
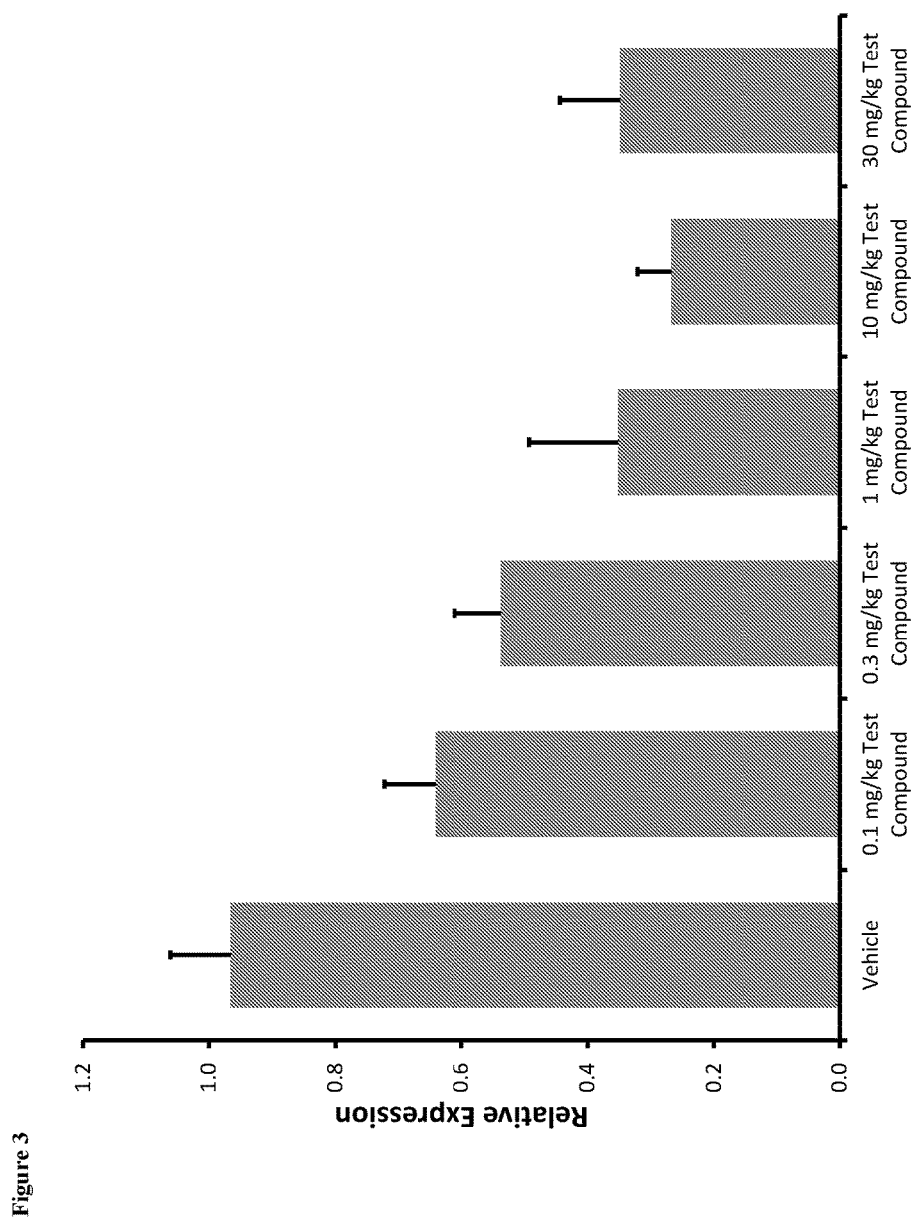
FIG. 3 is a bar graph showing assay results, as described in Example 25.

Results are provided in graphical form in FIG. 3, demonstrating that the Test Compound achieves a dose-dependent decrease in the expression of BclxL in murine thymus.

Example 26

Murine Collagen-Induced Arthritis Model

The compound having the following formula (hereinafter the "Test Compound") was evaluated for ability to decrease total joint swelling circumference in a murine collagen-induced arthritis model:

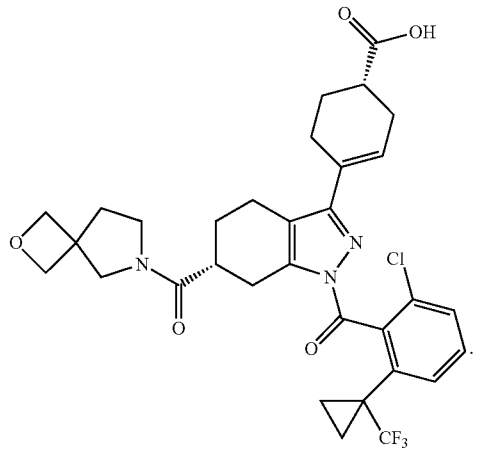 [SMILES: O=C(O)[C@@H]1CC=C(c2nn(C(=O)c3c(Cl)cccc3C3(C(F)(F)F)CC3)c3c2CC[C@@H](C(=O)N2CCC4(COC4)C2)C3)CC1]

Experimental procedures and results are provided below.
Part I—Procedure

Female DBA/1J mice (Jackson Laboratories, 7-8 weeks old) were received and allowed to acclimate for about one week. On the day of immunization, an emulsion was freshly prepared by homogenizing equal volumes of Complete Freund's Adjuvant (CFA, Chondrex #7001) and a collagen type-2 solution (bovine source, Chondrex #20022) using a tissue homogenizer, on ice. A volume of 0.1 mL of this emulsion was injected subcutaneously into the base of the tail of each mouse, which was lightly anesthetized with isoflurane. Mice recovered from anesthesia were allowed food and water ad libitum.

Eighteen days after immunization, the mice were injected intraperitoneally with 40 μg of lipopolysaccaride (LPS, Sigma#L4005) in 0.2 mL saline, in order to help synchronize the disease progression in all animals. Seven days after LPS injection, the mice were assessed for knee joint swelling by measurement of each knee joint using digital calipers and computing total joint circumference. The total knee joint circumference of the 4 knee joints was then used to randomize mice into treatment groups of equal average circumference.

After assignment to treatment groups, the mice were orally dosed (10 ml/kg) with 1% Tween 80 as vehicle or 3, 10, or 30 mg/kg of Test Compound. This dosing continued twice daily at 8- and 16-hour intervals for the duration of the study. As a positive control, one group of mice received 25 mg/kg Jak inhibitor (JAKi) tofacitinib once per day. Joints were measured 2-3 times per week.

Part II—Results

Figure 4:
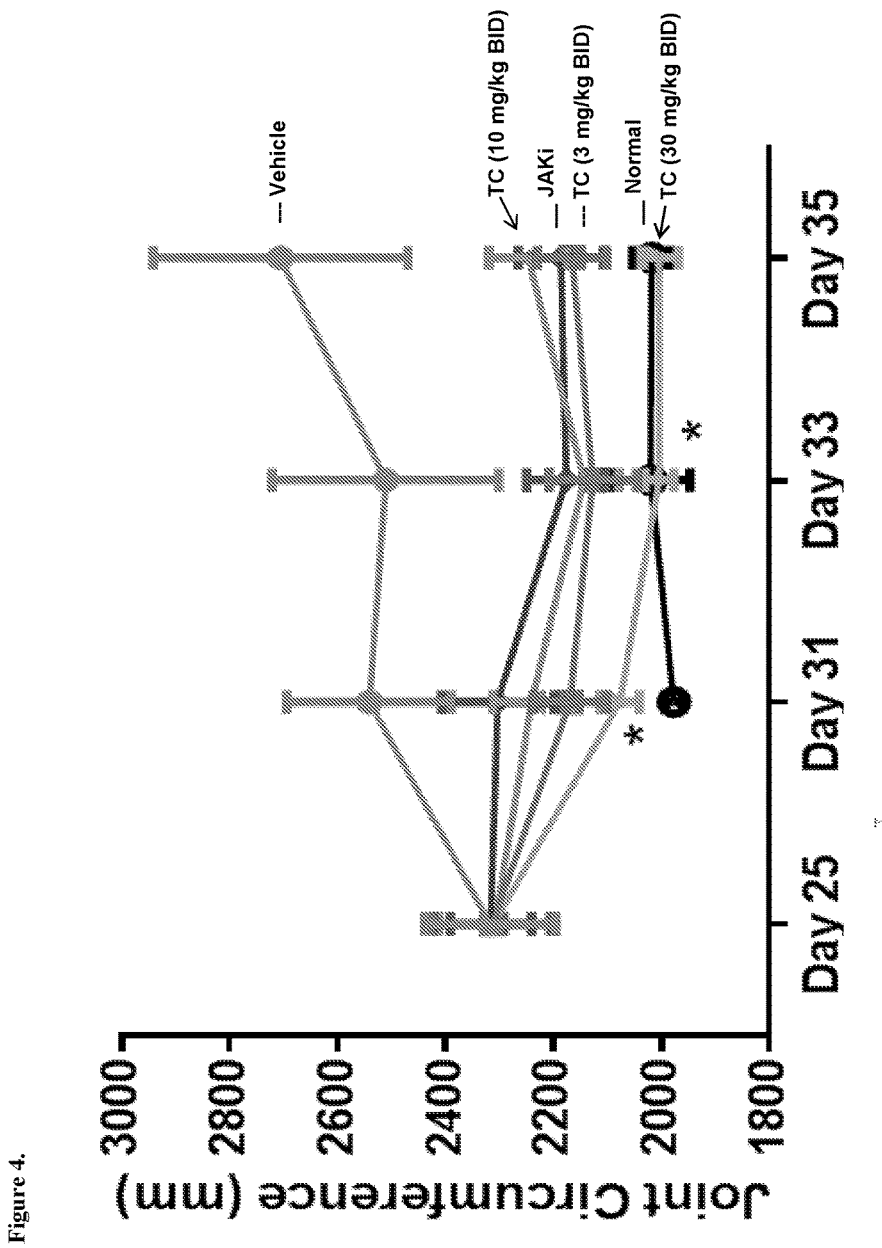
FIG. 4 is a line graph showing assay results, as described in Example 26, where the abbreviation "TC" refers to Test Compound, and the abbreviation JAKi refers to results observed using JAK inhibitor tofacitinib.

Results are provided in graphical form in FIG. 4, demonstrating that the Test Compound provided a dose-dependent decrease in total joint circumference.

Example 27

Human Ex Vivo IL-17 Expression Assay

The compound having the following formula (hereinafter the "Test Compound") was evaluated for ability to inhibit expression of interleukin-17 (IL-17) ex vivo in samples of human whole blood using qPCR:

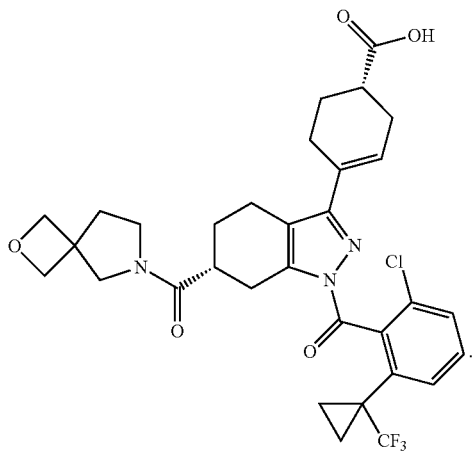 [SMILES: O=C(O)[C@@H]1CC=C(c2nn(C(=O)c3c(Cl)cccc3C3(C(F)(F)F)CC3)c3c2CC[C@@H](C(=O)N2CCC4(COC4)C2)C3)CC1]

Experimental procedures and results are provided below.

Part I—Procedure

Human whole blood was collected into sodium-heparin tubes, and T cell activators (0.5 μg/mL soluble anti-CD3/28, 10 ng/mL IL-1β, and 10 ng/mL IL-23 [R&D Systems]) were added. Test Compound was added to 1.5 mL aliquots of blood, and samples were incubated for 18-22 hours at 37° C. with 5% $CO_2$.

After incubation, whole blood samples were transferred to 2 mL Eppendorf tubes and spun down at 6000 rpm for 3 minutes. After discarding the supernatant, 1.0 mL of TRIsure (Bioline) was added into each tube, the contents were mixed by vertexing, and the samples were spun down at 14000 rpm for 10 min at 4° C. The resulting supernatant was transferred to a 2 mL Eppendorf tube, 0.27 mL of Chloroform was added, and the samples were maintained at room temperature for 15 minutes. After centrifugation at 12000×g for 10 min at 4° C., 0.6 mL of the RNA-containing upper phase was transferred to a new tube. Isopropanol (100%, 1 mL) was added, and the tubes were cooled on ice for 15 minutes to precipitate RNA. After centrifugation at 12000×g for 10 min at 4° C., the resulting RNA pellet was stored at −20° C. until further processing.

Further processing consisted of RNA isolation and cDNA synthesis. RNA was isolated and purified using the Qiagen RNeasy Mini Kit. cDNA was synthesized with reverse transcription using 20 μL reactions, as dictated in the High-Capacity RNA-to-cDNA Kit (Applied Biosystems). Each cDNA sample was diluted with 30 μL water.

Gene expression of IL-17 in the samples was analyzed via real-time qPCR using the StepOnePlus Real-Time PCR system (Applied Biosystems). qPCR was performed in 20 μL reactions according to manufacturer protocol using 4 μL of each cDNA sample and Power SYBR Green PCR master mix with conditions as follows: denaturation and activation at 95° C. for 10 minutes, amplification for 40 cycles (95° C. for 15 seconds, 60° C. for 1 minute), cooling at 25° C. The thresholds for significant amplification were manually set in the StepOne v2.1 software. The threshold cycle ($C_t$) for each gene was automatically calculated in the software based on expression of the housekeeping gene Cyclophilin A. Relative quantification of select genes of interest was calculated using the $\Delta\Delta C_t$ method.

Part II—Results

Figure 5:
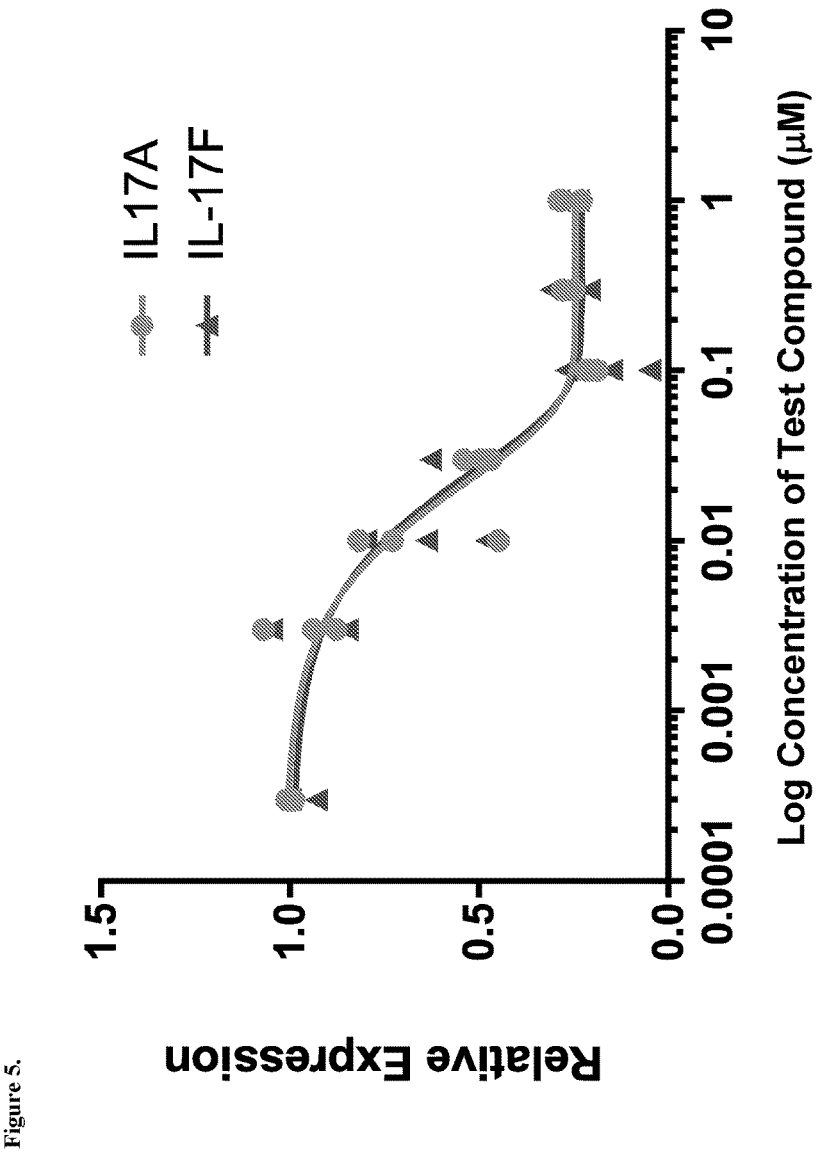
FIG. 5 is a line graph showing assay results, as described in Example 27.

Results are provided in graphical form in FIG. 5, demonstrating an $IC_{50}$ of 15 nM for inhibition of IL-17 expression by the Test Compound in this assay.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within.

What is claimed is:
1. A compound according to Formula I:

$$\text{(I)}$$

wherein:
- Rz and Rz' are independently selected from H, $(C_{1-4})$alkyl, $O(C_{1-4})$alkyl, $(C=O)O$ $(C_{1-4})$alkyl, halogen, OH, oxo, cycloalkyl, $-((C_{1-4})$alkylene)-cycloalkyl, heterocyclyl, phenyl, $NH_2$, $N(R_b)_2$, $S(O)_2-Z$, $CF_3$, $CHF_2$ and CN, said $N(R_b)_2$, alkyl, cycloalkyl and heterocyclyl are optionally substituted with OH, oxo, CN, halogen, $NH_2$, $(C_{1-4})$alkyl, $O(C_{1-4})$alkyl, heterocyclyl and $N(R_b)_2$, and said alkyl and phenyl are optionally substituted with halogen, $O(C_{1-4})$alkyl and $N(R_b)_2$; or
- Rz and Rz' can come together with the nitrogen to which they are attached and form a cyclic, bicyclic or spirocyclic moiety containing 3-9 atoms selected from C, O, N and S, said cyclic, bicylic or spirocyclic moiety optionally substituted with one to three substituents independently selected from H, $(C_{1-4})$alkyl $O(C_{1-4})$alkyl, $(C=O)O(C_{1-4})$alkyl, halogen, OH, oxo, cycloalkyl, heterocyclyl, $NH_2$, $N(R_b)_2$, $S(O)_2-Z$, $CF_3$, $CHF_2$ and CN, wherein said $N(R_b)_2$, alkyl, cycloalkyl and heterocyclyl are optionally substituted with OH, oxo, halogen, $NH_2$, $(C_{1-4})$alkyl, $O(C_{1-4})$alkyl and $N(R_b)_2$, and said alkyl is optionally substituted with halogen, $O(C_{1-4})$alkyl and $N(R_b)_2$;
- Z is $(C_{1-4})$alkyl;
- X is N or C, wherein when X is N then the dashed line is absent and when X is C the dashed line represents a double bond;
- Y is N or CH;
- $R_{1a}$ is H or $(C_{1-4})$alkyl;
- $R_{1b}$ is H, OH or $(C_{1-4})$alkyl;
- $R_{2a}$ is Cl or $(C_{1-4})$alkyl;
- $R_{2b}$ is cyclopropyl, cyclobutyl, oxetanyl or azetidinyl, each optionally substituted with $(C_{1-4})$alkyl, F, $CF_3$, $CHF_2$ or CN;
- $R_{2c}$ is H or F;
- $R_b$ is selected from H and $(C_{1-4})$alkyl; and
- $R_3$ is H or $(C_{1-4})$alkyl;
- or a pharmaceutically acceptable salt thereof.

2. A compound according to claim 1, wherein Rz and Rz' are taken together with the nitrogen to which they are attached and form a cyclic, bicyclic or spirocyclic moiety containing 3-9 atoms selected from C, O, N and S, said cyclic, bicyclic or spirocyclic moiety are optionally substituted with one to three substituents independently selected from H, $(C_{1-4})$alkyl, $O(C_{1-4})$alkyl, $(C=O)O(C_{1-4})$alkyl, halogen, OH, oxo, cycloalkyl, heterocyclyl, $NH_2$, $N(R_b)_2$, $S(O)_2-Z$, $CF_3$, $CHF_2$ and CN, wherein said $N(R_b)_2$, alkyl, cycloalkyl and heterocyclyl are optionally substituted with OH, oxo, halogen, $NH_2$, $(C_{1-4})$alkyl, $O(C_{1-4})$alkyl and N $(R_b)_2$, and said alkyl is optionally substituted with halogen, $O(C_{1-4})$alkyl and $N(R_b)_2$.

3. A compound according to claim 1, wherein Rz and Rz' are taken together with the nitrogen to which they are attached and form a spirocyclic moiety containing 7-9 atoms selected from C, O, and N, wherein said spirocyclic moiety is optionally substituted with one to two substituents independently selected from H, $(C_{1-4})$alkyl, $O(C_{1-4})$alkyl, halogen, and OH.

4. A compound according to claim 3, wherein X is C.

5. A compound according to claim 4, wherein Y is CH.

6. A compound according to claim 5, wherein $R_{1a}$ is H.

7. A compound according to claim 6, wherein $R_{1b}$ is H.

8. A compound according to claim 7, wherein $R_{2a}$ Cl.

9. A compound according to claim 7, wherein $R_{2b}$ is cyclopropyl optionally substituted with $CF_3$.

10. A compound according to claim 1, wherein:

Rz and Rz' are independently selected from H, $(C_{1-4})$ alkyl, $O(C_{1-4})$alkyl, $(C=O)O(C_{1-4})$alkyl, halogen, OH, oxo, cycloalkyl, heterocyclyl, $NH_2$, $N(R_b)_2$, $S(O)_2-Z$, $CF_3$, $CHF_2$ and CN, said $N(R_b)_2$, alkyl, cycloalkyl and heterocyclyl are optionally substituted with OH, oxo, CN, halogen, $NH_2$, $(C_{1-4})$alkyl, $O(C_{1-4})$alkyl, heterocyclyl and $N(R_b)_2$, and said alkyl is optionally substituted with halogen, $O(C_{1-4})$alkyl and $N(R_b)_2$; or Rz and Rz' can come together with the nitrogen to which they are attached and form a cyclic, bicyclic or spirocyclic moiety containing 3-9 atoms selected from C, O, N and S, said cyclic, bicylic or spirocyclic moiety are optionally substituted with one to three substituents independently selected from H, $(C_{1-4})$alkyl, $O(C_{1-4})$ alkyl, $(C=O)O(C_{1-4})$alkyl, halogen, OH, oxo, cycloalkyl, heterocyclyl, $NH_2$, $N(R_b)_2$, $S(O)_2-Z$, $CF_3$, $CHF_2$ and CN, wherein said $N(R_b)_2$, alkyl, cycloalkyl and heterocyclyl are optionally substituted with OH, oxo, halogen, $NH_2$, $(C_{1-4})$alkyl, $O(C_{1-4})$alkyl and $N(R_b)_2$, and said alkyl is optionally substituted with halogen, $O(C_{1-4})$alkyl and $N(R_b)_2$;

Z is $(C_{1-4})$alkyl;

X is N or C, wherein when X is N then the dashed line is absent and when X is C the dashed line represents a double bond;

Y is N or CH;

$R_{1a}$ is H or methyl;

$R_{1b}$ is H, OH or methyl;

$R_{2a}$ is Cl or methyl;

$R_{2b}$ is cyclopropyl, cyclobutyl, oxetanyl or azetidinyl, each optionally substituted with methyl, F, $CF_3$, $CHF_2$ and CN;

$R_{2c}$ is H or F; and $R_3$ is H;

or a pharmaceutically acceptable salt thereof.

11. A compound according to claim 1, wherein the compound is represented by Formula II:

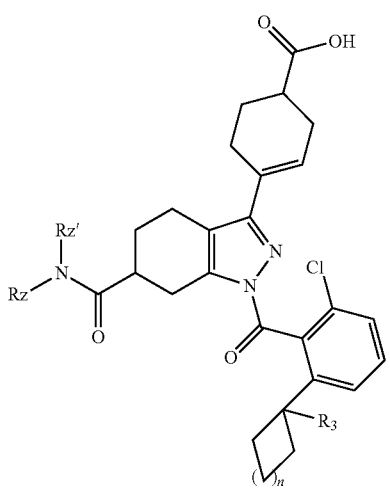

(II)

wherein:
Rz and Rz' are independently selected from H, $(C_{1-4})$alkyl, $O(C_{1-4})$alkyl, $(C=O)O(C_{1-4})$alkyl, halogen, OH, oxo, cycloalkyl, heterocyclyl, $NH_2$, $N(R_b)_2$, $S(O)_2$—Z, $CF_3$, $CHF_2$ and CN, wherein said $N(R_b)_2$, alkyl, cycloalkyl and heterocyclyl are optionally substituted with OH, oxo, CN, halogen, $NH_2$, $(C_{1-4})$alkyl, $O(C_{1-4})$alkyl, heterocyclyl and $N(R_b)_2$, and said alkyl is optionally substituted with halogen, $O(C_{1-4})$alkyl and $N(R_b)_2$; or Rz and Rz' can come together with the nitrogen to which they are attached and form a cyclic, bicyclic or spirocyclic moiety containing 3-9 atoms selected from C, O, N and S, said cyclic, bicyclic or spirocyclic moiety are optionally substituted with one to three substituents independently selected from H, $(C_{1-4})$alkyl, $O(C_{1-4})$alkyl, $(C=O)O(C_{1-4})$alkyl, halogen, OH, oxo, cycloalkyl, heterocyclyl, $NH_2$, $N(R_b)_2$, $S(O)_2$—Z, $CF_3$, $CHF_2$ and CN, wherein said $N(R_b)_2$, alkyl, cycloalkyl and heterocyclyl are optionally substituted with OH, oxo, halogen, $NH_2$, $(C_{1-4})$alkyl, $O(C_{1-4})$alkyl and $N(R_b)_2$, and said alkyl is optionally substituted with halogen, $O(C_{1-4})$alkyl and $N(R_b)_2$;

Z is $(C_{1-4})$alkyl;
n is 0 or 1;
$R_b$ is selected from H and $(C_{1-4})$alkyl; and
$R_3$ is methyl, F, $CF_3$, $CHF_2$ or CN;
or a pharmaceutically acceptable salt thereof.

12. A compound according to claim 11, wherein the compound is in the form of a free acid.

13. A compound selected from:
4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-methoxyazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(6-methyl-2,6-diazaspiro[3.3]heptane-2-carbonyl)-4,5,6,7-tetrahydro-1H-indazol-3-yl)cyclohex-3-ene-1-carboxylic acid;
4-((R or S)-6-(azetidine-1-carbonyl)-1-(2-chloro-6-cyclopropylbenzoyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-fluoroazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3,3-difluoroazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-hydroxyazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-cyclopropyl-3-hydroxyazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-hydroxy-3-(trifluoromethyl)azetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-hydroxy-3-methylazetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-methoxy-3-methylazetidine-1-carbonyl)-4,5,6,7-tetrahydro-1H-indazol-3-yl)cyclohex-3-ene-1-carboxylic acid;
4-((R or S)-6-(3-(1H-pyrazol-1-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid;
4-((R or S)-6-(3-(1H-imidazol-1-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid;
4-((R or S)-6-(3-(4H-1,2,4-triazol-4-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid;
4-((R or S)-6-(3-(4H-1,2,4-triazol-3-yl)azetidine-1-carbonyl)-1-(2-chloro-6-cyclopropylbenzoyl)-4,5,6,7-tetrahydro-1H-indazol-3-yl)cyclohex-3-ene-1-carboxylic acid;
4-((R or S)-6-(3-aminoazetidine-1-carbonyl)-1-(2-chloro-6-cyclopropylbenzoyl)-4,5,6,7-tetrahydro-1H-indazol-3-yl)cyclohex-3-ene-1-carboxylic acid;
4-((R or S)-6-(3-(aminomethyl)-3-methylazetidine-1-carbonyl)-1-(2-chloro-6-cyclopropylbenzoyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-(2-hydroxypropan-2-yl)azetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-(dimethylamino)azetidine-1-carbonyl)-4,5,6,7-tetrahydro-1H-indazol-3-yl)cyclohex-3-ene-1-carboxylic acid;
4-((R or S)-1-(2-chloro-6-cyclopropylbenzoyl)-6-(5-methyl-2,5-diazaspiro[3.4]octane-2-carbonyl)-4,5,6,7-tetrahydro-1H-indazol-3-yl)cyclohex-3-ene-1-carboxylic acid;
4-((R or S)-6-(azetidin-3-yl(methyl)carbamoyl)-1-(2-chloro-6-cyclopropylbenzoyl)-4,5,6,7-tetrahydro-1H-indazol-3-yl)cyclohex-3-ene-1-carboxylic acid;
4-((R or S)-1-(2-chloro-6-cyclopropylbenzoyl)-6-(3-(difluoromethyl)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-cyano-3-fluoroazetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-2-(hydroxymethyl)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(1-oxa-6-azaspiro[3.3]heptane-6-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(5-oxa-2-azaspiro[3.4]octane-2-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(1-methyloctahydropyrrolo[3,4-b]pyrrole-5-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-2-(methoxymethyl)pyrrolidine-1-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(2-(1-methyl-1H-1,2,4-triazol-3-yl)pyrrolidine-1-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(2-((methylamino)methyppyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-2-(methoxymethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-2-(fluoromethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-2-(fluoromethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-2-(hydroxymethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-2-(hydroxymethyl)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-3-methoxypyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-3-methoxypyrrolidine-1-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(3-hydroxy-3-methylpyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(5-methyl-2-oxa-5,8-diazaspiro[3.5]nonane-8-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((S)-3-(dimethylamino)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((R)-3-(dimethylamino)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(6-oxa-2-azaspiro[3.4]octane-2-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(1-oxa-6-azaspiro[3.4]octane-6-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(2-oxa-7-azaspiro[4.4]nonane-7-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(hexahydro-1H-furo[3,4-c]pyrrole-5-carbonyl)-4,5,6,7-tetrahydro-1H-indazol-3-yl)cyclohex-3-ene-1-carboxylic acid;

4-((6R or S)-1-(2-chloro-6-cyclopropylbenzoyl)-6-(1-oxa-7-azaspiro[4.4]nonane-7-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-fluoro-[1,3'-biazetidine]-l'-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(2-oxa-6-azaspiro[3.4]octane-6-carbonyl) -4,5,6,7-tetrahydro-1H-indazol-3-yl)cyclohex-3-ene-1-carboxylic acid;

4-((6R or S)-1-(2-chloro-6-cyclopropylbenzoyl)-6-(1-methyl-1,6-diazaspiro[3.4]octane-6-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-((3aR,6aS)-hexahydro-1H-furo[3,4-c]pyrrole-5-carbonyl)-4,5,6,7-tetrahydro-1H-indazol-3-yl)cyclohex-3-ene-1-carboxylic acid;

4-[(6R or S)-1-[(2-chloro-6-cyclopropylphenyl)carbonyl]-6-{[6-(1-methylethyl)-2,6-diazaspiro[3.3]hept-2-yl]carbonyl}-4,5,6,7-tetrahydro-1H-indazol-3-yl]cyclohex-3-ene-1-carboxylic acid;

4-{(6R or S)-1-[(2-chloro-6-cyclopropylphenyl)carbonyl]-6-[(6-pyrimidin-2-yl-2,6-diazaspiro[3.3]hept-2-yl)carbonyl]-4,5,6,7-tetrahydro-1H-indazol-3-yl}cyclohex-3-ene-1-carboxylic acid;

4-{(6R or S)-6-{[6-(tert-butoxycarbonyl)-2,6-diazaspiro[3.3]hept-2-yl]carbonyl}-1-[(2-chloro-6-cyclopropylphenyl)carbonyl]-4,5,6,7-tetrahydro-1H-indazol-3-yl}cyclohex-3-ene-1-carboxylic acid;

4-((6R or S)-1-(2-chloro-6-cyclopropylbenzoyl)-6-(((1-methylpyrrolidin-3-yl)oxy)carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(4-methyl-3-oxopiperazine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-(methylsulfonyl)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(2-oxa-6-azaspiro[3.3]heptane-6-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(3-(methylsulfonyl)azetidine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(4-methyl-3-oxopiperazine-1-carbonyl)-4,5,6,7-tetrahydro-1H-indazol-3-yl)cyclohex-3-ene-1-carboxylic acid;

4-((R or S)-1-(2-chloro-6-cyclopropylbenzoyl)-6-(2-oxa-6-azaspiro[3.3]heptane-6-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-((R)-3-(dimethylamino)pyrrolidine-1-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-(3-fluoro-[1,3'-biazetidine]-1'-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-(6-oxa-2-azaspiro[3.4]octane-2-carbonyl)-4,5,6,7-tetrahydro-1H-indazol-3-yl)cyclohex-3-ene-1-carboxylic acid;

4-((6R or S)-1-(2-chloro-6-cyclopropyl-3-fluorobenzoyl)-6-(1,6-diazaspiro[3.4]octane-6-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-(3-methoxyazetidine-1-carbonyl)-4,5,6,7-tetrahydro-1H-indazol-3-yl)cyclohex-3-ene-1-carboxylic acid;

4-((R or S)-1-(2-chloro-6-cyclopropyl-3-fluorobenzoyl)-6-(5-oxa-2-azaspiro[3.4]octane-2-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((1R,2S)-2-hydroxycyclopentyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((1S,2R)-2-fluorocyclopentyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((1R,2R)-2-hydroxycyclopentyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((1S,2R)-2-hydroxycyclopentyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3R,4S)-4-fluoropyrrolidin-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3S,4S)-4-fluoropyrrolidin-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3R,4R)-4-fluorotetrahydrofuran-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3S,4R)-4-fluorotetrahydrofuran-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((3-fluoroazetidin-3-yl)methyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(((4-fluoropiperidin-4-yl)methyl)carbamoyl)-4,5,6,7-tetrahydro-1H-indazol-3-yl)cyclohex-3-ene-1-carboxylic acid;

(1R or S)-4-((6R or S)-1-(2-chloro-6-(1-(trifluoromethyl)cyclopropyl)benzoyl)-6-((3,3-difluoropiperidin-4-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((((S)-3-fluoropiperidin-3-yl)methyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3-(dimethylamino)-2,2-difluoropropyl)carbamoyl)-4,5,6,7-tetrahydro-1H-indazol-3-yl)cyclohex-3-ene-1-carboxylic acid;

(1R or S)-4-((6R or S)-1-(2-chloro-6-(1-(trifluoromethyl)cyclopropyl)benzoyl)-6-((2,2-difluorocyclopropyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((1-(2,2,2-trifluoroethyl)-1H-pyrazol-3-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((2-fluorophenyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3-fluoropyridin-2-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(methyl(pyridin-2-yl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(pyridin-2-ylcarbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4S)-3-hydroxy-4-methoxypyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4S)-3-(dimethylamino)-4-hydroxypyrrolidine-1-carbonyl)-4,5,6,7-tetrahydro-1H-indazol-3-ylcyclohex-3-ene-1-carboxylic acid;

(R or S)-4-((R or S)-1-(2-chloro-6-(1-(trifluoromethyl)cyclopropyl)benzoyl)-6-((3S,4R)-3-fluoro-4-hydroxypyrrolidine-1-carbonyl)-4,5,6,7-tetrahydro-1H-indazol-3-yl)cyclohex-3-ene-1-carboxylic acid;

(1R or S)-4-((6R or S)-1-(2-chloro-6-(1-(trifluoromethyl)cyclopropyl)benzoyl)-6-(4-(dimethylamino)-3,3-difluoropyrrolidine-1-carbonyl)-4,5,6,7-tetrahydro-1H-indazol-3-ylcyclohex-3-ene-1-carboxylic acid;

(1R or S)-4-((6R or S)-6-(3-(azetidin-1-yl)pyrrolidine-1-carbonyl)-1-(2-chloro-6-(1-(trifluoromethyl)cyclopropyl)benzoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4R)-3-(dimethylamino)-4-fluoropyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-methoxy-3-methylazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4S)-3-(dimethylamino)-4-fluoropyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(methyl((1-methyl-1H-pyrazol-4-yOmethyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(1-methyl-1,4,5,6-tetrahydropyrrolo[3,4-c]pyrazole-5-carbonyl)-4,5,6,7-tetrahydro-1H-indazol-3-ylcyclohex-3-ene-1-carboxylic acid;

(R or S)-4-((R or S)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-((R)-3-cyanopyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(methyl((1-methyl-1H-pyrazol-4-yl)methyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(1-methyl-1,4,5,6-tetrahydropyrrolo[3,4-c]pyrazole-5-carbonyl)-4,5,6,7-tetrahydro-1H-indazol-3-ylcyclohex-3-ene-1-carboxylic acid;

(R or S)-4-((R or S)-1-(2-chloro-6-(1-(trifluoromethyl)cyclopropyl)benzoyl)-6-((3S,4S)-3-(dimethylamino)-4-fluoropyrrolidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-methoxy-3-methylazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4R)-3-(dimethylamino)-4-fluoropyrrolidine-1-carbonyl)-4,5,6,7-tetrahydro-1H-indazol-3-yl)cyclohex-3-ene-1-carboxylic acid;

(1R or S)-4-((6R or S)-6-(3-(azetidin-1-yl)pyrrolidine-1-carbonyl)-1-(2-chloro-6-(1-(trifluoromethyl)cyclopropyl)benzoyl)-4,5,6,7-tetrahydro-1H-indazol-3-yl)cyclohex-3-ene-1-carboxylic acid;

(1R or S)-4-((6R or S)-1-(2-chloro-6-(1-(trifluoromethyl)cyclopropyl)benzoyl)-6-(4-(dimethylamino)-3,3-difluoropyrrolidine-1-carbonyl)-4,5,6,7-tetrahydro-1H-indazol-3-ylcyclohex-3-ene-1-carboxylic acid;

(R or S)-4-((R or S)-1-(2-chloro-6-(1-(trifluoromethyl)cyclopropyl)benzoyl)-6-(methyl(pyrazin-2-ylmethyl)carbamoyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-hydroxyazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(3-hydroxy-3-methylazetidine-1-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-((3S,4R)-3-fluoro-4-hydroxypyrrolidine-1-carbonyl)-4,5,6,7-tetrahydro-1H-indazol-3-yl)cyclohex-3-ene-1-carboxylic acid;

4-((R or S)-1-(2-chloro-6-(1-(difluoromethyl)cyclopropyl)benzoyl)-6-(2-oxa-6-azaspiro[3.4]octane-6-carbonyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-(3-fluoro-[1,3'-biazetidine]-1'-carbonyl)-4,5,6,7-tetrahydro-1H-indazol-3-yl)cyclohex-3-ene-1-carboxylic acid;

(R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-(5-oxa-2-azaspiro[3.4]octane-2-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(trifluoromethyl)cyclopropyl)benzoyl)-6-((R)-3-(dimethylamino)pyrrolidine-1-carbonyl)-4,5,6,7-tetrahydro-1H-indazol-3-yl)-1-methylcyclohex-3-ene-1-carboxylic acid;

(R or S)-4-((R or S)-1-(2-chloro-6-(1-(difluoromethyl)cyclopropyl)benzoyl)-6-(3-methoxyazetidine-1-carbonyl)-4,5,6,7-tetrahydro-1H-indazol-3-yl)-1-methylcyclohex-3-ene-1-carboxylic acid;

4-((R or S)-1-(2-chloro-6-cyclopropylbenzoyl)-6-(3-methoxyazetidine-1-carbonyl)-6-methyl-4,5,6,7-tetrahydro-1H-indazol-3-yl)cyclohex-3-ene-1-carboxylic acid;

4-((R or S)-1-(2-(azetidin-1-yl)-4-methylnicotinoyl)-6-(3-methoxyazetidine-1-carbonyl)-4,5,6,7-tetrahydro-1H-indazol-3-yl)cyclohex-3-ene-1-carboxylic acid;

4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid;

4-((R or S)-1-(2-chloro-6-(1-fluorocyclobutyl)benzoyl)-6-((R)-3-(dimethylamino)pyrrolidine-1-carbonyl)-4,5,6,7-tetrahydro-1H-indazol-3-yl)cyclohex-3-ene-1-carboxylic acid;

4-((6R or S)-1-(2-chloro-6-(1-(trifluoromethyl)cyclopropyl)benzoyl)-6-(3-hydroxypyrrolidine-1-carbonyl)-4,5,6,7-tetrahydro-1H-indazol-3-yl)cyclohex-3-ene-1-carboxylic acid;

4-((6R or S)-1-(2-chloro-6-(1-(trifluoromethyl)cyclopropyl)benzoyl)-6-(3-methoxy-3-methylpyrrolidine-1-carbonyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-((2-methoxyethyl)(methyl)carbamoyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-((2-(dimethylamino)ethyl)(methyl)carbamoyl)-4,5,6,7-tetrahydro-1H-indazol-3-yl)cyclohex-3-ene-1-carboxylic acid;

4-((R or S)-1-(2-chloro-6-(1-(trifluoromethyl)cyclopropyl)benzoyl)-6-((2-(dimethylamino)ethyl)carbamoyl)-4,5,6,7-tetrahydro-1H-indazol-3-yl)cyclohex-3-ene-1-carboxylic acid;

4-((6R or S)-1-(2-chloro-6-(1-(trifluoromethyl)cyclopropyl)benzoyl)-6-(3-hydroxy-3-methylpyrrolidine-1-carbonyl)-4,5,6,7-tetrahydro-1H-indazol-3-yl)cyclohex-3-ene-1-carboxylic acid;

4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylic acid;

4-((R or S)-1-(2-chloro-6-(1-fluorocyclobutyl)benzoyl)-6-(3-methoxyazetidine-1-carbonyl)-4,5,6,7-tetrahydro-1H-indazol-3-yl)cyclohex-3-ene-1-carboxylic acid;

(1R,2S or 1S,2R)-4-((R or S)-1-(2-chloro-6-(1-(trifluoromethyl)cyclopropyl)benzoyl)-6-(3-hydroxy-3-methylazetidine-1-carbonyl)-4,5,6,7-tetrahydro-1H-indazol-3-yl)-2-methylcyclohex-3-ene-1-carboxylic acid;

(1R,2S or 1S,2R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-2-methylcyclohex-3-ene-1-carboxylic acid;

(1R,2S or 1S,2R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-2-methylcyclohex-3-ene-1-carboxylic acid;

(1R,6S or 1S, 6R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-6-methylcyclohex-3-ene-1-carboxylic acid;

(1R,6S or 1S, 6R)-4-((S or R)-1-(2-chloro-6-(1-(trifluoromethyl)cyclopropyl)benzoyl)-6-(3-methoxyazetidine-1-carbonyl)-4,5,6,7-tetrahydro-1H-indazol-3-yl)-6-methylcyclohex-3-ene-1-carboxylic acid;

(1R,2S or 1S,2R)-4-((S or R)-1-(2-chloro-6-(1-(trifluoromethyl)cyclopropyl)benzoyl)-6-(3-hydroxyazetidine-1-carbonyl)-4,5,6,7-tetrahydro-1H-indazol-3-yl)-2-methylcyclohex-3-ene-1-carboxylic acid;

(1R,6S or 1S,6R)-4-((S or R)-1-(2-chloro-6-(1-(trifluoromethyl)cyclopropyl)benzoyl)-6-(2-oxa-6-azaspiro[3.4]octane-6-carbonyl)-4,5,6,7-tetrahydro-1H-indazol-3-yl)-6-methylcyclohex-3-ene-1-carboxylic acid;

(1R,6S or 1S,6R)-4-((S or R)-1-(2-chloro-6-(1-(trifluoromethyl)cyclopropyl)benzoyl)-6-(4-hydroxypiperidine-1-carbonyl)-4,5,6,7-tetrahydro-1H-indazol-3-yl)-6-methylcyclohex-3-ene-1-carboxylic acid;

(R or S)-1-(1-(2-chloro-6-cyclopropylbenzoyl)-6-(3-methoxyazetidine-1-carbonyl)-4,5,6,7-tetrahydro-1H-indazol-3-yl)piperidine-4-carboxylic acid; and (R or S)-1-(1-(2-chloro-6-(1-(trifluoromethyl)cyclopropyl)benzoyl)-6-(3-methoxyazetidine-1-carbonyl)-4,5,6,7-tetrahydro-1H-indazol-3-yl)piperidine-4-carboxylic acid;

or a pharmaceutically acceptable salt thereof.

14. A compound according to claim 1, wherein the compound is

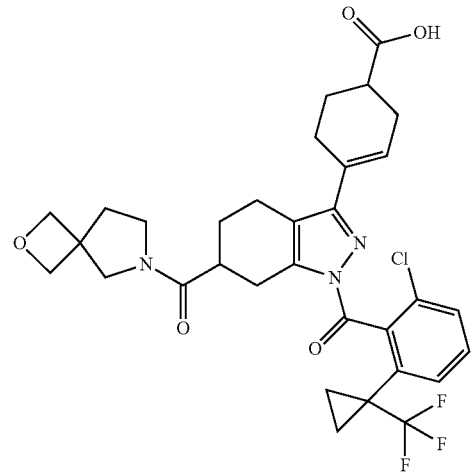 [SMILES: O=C(O)C1CC=C(c2nn(C(=O)c3c(Cl)cccc3C3(C(F)(F)F)CC3)c3c2CCC(C(=O)N2CCC4(COC4)C2)C3)CC1]

or a pharmaceutically acceptable salt thereof.

15. A compound according to claim 1, wherein the compound is

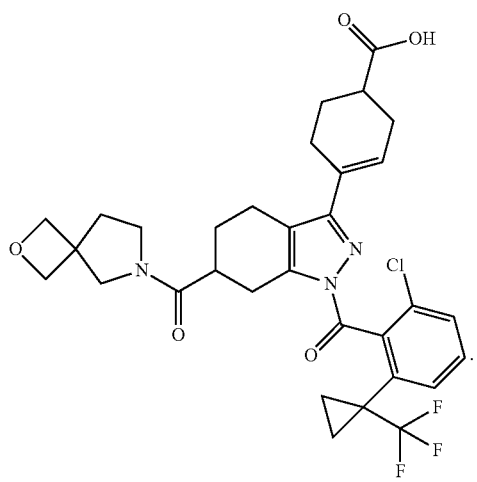 [SMILES: O=C(O)C1CC=C(c2nn(C(=O)c3c(Cl)cccc3C3(C(F)(F)F)CC3)c3c2CCC(C(=O)N2CCC4(COC4)C2)C3)CC1]

or a pharmaceutically acceptable salt thereof.

16. A compound according to claim 1, wherein the compound is

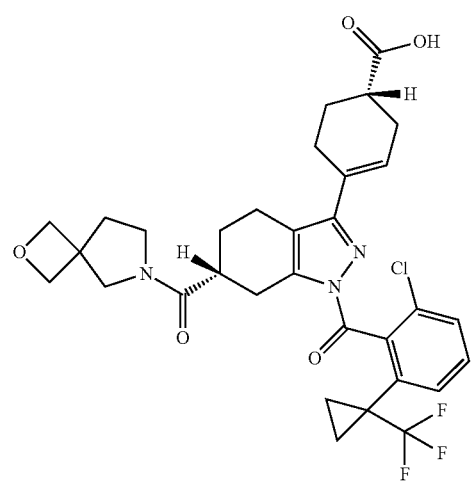 [SMILES: O=C(O)[C@@H]1CC=C(c2nn(C(=O)c3c(Cl)cccc3C3(C(F)(F)F)CC3)c3c2CC[C@@H](C(=O)N2CCC4(COC4)C2)C3)CC1]

or a pharmaceutically acceptable salt thereof.

17. A compound according to claim 1, wherein the compound is

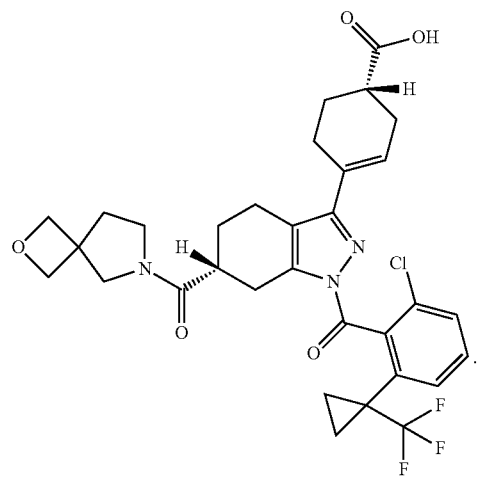 [SMILES: O=C(O)[C@@H]1CC=C(c2nn(C(=O)c3c(Cl)cccc3C3(C(F)(F)F)CC3)c3c2CC[C@@H](C(=O)N2CCC4(COC4)C2)C3)CC1]

18. A compound according to claim 1, wherein the compound is

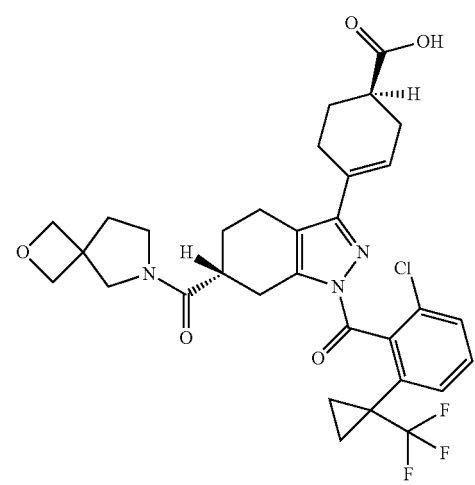 [SMILES: O=C(O)[C@H]1CC=C(c2nn(C(=O)c3c(Cl)cccc3C3(C(F)(F)F)CC3)c3c2CC[C@@H](C(=O)N2CCC4(COC4)C2)C3)CC1]

or a pharmaceutically acceptable salt thereof.

19. A compound according to claim 1, wherein the compound is
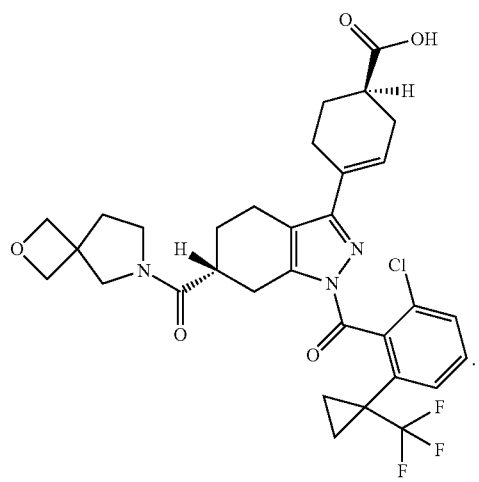 [SMILES: O=C(O)[C@H]1CC=C(c2nn(C(=O)c3c(Cl)cccc3C3(C(F)(F)F)CC3)c3c2CC[C@@H](C(=O)N2CCC4(COC4)C2)C3)CC1]
20. A compound according to claim 1, wherein the compound is
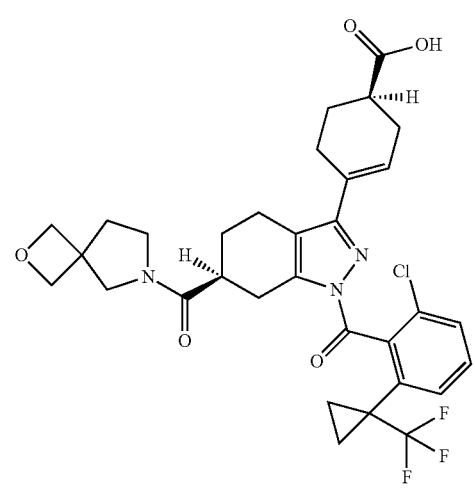 [SMILES: O=C(O)[C@H]1CC=C(c2nn(C(=O)c3c(Cl)cccc3C3(C(F)(F)F)CC3)c3c2CC[C@H](C(=O)N2CCC4(COC4)C2)C3)CC1]
or a pharmaceutically acceptable salt thereof.
21. A compound according to claim 1, wherein the compound is
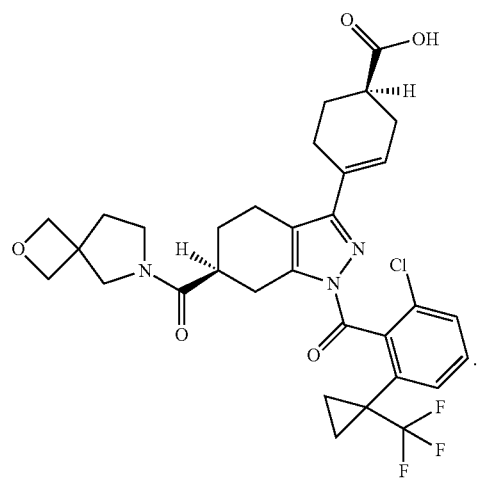 [SMILES: O=C(O)[C@H]1CC=C(c2nn(C(=O)c3c(Cl)cccc3C3(C(F)(F)F)CC3)c3c2CC[C@H](C(=O)N2CCC4(COC4)C2)C3)CC1]
22. A compound according to claim 1, wherein the compound is
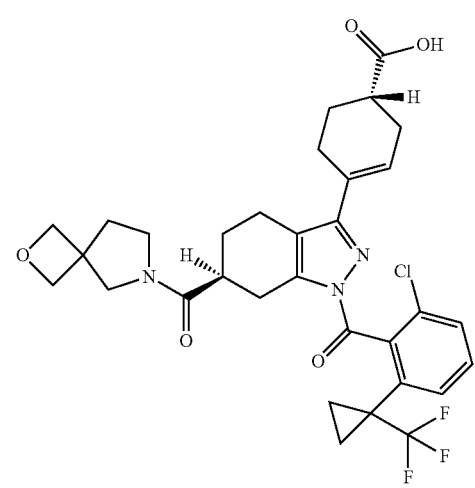 [SMILES: O=C(O)[C@@H]1CC=C(c2nn(C(=O)c3c(Cl)cccc3C3(C(F)(F)F)CC3)c3c2CC[C@H](C(=O)N2CCC4(COC4)C2)C3)CC1]
or a pharmaceutically acceptable salt thereof.

23. A compound according to claim 1, wherein the compound is

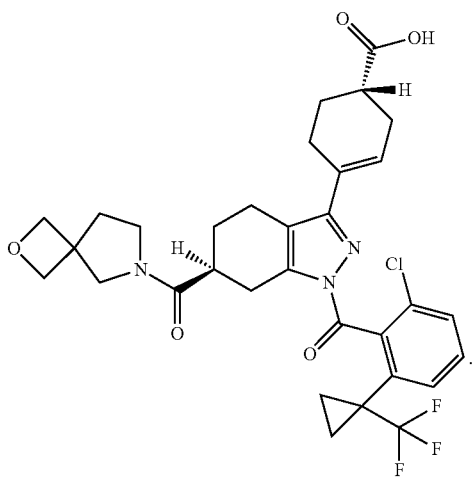 [SMILES: O=C(O)[C@@H]1CC=C(c2nn(C(=O)c3c(Cl)cccc3C3(C(F)(F)F)CC3)c3c2CC[C@H](C(=O)N2CCC4(COC4)C2)C3)CC1]

24. A pharmaceutical composition comprising a compound of claim 1, and one or more pharmaceutically acceptable carriers.

25. A pharmaceutical composition comprising a compound of claim 13 or a pharmaceutically acceptable salt thereof, and one or more pharmaceutically acceptable carriers.

26. A pharmaceutical composition comprising a compound of claim 14 and one or more pharmaceutically acceptable carriers.

27. A pharmaceutical composition comprising a compound of claim 16 and one or more pharmaceutically acceptable carriers.

28. A method of treating a disorder selected from the group consisting of an autoimmune disorder and an inflammatory disorder, comprising administering to a subject in need thereof a therapeutically effective amount of a compound of claim 1, to treat the disorder.

29. The method of claim 28, wherein the disorder is rheumatoid arthritis, psoriasis, Crohn's disease, inflammatory bowel disease, multiple sclerosis, ankylosing spondylitis, systemic lupus erythematosus, chronic graft-versus-host disease, acute graft-versus-host disease, Celiac Sprue, idiopathic thrombocytopenic thrombotic purpura, myasthenia gravis, Sjogren's syndrome, scleroderma, ulcerative colitis, or epidermal hyperplasia.

30. A method of inhibiting the activity of a RORγ, comprising exposing a RORγ to an effective amount of a compound of claim 1 to inhibit the activity of said RORγ.

* * * * *